US007132291B2

(12) United States Patent
Cardineau et al.

(10) Patent No.: US 7,132,291 B2
(45) Date of Patent: Nov. 7, 2006

(54) VECTORS AND CELLS FOR PREPARING IMMUNOPROTECTIVE COMPOSITIONS DERIVED FROM TRANSGENIC PLANTS

(75) Inventors: Guy A. Cardineau, Tempe, AZ (US); Hugh Stanley Mason, Phoenix, AZ (US); Joyce M. VanEck, Ithaca, NY (US); Dwayne D. Kirk, Mesa, AZ (US); Amanda Maree Walmsley, Mesa, AZ (US)

(73) Assignees: Dow Agro Sciences LLC, Indianapolis, IN (US); Boyce Thompson Institute for Plant Research, Ithaca, NY (US)

( * ) Notice: Subject to any disclaimer, the term of this patent is extended or adjusted under 35 U.S.C. 154(b) by 35 days.

(21) Appl. No.: 10/838,834

(22) Filed: May 4, 2004

(65) Prior Publication Data

US 2005/0048074 A1 Mar. 3, 2005

Related U.S. Application Data

(60) Provisional application No. 60/467,998, filed on May 5, 2003.

(51) Int. Cl.

*C12N 15/82* (2006.01)
*A01H 5/00* (2006.01)
*C07H 21/04* (2006.01)

(52) U.S. Cl. .................. 435/468; 435/419; 435/320.1; 526/23.72

(58) Field of Classification Search ..................... None
See application file for complete search history.

(56) References Cited

U.S. PATENT DOCUMENTS

| | | | | |
|---|---|---|---|---|
| 5,484,717 | A | 1/1996 | Zaccardi | 435/119 |
| 5,654,184 | A | 8/1997 | Curtiss, III et al. | 435/172.3 |
| 5,679,880 | A | 10/1997 | Curtiss, III et al. | 800/205 |
| 5,686,079 | A | 11/1997 | Curtiss, III et al. | 424/234.1 |
| 5,733,556 | A | 3/1998 | Schrier | |
| 5,914,123 | A | 6/1999 | Arntzen et al. | 424/439 |
| 6,034,298 | A | 3/2000 | Lam et al. | 800/298 |
| 6,136,320 | A | 10/2000 | Arntzen et al. | 424/204.1 |
| 6,194,560 | B1 | 2/2001 | Arntzen et al. | 536/23.7 |
| 6,395,964 | B1 | 5/2002 | Arntzen et al. | 800/288 |
| 2001/0053367 | A1 | 12/2001 | Arntzen | |

FOREIGN PATENT DOCUMENTS

| | | |
|---|---|---|
| EP | 0 974 660 | 1/2000 |
| WO | WO 90/02484 | 3/1990 |
| WO | WO 94/20135 | 9/1994 |
| WO | WO02/00169 A2 | 1/2002 |
| WO | WO 02/083072 | 10/2002 |

OTHER PUBLICATIONS

Bienenstock, et al., "A Common Mucosal Immunologic System Involving the Bronchus, Breast and Bowel," *Adv. Exp. Med. Biol.* 107:53-66 (1978).

Cebra, et al., "Origin and Differentiation of Lymphocytes Involved in the Secretory IgA Response," *Cold Spring Harbor Symp. Quant. Biol.* 41:201-215 (1976).

McGhee, et al., "The Secretory Immune System," *Annals N.Y. Acad. Sci.* 409(1983).

McNabb, P.C., "Host Defense Mechanisms at Mucosal Surfaces," *Ann. Rev. Microbiol.* 35:477-496 (1981).

Sneller, et al., "M Cells and Host Defense," *J. Inf. Dis.* 154(5):737-741 (1986).

Weisz-Carrington, et al., "Organ and Isotype Distribution of Plasma Cells Producing Specific Antibody After Oral Immunization: Evidence for Generalized Secretory Immune System," *J. Immunol.* 123(4):1705-1708 (1979).

Williams, et al., "Inhibition of Bacterial Adherence by Secretory Immunoglobulin A: A Mechanism of Antigen Disposal," *Science* 177:697-699 (1972).

Young, J.A., "Immune System of the Gastrointestinal Tract," *Int. Rev. Physiol.* 28:131-157 (1983).

Richter et al., Transgenic Plants as Edible Plant Vaccines. Current Topics in Microbiology. Plant Biotech. 1999. vol. 240, pp. 159-176.

Copy of International Search Report regarding PCT/US04/14182, unknown date.

Supplementary Partial European Search Report (re: EP 04 75 1538), Apr. 28, 2006.

*Primary Examiner*—Ashwin D. Mehta
*Assistant Examiner*—Cathy Kingdon Worley
(74) *Attorney, Agent, or Firm*—Elizabeth N. Spar; Kathleen M. Williams; Edwards Angell Palmer & Dodge LLP

(57) ABSTRACT

The inventions is drawn towards vectors and methods useful for preparing genetically transformed plant cells that express immunogens from pathogenic organisms which are used to produce immunoprotective particles useful in vaccine preparations. The invention includes plant optimized genes that encode the HN protein of Newcastle Disease Virus. The invention also relates to methods of producing an antigen in a transgenic plant.

6 Claims, 60 Drawing Sheets

Figure 1a (SEQ ID NOS: 1 and 2)

```
NcoI
cc ATG GAC CGA GCA GTT TCA CAA GTG GCT CTT GAG AAT GAT GAG AGG GAA GCC
  > M   D   R   A   V   S   Q   V   A   L   E   N   D   E   R   E   A
AAG AAC ACT TGG AGG CTT ATC TTT CGG ATA GCC ATT CTC TTT CTT ACT GTT GTC
 K   N   T   W   R   L   I   F   R   I   A   I   L   F   L   T   V   V
                                    BseRI
                    BseRI cut site
ACC CTA GCA ATC TCT GTT GCA TCA TTA CTC TAT TCT ATG GGA GCA AGC ACC CCC
 T   L   A   I   S   V   A > S   L   L   Y   S   M   G   A   S   T   P
TCA GAC TTA GTT GGC ATA CCC ACA CGA ATC TCT AGG GCT GAA GAG AAG ATT ACC
 S   D   L   V   G   I   P   T   R   I   S   R   A   E   E   K   I   T
AGT ACC CTA GGC TCC AAC CAG GAT GTT GTG GAC CGA ATC TAC AAA CAA GTT GCA
 S   T   L   G   S   N   Q   D   V   V   D   R   I   Y   K   Q   V   A
CTT GAA AGT CAA CTT GCA TTA CTC AAC ACA GAA ACT ACC ATC ATG AAT GCA ATC
 L   E   S   P   L   A   L   L   N   T   E   T   T   I   M   N   A   I
ACC AGC CTA TCC TAT CAG ATC AAT GGG GCT GCC AAC AAT TCA GGT TGG GGA GCC
 T   S   L   S   Y   Q   I   N   G   A   A   N   N   S   G   W   G   A
CCA ATT CAT GAT CCA GAC TAC ATT GGA GGT ATT GGC AAA GAA CTC ATT GTA GAT
 P   I   H   D   P   D   Y   I   G   G   I   G   K   E   L   I   V   D
GAT GCT TCA GAT GTT ACA TCT TTC TAT CCT TCA GCT TTC CAG GAA CAT CTG AAC
 D   A   S   D   V   T   S   F   Y   P   S   A   F   Q   E   H   L   N
TTC ATT CCT GCA CCC ACA ACT GGG AGT GGG TGC ACT CGG ATA CCC TCA TTT GAC
 F   I   P   A   P   T   T   G   S   G   C   T   R   I   P   S   F   D
ATG AGT GCT ACA CAC TAT TGC TAT ACA CAC AAT GTC ATT CTA TCT GGC TGT CGT
 M   S   A   T   H   Y   C   Y   T   H   N   V   I   L   S   G   C   R
GAC CAT TCT CAC TCT TAT CAG TAC TTA GCA CTT GGA GTT CTT CGT ACA TCT GCT
 D   H   S   H   S   Y   Q   Y   L   A   L   G   V   L   R   T   S   A
ACT GGT AGA GTG TTC TTC TCA ACT CTT CGC AGT ATC AAT CTT GAT GAT ACA CAG
 T   G   R   V   F   F   S   T   L   R   S   I   N   L   D   D   T   Q
AAT CGC AAA AGT TGC TCT GTA TCT GCT ACA CCT TTG GGC TGT GAT ATG CTA TGC
 N   R   K   S   C   S   V   S   A   T   P   L   G   C   D   M   L   C
AGT AAA GTA ACA GAA ACT GAA GAA GAG GAC TAC AAT TCT GCA GTC CCT ACA AGG
 S   K   V   T   E   T   E   E   E   D   Y   N   S   A   V   P   T   R
ATG GTG CAT GGC AGA TTG GGT TTT GAT GGT CAA TAC CAT GAG AAA GAT TTG GAT
 M   V   H   G   R   L   G   F   D   G   Q   Y   H   E   K   D   L   D
GTC ACT ACA TTG TTT GGG GAT TGG GTA GCT AAC TAT CCA GGA GTT GGA GGT GGT
 V   T   T   L   F   G   D   W   V   A   N   Y   P   G   V   G   G   G
AGC TTC ATT GAC TCC AGA GTC TGG TTC TCT GTC TAT GGT GGT TTG AAA CCT AAC
 S   F   I   D   S   R   V   W   F   S   V   Y   G   G   L   K   P   N
AGT CCT AGT GAT ACT GTG CAA GAG GGA AAG TAT GTT ATC TAC AAG AGG TAC AAT
 S   P   S   D   T   V   Q   E   G   K   Y   V   I   Y   K   R   Y   N
GAT ACT TGT CCT GAT GAG CAA GAC TAT CAG ATT CGA ATG GCT AAG TCA TCA TAC
 D   T   C   P   D   E   Q   D   Y   Q   I   R   M   A   K   S   S   Y
AAA CCA GGA AGA TTT GGA GGT AAG AGG ATA CAA CAA GCT ATT CTC AGT ATC AAG
 K   P   G   R   F   G   G   K   R   I   Q   Q   A   I   L   S   I   K
GTT AGC ACA TCA TTG GGA GAA GAT CCA GTC CTT ACT GTT CCA CCA AAC ACT GTA
 V   S   T   S   L   G   E   D   P   V   L   T   V   P   P   N   T   V
ACA TTG ATG GGA GCT GAG GGA AGG ATT CTT ACT GTT GGT ACT AGC CAC TTT CTC
 T   L   M   G   A   E   G   R   I   L   T   V   G   T   S   H   F   L
TAT CAA CGT GGA AGT TCC TAC TTT AGC CCA GCG TTA CTG TAT CCA ATG ACT GTG
 Y   Q   R   G   S   S   Y   F   S   P   A   L   L   Y   P   M   T   V
AGC AAC AAG ACA GCT ACA TTA CAT TCA CCA TAT ACT TTC AAT GCC TTT ACA AGA
 S   N   K   T   A   T   L   H   S   P   Y   T   F   N   A   F   T   R
```

Figure 1b

```
CCT GGA TCG ATT CCT TGC CAA GCT TCA GCT AGA TGT CCG AAT TCG TGT GTG ACT
 P   G   S   I   P   C   Q   A   S   A   R   C   P   N   S   C   V   T
GGA GTT TAC ACT GAT CCT TAC CCT TTG ATC TTC TAC CGT AAT CAT ACC TTG AGA
 G   V   Y   T   D   P   Y   P   L   I   F   Y   R   N   H   T   L   R
GGG GTG TTT GGA ACA ATG TTA GAT GGT GTT CAA GCT AGG TTG AAT CCT GCC TCT
 G   V   F   G   T   M   L   D   G   V   Q   A   R   L   N   P   A   S
GCT GTG TTT GAT TCT ACA TCC AGA TCA AGG ATA ACC AGA GTT TCC TCT AGT TCT
 A   V   F   D   S   T   S   R   S   R   I   T   R   V   S   S   S   S
ACT AAG GCA GCA TAC ACT ACC TCC ACA TGT TTC AAA GTT GTA AAG ACG AAC AAG
 T   K   A   A   Y   T   T   S   T   C   F   K   V   V   K   T   N   K
                           BglII
ACC TAT TGT CTG AGC ATA GCT GAG ATT TCT AAC ACT CTC TTT GGG GAA TTC AGA
 T   Y   C   L   S   I   A   E   I   S   N   T   L   F   G   E   F   R
                                                                   BglII
ATT GTT CCA CTT TTG GTG GAG ATT CTG AAA GAT GAT GGT GTA CGT GAA GCA AGA
 I   V   P   L   L   V   E   I   L   K   D   D   G   V   R   E   A   R
                 KpnI
    BbsI cut site       SacI
          BbsI
TCA GGT TAA gtcttcggat ccggtaccga gctc
 S   G   •
```

Figure 10

```
   1 gaccaaatct gcatcggtta tcatgcaaac aattcaacaa aacaagttga cacaatcatg
  61 gagaagaatg tgacggtcac acatgctcaa gatatactgg aaaaagagca caacgggaaa
 121 ctctgcagtc tcaaaggagt gaggcccctc attctgaagg attgcagtgt ggctggatgg
 181 cttcttggga acccaatgtg tgatgagttc ctaaatgtac cggaatggtc atatattgta
 241 gagaaggaca atccaaccaa tggcttatgt tatccgggag acttcaatga ttatgaagaa
 301 ctgaagtatt taatgagcaa cacaaaccat tttgagaaaa ttcaaataat ccctaggaac
 361 tcttggtcca atcatgatgc ctcatcagga gtgagctcag catgcccata caatggtagg
 421 tcttcctttt tcaggagtgt ggtgtggttg atcaagaaga gtaatgtata cccaacaata
 481 aagaggacct acaataacac caatgtagag gaccttctga tattgtgggg aatccatcac
 541 cctaatgatg cagcggaaca aacggaactc tatcagaact cgaacactta tgtgtctgta
 601 ggaacatcaa cactaaatca gaggtcaatt ccagaaatag ctaccaggcc caaagtgaat
 661 ggacaaagtg gaagaataga atttttctgg acaatactaa ggccgaacga tgcaatcagc
 721 tttgaaagta atgggaactt tatagctcct gaatatgcat acaagatagt taaaaaggga
 781 gattcagcaa tcatgagaag cgaactggag tatggcaact gtgataccaa atgtcagacc
 841 ccagtgggtg ctataaattc cagtatgcct tttcacaatg ttcatcccct taccattgga
 901 gagtgtccca aatatgtcaa atcagataaa ctggtccttg caacaggact gaggaacgtg
 961 cctcagagag aaacaagagg tctgtttgga gcaatagcag gattcataga aggggggtgg
1021 caaggaatgg tagatggatg gtatggttac catcatagca acgagcaggg aagtggatat
1081 gctgcagaca aagagtccac tcagaaagca atcgacggga tcaccaataa agtcaactca
1141 atcattgaca aaatgaacac tcaattcgaa gccgttggga aagaattcaa caacttagaa
1201 aggagaatag aaaatttgaa taagaaaatg gaagatggat ttctagatgt atggacttac
1261 aatgcagaac ttctggtgct catggaaaat gaaagaactc tggatttcca tgattcatat
1321 gtcaagaacc tatacgataa ggtccgactc cagctgagag ataatgcaaa agaattgggc
1381 aatgggtgtt tggagttctc ccacaaatgt gacaatgaat gcatggaaag tgtgagaaac
1441 ggaacgtatg actatccaca atactcagaa gaatcaaggc tgaacagaga ggaaatagat
1501 ggagtcaaat tggagtcaat gggcacctat cagatactat caatttactc aacagtggcg
1561 agttccctag cactggcaat catggtagct ggtctgtctt tttggatgtg ctccaatgga
1621 tcattgcaat gcagaatttg catctag
```

(SEQ ID NO:3)

```
                     DQICIGYHANNSTKQVDTIMEKNVTVTHAQDILEKEHNGKLCSL
KGVRPLILKDCSVAGWLLGNPMCDEFLNVPEWSYIVEKDNPTNGLCYPGDFNDYEELK
YLMSNTNHFEKIQIIPRNSWSNHDASSGVSSACPYNGRSSFFRSVVWLIKKSNVYPTI
KRTYNNTNVEDLLILWGIHHPNDAAEQTELYQNSNTYVSVGTSTLNQRSIPEIATRPK
VNGQSGRIEFFWTILRPNDAISFESNGNFIAPEYAYKIVKKGDSAIMRSELEYGNCDT
KCQTPVGAINSSMPFHNVHPLTIGECPKYVKSDKLVLATGLRNVPQRETRGLFGAIAG
FIEGGWQGMVDGWYGYHHSNEQGSGYAADKESTQKAIDGITNKVNSIIDKMNTQFEAV
GKEFNNLERRIENLNKKMEDGFLDVWTYNAELLVLMENERTLDFHSYVKNLYDKVRL
QLRDNAKELGNGCLEFSHKCDNECMESVRNGTYDYPQYSEESRLNREEIDGVKLESMG
TYQILSIYSTVASSLALAIMVAGLSFWMCSNGSLQCRICI
```

(SEQ ID NO:4)

Figure 14. Repeated assays of pCHA-transformed NT1 cell lines.

Cells were extracted and assayed as indicated in Figure 3.

Figure 20. Expression of HN per cell mass in pCHN-transformed NT1 lines.

Expression in lines CHN-1 and CHN-5 (Figure 6) is normalized based on cell mass.

Figure 21. Stability of expression of HN in pCHN-transformed NT1 cell lines.

Cells growing on solid media were transferred to fresh media at 2-week intervals. Expression in cell extracts was measured by ELISA and displayed on the basis of TSP.

5P=LINE 5 PLATED; 5-6=LINE 5 SUSPENSION SUBCULTURED 12-6-01; 5-13=LINE 5 SUSPENSION SUBCULTURED 12-13-01

7P=LINE 7 PLATED; 7-6=LINE 7 SUSPENSION SUBCULTURED 12-6-01; 7-13=LINE 7 SUSPENSION SUBCULTURED 12-13-01

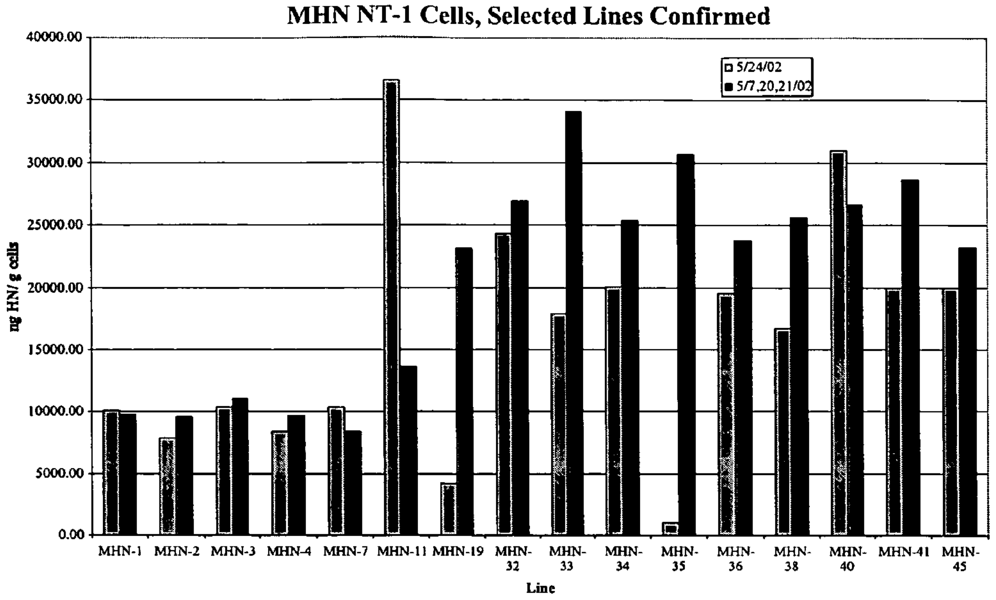
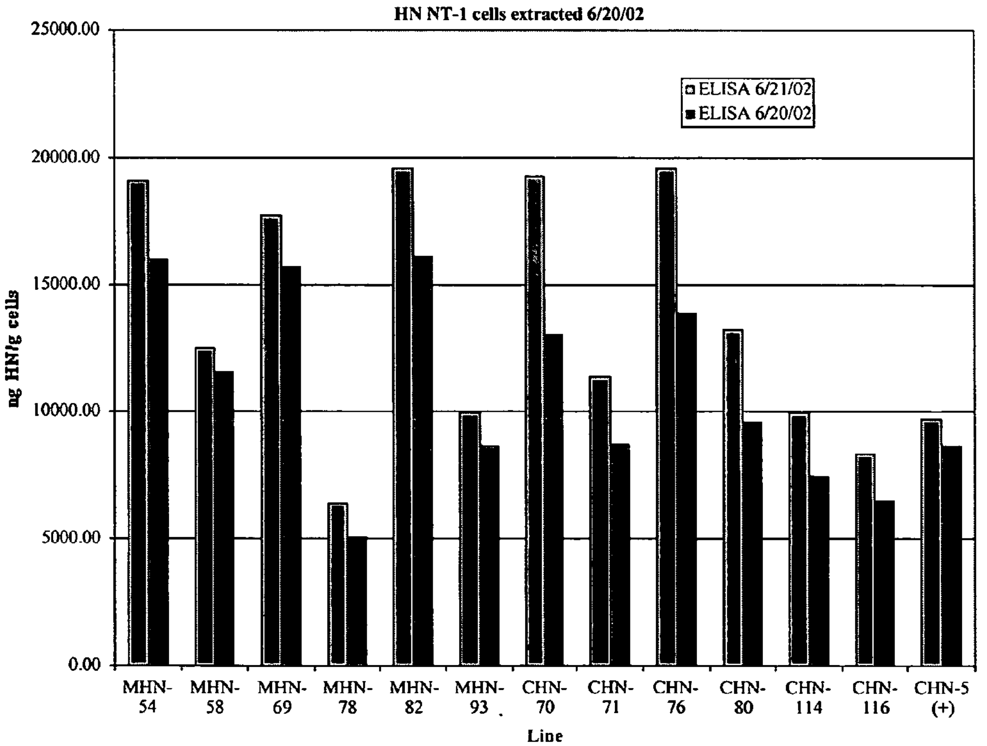
Figure 25. Expression of HN in pMHN- and pCHN-transformed NT1 cell lines.

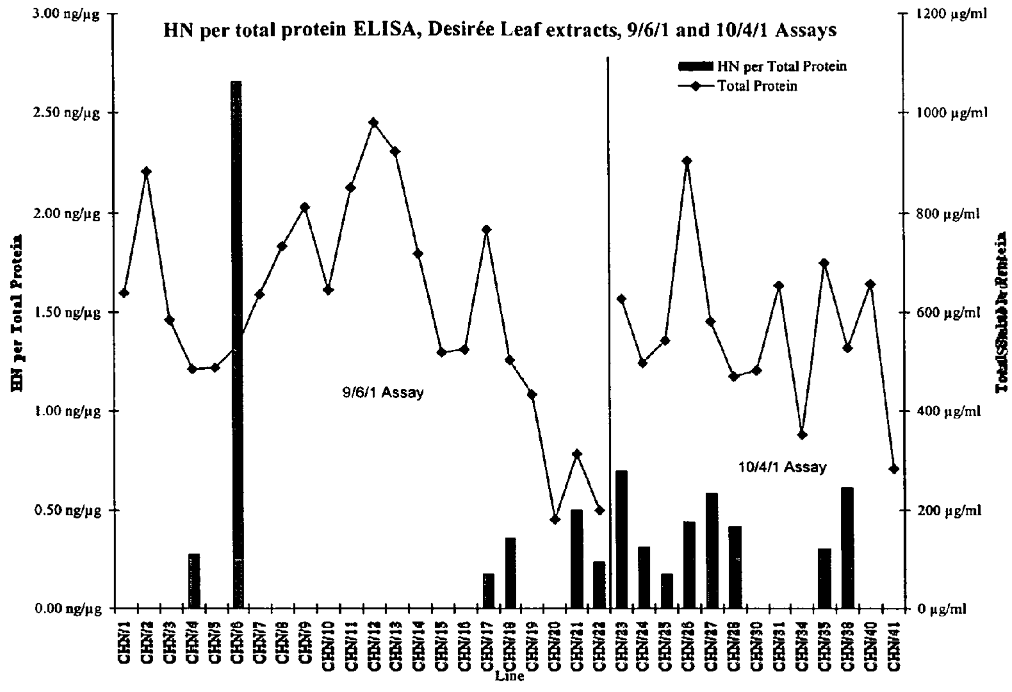
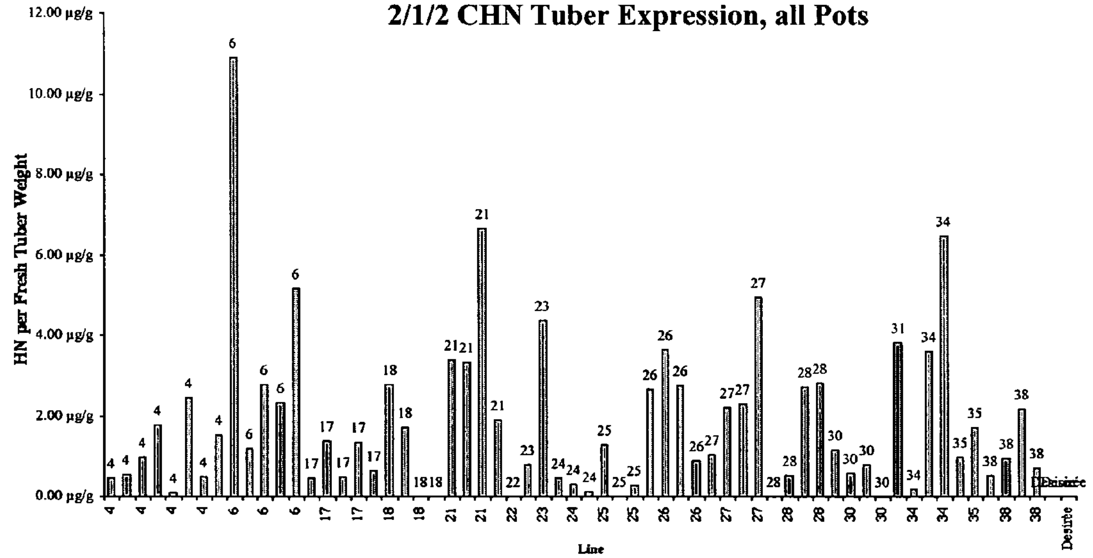
Figure 26. HN expression in pCHN-transformed potato.
Upper panel, expression in leaves of tissue culture plantlets. Lower panel, expression in tubers (each bar represents value obtained from a separate tuber of the same line.

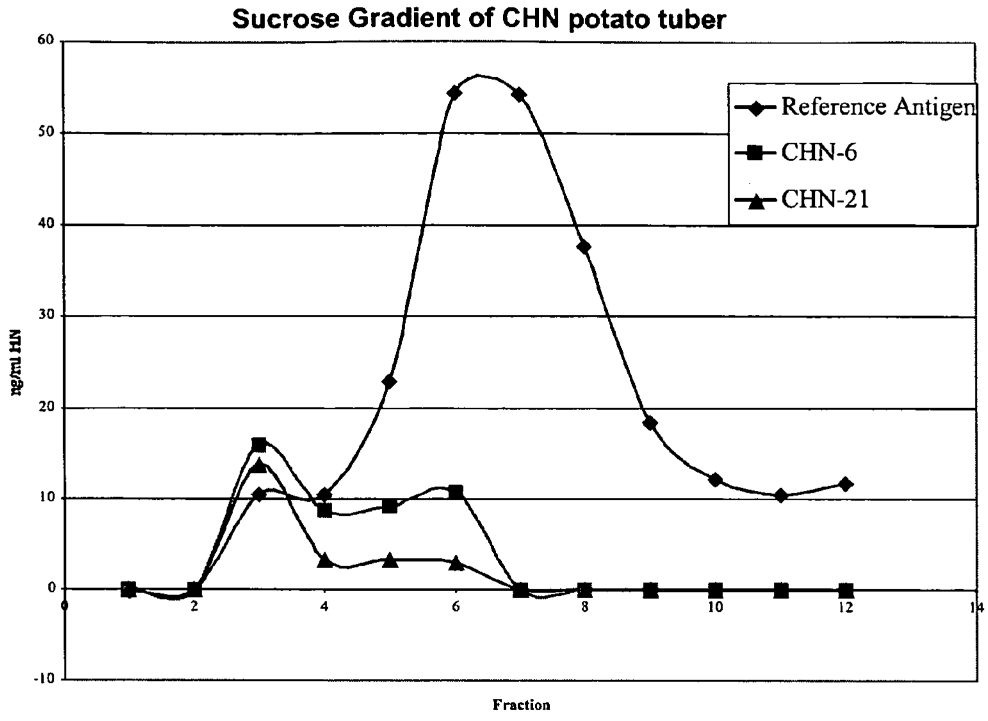
Figure 27. Particle behavior of HN antigen extracted from pCHN-transformed potato tubers. Extracts were prepared and analyzed as for NT1 extracts in Figure 11. CHN-6, CHN-21 are independent pCHN-transformed potato lines. Reference antigen is inactivated NDV.

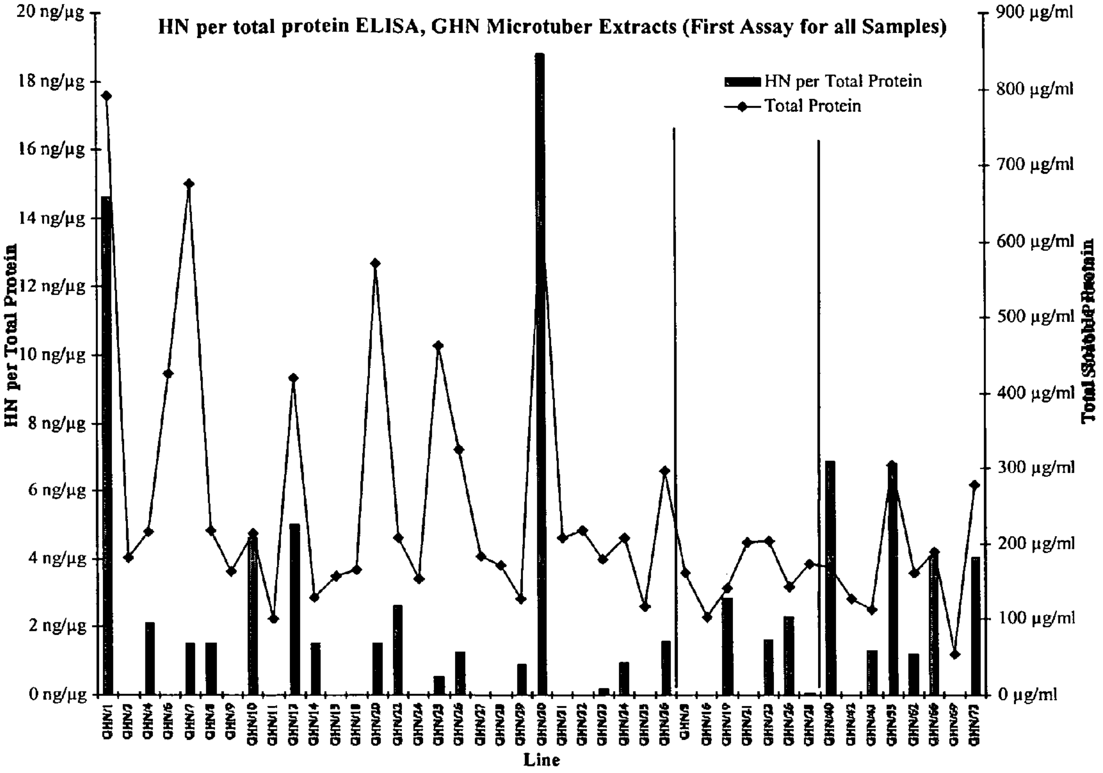
Figure 28. HN expression in microtubers of pGHN-transformed potato plants.
Microtubers were generated *in vitro* from stem node cuttings of transformed plants. HN was assayed by ELISA and total protein was assayed by the Bradford method.

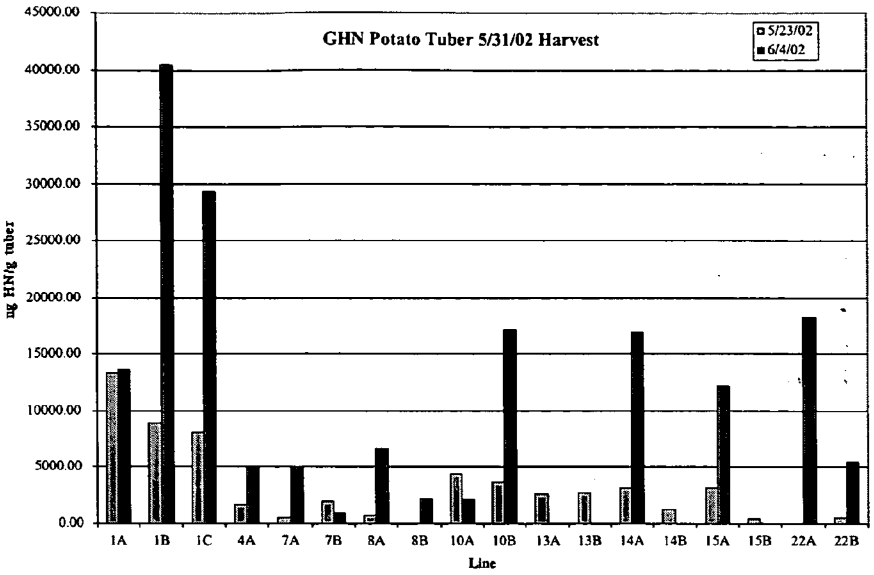
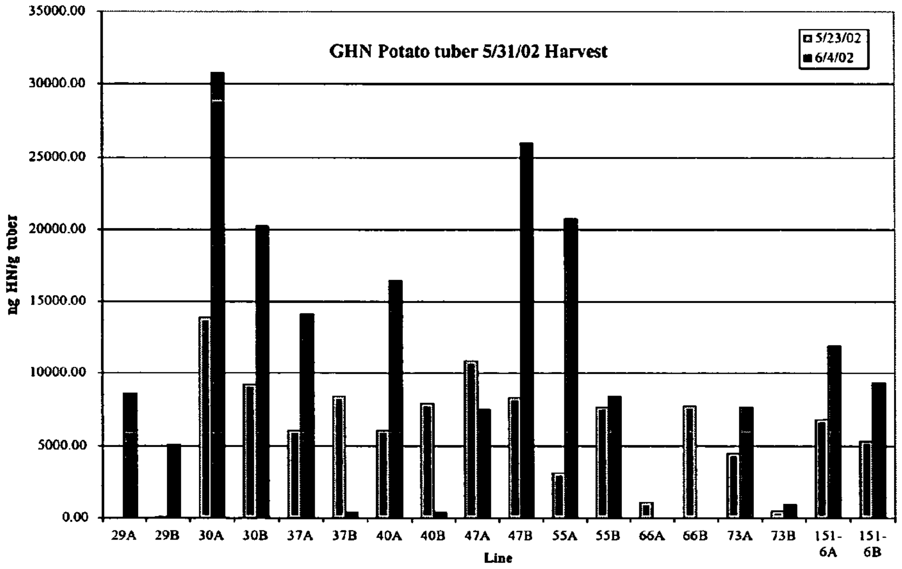
Figure 29. Expression of HN in tubers of pGHN -and pGHN151-transformed potato plants.
Tubers were sampled either before total harvest (5/23/02) or after total harvest on 5/31/02 and storage at 23°C until sampling on 6/4/02), extracted and subjected to ELISA for HN.

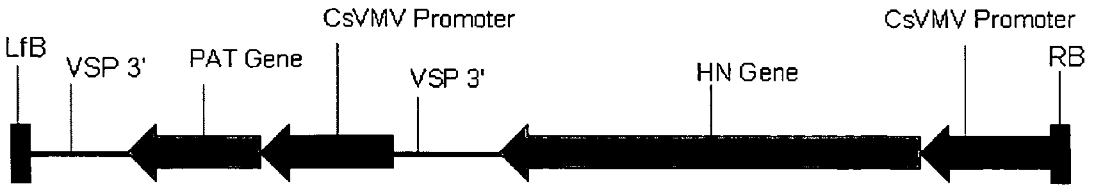
Figure 30. T-DNA region from the construct pCHN. LfB represents the left border repeat, VSP 3' the terminator of the soyabean vegetative storage protein, PAT the coding region of the phosphinothricin acetyl transferase gene, CsVMV the promoter of the casava vein mosaic virus, HN the coding region of the heamagglutinin neuraminidase gene, RB the right border repeat.

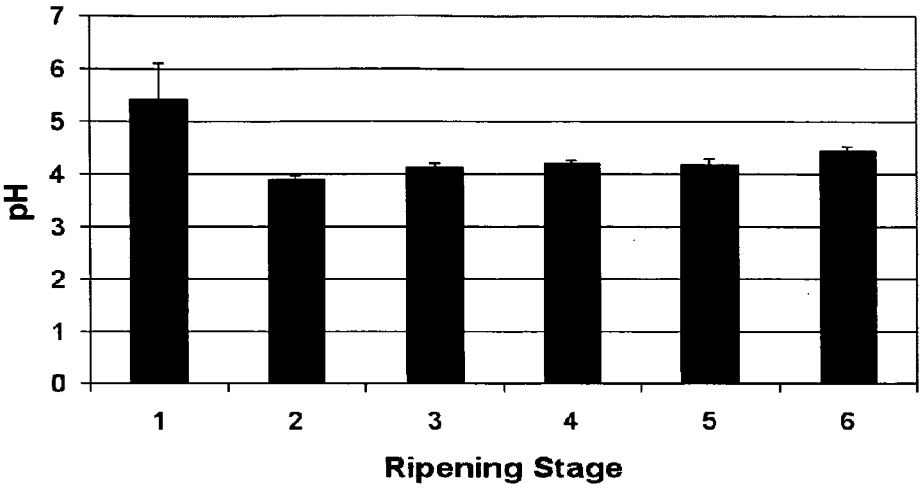
Figure 31. Effect of ripening on wild type TA234 tomato fruit pH. Bars represent the average of 3 readings while the error bars represent the standard error of the mean. Bars labeled with the same letter are not significantly different.

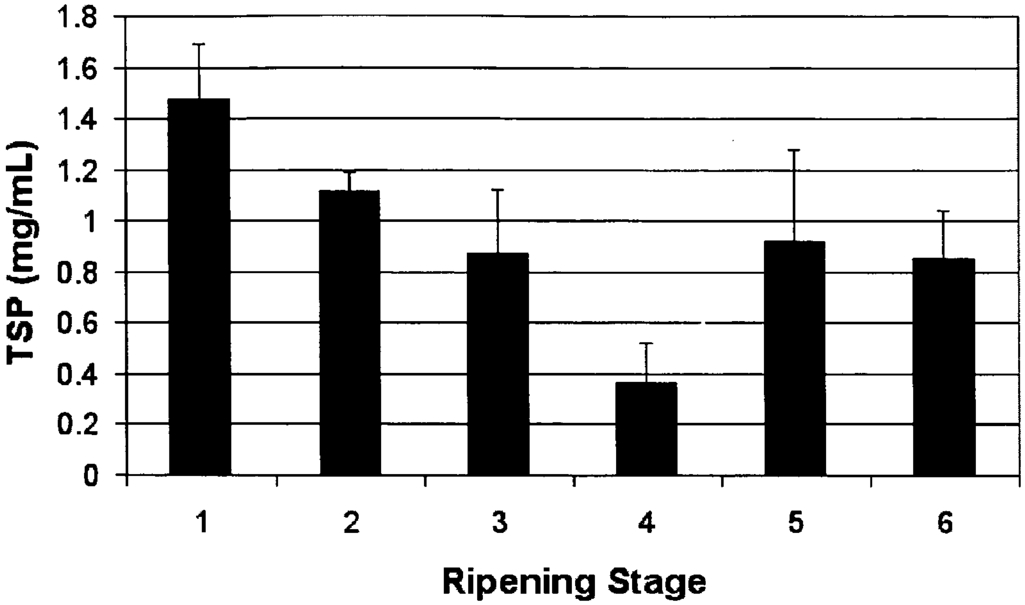
Figure 32. Effect of ripening on wild type TA234 tomato fruit total soluble protein. Bars represent the average of 3 readings while the error bars represent the standard error of the mean.

CHN-32

CHN-12

CHN-10

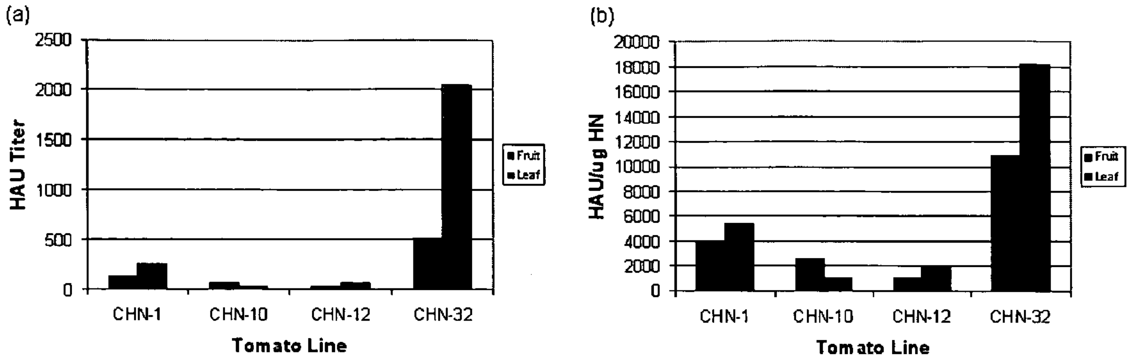
Figure 37. Haemagglutination activity in the fruit and leaves of CHN tomatoes.

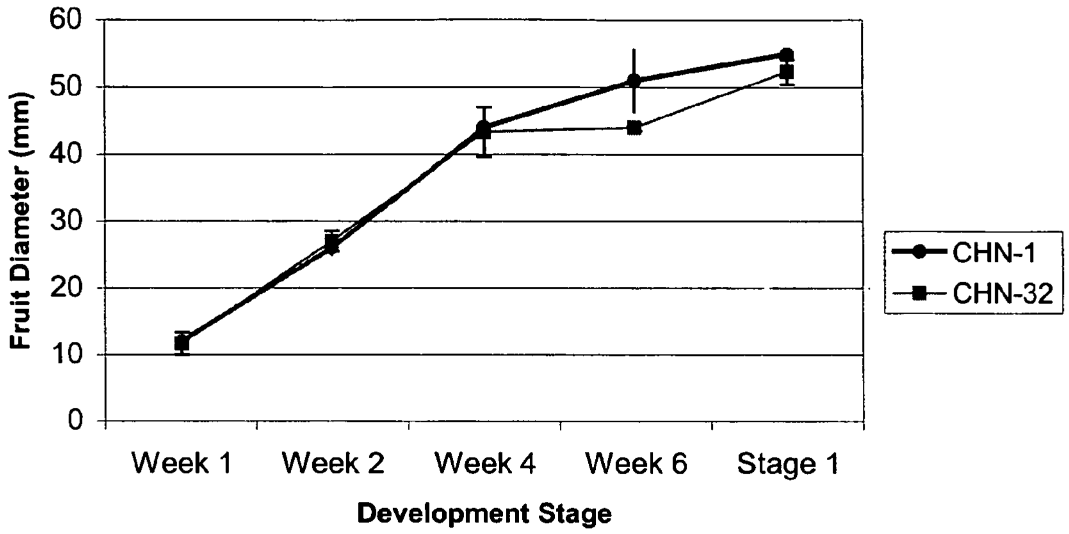
Figure 38. Change in maturing fruit diameter

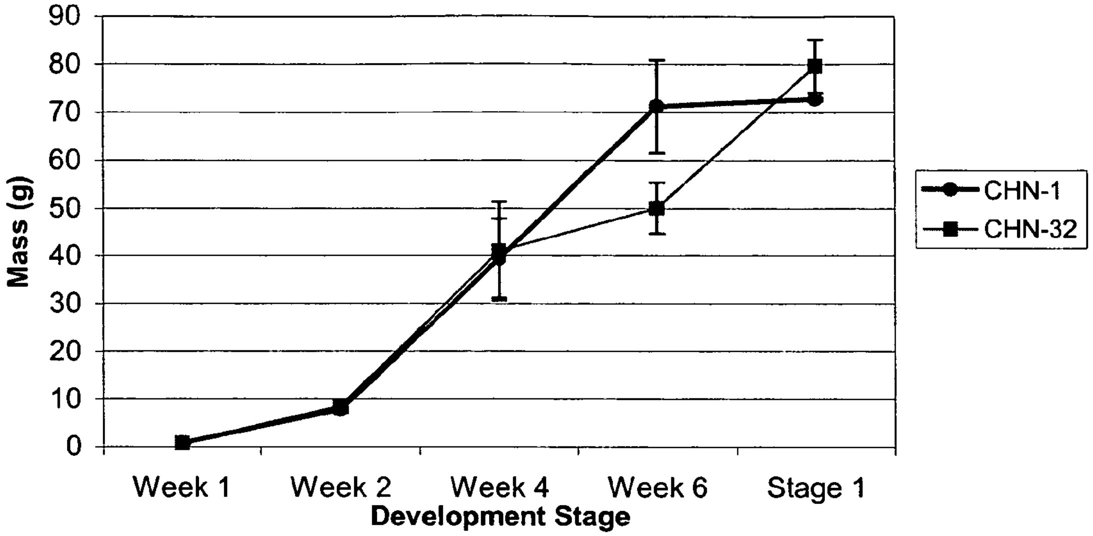
Figure 39. Change in fruit mass of maturing tomato fruit.

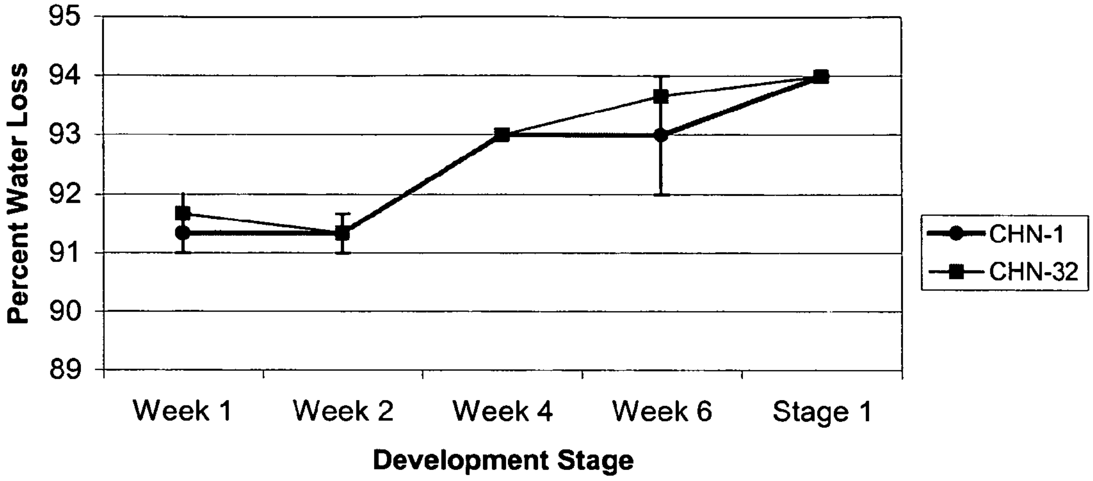
Figure 40. Amount of water lost from maturing tomato fruit upon lyophillization.

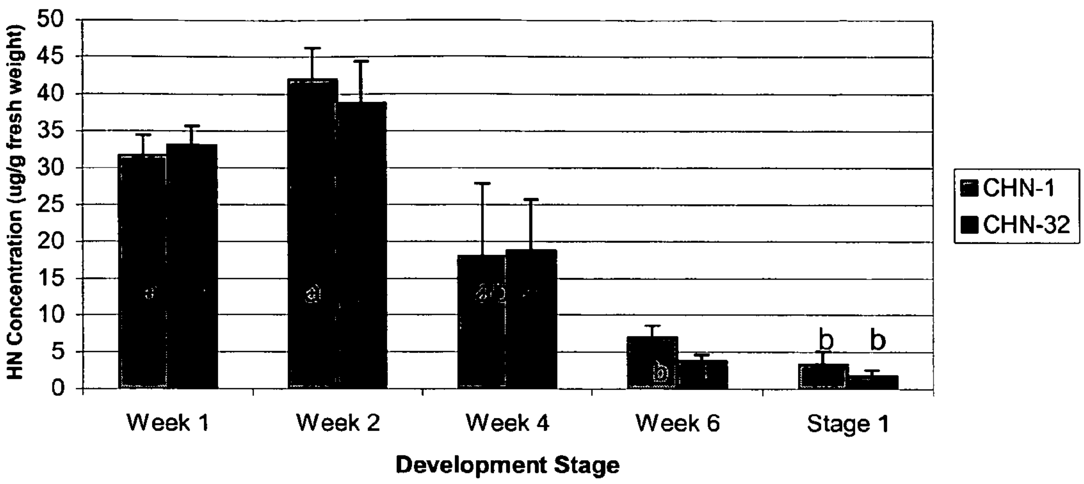
Figure 41: Concentration of HN per gram of fresh tomato fruit

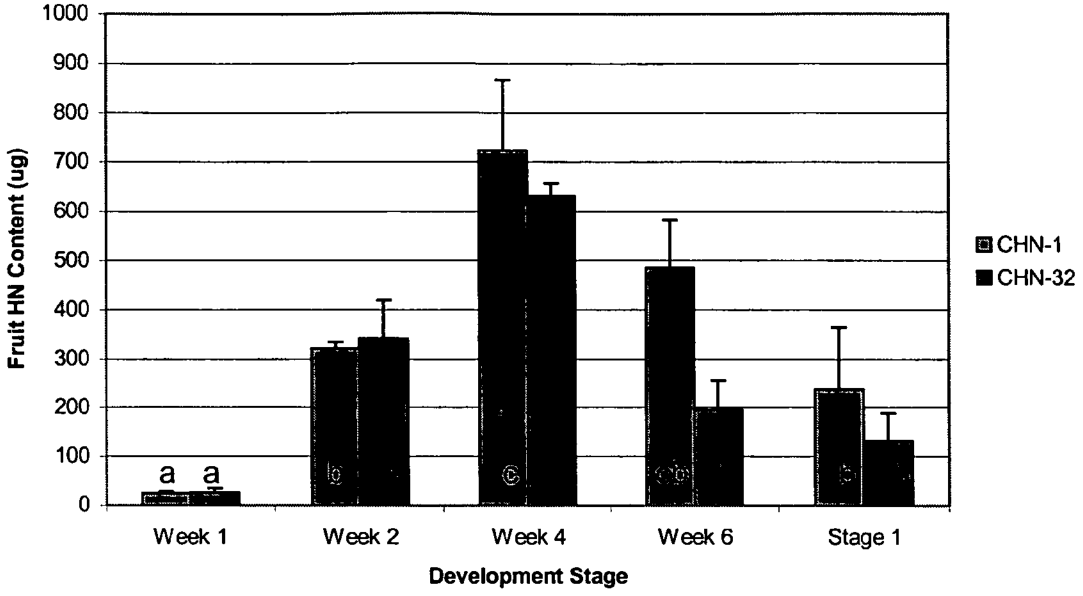
Figure 42. Amount of HN in maturing tomato fruit.

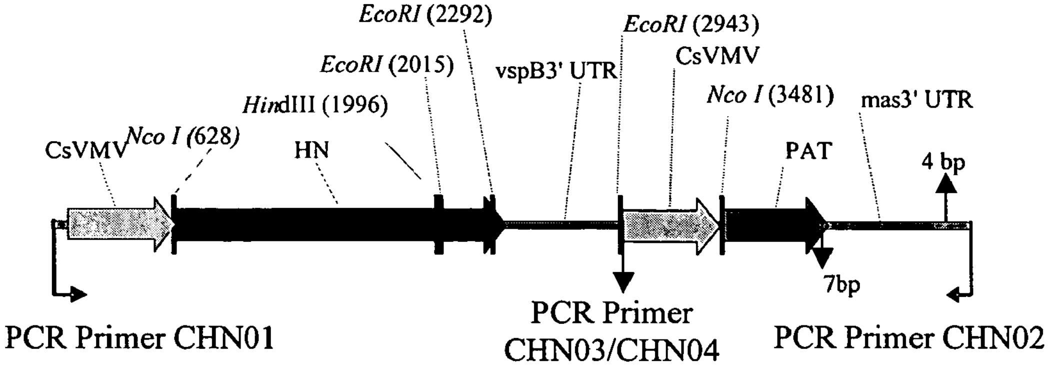
Figure 43. The Regulated Biological Agent (pCHN) insert in CHN-18 Master Seed

Figure 44. DNA Sequence of the whole gene insert in CHN-18 Master Seed

Annotation:

Base 1 -24: Primer CHN01
Base 1-102: polycloning region
Base 103 -618: Gene promoter isolated from Cassava Vein Mosaic Virus (CsVMV)
Base 629-2362: Hemagglutinin-neuraminidase gene
Base 2363-2374: polycloning region
Base 2375-2947: 3' polyadenylation sequence of a vegetative storage protein gene in soybean (vspB3)
Base 2924-2947: Primer CHN03 (complementary) and CHN04
Base 2948-2955: polycloning region
Base 2956-3471: Gene promoter isolated from Cassava Vein Mosaic Virus (CsVMV)
Base 3472-3482: polycloning region
Base 3483-4037: Phosphinothricin N-acetyltransferase gene (*PAT*)
Base 4036-4058: polycloning region
Base 4059-4595: 3' polyadenylation sequence of Mannopine synthetase gene in *Agrobacterium tumefaciens* Ti plasmid pTi15955 (MAS3)
Base 4596-4768: polycloning region
Base 4743-4768: Primer CHN02 (complementary)

```
   1  GAGGTCTACA GGCCAAATTC GCTCTTAGCC GTACAATATT ACTCACCGGA
  51  TCGGCCGCTT AATTAAGTTT AAACCCTGCA GGAAAGCCCG GGCAAAGGCG
 101  CGCCAGAAGG TAATTATCCA GATGTAGCAT CAAGAATCCA ATGTTTACGG
 151  GAAAAACTAT GGAAGTATTA TGTGAGCTCA GCAAGAAGCA GATCAATATG
 201  CGGCACATAT GCAACCTATG TTCAAAAATG AAGAATGTAC AGATACAAGA
 251  TCCTATACTG CCAGAATACG AAGAAGAATA CGTAGAAATT GAAAAAGAAG
 301  AACCAGGCGA AGAAAAGAAT CTTGAAGACG TAAGCACTGA CGACAACAAT
 351  GAAAAGAAGA AGATAAGGTC GGTGATTGTG AAAGAGACAT AGAGGACACA
 401  TGTAAGGTGG AAAATGTAAG GGCGGAAAGT AACCTTATCA CAAAGGAATC
 451  TTATCCCCCA CTACTTATCC TTTTATATTT TTCCGTGTCA TTTTTGCCCT
 501  TGAGTTTTCC TATATAAGGA ACCAAGTTCG GCATTTGTGA AAACAAGAAA
 551  AAATTTGGTG TAAGCTATTT TCTTTGAAGT ACTGAGGATA CAACTTCAGA
 601  GAAATTTGTA AGTTTGTGGA TCCAAACCAT GGACCGAGCA GTTTCACAAG
 651  TGGCTCTTGA GAATGATGAG AGGGAAGCCA AGAACACTTG GAGGCTTATC
 701  TTTCGGATAG CCATTCTCTT TCTTACTGTT GTCACCCTAG CAATCTCTGT
 751  TGCATCATTA CTCTATTCTA TGGGAGCAAG CACCCCCTCA GACTTAGTTG
 801  GCATACCCAC ACGAATCTCT AGGGCTGAAG AGAAGATTAC CAGTACCCTA
 851  GGCTCCAACC AGGATGTTGT GGACCGAATC TACAAACAAG TTGCACTTGA
 901  AAGTCCACTT GCATTACTCA ACACAGAAAC TACCATCATG AATGCAATCA
 951  CCAGCCTATC CTATCAGATC AATGGGGCTG CCAACAATTC AGGTTGGGGA
1001  GCCCCAATTC ATGATCCAGA CTACATTGGA GGTATTGGCA AAGAACTCAT
1051  TGTAGATGAT GCTTCAGATG TTACATCTTT CTATCCTTCA GCTTTCCAGG
1101  AACATCTGAA CTTCATTCCT GCACCCACAA CTGGGAGTGG GTGCACTCGG
1151  ATACCCTCAT TTGACATGAG TGCTACACAC TATTGCTATA CACACAATGT
1201  CATTCTATCT GGCTGTCGTG ACCATTCTCA CTCTTATCAG TACTTAGCAC
1251  TTGGAGTTCT TCGTACATCT GCTACTGGTA GAGTGTTCTT CTCAACTCTT
1301  CGCAGTATCA ATCTTGATGA TACACAGAAT CGCAAAAGTT GCTCTGTATC
1351  TGCTACACCT TTGGGCTGTG ATATGCTATG CAGTAAAGTA ACAGAAACTG
1401  AAGAAGAGGA CTACAATTCT GCAGTCCCTA CAAGGATGGT GCATGGCAGA
1451  TTGGGTTTTG ATGGTCAATA CCATGAGAAA GATTTGGATG TCACTACATT
1501  GTTTGGGGAT TGGGTAGCTA ACTATCCAGG AGTTGGAGGT GGTAGCTTCA
```

Figure 44 (Continued)

```
1551  TTGACTCCAG AGTCTGGTTC TCTGTCTATG GTGGTTTGAA ACCTAACAGT
1601  CCTAGTGATA CTGTGCAAGA GGGAAAGTAT GTTATCTACA AGAGGTACAA
1651  TGATACTTGT CCTGATGAGC AAGACTATCA GATTCGAATG GCTAAGTCAT
1701  CATACAAACC AGGAAGATTT GGAGGTAAGA GGATACAACA AGCTATTCTC
1751  AGTATCAAGG TTAGCACATC ATTGGGAGAA GATCCAGTCC TTACTGTTCC
1801  ACCAAACACT GTAACATTGA TGGGAGCTGA GGGAAGGATT CTTACTGTTG
1851  GTACTAGCCA CTTTCTCTAT CAACGTGGAA GTTCCTACTT TAGCCCAGCG
1901  TTACTGTATC CAATGACTGT GAGCAACAAG ACAGCTACAT TACATTCACC
1951  ATATACTTTC AATGCCTTTA CAAGACCTGG ATCGATTCCT TGCCAAGCTT
2001  CAGCTAGATG TCCGAATTCG TGTGTGACTG GAGTTTACAC TGATCCTTAC
2051  CCTTTGATCT TCTACCGTAA TCATACCTTG AGAGGGGTGT TTGGAACAAT
2101  GTTAGATGGT GTTCAAGCTA GGTTGAATCC TGCCTCTGCT GTGTTTGATT
2151  CTACATCCAG ATCAAGGATA ACCAGAGTTT CCTCTAGTTC TACTAAGGCA
2201  GCATACACTA CCTCCACATG TTTCAAAGTT GTAAAGACGA ACAAGACCTA
2251  TTGTCTGAGC ATAGCTGAGA TTTCTAACAC TCTCTTTGGG GAATTCAGAA
2301  TTGTTCCACT TTTGGTGGAG ATTCTGAAAG ATGATGGTGT ACGTGAAGCA
2351  AGATCAGGTT AAGTCTTCGG ATCCGGTACC GAGCTCTCTC AACAATCTAG
2401  CTAGAGTTTG CTCCTATCTA TATGTAATAA GGTATGCTGA TATGCACTAT
2451  TCAAATAGGA GCATTAGCTA TGTTTGTTAA TGTCACTTTA TGTTATGTGG
2501  GTAAGTCACC TAAGACACTC CACGTACCTA CTTGTTGTCT CTTACGCGGC
2551  TTTAATAAAT CTTCTGCCCT TGTTCCATAT TTACTAATTA TCCCTTTCTT
2601  CACTAAAAGA AAATTGTTAT CATTAAGTAT TAGTCTTTAG AACATATGAG
2651  GTCTTTAATT GGGTAGGTTT TACAAATTAA CTAATATAAA ATGTCATAAA
2701  ATCCACGTGG TTAAACAAAT GCAGAAAATC GACGTCGTCT ATTGGACCGA
2751  CAGTTGCTAT TAATATAATG GGCCACCATA GTAGACTGAC AAATAAATTA
2801  CCTGACAACA TCGTTTCACA AAAAAACAAA CACAAAAAGG GAGTGCATTT
2851  TCCAGGGCAT TTTTGTAATA AAAAACAGAT AAAAGGGAGT GCAATAGAAA
2901  TATAGGGGTG TGGAAATAGT GATTTGAGCA CGTCTTGAAG CGAATTCGCG
2951  GCCGGCCAGA AGGTAATTAT CCAAGATGTA GCATCAAGAA TCCAATGTTT
3001  ACGGGAAAAA CTATGGAAGT ATTATGTGAG CTCAGCAAGA AGCAGATCAA
3051  TATGCGGCAC ATATGCAACC TATGTTCAAA AATGAAGAAT GTACAGATAC
3101  AAGATCCTAT ACTGCCAGAA TACGAAGAAG AATACGTAGA AATTGAAAAA
3151  GAAGAACCAG GCGAAGAAAA GAATCTTGAA GACGTAAGCA CTGACGACAA
3201  CAATGAAAAG AAGAAGATAA GGTCGGTGAT TGTGAAAGAG ACATAGAGGA
3251  CACATGTAAG GTGGAAAATG TAAGGGCGGA AAGTAACCTT ATCACAAAGG
3301  AATCTTATCC CCCACTACTT ATCCTTTTAT ATTTTTCCGT GTCATTTTTG
3351  CCCTTGAGTT TTCCTATATA AGGAACCAAG TTCGGCATTT GTGAAAACAA
3401  GAAAAAATTT GGTGTAAGCT ATTTTCTTTG AAGTACTGAG GATACAACTT
3451  CAGAGAAATT TGTAAGTTTG TGGATCCAAA CCATGGCTTC TCCGGAGAGG
3501  AGACCAGTTG AGATTAGGCC AGCTACAGCA GCTGATATGG CCGCGGTTTG
3551  TGATATCGTT AACCATTACA TTGAGACGTC TACAGTGAAC TTTAGGACAG
3601  AGCCACAAAC ACCACAAGAG TGGATTGATG ATCTAGAGAG GTTGCAAGAT
3651  AGATACCCTT GGTTGGTTGC TGAGGTTGAG GGTGTTGTGG CTGGTATTGC
3701  TTACGCTGGG CCCTGGAAGG CTAGGAACGC TTACGATTGG ACAGTTGAGA
3751  GTACTGTTTA CGTGTCACAT AGGCATCAAA GGTTGGGCCT AGGATCCACA
3801  TTGTACACAC ATTTGCTTAA GTCTATGGAG GCGCAAGGTT TTAAGTCTGT
3851  GGTTGCTGTT ATAGGCCTTC CAAACGATCC ATCTGTTAGG TTGCATGAGG
3901  CTTTGGGATA CACAGCCCGG GGTACATTGC GCGCAGCTGG ATACAAGCAT
3951  GGTGGATGGC ATGATGTTGG TTTTTGGCAA AGGGATTTTG AGTTGCCAGC
4001  TCCTCCAAGG CCAGCTAGGC CAGTTACCCA GATCTGAGGT ACCCTGAGCT
4051  CGGTCACCTG TCCAACAGTC TCAGGGTTAA TGTCTATGTA TCTTAAATAA
4101  TGTTGTCGGT ATTTTGTAAT CTCATATAGA TTTTCACTGT GCGACGCAAA
4151  AATATTAAAT AAATATTATT ATTATCTACG TTTTGATTGA GATATCATCA
4201  ATATTATAAT AAAAATATCC ATTAAACACG ATTTGATACA AATGACAGTC
4251  AATAATCTGA TTTGAATATT TATTAATTGT AACGAATTAC ATAAAGATCG
4301  AATAGAAAAT ACTGCACTGC AAATGAAAAT TAACACATAC TAATAAATGC
```

Figure 44 (Continued)

| | | | | | |
|---|---|---|---|---|---|
| 4351 | GTCAAATATC | TTTGCCAAGA | TCAAGCGGAG | TGAGGGCCTC | ATATCCGGTC |
| 4401 | TCAGTTACAA | GCACGGTATC | CCCGAAGCGC | GCTCCACCAA | TGCCCTCGAC |
| 4451 | ATAGATGCCG | GGCTCGACGC | TGAGGACATT | GCCTACCTTG | AGCATGGTCT |
| 4501 | CAGCGCCGGC | TTTAAGCTCA | ATCCCATCCC | AATCTGAATA | TCCTATCCCG |
| 4551 | CGCCCAGTCC | GGTGTAAGAA | CGGGTCTGTC | CATCCACCTC | TGTTGCGGCC |
| 4601 | AATTCTGATC | TGGCCCCCAT | TTGGACGTGA | ATGTAGACAC | GTCGATATAA |
| 4651 | AGATTTCCGA | ATTAGAATAA | TTTGTTTATT | GCTTTCGCCT | ATAAATACGA |
| 4701 | CGGATCGTAA | TTTGTCGTTT | TATCAAAATG | TACTTTCATT | TTATAATAAC |
| 4751 | | | GCTGCGGACA | TCTACAT | |

(SEQ ID NO: 12)

Figure 45 pCHA Sequence

GGCCGCAACAGAGGTGGATGGACAGACCCGTTCTTACACCGGACTGGGCGCGGGATAGGATATT
CAGATTGGGATGGGATTGAGCTTAAAGCCGGCGCTGAGACCATGCTCAAGGTAGGCAATGTCCT
CAGCGTCGAGCCCGGCATCTATGTCGAGGGCATTGGTGGAGCGCGCTTCGGGGATACCGTGCTT
GTAACTGAGACCGGATATGAGGCCCTCACTCCGCTTGATCTTGGCAAAGATATTTGACGCATTT
ATTAGTATGTGTTAATTTTCATTTGCAGTGCAGTATTTTCTATTCGATCTTTATGTAATTCGTT
ACAATTAATAAATATTCAAATCAGATTATTGACTGTCATTTGTATCAAATCGTGTTTAATGGAT
ATTTTTATTATAATATTGATGATATCTCAATCAAAACGTAGATAATAATAATATTTATTTAATA
TTTTTGCGTCGCACAGTGAAAATCTATATGAGATTACAAAATACCGACAACATTATTTAAGATA
CATAGACATTAACCCTGAGACTGTTGGACAGAGCTCATTGGTACCTCAGATCTGGGTAACTGGC
CTAACTGGCCTTGGAGGAGCTGGCAACTCAAAATCCCTTTGCCAAAAACCAACATCATGCCATC
CACCATGCTTGTATCCAGCTGCGCGCAATGTACCCCGGGCTGTGTATCCCAAAGCCTCATGCAA
CCTAACAGATGGATCGTTTGGAAGGCCTATAACAGCAACCACAGACTTAAAACCTTGCGCCTCC
ATAGACTTAAGCAAATGTGTGTACAATGTGGATCCTAGGCCCAACCTTTGATGCCTATGTGACA
CGTAAACAGTACTCTCAACTGTCCAATCGTAAGCGTTCCTAGCCTTCCAGGGCCCAGCGTAAGC
AATACCAGCCACAACACCCTCAACCTCAGCAACCAACCAAGGGTATCTATCTTGCAACCTCTCT
AGATCATCAATCCACTCTTGTGGTGTTTGTGGCTCTGTCCTAAAGTTCACTGTAGACGTCTCAA
TGTAATGGTTAACGATATCACAAACCGCGGCCATATCAGCTGCTGTAGCTGGCCTAATCTCAAC
TGGTCTCCTCTCCGGAGAAGCCATGGTTTGGATCCACAAACTTACAAATTTCTCTGAAGTTGTA
TCCTCAGTACTTCAAAGAAAATAGCTTACACCAATTTTTTCTTGTTTTCACAAATGCCGAACTT
GGTTCCTTATATAGGAAAACTCAAGGGCAAAAATGACACGGAAAAATATAAAAGGATAAGTAGT
GGGGGATAAGATTCCTTTGTGATAAGGTTACTTTCCGCCCTTACATTTTCCACCTTACATGTGT
CCTCTATGTCTCTTTCACAATCACCGACCTTATCTTCTTCTTTTCATTGTTGTCGTCAGTGCTT
ACGTCTTCAAGATTCTTTTCTTCGCCTGGTTCTTCTTTTTCAATTTCTACGTATTCTTCTTCGT
ATTCTGGCAGTATAGGATCTTGTATCTGTACATTCTTCATTTTTGAACATAGGTTGCATATGTG
CCGCATATTGATCTGCTTCTTGCTGAGCTCACATAATACTTCCATAGTTTTTCCCGTAAACATT
GGATTCTTGATGCTACATCTTGGATAATTACCTTCTGGCCGGCCGCGAATTCGCTTCAAGACGT
GCTCAAATCACTATTTCCACACCCCTATATTTCTATTGCACTCCCTTTTAACTGTTTTTTATTA
CAAAAATGCCCTGGAAAATGCACTCCCTTTTTGTGTTTGTTATTTAGTGAAACGATGTTGTCAG
GTAATTTATTTGTCAGTCTACTATGGTGGCCCATTATATTAATAGCAACTGTCGGTCCAATAGA
CGACGTCGATTTTCTGCATTTGTTTAACCACGTGGATTTTATGACATTTTATATTAGTTAATTT
GTAAAACCTACCCAATTAAAGACCTCATATGTTCTAAAGACTAATACTTAATGATAACAATTTT
CTTTTAGTGAAGAAAGGGATAATTAGTAAATATGGAACAAGGGCAGAAGATTTATTAAAGCCGG
TAAGAGACAACAACGTAGGTACGTGGAGTGTCTTAGGTGACTTACCCACATAACATAAAGTGAC
ATTAACAAACATAGCTAATGCTCCTATTTGAATAGTGCATATCAGCATACCTTATTACATATAG
ATAGGAGCAAACTCTAGCTAGATTGTTGAGAGAGCTCGGTACCTTAAAATCTGAACTCACAATC
CTAGATGCAAATTCTGCACTGCAATGATCCATTGGAGCACATCCAAAAAGACAGACCAGCTACC
ATGATTGCCAGTGCTAGGGAACTCGCCACTGTTGAGTAGATTGATAGTATCTGATAGGTGCCCA
TTGACTCCAATTTGACTCCATCTATTTCCTCTCTGTTCAGCCTTGATTCTTCTGAGTATTGTGG
ATAGTCATACGTTCCGTTTCTCACACTTTCCATGCATTCATTGTCACATTTGTGGTAGAACTCA
AAACACCCATTGCCCAATTCTTTTGCATTATCTCTCAGCTGGAGTCGGACCTTATCGTATAGGT
TCTTGACATATGAATCATGGAAATCCAGAGTTCTTTCATTTTCCATGAGCACCAGAAGTTCTGC
ATTGTAAGTCCATACATCTAGAAATCCATCTTCCATTTTCTTATTCAAATTTTCTATTCTCCTT
TCTAAGTTGTTGAATTCTTTCCCAACGGCTTCGAATTGAGTGTTCATTTTGTCAATGATTGAGT
TGACTTTATTGGTGATCCCGTCGATTGCTTTCTGAGTGGACTCTTTGTCTGCAGCATATCCACT
TCCCTGCTCGTTGCTATGATGGTAACCATACCATCCATCTACCATTCCTTGCCACCCCCCTTCT

FIGURE 45 CONTINUED

ATGAATCCTGCTATTGCTCCAAACAGACCTCTTGTTTCTCTCTGAGGCACGTTCCTCAGTCCTG
TTGCAAGGACCAGTTTATCTGATTTGACATATTTGGGACACTCTCCAATGGTAAGGGGATGAAC
ATTGTGAAAAGGCATACTGGAATTTATAGCACCCACTGGGGTCTGACATTTGGTATCACAGTTG
CCATACTCCAGTTCGCTTCTCATGATTGCTGAATCTCCCTTTTTAACTATCTTGTATGCATATT
CAGGAGCTATAAAGTTCCCATTACTTTCAAAGCTGATTGCATCGTTCGGCCTTAGTATTGTCCA
GAAAAATTCTATTCTTCCACTTTGTCCATTCACTTTGGGCCTGGTAGCTATTTCTGGAATTGAC
CTCTGATTTAGTGTTGATGTTCCTACAGACACATAAGTGTTCGAGTTCTGATAGAGTTCCGTTT
GTTCCGCTGCATCATTAGGGTGATGGATTCCCCACAATATCAGAAGGTCCTCTACATTGGTGTT
ATTGTAGGTCCTCTTTATTGTTGGGTATGCATTACTCTTCTTGATCAACCACACCACATTCCTG
AAAAAGGAAGATCTACCATTGTATGGGCATGCTGAGCTCACTCCTGATGAGGCATCATGATTGG
ACCAAGAGTTCCTAGGGATTATTTGAATTTTCTCAAAATGGTTTGTGTTGCTCATTAAATACTT
CAGTTCTTCATAATCATTGAAGTCTCCCGGATAACATAAGCCATTGGTTGGATTGTCCTTCTCT
ACAATATATGACCATTCCGGTACATTTAGGAACTCATCACACATTGGGTTCCCAAGAAGCCATC
CAGCCACACTGCAATCCTTCAGAATGAGGGGCCTCACTCCTTTGAGACTGCAGAGTTTCCCGTT
GTGCTCTTTTTCCAGTATATCTTGAGCATGTGTGACCGTAACATTCTTCTCCATGATTGTGTCA
ACTTGTTTTGTTGAATTGTTTGCATGATAACCGATGCAGATTTGGTCACCTTTGACAACGCTGA
TTATTGCAAGGGCAATCACTATTCTTTCCATCCATGGTTTGGATCCACAAACTTACAAATTTCT
CTGAAGTTGTATCCTCAGTACTTCAAAGAAAATAGCTTACACCAATTTTTTCTTGTTTTCACAA
ATGCCGAACTTGGTTCCTTATATAGGAAAACTCAAGGGCAAAAATGACACGGAAAAATATAAAA
GGATAAGTAGTGGGGGATAAGATTCCTTTGTGATAAGGTTACTTTCCGCCCTTACATTTTCCAC
CTTACATGTGTCCTCTATGTCTCTTTCACAATCACCGACCTTATCTTCTTCTTTTCATTGTTGT
CGTCAGTGCTTACGTCTTCAAGATTCTTTTCTTCGCCTGGTTCTTCTTTTTCAATTTCTACGTA
TTCTTCTTCGTATTCTGGCAGTATAGGATCTTGTATCTGTACATTCTTCATTTTTGAACATAGG
TTGCATATGTGCCGCATATTGATCTGCTTCTTGCTGAGCTCACATAATACTTCCATAGTTTTTC
CCGTAAACATTGGATTCTTGATGCTACATCTTGGATAATTACCTTCTGGCGCGCCTTTGCCCGG
GCTTTCCTGCAGGGTTTAAACTTAATTAAGCGGCCGATCCGGTGAGTAATATTGTACGGCTAAG
AGCGAATTTGGCCTGTAGACCTCAATTGCGAGCTTTCTAATTTCAAACTATTCGGGCCTAACTT
TTGGTGTGATGATGCTGACTGGCAGGATATATACCGTTGTAATTTGAGCTCGTGTGAATAAGTC
GCTGTGTATGTTTGTTTGATTGTTTCTGTTGGAGTGCAGCCCATTTCACCGGACAAGTCGGCTA
GATTGATTTAGCCCTGATGAACTGCCGAGGGGAAGCCATCTTGAGCGCGGAATGGGAATGGATC
GAACCGGGAGCACAGGATGACGCCTAACAATTCATTCAAGCCGACACCGCTTCGCGGCGCGGCT
TAATTCAGGAGTTAAACATCATGAGGGAAGCGGTGATCGCCGAAGTATCGACTCAACTATCAGA
GGTAGTTGGCGTCATCGAGCGCCATCTCGAACCGACGTTGCTGGCCGTACATTTGTACGGCTCC
GCAGTGGATGGCGGCCTGAAGCCACACAGTGATATTGATTTGCTGGTTACGGTGACCGTAAGGC
TTGATGAAACAACGCGGCGAGCTTTGATCAACGACCTTTTGGAAACTTCGGCTTCCCCTGGAGA
GAGCGAGATTCTCCGCGCTGTAGAAGTCACCATTGTTGTGCACGACGACATCATTCCGTGGCGT
TATCCAGCTAAGCGCGAACTGCAATTTGGAGAATGGCAGCGCAATGACATTCTTGCAGGTATCT
TCGAGCCAGCCACGATCGACATTGATCTGGCTATCTTGCTGACAAAAGCAAGAGAACATAGCGT
TGCCTTGGTAGGTCCAGCGGCGGAGGAACTCTTTGATCCGGTTCCTGAACAGGATCTATTTGAG
GCGCTAAATGAAACCTTAACGCTATGGAACTCGCCGCCCGACTGGGCTGGCGATGAGCGAAATG
TAGTGCTTACGTTGTCCCGCATTTGGTACAGCGCAGTAACCGGCAAAATCGCGCCGAAGGATGT
CGCTGCCGACTGGGCAATGGAGCGCCTGCCGGCCCAGTATCAGCCCGTCATACTTGAAGCTAGG
CAGGCTTATCTTGGACAAGAAGATCGCTTGGCCTCGCGCGCAGATCAGTTGGAAGAATTTGTTC
ACTACGTGAAAGGCGAGATCACCAAGGTAGTCGGCAAATAATGTCTAACAATTCGTTCAAGCCG
ACGCCGCTTCGCGGCGCGGCTTAACTCAAGCGTTAGAGAGCTGGGGAAGACTATGCGCGATCTG
TTGAAGGTGGTTCTAAGCCTCGTACTTGCGATGGCATTTCGATCGAAAGGGGTACAAATTCCCA

FIGURE 45 CONTINUED

CTAAGCGCTCGGGGGCTGAGAAAGCCCAGTAAGGAAACAACTGTAGGTTCGAGTCGCGAGATCC
CCCGGAACCAAAGGAAGTAGGTTAAACCCGCTCCGATCAGGCCGAGCCACGCCAGGCCGAGAAC
ATTGGTTCCTGTAGGCATCGGGATTGGCGGATCAAACACTAAAGCTACTGGAACGAGCAGAAGT
CCTCCGGCCGCCAGTTGCCAGGCCGTAAAGGTGAGCAGAGGCACGGGAGGTTGCCACTTGCGGG
TCAGCACGGTTCCGAACGCCATGGAAACCGCCCCCGCCAGGCCCGCTGCGACGCCGACAGGATC
TAGCGCTGCGTTTGGTGTCAACACCAACAGCGCCACGCCCGCAGTTCCGCAAATAGCCCCCAGG
ACCGCCATCAATCGTATCGGGCTACCTAGCAGAGCGGCAGAGATGAACACGACCATCAGCGGCT
GCACAGCGCCTACCGTCGCCGCGACCCGCCCGGCAGGCGGTAGACCGAAATAAACAACAAGCTC
CAGAATAGCGAAATATTAAGTGCGCCGAGGATGAAGATGCGCATCCACCAGATTCCCGTTGGAA
TCTGTCGGACGATCATCACGAGCAATAAACCCGCCGGCAACGCCCGCAGCAGCATACCGGCGAC
CCCTCGGCCTCGCTGTTCGGGCTCCACGAAAACGCCGGACAGATGCGCCTTGTGAGCGTCCTTG
GGGCCGTCCTCCTGTTTGAAGACCGACAGCCCAATGATCTCGCCGTCGATGTAGGCGCCGAATG
CCACGGCATCTCGCAACCGTTCAGCGAACGCCTCCATGGGCTTTTTCTCCTCGTGCTCGTAAAC
GGACCCGAACATCTCTGGAGCTTTCTTCAGGGCCGACAATCGGATCTCGCGGAAATCCTGCACG
TCGGCCGCTCCAAGCCGTCGAATCTGAGCCTTAATCACAATTGTCAATTTTAATCCTCTGTTTA
TCGGCAGTTCGTAGAGCGCGCCGTGCGCCCGAGCGATACTGAGCGAAGCAAGTGCGTCGAGCAG
TGCCCGCTTGTTCCTGAAATGCCAGTAAAGCGCTGGCTGCTGAACCCCCAGCCGGAACTGACCC
CACAAGGCCCTAGCGTTTGCAATGCACCAGGTCATCATTGACCCAGGCGTGTTCCACCAGGCCG
CTGCCTCGCAACTCTTCGCAGGCTTCGCCGACCTGCTCGCGCCACTTCTTCACGCGGGTGGAAT
CCGATCCGCACATGAGGCGGAAGGTTTCCAGCTTGAGCGGGTACGGCTCCCGGTGCGAGCTGAA
ATAGTCGAACATCCGTCGGGCCGTCGGCGACAGCTTGCGGTACTTCTCCCATATGAATTTCGTG
TAGTGGTCGCCAGCAAACAGCACGACGATTTCCTCGTCGATCAGGACCTGGCAACGGGACGTTT
TCTTGCCACGGTCCAGGACGCGGAAGCGGTGCAGCAGCGACACCGATTCCAGGTGCCCAACGCG
GTCGGACGTGAAGCCCATCGCCGTCGCCTGTAGGCGCGACAGGCATTCCTCGGCCTTCGTGTAA
TACCGGCCATTGATCGACCAGCCCAGGTCCTGGCAAAGCTCGTAGAACGTGAAGGTGATCGGCT
CGCCGATAGGGGTGCGCTTCGCGTACTCCAACACCTGCTGCCACACCAGTTCGTCATCGTCGGC
CCGCAGCTCGACGCCGGTGTAGGTGATCTTCACGTCCTTGTTGACGTGGAAAATGACCTTGTTT
TGCAGCGCCTCGCGCGGGATTTTCTTGTTGCGCGTGGTGAACAGGGCAGAGCGGGCCGTGTCGT
TTGGCATCGCTCGCATCGTGTCCGGCCACGGCGCAATATCGAACAAGGAAAGCTGCATTTCCTT
GATCTGCTGCTTCGTGTGTTTCAGCAACGCGGCCTGCTTGGCCTCGCTGACCTGTTTTGCCAGG
TCCTCGCCGGCGGTTTTTCGCTTCTTGGTCGTCATAGTTCCTCGCGTGTCGATGGTCATCGACT
TCGCCAAACCTGCCGCCTCCTGTTCGAGACGACGCGAACGCTCCACGGCGGCCGATGGCGCGGG
CAGGGCAGGGGGAGCCAGTTGCACGCTGTCGCGCTCGATCTTGGCCGTAGCTTGCTGGACCATC
GAGCCGACGGACTGGAAGGTTTCGCGGGGCGCACGCATGACGGTGCGGCTTGCGATGGTTTCGG
CATCCTCGGCGGAAAACCCCGCGTCGATCAGTTCTTGCCTGTATGCCTTCCGGTCAAACGTCCG
ATTCATTCACCCTCCTTGCGGGATTGCCCCGACTCACGCCGGGGCAATGTGCCCTTATTCCTGA
TTTGACCCGCCTGGTGCCTTGGTGTCCAGATAATCCACCTTATCGGCAATGAAGTCGGTCCCGT
AGACCGTCTGGCCGTCCTTCTCGTACTTGGTATTCCGAATCTTGCCCTGCACGAATACCAGCGA
CCCCTTGCCCAAATACTTGCCGTGGGCCTCGGCCTGAGAGCCAAAACACTTGATGCGGAAGAAG
TCGGTGCGCTCCTGCTTGTCGCCGGCATCGTTGCGCCACTCTTCATTAACCGCTATATCGAAAA
TTGCTTGCGGCTTGTTAGAATTGCCATGACGTACCTCGGTGTCACGGGTAAGATTACCGATAAA
CTGGAACTGATTATGGCNNCTCGAAATTCCCTCGGTCTTGCCTTGCTCGTCGGTGATGTACTTC
ACCAGCTCCGCGAAGTCGCTCTTCTTGATGGAGCGCATGGGGACGTGCTTGGCAATCACGCGCA
CCCCCCGGCCGTTTTAGCGGCTAAAAAAGTCATGGCTCTGCCCTCGGGCGGACCACGCCCATCA
TGACCTTGCCAAGCTCGTCCTGCTTCTCTTCGATCTTCGCCAGCAGGGCGAGGATCGTGGCATC
ACCGAACCGCGCCGTGCGCGGGTCGTCGGTGAGCCAGAGTTTCAGCAGGCCGCCCAGGCGGCCC
AGGTCGCCATTGATGCGGGCCAGCTCGCGGACGTGCTCATAGTCCACGACGCCCGTGATTTTGT

FIGURE 45 CONTINUED

AGCCCTGGCCGACGGCCAGCAGGTAGGCCGACAGGCTCATGCCGGCCGCCGCCGCCTTTTCCTC
AATCGCTCTTCGTTCGTCTGGAAGGCAGTACACCTTGATAGGTGGGCTGCCCTTCCTGGTTGGC
TTGGTTTCATCAGCCATCCGCTTGCCCTCATCTGTTACGCCGGCGGTAGCCGGCCAGCCTCGCA
GAGCAGGATTCCCGTTGAGCACCGCCAGGTGCGAATAAGGGACAGTGAAGAAGGAACACCCGCT
CGCGGGTGGGCCTACTTCACCTATCCTGCCCGGCTGACGCCGTTGGATACACCAAGGAAAGTCT
ACACGAACCCTTTGGCAAAATCCTGTATATCGTGCGAAAAAGGATGGATATACCGAAAAAATCG
CTATAATGACCCCGAAGCAGGGTTATGCAGCGGAAAAGATCCGTCGACCCTTTCCGACGCTCAC
CGGGCTGGTTGCCCTCGCCGCTGGGCTGGCGGCCGTCTATGGCCCTGCAAACGCGCCAGAAACG
CCGTCGAAGCCGTGTGCGAGACACCGCGGCCGCCGGCGTTGTGGATACCACGCGGAAAACTTGG
CCCTCACTGACAGATGAGGGGCGGACGTTGACACTTGAGGGGCCGACTCACCCGGCGCGGCGTT
GACAGATGAGGGGCAGGCTCGATTTCGGCCGGCGACGTGGAGCTGGCCAGCCTCGCAAATCGGC
GAAAACGCCTGATTTTACGCGAGTTTCCCACAGATGATGTGGACAAGCCTGGGGATAAGTGCCC
TGCGGTATTGACACTTGAGGGGCGCGACTACTGACAGATGAGGGGCGCGATCCTTGACACTTGA
GGGGCAGAGTGATGACAGATGAGGGGCGCACCTATTGACATTTGAGGGGCTGTCCACAGGCAGA
AAATCCAGCATTTGCAAGGGTTTCCGCCCGTTTTTCGGCCACCGCTAACCTGTCTTTTAACCTG
CTTTTAAACCAATATTTATAAACCTTGTTTTTAACCAGGGCTGCGCCCTGGCGCGTGACCGCGC
ACGCCGAAGGGGGGTGCCCCCCCTTCTCGAACCCTCCCGGCCCGCTAACGCGGGCCTCCCATCC
CCCCAGGGGCTGCGCCCCTCGGCCGCGAACGGCCTCACCCCAAAAATGGCAGGCCAAGCTAGCT
TGCTTGGTCGTTCCGGTACGTACCGTGAACGTCGGCTCGATTGTACCTGCGTTCAAATACTTTG
CGATCGTGTTGCGCGCCTGCCCGGTGCGTCGGCTGATCTCACGGATCGACTGCTTCTCTCGCAA
CGCCATCCGACGGATGATGTTTAAAAGTCCCATGTGGATCACTCCGTTGCCCCGTCGCTCACCG
TGTTGGGGGGAAGGTGCACATGGCTCAGTTCTCAATGGAAATTATCTGCCTAACCGGCTCAGTT
CTGCGTAGAAACCAACATGCAAGCTCCACCGGGTGCAAAGCGGCAGCGGCGGCAGGATATATTC
AATTGTAAATGGCTTCATGTCCGGGAAATCTACATGGATCAGCAATGAGTATGATGGTCAATAT
GGAGAAAAAGAAAGAGTAATTACCAATTTTTTTTCAATTCAAAAATGTAGATGTCCGCAGCGTT
ATTATAAAATGAAAGTACATTTTGATAAAACGACAAATTACGATCCGTCGTATTTATAGGCGAA
AGCAATAAACAAATTATTCTAATTCGGAAATCTTTATTTCGACGTGTCTACATTCACGTCCAAA
TGGGGGCGGCGAATT (SEQ ID NO: 24)

Figure 46. pMHN Sequence

GGCCGCAACAGAGGTGGATGGACAGACCCGTTCTTACACCGGACTGGGCGCGGGATAGGATATT
CAGATTGGGATGGGATTGAGCTTAAAGCCGGCGCTGAGACCATGCTCAAGGTAGGCAATGTCCT
CAGCGTCGAGCCCGGCATCTATGTCGAGGGCATTGGTGGAGCGCGCTTCGGGGATACCGTGCTT
GTAACTGAGACCGGATATGAGGCCCTCACTCCGCTTGATCTTGGCAAAGATATTTGACGCATTT
ATTAGTATGTGTTAATTTTCATTTGCAGTGCAGTATTTTCTATTCGATCTTTATGTAATTCGTT
ACAATTAATAAATATTCAAATCAGATTATTGACTGTCATTTGTATCAAATCGTGTTTAATGGAT
ATTTTTATTATAATATTGATGATATCTCAATCAAAACGTAGATAATAATAATATTTATTTAATA
TTTTTGCGTCGCACAGTGAAAATCTATATGAGATTACAAAATACCGACAACATTATTTAAGATA
CATAGACATTAACCCTGAGACTGTTGGACAGAGCTCATTGGTACCTCAGATCTGGGTAACTGGC
CTAACTGGCCTTGGAGGAGCTGGCAACTCAAAATCCCTTTGCCAAAAACCAACATCATGCCATC
CACCATGCTTGTATCCAGCTGCGCGCAATGTACCCCGGGCTGTGTATCCCAAAGCCTCATGCAA
CCTAACAGATGGATCGTTTGGAAGGCCTATAACAGCAACCACAGACTTAAAACCTTGCGCCTCC
ATAGACTTAAGCAAATGTGTGTACAATGTGGATCCTAGGCCCAACCTTTGATGCCTATGTGACA
CGTAAACAGTACTCTCAACTGTCCAATCGTAAGCGTTCCTAGCCTTCCAGGGCCCAGCGTAAGC
AATACCAGCCACAACACCCTCAACCTCAGCAACCAACCAAGGGTATCTATCTTGCAACCTCTCT
AGATCATCAATCCACTCTTGTGGTGTTTGTGGCTCTGTCCTAAAGTTCACTGTAGACGTCTCAA
TGTAATGGTTAACGATATCACAAACCGCGGCCATATCAGCTGCTGTAGCTGGCCTAATCTCAAC
TGGTCTCCTCTCCGGAGAAGCCATGGTTTGGATCCACAAACTTACAAATTTCTCTGAAGTTGTA
TCCTCAGTACTTCAAAGAAAATAGCTTACACCAATTTTTTCTTGTTTTCACAAATGCCGAACTT
GGTTCCTTATATAGGAAAACTCAAGGGCAAAAATGACACGGAAAAATATAAAAGGATAAGTAGT
GGGGGATAAGATTCCTTTGTGATAAGGTTACTTTCCGCCCTTACATTTTCCACCTTACATGTGT
CCTCTATGTCTCTTTCACAATCACCGACCTTATCTTCTTCTTTTCATTGTTGTCGTCAGTGCTT
ACGTCTTCAAGATTCTTTTCTTCGCCTGGTTCTTCTTTTTCAATTTCTACGTATTCTTCTTCGT
ATTCTGGCAGTATAGGATCTTGTATCTGTACATTCTTCATTTTTGAACATAGGTTGCATATGTG
CCGCATATTGATCTGCTTCTTGCTGAGCTCACATAATACTTCCATAGTTTTTCCCGTAAACATT
GGATTCTTGATGCTACATCTTGGATAATTACCTTCTGGCCGGCCGCGAATTCGCTTCAAGACGT
GCTCAAATCACTATTTCCACACCCCTATATTTCTATTGCACTCCCTTTTAACTGTTTTTTATTA
CAAAAATGCCCTGGAAAATGCACTCCCTTTTTGTGTTTGTTATTTAGTGAAACGATGTTGTCAG
GTAATTTATTTGTCAGTCTACTATGGTGGCCCATTATATTAATAGCAACTGTCGGTCCAATAGA
CGACGTCGATTTTCTGCATTTGTTTAACCACGTGGATTTTATGACATTTTATATTAGTTAATTT
GTAAAACCTACCCAATTAAAGACCTCATATGTTCTAAAGACTAATACTTAATGATAACAATTTT
CTTTTAGTGAAGAAAGGGATAATTAGTAAATATGGAACAAGGGCAGAAGATTTATTAAAGCCGG
TAAGAGACAACAACGTAGGTACGTGGAGTGTCTTAGGTGACTTACCCACATAACATAAAGTGAC
ATTAACAAACATAGCTAATGCTCCTATTTGAATAGTGCATATCAGCATACCTTATTACATATAG
ATAGGAGCAAACTCTAGCTAGATTGTTGAGAGAGCTCGGTACCGGATCCGAAGACTTAACCTGA
TCTTGCTTCACGTACACCATCATCTTTCAGAATCTCCACCAAAAGTGGAACAATTCTGAATTCC
CCAAAGAGAGTGTTAGAAATCTCAGCTATGCTCAGACAATAGGTCTTGTTCGTCTTTACAACTT
TGAAACATGTGGAGGTAGTGTATGCTGCCTTAGTAGAACTAGAGGAAACTCTGGTTATCCTTGA
TCTGGATGTAGAATCAAACACAGCAGAGGCAGGATTCAACCTAGCTTGAACACCATCTAACATT
GTTCCAAACACCCCTCTCAAGGTATGATTACGGTAGAAGATCAAAGGGTAAGGATCAGTGTAAA
CTCCAGTCACACACGAATTCGGACATCTAGCTGAAGCTTGGCAAGGAATCGATCCAGGTCTTGT
AAAGGCATTGAAAGTATATGGTGAATGTAATGTAGCTGTCTTGTTGCTCACAGTCATTGGATAC
AGTAACGCTGGGCTAAAGTAGGAACTTCCACGTTGATAGAGAAAGTGGCTAGTACCAACAGTAA
GAATCCTTCCCTCAGCTCCCATCAATGTTACAGTGTTTGGTGGAACAGTAAGGACTGGATCTT

FIGURE 46 CONTINUED

TCCCAATGATGTGCTAACCTTGATACTGAGAATAGCTTGTTGTATCCTCTTACCTCCAAATCTT
CCTGGTTTGTATGATGACTTAGCCATTCGAATCTGATAGTCTTGCTCATCAGGACAAGTATCAT
TGTACCTCTTGTAGATAACATACTTTCCCTCTTGCACAGTATCACTAGGACTGTTAGGTTTCAA
ACCACCATAGACAGAGAACCAGACTCTGGAGTCAATGAAGCTACCACCTCCAACTCCTGGATAG
TTAGCTACCCAATCCCCAAACAATGTAGTGACATCCAAATCTTTCTCATGGTATTGACCATCAA
AACCCAATCTGCCATGCACCATCCTTGTAGGGACTGCAGAATTGTAGTCCTCTTCTTCAGTTTC
TGTTACTTTACTGCATAGCATATCACAGCCCAAAGGTGTAGCAGATACAGAGCAACTTTTGCGA
TTCTGTGTATCATCAAGATTGATACTGCGAAGAGTTGAGAAGAACACTCTACCAGTAGCAGATG
TACGAAGAACTCCAAGTGCTAAGTACTGATAAGAGTGAGAATGGTCACGACAGCCAGATAGAAT
GACATTGTGTGTATAGCAATAGTGTGTAGCACTCATGTCAAATGAGGGTATCCGAGTGCACCCA
CTCCCAGTTGTGGGTGCAGGAATGAAGTTCAGATGTTCCTGGAAAGCTGAAGGATAGAAAGATG
TAACATCTGAAGCATCATCTACAATGAGTTCTTTGCCAATACCTCCAATGTAGTCTGGATCATG
AATTGGGGCTCCCCAACCTGAATTGTTGGCAGCCCCATTGATCTGATAGGATAGGCTGGTGATT
GCATTCATGATGGTAGTTTCTGTGTTGAGTAATGCAAGTGGACTTTCAAGTGCAACTTGTTTGT
AGATTCGGTCCACAACATCCTGGTTGGAGCCTAGGGTACTGGTAATCTTCTCTTCAGCCCTAGA
GATTCGTGTGGGTATGCCAACTAAGTCTGAGGGGGTGCTTGCTCCCATAGAATAGAGTAATGAT
GCAACAGAGATTGCTAGGGTGACAACAGTAAGAAAGAGAATGGCTATCCGAAAGATAAGCCTCC
AAGTGTTCTTGGCTTCCCTCTCATCATTCTCAAGAGCCACTTGTGAAACTGCTCGGTCCATGGT
TTGGATCCGCGATTTGGTGTATCGAGATTGGTTATGAAATTCAGATGCTAGTGTAATGTATTGG
TAATTTGGGAAGATATAATAGGAAGCAAGGCTATTTATCCATTTCTGAAAAGGCGAAATGGCGT
CACCGCGAGCGTCACGCTCTAGTCGACCATGTACGTAAGCGCTTACGTTTTTGGTGGACCCCCT
CGACCATGTACGTAAGCGCTTACGTTTTTGGTGGACCCCCTCGACCATGTACGTAAGCGCTTAC
GTTTTTGGTGGACCCCCTCGACCATGTACGTAAGCGCTTACGTTTTTGGTGGACCCCCTCGACG
GATCCCCCCTCGACCCTAGACGTATCTATTCAAAAGTCGTTAATGGCTGCGGATCAAGAAAAAG
TTGGAATAGAAACAGAATACCCGCGAAATTCAGGCCCGGTTGCCATGTCCTACACGCCGAAATA
AACGACCAAATTAGTAGAAAAATAAAAACTAGCTCAGATACTTACGTCACGTCTTGCGCACTGA
TTTGAAAAATCTCAATATAAACAAAGACGGCCACAAGAAAAAACCAAAACACCGATATTCATTA
ATCTTATCTAGTTTCTCAAAAAAATTCATATCTTCCACACCCTCGAGATCTAGATAAACTTAAT
TAAGCGGCCGATCCGGTGAGTAATATTGTACGGCTAAGAGCGAATTTGGCCTGTAGACCTCAAT
TGCGAGCTTTCTAATTTCAAACTATTCGGGCCTAACTTTTGGTGTGATGATGCTGACTGGCAGG
ATATATACCGTTGTAATTTGAGCTCGTGTGAATAAGTCGCTGTGTATGTTTGTTTGATTGTTTC
TGTTGGAGTGCAGCCCATTTCACCGGACAAGTCGGCTAGATTGATTTAGCCCTGATGAACTGCC
GAGGGGAAGCCATCTTGAGCGCGGAATGGGAATGGATCGAACCGGGAGCACAGGATGACGCCTA
ACAATTCATTCAAGCCGACACCGCTTCGCGGCGCGGCTTAATTCAGGAGTTAAACATCATGAGG
GAAGCGGTGATCGCCGAAGTATCGACTCAACTATCAGAGGTAGTTGGCGTCATCGAGCGCCATC
TCGAACCGACGTTGCTGGCCGTACATTTGTACGGCTCCGCAGTGGATGGCGGCCTGAAGCCACA
CAGTGATATTGATTTGCTGGTTACGGTGACCGTAAGGCTTGATGAAACAACGCGGCGAGCTTTG
ATCAACGACCTTTTGGAAACTTCGGCTTCCCCTGGAGAGAGCGAGATTCTCCGCGCTGTAGAAG
TCACCATTGTTGTGCACGACGACATCATTCCGTGGCGTTATCCAGCTAAGCGCGAACTGCAATT
TGGAGAATGGCAGCGCAATGACATTCTTGCAGGTATCTTCGAGCCAGCCACGATCGACATTGAT
CTGGCTATCTTGCTGACAAAAGCAAGAGAACATAGCGTTGCCTTGGTAGGTCCAGCGGCGGAGG
AACTCTTTGATCCGGTTCCTGAACAGGATCTATTTGAGGCGCTAAATGAAACCTTAACGCTATG
GAACTCGCCGCCCGACTGGGCTGGCGATGAGCGAAATGTAGTGCTTACGTTGTCCCGCATTTGG
TACAGCGCAGTAACCGGCAAAATCGCGCCGAAGGATGTCGCTGCCGACTGGGCAATGGAGCGCC
TGCCGGCCCAGTATCAGCCCGTCATACTTGAAGCTAGGCAGGCTTATCTTGGACAAGAAGATCG
CTTGGCCTCGCGCGCAGATCAGTTGGAAGAATTTGTTCACTACGTGAAAGGCGAGATCACCAAG

FIGURE 46 CONTINUED

GTAGTCGGCAAATAATGTCTAACAATTCGTTCAAGCCGACGCCGCTTCGCGGCGCGGCTTAACT
CAAGCGTTAGAGAGCTGGGGAAGACTATGCGCGATCTGTTGAAGGTGGTTCTAAGCCTCGTACT
TGCGATGGCATTTCGATCGAAAGGGGTACAAATTCCCACTAAGCGCTCGGGGGCTGAGAAAGCC
CAGTAAGGAAACAACTGTAGGTTCGAGTCGCGAGATCCCCCGGAACCAAAGGAAGTAGGTTAAA
CCCGCTCCGATCAGGCCGAGCCACGCCAGGCCGAGAACATTGGTTCCTGTAGGCATCGGGATTG
GCGGATCAAACACTAAAGCTACTGGAACGAGCAGAAGTCCTCCGGCCGCCAGTTGCCAGGCCGT
AAAGGTGAGCAGAGGCACGGGAGGTTGCCACTTGCGGGTCAGCACGGTTCCGAACGCCATGGAA
ACCGCCCCCGCCAGGCCCGCTGCGACGCCGACAGGATCTAGCGCTGCGTTTGGTGTCAACACCA
ACAGCGCCACGCCCGCAGTTCCGCAAATAGCCCCCAGGACCGCCATCAATCGTATCGGGCTACC
TAGCAGAGCGGCAGAGATGAACACGACCATCAGCGGCTGCACAGCGCCTACCGTCGCCGCGACC
CGCCCGGCAGGCGGTAGACCGAAATAAACAACAAGCTCCAGAATAGCGAAATATTAAGTGCGCC
GAGGATGAAGATGCGCATCCACCAGATTCCCGTTGGAATCTGTCGGACGATCATCACGAGCAAT
AAACCCGCCGGCAACGCCCGCAGCAGCATACCGGCGACCCCTCGGCCTCGCTGTTCGGGCTCCA
CGAAAACGCCGGACAGATGCGCCTTGTGAGCGTCCTTGGGGCCGTCCTCCTGTTTGAAGACCGA
CAGCCCAATGATCTCGCCGTCGATGTAGGCGCCGAATGCCACGGCATCTCGCAACCGTTCAGCG
AACGCCTCCATGGGCTTTTTCTCCTCGTGCTCGTAAACGGACCCGAACATCTCTGGAGCTTTCT
TCAGGGCCGACAATCGGATCTCGCGGAAATCCTGCACGTCGGCCGCTCCAAGCCGTCGAATCTG
AGCCTTAATCACAATTGTCAATTTTAATCCTCTGTTTATCGGCAGTTCGTAGAGCGCGCCGTGC
GCCCGAGCGATACTGAGCGAAGCAAGTGCGTCGAGCAGTGCCCGCTTGTTCCTGAAATGCCAGT
AAAGCGCTGGCTGCTGAACCCCCAGCCGGAACTGACCCCACAAGGCCCTAGCGTTTGCAATGCA
CCAGGTCATCATTGACCCAGGCGTGTTCCACCAGGCCGCTGCCTCGCAACTCTTCGCAGGCTTC
GCCGACCTGCTCGCGCCACTTCTTCACGCGGGTGGAATCCGATCCGCACATGAGGCGGAAGGTT
TCCAGCTTGAGCGGGTACGGCTCCCGGTGCGAGCTGAAATAGTCGAACATCCGTCGGGCCGTCG
GCGACAGCTTGCGGTACTTCTCCCATATGAATTTCGTGTAGTGGTCGCCAGCAAACAGCACGAC
GATTTCCTCGTCGATCAGGACCTGGCAACGGGACGTTTTCTTGCCACGGTCCAGGACGCGGAAG
CGGTGCAGCAGCGACACCGATTCCAGGTGCCCAACGCGGTCGGACGTGAAGCCCATCGCCGTCG
CCTGTAGGCGCGACAGGCATTCCTCGGCCTTCGTGTAATACCGGCCATTGATCGACCAGCCCAG
GTCCTGGCAAAGCTCGTAGAACGTGAAGGTGATCGGCTCGCCGATAGGGGTGCGCTTCGCGTAC
TCCAACACCTGCTGCCACACCAGTTCGTCATCGTCGGCCCGCAGCTCGACGCCGGTGTAGGTGA
TCTTCACGTCCTTGTTGACGTGGAAAATGACCTTGTTTTGCAGCGCCTCGCGCGGGATTTTCTT
GTTGCGCGTGGTGAACAGGGCAGAGCGGGCCGTGTCGTTTGGCATCGCTCGCATCGTGTCCGGC
CACGGCGCAATATCGAACAAGGAAAGCTGCATTTCCTTGATCTGCTGCTTCGTGTGTTTCAGCA
ACGCGGCCTGCTTGGCCTCGCTGACCTGTTTTGCCAGGTCCTCGCCGGCGGTTTTTCGCTTCTT
GGTCGTCATAGTTCCTCGCGTGTCGATGGTCATCGACTTCGCCAAACCTGCCGCCTCCTGTTCG
AGACGACGCGAACGCTCCACGGCGGCCGATGGCGCGGGCAGGGCAGGGGGAGCCAGTTGCACGC
TGTCGCGCTCGATCTTGGCCGTAGCTTGCTGGACCATCGAGCCGACGGACTGGAAGGTTTCGCG
GGGCGCACGCATGACGGTGCGGCTTGCGATGGTTTCGGCATCCTCGGCGGAAAACCCCGCGTCG
ATCAGTTCTTGCCTGTATGCCTTCCGGTCAAACGTCCGATTCATTCACCCTCCTTGCGGGATTG
CCCCGACTCACGCCGGGGCAATGTGCCCTTATTCCTGATTTGACCCGCCTGGTGCCTTGGTGTC
CAGATAATCCACCTTATCGGCAATGAAGTCGGTCCCGTAGACCGTCTGGCCGTCCTTCTCGTAC
TTGGTATTCCGAATCTTGCCCTGCACGAATACCAGCGACCCCTTGCCCAAATACTTGCCGTGGG
CCTCGGCCTGAGAGCCAAAACACTTGATGCGGAAGAAGTCGGTGCGCTCCTGCTTGTCGCCGGC
ATCGTTGCGCCACTCTTCATTAACCGCTATATCGAAAATTGCTTGCGGCTTGTTAGAATTGCCA
TGACGTACCTCGGTGTCACGGGTAAGATTACCGATAAACTGGAACTGATTATGGCNNCTCGAAA
TTCCCTCGGTCTTGCCTTGCTCGTCGGTGATGTACTTCACCAGCTCCGCGAAGTCGCTCTTCTT
GATGGAGCGCATGGGGACGTGCTTGGCAATCACGCGCACCCCCCGGCCGTTTTAGCGGCTAAAA

FIGURE 46 CONTINUED

AAGTCATGGCTCTGCCCTCGGGCGGACCACGCCCATCATGACCTTGCCAAGCTCGTCCTGCTTC
TCTTCGATCTTCGCCAGCAGGGCGAGGATCGTGGCATCACCGAACCGCGCCGTGCGCGGGTCGT
CGGTGAGCCAGAGTTTCAGCAGGCCGCCCAGGCGGCCCAGGTCGCCATTGATGCGGGCCAGCTC
GCGGACGTGCTCATAGTCCACGACGCCCGTGATTTTGTAGCCCTGGCCGACGGCCAGCAGGTAG
GCCGACAGGCTCATGCCGGCCGCCGCCGCCTTTTCCTCAATCGCTCTTCGTTCGTCTGGAAGGC
AGTACACCTTGATAGGTGGGCTGCCCTTCCTGGTTGGCTTGGTTTCATCAGCCATCCGCTTGCC
CTCATCTGTTACGCCGGCGGTAGCCGGCCAGCCTCGCAGAGCAGGATTCCCGTTGAGCACCGCC
AGGTGCGAATAAGGGACAGTGAAGAAGGAACACCCGCTCGCGGGTGGGCCTACTTCACCTATCC
TGCCCGGCTGACGCCGTTGGATACACCAAGGAAAGTCTACACGAACCCTTTGGCAAAATCCTGT
ATATCGTGCGAAAAAGGATGGATATACCGAAAAAATCGCTATAATGACCCCGAAGCAGGGTTAT
GCAGCGGAAAAGATCCGTCGACCCTTTCCGACGCTCACCGGGCTGGTTGCCCTCGCCGCTGGGC
TGGCGGCCGTCTATGGCCCTGCAAACGCGCCAGAAACGCCGTCGAAGCCGTGTGCGAGACACCG
CGGCCGCCGGCGTTGTGGATACCACGCGGAAAACTTGGCCCTCACTGACAGATGAGGGGCGGAC
GTTGACACTTGAGGGGCCGACTCACCCGGCGCGGCGTTGACAGATGAGGGGCAGGCTCGATTTC
GGCCGGCGACGTGGAGCTGGCCAGCCTCGCAAATCGGCGAAAACGCCTGATTTTACGCGAGTTT
CCCACAGATGATGTGGACAAGCCTGGGGATAAGTGCCCTGCGGTATTGACACTTGAGGGGCGCG
ACTACTGACAGATGAGGGGCGCGATCCTTGACACTTGAGGGGCAGAGTGATGACAGATGAGGGG
CGCACCTATTGACATTTGAGGGGCTGTCCACAGGCAGAAAATCCAGCATTTGCAAGGGTTTCCG
CCCGTTTTTCGGCCACCGCTAACCTGTCTTTTAACCTGCTTTTAAACCAATATTTATAAACCTT
GTTTTTAACCAGGGCTGCGCCCTGGCGCGTGACCGCGCACGCCGAAGGGGGGTGCCCCCCCTTC
TCGAACCCTCCCGGCCCGCTAACGCGGGCCTCCCATCCCCCCAGGGGCTGCGCCCCTCGGCCGC
GAACGGCCTCACCCCAAAAATGGCAGGCCAAGCTAGCTTGCTTGGTCGTTCCGGTACGTACCGT
GAACGTCGGCTCGATTGTACCTGCGTTCAAATACTTTGCGATCGTGTTGCGCGCCTGCCCGGTG
CGTCGGCTGATCTCACGGATCGACTGCTTCTCTCGCAACGCCATCCGACGGATGATGTTTAAAA
GTCCCATGTGGATCACTCCGTTGCCCCGTCGCTCACCGTGTTGGGGGGAAGGTGCACATGGCTC
AGTTCTCAATGGAAATTATCTGCCTAACCGGCTCAGTTCTGCGTAGAAACCAACATGCAAGCTC
CACCGGGTGCAAAGCGGCAGCGGCGGCAGGATATATTCAATTGTAAATGGCTTCATGTCCGGGA
AATCTACATGGATCAGCAATGAGTATGATGGTCAATATGGAGAAAAAGAAAGAGTAATTACCAA
TTTTTTTTCAATTCAAAAATGTAGATGTCCGCAGCGTTATTATAAAATGAAAGTACATTTTGAT
AAAACGACAAATTACGATCCGTCGTATTTATAGGCGAAAGCAATAAACAAATTATTCTAATTCG
GAAATCTTTATTTCGACGTGTCTACATTCACGTCCAAATGGGGGCGGCGAATT (SEQ ID NO: 25)

Figure 47. pCHN Sequence

TGCGTAGAAACCAACATGCAAGCTCCACCGGGTGCAAAGCGGCAGCGGCGGCAGGATATATTCA
ATTGTAAATGGCTTCATGTCCGGGAAATCTACATGGATCAGCAATGAGTATGATGGTCAATATG
GAGAAAAAGAAAGAGTAATTACCAATTTTTTTTCAATTCAAAAATGTAGATGTCCGCAGCGTTA
TTATAAAATGAAAGTACATTTTGATAAAACGACAAATTACGATCCGTCGTATTTATAGGCGAAA
GCAATAAACAAATTATTCTAATTCGGAAATCTTTATTTCGACGTGTCTACATTCACGTCCAAAT
GGGGGCGGCGAATTGGCCGCAACAGAGGTGGATGGACAGACCCGTTCTTACACCGGACTGGGCG
CGGGATAGGATATTCAGATTGGGATGGGATTGAGCTTAAAGCCGGCGCTGAGACCATGCTCAAG
GTAGGCAATGTCCTCAGCGTCGAGCCCGGCATCTATGTCGAGGGCATTGGTGGAGCGCGCTTCG
GGGATACCGTGCTTGTAACTGAGACCGGATATGAGGCCCTCACTCCGCTTGATCTTGGCAAAGA
TATTTGACGCATTTATTAGTATGTGTTAATTTTCATTTGCAGTGCAGTATTTTCTATTCGATCT
TTATGTAATTCGTTACAATTAATAAATATTCAAATCAGATTATTGACTGTCATTTGTATCAAAT
CGTGTTTAATGGATATTTTTATTATAATATTGATGATATCTCAATCAAAACGTAGATAATAATA
ATATTTATTTAATATTTTTGCGTCGCACAGTGAAAATCTATATGAGATTACAAAATACCGACAA
CATTATTTAAGATACATAGACATTAACCCTGAGACTGTTGGACAGAGCTCATTGGTACCTCAGA
TCTGGGTAACTGGCCTAACTGGCCTTGGAGGAGCTGGCAACTCAAAATCCCTTTGCCAAAAACC
AACATCATGCCATCCACCATGCTTGTATCCAGCTGCGCGCAATGTACCCCGGGCTGTGTATCCC
AAAGCCTCATGCAACCTAACAGATGGATCGTTTGGAAGGCCTATAACAGCAACCACAGACTTAA
AACCTTGCGCCTCCATAGACTTAAGCAAATGTGTGTACAATGTGGATCCTAGGCCCAACCTTTG
ATGCCTATGTGACACGTAAACAGTACTCTCAACTGTCCAATCGTAAGCGTTCCTAGCCTTCCAG
GGCCCAGCGTAAGCAATACCAGCCACAACACCCTCAACCTCAGCAACCAACCAAGGGTATCTAT
CTTGCAACCTCTCTAGATCATCAATCCACTCTTGTGGTGTTTGTGGCTCTGTCCTAAAGTTCAC
TGTAGACGTCTCAATGTAATGGTTAACGATATCACAAACCGCGGCCATATCAGCTGCTGTAGCT
GGCCTAATCTCAACTGGTCTCCTCTCCGGAGAAGCCATGGTTTGGATCCACAAACTTACAAATT
TCTCTGAAGTTGTATCCTCAGTACTTCAAAGAAAATAGCTTACACCAAATTTTTTCTTGTTTTC
ACAAATGCCGAACTTGGTTCCTTATATAGGAAAACTCAAGGGCAAAAATGACACGGAAAAATAT
AAAAGGATAAGTAGTGGGGGATAAGATTCCTTTGTGATAAGGTTACTTTCCGCCCTTACATTTT
CCACCTTACATGTGTCCTCTATGTCTCTTTCACAATCACCGACCTTATCTTCTTCTTTTCATTG
TTGTCGTCAGTGCTTACGTCTTCAAGATTCTTTTCTTCGCCTGGTTCTTCTTTTTCAATTTCTA
CGTATTCTTCTTCGTATTCTGGCAGTATAGGATCTTGTATCTGTACATTCTTCATTTTTGAACA
TAGGTTGCATATGTGCCGCATATTGATCTGCTTCTTGCTGAGCTCACATAATACTTCCATAGTT
TTTCCCGTAAACATTGGATTCTTGATGCTACATCTTGGATAATTACCTTCTGGCCGGCCGCGAA
TTCGCTTCAAGACGTGCTCAAATCACTATTTCCACACCCCTATATTTCTATTGCACTCCCTTTT
AACTGTTTTTTATTACAAAAATGCCCTGGAAAATGCACTCCCTTTTTGTGTTTGTTATTTAGTG
AAACGATGTTGTCAGGTAATTTATTTGTCAGTCTACTATGGTGGCCCATTATATTAATAGCAAC
TGTCGGTCCAATAGACGACGTCGATTTTCTGCATTTGTTTAACCACGTGGATTTTATGACATTT
TATATTAGTTAATTTGTAAAACCTACCCAATTAAAGACCTCATATGTTCTAAAGACTAATACTT
AATGATAACAATTTTCTTTTAGTGAAGAAAGGATAATTAGTAAATATGGAACAAGGGCAGAAG
ATTTATTAAAGCCGGTAAGAGACAACAACGTAGGTACGTGGAGTGTCTTAGGTGACTTACCCAC
ATAACATAAAGTGACATTAACAAACATAGCTAATGCTCCTATTTGAATAGTGCATATCAGCATA
CCTTATTACATATAGATAGGAGCAAACTCTAGCTAGATTGTTGAGAGAGCTCGGTACCGGATCC
GAAGACTTAACCTGATCTTGCTTCACGTACACCATCATCTTTCAGAATCTCCACCAAAAGTGGA
ACAATTCTGAATTCCCCAAAGAGAGTGTTAGAAATCTCAGCTATGCTCAGACAATAGGTCTTGT
TCGTCTTTACAACTTTGAAACATGTGGAGGTAGTGTATGCTGCCTTAGTAGAACTAGAGGAAAC

FIGURE 47 CONTINUED

TCTGGTTATCCTTGATCTGGATGTAGAATCAAACACAGCAGAGGCAGGATTCAACCTAGCTTGA
ACACCATCTAACATTGTTCCAAACACCCCTCTCAAGGTATGATTACGGTAGAAGATCAAAGGGT
AAGGATCAGTGTAAACTCCAGTCACACACGAATTCGGACATCTAGCTGAAGCTTGGCAAGGAAT
CGATCCAGGTCTTGTAAAGGCATTGAAAGTATATGGTGAATGTAATGTAGCTGTCTTGTTGCTC
ACAGTCATTGGATACAGTAACGCTGGGCTAAAGTAGGAACTTCCACGTTGATAGAGAAAGTGGC
TAGTACCAACAGTAAGAATCCTTCCCTCAGCTCCCATCAATGTTACAGTGTTTGGTGGAACAGT
AAGGACTGGATCTTCTCCCAATGATGTGCTAACCTTGATACTGAGAATAGCTTGTTGTATCCTC
TTACCTCCAAATCTTCCTGGTTTGTATGATGACTTAGCCATTCGAATCTGATAGTCTTGCTCAT
CAGGACAAGTATCATTGTACCTCTTGTAGATAACATACTTTCCCTCTTGCACAGTATCACTAGG
ACTGTTAGGTTTCAAACCACCATAGACAGAGAACCAGACTCTGGAGTCAATGAAGCTACCACCT
CCAACTCCTGGATAGTTAGCTACCCAATCCCCAAACAATGTAGTGACATCCAAATCTTTCTCAT
GGTATTGACCATCAAAACCCAATCTGCCATGCACCATCCTTGTAGGGACTGCAGAATTGTAGTC
CTCTTCTTCAGTTTCTGTTACTTTACTGCATAGCATATCACAGCCCAAAGGTGTAGCAGATACA
GAGCAACTTTTGCGATTCTGTGTATCATCAAGATTGATACTGCGAAGAGTTGAGAAGAACACTC
TACCAGTAGCAGATGTACGAAGAACTCCAAGTGCTAAGTACTGATAAGAGTGAGAATGGTCACG
ACAGCCAGATAGAATGACATTGTGTGTATAGCAATAGTGTGTAGCACTCATGTCAAATGAGGGT
ATCCGAGTGCACCCACTCCCAGTTGTGGGTGCAGGAATGAAGTTCAGATGTTCCTGGAAAGCTG
AAGGATAGAAAGATGTAACATCTGAAGCATCATCTACAATGAGTTCTTTGCCAATACCTCCAAT
GTAGTCTGGATCATGAATTGGGGCTCCCCAACCTGAATTGTTGGCAGCCCCATTGATCTGATAG
GATAGGCTGGTGATTGCATTCATGATGGTAGTTTCTGTGTTGAGTAATGCAAGTGGACTTTCAA
GTGCAACTTGTTTGTAGATTCGGTCCACAACATCCTGGTTGGAGCCTAGGGTACTGGTAATCTT
CTCTTCAGCCCTAGAGATTCGTGTGGGTATGCCAACTAAGTCTGAGGGGGTGCTTGCTCCCATA
GAATAGAGTAATGATGCAACAGAGATTGCTAGGGTGACAACAGTAAGAAAGAGAATGGCTATCC
GAAAGATAAGCCTCCAAGTGTTCTTGGCTTCCCTCTCATCATTCTCAAGAGCCACTTGTGAAAC
TGCTCGGTCCATGGTTTGGATCCACAAACTTACAAATTTCTCTGAAGTTGTATCCTCAGTACTT
CAAAGAAAATAGCTTACACCAAATTTTTTCTTGTTTTCACAAATGCCGAACTTGGTTCCTTATA
TAGGAAAACTCAAGGGCAAAAATGACACGGAAAAATATAAAAGGATAAGTAGTGGGGGATAAGA
TTCCTTTGTGATAAGGTTACTTTCCGCCCTTACATTTTCCACCTTACATGTGTCCTCTATGTCT
CTTTCACAATCACCGACCTTATCTTCTTCTTTTCATTGTTGTCGTCAGTGCTTACGTCTTCAAG
ATTCTTTTCTTCGCCTGGTTCTTCTTTTTCAATTTCTACGTATTCTTCTTCGTATTCTGGCAGT
ATAGGATCTTGTATCTGTACATTCTTCATTTTTGAACATAGGTTGCATATGTGCCGCATATTGA
TCTGCTTCTTGCTGAGCTCACATAATACTTCCATAGTTTTTCCCGTAAACATTGGATTCTTGAT
GCTACATCTTGGATAATTACCTTCTGGCGCGCCTTTGCCCGGGCTTTCCTGCAGGGTTTAAACT
TAATTAAGCGGCCGATCCGGTGAGTAATATTGTACGGCTAAGAGCGAATTTGGCCTGTAGACCT
CAATTGCGAGCTTTCTAATTTCAAACTATTCGGGCCTAACTTTTGGTGTGATGATGCTGACTGG
CAGGATATATACCGTTGTAATTTGAGCTCGTGTGAATAAGTCGCTGTGTATGTTTGTTTGATTG
TTTCTGTTGGAGTGCAGCCCATTTCACCGGACAAGTCGGCTAGATTGATTTAGCCCTGATGAAC
TGCCGAGGGGAAGCCATCTTGAGCGCGGAATGGGAATGGATCGAACCGGGAGCACAGGATGACG
CCTAACAATTCATTCAAGCCGACACCGCTTCGCGGCGCGGCTTAATTCAGGAGTTAAACATCAT
GAGGGAAGCGGTGATCGCCGAAGTATCGACTCAACTATCAGAGGTAGTTGGCGTCATCGAGCGC
CATCTCGAACCGACGTTGCTGGCCGTACATTTGTACGGCTCCGCAGTGGATGGCGGCCTGAAGC
CACACAGTGATATTGATTTGCTGGTTACGGTGACCGTAAGGCTTGATGAAACAACGCGGCGAGC
TTTGATCAACGACCTTTTGGAAACTTCGGCTTCCCCTGGAGAGAGCGAGATTCTCCGCGCTGTA
GAAGTCACCATTGTTGTGCACGACGACATCATTCCGTGGCGTTATCCAGCTAAGCGCGAACTGC
AATTTGGAGAATGGCAGCGCAATGACATTCTTGCAGGTATCTTCGAGCCAGCCACGATCGACAT
TGATCTGGCTATCTTGCTGACAAAAGCAAGAGAACATAGCGTTGCCTTGGTAGGTCCAGCGGCG

FIGURE 47 CONTINUED

GAGGAACTCTTTGATCCGGTTCCTGAACAGGATCTATTTGAGGCGCTAAATGAAACCTTAACGC
TATGGAACTCGCCGCCCGACTGGGCTGGCGATGAGCGAAATGTAGTGCTTACGTTGTCCCGCAT
TTGGTACAGCGCAGTAACCGGCAAAATCGCGCCGAAGGATGTCGCTGCCGACTGGGCAATGGAG
CGCCTGCCGGCCCAGTATCAGCCCGTCATACTTGAAGCTAGGCAGGCTTATCTTGGACAAGAAG
ATCGCTTGGCCTCGCGCGCAGATCAGTTGGAAGAATTTGTTCACTACGTGAAAGGCGAGATCAC
CAAGGTAGTCGGCAAATAATGTCTAACAATTCGTTCAAGCCGACGCCGCTTCGCGGCGCGGCTT
AACTCAAGCGTTAGAGAGCTGGGGAAGACTATGCGCGATCTGTTGAAGGTGGTTCTAAGCCTCG
TACTTGCGATGGCATTTCGATCGAAAGGGGTACAAATTCCCACTAAGCGCTCGGGGGCTGAGAA
AGCCCAGTAAGGAAACAACTGTAGGTTCGAGTCGCGAGATCCCCCGGAACCAAAGGAAGTAGGT
TAAACCCGCTCCGATCAGGCCGAGCCACGCCAGGCCGAGAACATTGGTTCCTGTAGGCATCGGG
ATTGGCGGATCAAACACTAAAGCTACTGGAACGAGCAGAAGTCCTCCGGCCGCCAGTTGCCAGG
CCGTAAAGGTGAGCAGAGGCACGGGAGGTTGCCACTTGCGGGTCAGCACGGTTCCGAACGCCAT
GGAAACCGCCCCCGCCAGGCCCGCTGCGACGCCGACAGGATCTAGCGCTGCGTTTGGTGTCAAC
ACCAACAGCGCCACGCCCGCAGTTCCGCAAATAGCCCCCAGGACCGCCATCAATCGTATCGGGC
TACCTAGCAGAGCGGCAGAGATGAACACGACCATCAGCGGCTGCACAGCGCCTACCGTCGCCGC
GACCCGCCCGGCAGGCGGTAGACCGAAATAAACAACAAGCTCCAGAATAGCGAAATATTAAGTG
CGCCGAGGATGAAGATGCGCATCCACCAGATTCCCGTTGGAATCTGTCGGACGATCATCACGAG
CAATAAACCCGCCGGCAACGCCCGCAGCAGCATACCGGCGACCCCTCGGCCTCGCTGTTCGGGC
TCCACGAAAACGCCGGACAGATGCGCCTTGTGAGCGTCCTTGGGGCCGTCCTCCTGTTTGAAGA
CCGACAGCCCAATGATCTCGCCGTCGATGTAGGCGCCGAATGCCACGGCATCTCGCAACCGTTC
AGCGAACGCCTCCATGGGCTTTTTCTCCTCGTGCTCGTAAACGGACCCGAACATCTCTGGAGCT
TTCTTCAGGGCCGACAATCGGATCTCGCGGAAATCCTGCACGTCGGCCGCTCCAAGCCGTCGAA
TCTGAGCCTTAATCACAATTGTCAATTTTAATCCTCTGTTTATCGGCAGTTCGTAGAGCGCGCC
GTGCGCCCGAGCGATACTGAGCGAAGCAAGTGCGTCGAGCAGTGCCCGCTTGTTCCTGAAATGC
CAGTAAAGCGCTGGCTGCTGAACCCCCAGCCGGAACTGACCCCACAAGGCCCTAGCGTTTGCAA
TGCACCAGGTCATCATTGACCCAGGCGTGTTCCACCAGGCCGCTGCCTCGCAACTCTTCGCAGG
CTTCGCCGACCTGCTCGCGCCACTTCTTCACGCGGGTGGAATCCGATCCGCACATGAGGCGGAA
GGTTTCCAGCTTGAGCGGGTACGGCTCCCGGTGCGAGCTGAAATAGTCGAACATCCGTCGGGCC
GTCGGCGACAGCTTGCGGTACTTCTCCCATATGAATTTCGTGTAGTGGTCGCCAGCAAACAGCA
CGACGATTTCCTCGTCGATCAGGACCTGGCAACGGGACGTTTTCTTGCCACGGTCCAGGACGCG
GAAGCGGTGCAGCAGCGACACCGATTCCAGGTGCCCAACGCGGTCGGACGTGAAGCCCATCGCC
GTCGCCTGTAGGCGCGACAGGCATTCCTCGGCCTTCGTGTAATACCGGCCATTGATCGACCAGC
CCAGGTCCTGGCAAAGCTCGTAGAACGTGAAGGTGATCGGCTCGCCGATAGGGGTGCGCTTCGC
GTACTCCAACACCTGCTGCCACACCAGTTCGTCATCGTCGGCCCGCAGCTCGACGCCGGTGTAG
GTGATCTTCACGTCCTTGTTGACGTGGAAAATGACCTTGTTTTGCAGCGCCTCGCGCGGGATTT
TCTTGTTGCGCGTGGTGAACAGGGCAGAGCGGGCCGTGTCGTTTGGCATCGCTCGCATCGTGTC
CGGCCACGGCGCAATATCGAACAAGGAAAGCTGCATTTCCTTGATCTGCTGCTTCGTGTGTTTC
AGCAACGCGGCCTGCTTGGCCTCGCTGACCTGTTTTGCCAGGTCCTCGCCGGCGGTTTTTCGCT
TCTTGGTCGTCATAGTTCCTCGCGTGTCGATGGTCATCGACTTCGCCAAACCTGCCGCCTCCTG
TTCGAGACGACGCGAACGCTCCACGGCGGCCGATGGCGCGGGCAGGGCAGGGGGAGCCAGTTGC
ACGCTGTCGCGCTCGATCTTGGCCGTAGCTTGCTGGACCATCGAGCCGACGGACTGGAAGGTTT
CGCGGGGCGCACGCATGACGGTGCGGCTTGCGATGGTTTCGGCATCCTCGGCGGAAAACCCCGC
GTCGATCAGTTCTTGCCTGTATGCCTTCCGGTCAAACGTCCGATTCATTCACCCTCCTTGCGGG
ATTGCCCCGACTCACGCCGGGGCAATGTGCCCTTATTCCTGATTTGACCCGCCTGGTGCCTTGG
TGTCCAGATAATCCACCTTATCGGCAATGAAGTCGGTCCCGTAGACCGTCTGGCCGTCCTTCTC
GTACTTGGTATTCCGAATCTTGCCCTGCACGAATACCAGCGACCCCTTGCCCAAATACTTGCCG

FIGURE 47 CONTINUED

TGGGCCTCGGCCTGAGAGCCAAAACACTTGATGCGGAAGAAGTCGGTGCGCTCCTGCTTGTCGC
CGGCATCGTTGCGCCACTCTTCATTAACCGCTATATCGAAAATTGCTTGCGGCTTGTTAGAATT
GCCATGACGTACCTCGGTGTCACGGGTAAGATTACCGATAAACTGGAACTGATTATGGCNNCTC
GAAATTCCCTCGGTCTTGCCTTGCTCGTCGGTGATGTACTTCACCAGCTCCGCGAAGTCGCTCT
TCTTGATGGAGCGCATGGGGACGTGCTTGGCAATCACGCGCACCCCCCGGCCGTTTTAGCGGCT
AAAAAAGTCATGGCTCTGCCCTCGGGCGGACCACGCCCATCATGACCTTGCCAAGCTCGTCCTG
CTTCTCTTCGATCTTCGCCAGCAGGGCGAGGATCGTGGCATCACCGAACCGCGCCGTGCGCGGG
TCGTCGGTGAGCCAGAGTTTCAGCAGGCCGCCCAGGCGGCCCAGGTCGCCATTGATGCGGGCCA
GCTCGCGGACGTGCTCATAGTCCACGACGCCCGTGATTTTGTAGCCCTGGCCGACGGCCAGCAG
GTAGGCCGACAGGCTCATGCCGGCCGCCGCCGCCTTTTCCTCAATCGCTCTTCGTTCGTCTGGA
AGGCAGTACACCTTGATAGGTGGGCTGCCCTTCCTGGTTGGCTTGGTTTCATCAGCCATCCGCT
TGCCCTCATCTGTTACGCCGGCGGTAGCCGGCCAGCCTCGCAGAGCAGGATTCCCGTTGAGCAC
CGCCAGGTGCGAATAAGGGACAGTGAAGAAGGAACACCCGCTCGCGGGTGGGCCTACTTCACCT
ATCCTGCCCGGCTGACGCCGTTGGATACACCAAGGAAAGTCTACACGAACCCTTTGGCAAAATC
CTGTATATCGTGCGAAAAAGGATGGATATACCGAAAAAATCGCTATAATGACCCCGAAGCAGGG
TTATGCAGCGGAAAAGATCCGTCGACCCTTTCCGACGCTCACCGGGCTGGTTGCCCTCGCCGCT
GGGCTGGCGGCCGTCTATGGCCCTGCAAACGCGCCAGAAACGCCGTCGAAGCCGTGTGCGAGAC
ACCGCGGCCGCCGGCGTTGTGGATACCACGCGGAAAACTTGGCCCTCACTGACAGATGAGGGGC
GGACGTTGACACTTGAGGGGCCGACTCACCCGGCGCGGCGTTGACAGATGAGGGGCAGGCTCGA
TTTCGGCCGGCGACGTGGAGCTGGCCAGCCTCGCAAATCGGCGAAAACGCCTGATTTTACGCGA
GTTTCCCACAGATGATGTGGACAAGCCTGGGGATAAGTGCCCTGCGGTATTGACACTTGAGGGG
CGCGACTACTGACAGATGAGGGGCGCGATCCTTGACACTTGAGGGGCAGAGTGATGACAGATGA
GGGGCGCACCTATTGACATTTGAGGGGCTGTCCACAGGCAGAAAATCCAGCATTTGCAAGGGTT
TCCGCCCGTTTTTCGGCCACCGCTAACCTGTCTTTTAACCTGCTTTTAAACCAATATTTATAAA
CCTTGTTTTTAACCAGGGCTGCGCCCTGGCGCGTGACCGCGCACGCCGAAGGGGGGTGCCCCCC
CTTCTCGAACCCTCCCGGCCCGCTAACGCGGGCCTCCCATCCCCCCAGGGGCTGCGCCCCTCGG
CCGCGAACGGCCTCACCCCAAAAATGGCAGGCCAAGCTAGCTTGCTTGGTCGTTCCGGTACGTA
CCGTGAACGTCGGCTCGATTGTACCTGCGTTCAAATACTTTGCGATCGTGTTGCGCGCCTGCCC
GGTGCGTCGGCTGATCTCACGGATCGACTGCTTCTCTCGCAACGCCATCCGACGGATGATGTTT
AAAAGTCCCATGTGGATCACTCCGTTGCCCCGTCGCTCACCGTGTTGGGGGGAAGGTGCACATG
GCTCAGTTCTCAATGGAAATTATCTGCCTAACCGGCTCAGTTC (SEQ ID NO: 26)

Figure 48. Construction of pUHN
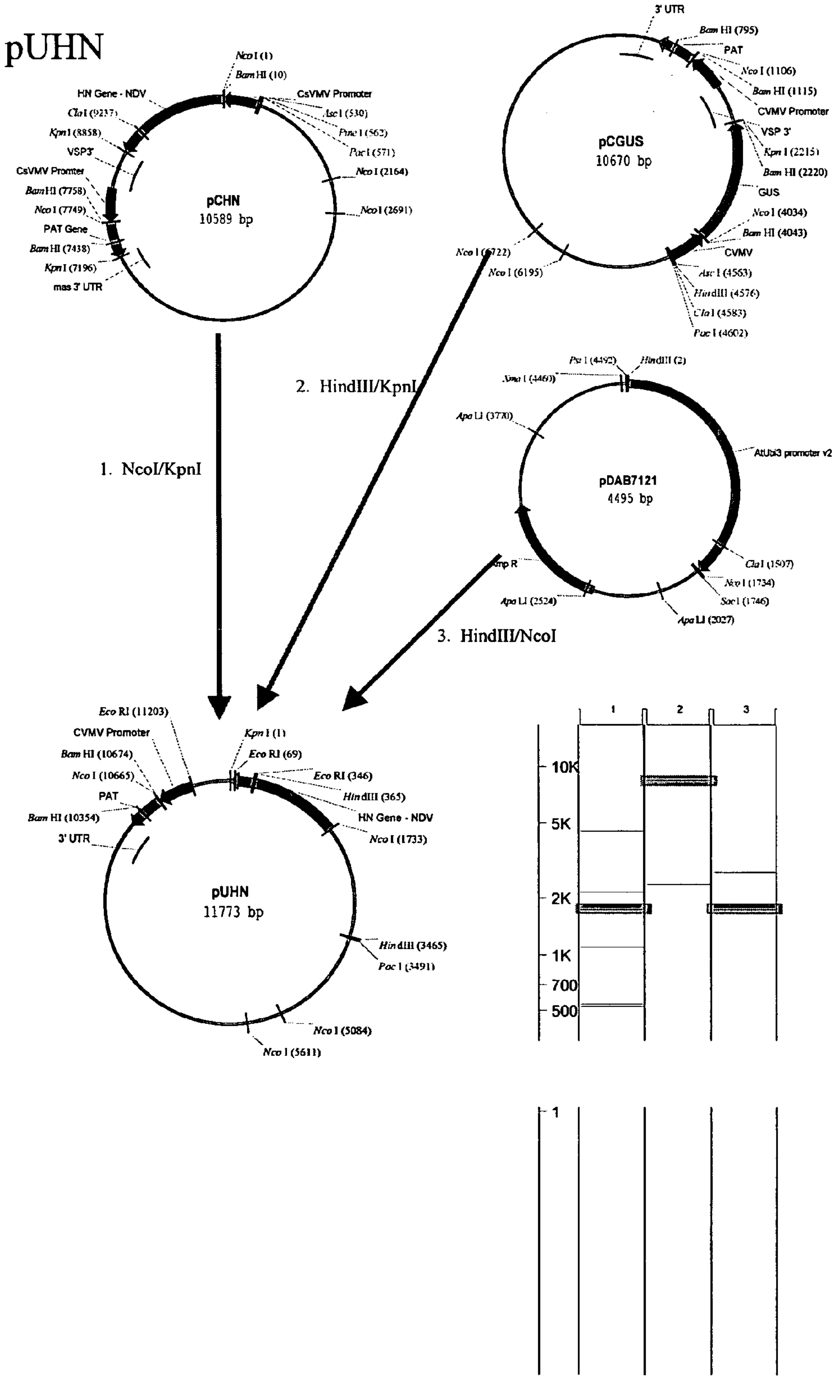

VECTORS AND CELLS FOR PREPARING IMMUNOPROTECTIVE COMPOSITIONS DERIVED FROM TRANSGENIC PLANTS

This application claims the benefit of U.S. Provisional Application No. 60/467,998, filed on May 5, 2003. The entire teachings of the above application is incorporated herein by reference.

FIELD OF INVENTION

The present invention generally relates to the field of plant molecular biology as it applies to the recombinant production of plant-made vaccines.

BACKGROUND OF THE INVENTION

Recombinant DNA technology has provided substantial improvements in the safety, quality, efficacy and cost of pharmaceutical and veterinary medicaments including vaccines. Plant produced mucosal vaccines were invented by Curtiss & Cardineau. See U.S. Pat. Nos. 5,654,184; 5,679,880 and 5,686,079 herein incorporated by reference. Others have described transgenic plants expressing immunoprotective antigens and methods for production including Arntzen, Mason and Lam. See U.S. Pat. Nos. 5,484,717; 5,914,123; 6,034,298; 6,136,320; 6,194,560; and 6,395,964 herein incorporated by reference.

Vaccines produced in plant systems offer a number of advantages over conventional production systems. Conventionally produced vaccines strains (live and vectored) may revert towards virulence or carry biological contaminants from the production process. Subunit vaccines may be difficult to produce and purify due to protein instability issues and will not be glycosylated when produced in prokaryotes.

Plant cell production avoids the need for animal-sourced components in growth media essentially eliminating the risk of transmitting pathogenic contaminants from the production process. Plant cells are capable of post translational glycosylation, and plant cell growth media is generally less expensive and easier to handle and prepare compared to conventional growth media presently used in the manufacture of vaccines.

Systemic immunity to a particular pathogen results from activation of the immune system in response to antigen presented by a particular pathogenic organism or via a vaccine designed to protect against a particular pathogenic agent. Exposure to a pathogen is often through mucosal surfaces that are constantly exposed and challenged by pathogenic organisms.

Mucosal and oral immunity results from the production of sIgA (secretory IgA) antibodies in secretions that bathe all mucosal surfaces of the respiratory tract, gastrointestinal tract and the genitourinary tract and in secretions from all secretory glands. McGhee, J. R. et al., *Annals N.Y. Acad. Sci.* 409, (1983). These sIgA antibodies act to prevent colonization of pathogens on a mucosal surface (Williams, R. C. et al., Science 177, 697 (1972); McNabb, P. C. et al., *Ann. Rev. Microbiol.* 35, 477 (1981) and thus act as a first line of defense to prevent colonization or invasion through a mucosal surface. The production of sIgA can be stimulated either by local immunization of the secretory gland or tissue or by presentation of an antigen to either the GALT (gut-associated lymphoid tissue or Peyer's patches) or the BALT (bronchial-associated lymphoid tissue). Cebra, J. J. et al., Cold Spring Harbor Symp. Quant. Biol. 41, 210 (1976); Bienenstock, J. M., *Adv. Exp. Med. Biol.* 107, 53 (1978); Weisz-Carrington, P. Et al., J. Inmunol 123, 1705 (1979); McCaughan, G. et al., *Internal Rev. Physiol* 28, 131 (1983). Membranous microfold cells, otherwise known as M Cells, cover the surface of the GALT and BALT and may be associated with other secretory mucosal surfaces. M cells act to sample antigens from the luminal space adjacent to the mucosal surface and transfer such antigens to antigen-presenting cells (dendritic cells and macrophages), which in turn present the antigen to a T lymphocyte (in the case of T-dependent antigens), which process the antigen for presentation to a committed B cell. B cells are then stimulated to proliferate, migrate and ultimately be transformed into an antibody-secreting plasma cell producing IgA against the presented antigen. When the antigen is taken up by M cells overlying the GALT and BALT, a generalized mucosal immunity results with sIgA against the antigen being produced by all secretory tissues in the body. Cebra et al., supra; Bienenstock et al., supra; Weinz-Carrington et al., supra; McCaughan et al., supra. Oral immunization is therefore a most important route to stimulate a generalized mucosal immune response and, in addition, leads to local stimulation of a secretory immune response in the oral cavity and in the gastrointestinal tract.

Mucosal immunity can also be advantageously transferred to offspring. Immunity in neonates may be passively acquired through colostrum and/or milk. This has been referred to as lactogenic immunity and is an efficient way to protect animals during early life. sIgA is the major immunoglobulin in milk and is most efficiently induced by mucosal immunization.

The M cells overlying the Peyer's patches of the gut-associated lymphoid tissue are capable of taking up a diversity of antigenic material and particles (Sneller, M. C. and Strober, W., J. *Inf. Dis.* 154, 737 (1986). Because of their abilities to take up latex and polystyrene spheres, charcoal, microcapsules and other soluble and particulate matter, it is possible to deliver a diversity of materials to the GALT independent of any specific adhesive-type property of the material to be delivered.

Vectors and cells useful for producing transgenic plant-derived immunoprotective antigens, and improved methods of antigen production would greatly facilitate the development, manufacture and efficacy plant-produced vaccines.

SUMMARY OF THE INVENTION

The invention is based on plant optimized sequences encoding an immunoprotective antigen of interest. In particular, the invention is based on a plant optimized DNA sequence encoding the HN antigen of Newcastle Disease Virus or a DNA sequence encoding the HA antigen of Avian Influenza Virus. The invention also includes a recombinant expression vector for effecting expression of an immunoprotective antigen gene in a plant cell, as well as plant cells and transgenic plants comprising the expression vector, as well as vaccines comprising a protein product of the expression vector. The invention also relates to methods of protecting against the effects of a pathogen utilizing the vaccines of the invention. The invention further relates to methods of producing an antigen in a transgenic plant.

The invention provides for an isolated plant optimized nucleotide sequence encoding the HN antigen of Newcastle Disease Virus comprising the sequence of SEQ ID NO:1, as well as a recombinant expression vector comprising SEQ ID NO:1.

In one embodiment, the vector is selected from the group consisting of pCHN, pGHN, pGHN151, pGHN153, pMHN, pUHN.

In another embodiment, the vector comprises a plant-functional promoter is operably linked to SEQ ID NO:1.

The invention also provides for a recombinant expression vector for expressing an immunoprotective antigen in a plant cell comprising a DNA sequence encoding the HA antigen of Avian Influenza Virus, wherein the vector is pCHA The invention further provides for a transgenic plant cell for expression of an immunogenic antigen comprising a vector of the invention. The plant cell includes a tomato plant cell or a tobacco plant cell, as well as a cell from any of the plant species described hereinbelow.

The invention further provides for a transgenic plant comprising a vector of the invention.

The invention also provides for a vaccine comprising a recombinant viral antigenic protein and a pharmaceutically acceptable carrier, wherein the viral antigenic protein is the HN antigen of Newcastle Disease virus produced by a vector of the invention, and wherein the vaccine is capable of eliciting an immune response upon administration to an animal.

In one embodiment, the HN protein of the vaccine comprises SEQ ID NO:2. The HN protein of the vaccine can be produced in a plant cell.

The invention also provides for a vaccine comprising a recombinant viral antigenic protein and a pharmaceutically acceptable carrier, wherein the viral antigenic protein is the HA antigen of Avian Influenza Virus produced by a vector of the invention, and wherein the vaccine is capable of eliciting an immune response upon administration to an animal. In one embodiment, the HA antigen of the vaccine is produced in a plant cell.

The invention also provides for a method for protecting an animal against NewCastle Disease Virus or Avian Influenza Virus comprising administering an effective amount of the appropriate vaccine of the invention to an animal. According to one embodiment of the method, wherein the vaccine is administered orally, intranasaly, intraperitonealy, intramuscularly, intravenously or subcutaneously. In one embodiment of the method, the effective amount of the vaccine is at a range of 1 μg to 50 μg per kilogram of body weight.

The invention also provides for a method of producing an antigen in a transgenic plant comprising the steps of: a) producing a transgenic plant comprising a vector encoding the antigen; b) incubating the plant under conditions wherein the plant expresses the antigen; and wherein the plant is incubated prior to the onset of ripening.

In one embodiment, the plant comprises a fruit that ripens.

In another embodiment, the plant is a tomato plant.

In another embodiment, the fruit of the plant is harvested prior to the onset of ripening. According to one embodiment of this method, the antigen is isolated from the harvested fruit.

In another embodiment, the antigen is selected from the group consisting of HN antigen of Newcastle Disease Virus, HA antigen of Avian Influenza Virus, LTB, NVCP, zona pellucida glycoprotein and HBsAg.

BRIEF DESCRIPTION OF THE FIGURES

FIGS. 1*a* and 1*b*. The plant optimized coding sequence (SEQ ID NO: 1) and protein sequence (SEQ ID NO: 2) of the HN gene of NDV strain "Lasota"

FIG. 10. The DNA (SEQ ID NO: 3) and protein (SEQ ID NO: 4) sequences of the HA gene of AIV A/turkey/Wisconsin/68 (H5N9).

FIG. 25. Expression of HN in pMHN- and pCHN-transformed NT1 cell lines.

FIG. 26. HN expression in pCHN-transformed potato.

FIG. 27. Particle behavior of HN antigen extracted from pCHN-transformed potato tubers.

FIG. 28. HN expression in microtubers of pGHN-transformed potato plants.

FIG. 29. Expression of HN in tubers of pGHN- and pGHN151-transformed potato plants.

FIG. 30. T-DNA region from the construct pCHN.

FIG. 31. Effect of ripening on wild type TA234 tomato fruit pH.

FIG. 32. Effect of ripening on wild type TA234 tomato fruit total soluble protein.

FIG. 37. Haemagglutination activity in the fruit and leaves of CHN tomatoes.

FIG. 38. Change in maturing fruit diameter. “Week” indicates the amount of time post pollination. Points indicate the mean of three measurements while the bars indicate the standard errors of the means.

FIG. 39. Change in fruit mass of maturing tomato fruit. “Week” indicates the amount of time post pollination. Each point represents the mean of the three measurements while the bars indicate the standard errors of the means.

FIG. 40. Water loss from maturing tomato fruit upon lyophilization. “Week” indicates the amount of time post pollination. Points represent the mean of three measurements while the bars indicate the standard errors of the means.

FIG. 41. Concentration of HN per gram of fresh tomato fruit. “Week” indicates the amount of time post pollination. Bars represent the average of three samples. Bars labeled with the same letter are not significantly different (α=0.05). Error bars indicate the standard error of the means.

FIG. 42. Amount of HN in maturing tomato fruit. “Week” indicates the amount of time post pollination. Bars represent the average of three replicate HN contents multiplied by the masses. Bars labeled with the same letter are not significantly different (α=0.05). Error bars indicate the standard error of the mean.

FIG. 43. The regulated biological agent (pCHN) insert in CHN-18 master seed.

FIG. 44. DNA sequence of the whole gene insert in CHN-18 master seed (SEQ ID NO: 12).

FIG. 45. pCHA vector sequence (SEQ ID NO: 24).

FIG. 46. pMHN vector sequence (SEQ ID NO: 25).

FIG. 47. pCHN vector sequence (SEQ ID NO: 26).

FIG. 48. Construction of pUHN.

SUMMARY OF THE SEQUENCES

Figure 2:
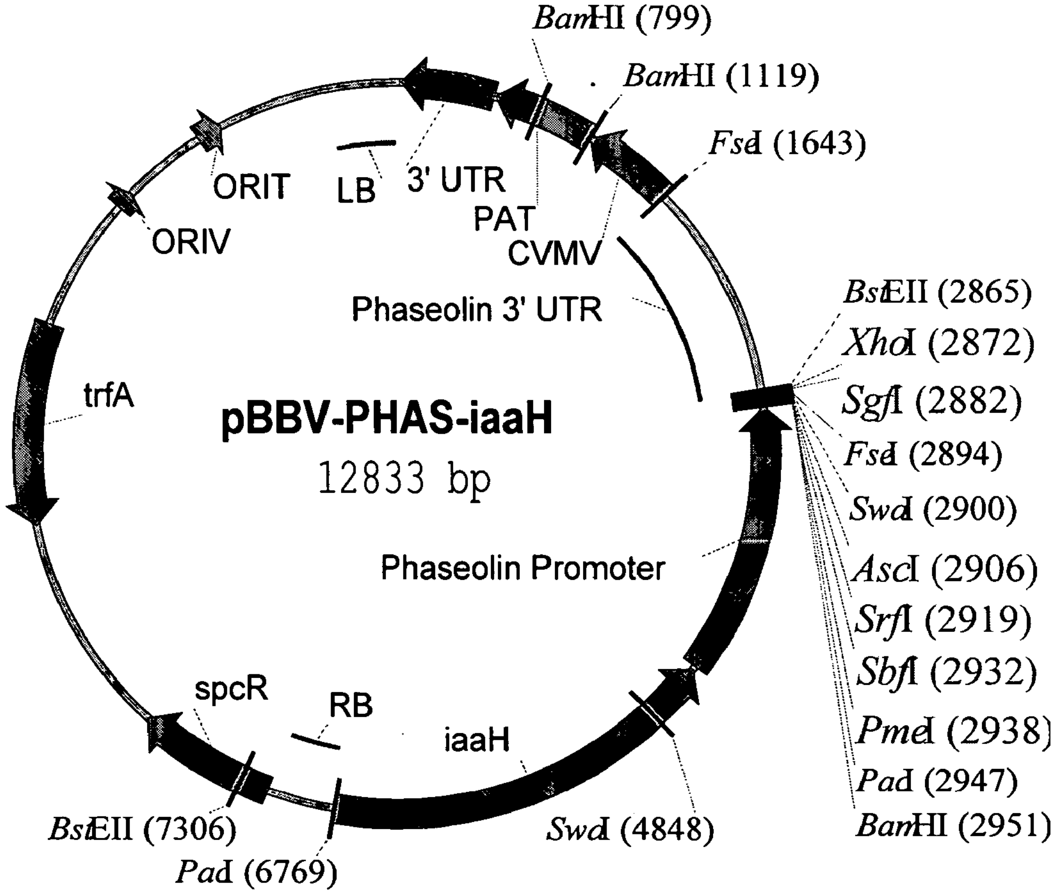
FIG. 2. Map of pBBV-PHAS-iaaH that contains the plant selectable marker PAT (phosphinothricin acetyl transferase), includes the constitutive CsVMV (cassava vein mosaic virus) promoter and is terminated by the MAS 3' (mannopine synthase) element. LB and RB (left and right T-DNA border) elements from *Agrobacterium* delineate the boundaries of the DNA that is integrated into the plant genome.

SEQ ID NOS: 1 and 2, shown in FIG. 1, are the plant optimized coding sequence and protein sequence of the HN gene of NDV strain "Lasota".

SEQ ID NOS: 3 and 4, shown in FIG. 10, are the DNA and protein sequences of the HA gene of AIV A/turkey/Wisconsin/68 (H5N9).

SEQ ID NO: 5 is a PCR primer used to end-tailor the CsVMV promoter on pCP!H.

SEQ ID NO: 6 is a PCR primer used to end-tailor the CsVMV promoter on pCP!H.

SEQ ID NO: 7 is a mutagenic primer used to create a Nco I site.

SEQ ID NO: 8 is a forward primer complimentary to the 5' region.

SEQ ID NO: 9 is a mutagenic primer used to create a XhoI I site.

SEQ ID NO: 10 is a PCR labeled probe made by using the primer HNa.

SEQ ID NO: 11 is a PCR labeled probe made by using the primer HNb.

SEQ ID NO: 12 is the DNA sequence of the whole gene insert in CHN-18 master seed.

SEQ ID NO: 13 is the DNA sequence encoding Hepatitis B virus Strain Gly D surface antigen, complete cds. (GenBank accession AF134148).

SEQ ID NO: 14 is the protein sequence of Hepatitis B virus Strain Gly D surface antigen. (GenBank accession AAD31865).

SEQ ID NO: 15 is the DNA sequence encoding Homo sapiens zona pellucida glycoprotein 3 (sperm receptor) (ZP3), mRNA. (GenBank accession NM_007155).

SEQ ID NO: 16 is the protein sequence of Homo sapiens zona pellucida glycoprotein 3 preproprotein (sperm receptor) (ZP3). (GenBank accession NP_009086).

SEQ ID NO: 17 is the DNA sequence encoding Avian influenza virus hemagglutinin (HA) MRNA, complete cds. (GenBank accession U67783).

SEQ ID NO: 18 is the protein sequence of Avian influenza virus hemagglutinin (HA). (GenBank accession AAC58999).

SEQ ID NO: 19 is the DNA sequence encoding Newcastle disease virus hemagglutinin-neuraminidase (HN), MRNA, complete cds. (GenBank accession AY510092).

SEQ ID NO: 20 is the protein sequence of Newcastle disease virus hemagglutinin-neuraminidase (HN). (GenBank accession AAS10195).

SEQ ID NO: 21 is the DNA sequence encoding Gallus gallus zona pellucida glycoprotein 3 (sperm receptor) (ZP3), mRNA. (GenBank accession NM_204389).

SEQ ID NO: 22 is the protein sequence of Gallus gallus zona pellucida glycoprotein 3 (sperm receptor) (ZP3). (GenBank accession NP_989720).

SEQ ID NO: 23 is the DNA sequence of Duck hepatitis B virus. (GenBank accession X58569).

SEQ ID NO: 24 is the DNA sequence of vector pCHA.

SEQ ID NO: 25 is the DNA sequence of vector pMHN.

SEQ ID NO: 26 is the DNA sequence of vector pCHN.

Definitions

As used herein, "an immunogen or immunoprotective antigen" is a non-self substance that elicits a humoral and/or cellular immune response in healthy animals such that the animal is protected against future exposure to a pathogen bearing the immunogen. The pathogens are typically agents such as viruses, bacteria, fungi and protozoa. Immunogens may also be antigenic portions of pathogens including cell wall components and viral coat proteins.

As used herein, "an immunoprotective particle" is a particle or vesicle derived from a transgenic plant cell that expresses an immunogen that, when appropriately administered to an animal, provides protection against future exposure to a pathogen bearing the immunogen.

As used herein, "vaccination or vaccinating" is defined as a means for providing protection against a pathogen by inoculating a host with an immunogenic preparation of a pathogenic agent, or a non-virulent form or part thereof, such that the host immune system is stimulated and prevents or attenuates subsequent host reactions to later exposures of the pathogen. "Providing protection" refers to stimulating an immune response as defined hereinbelow.

As used herein, "a vaccine" is a composition used to vaccinate an animal that contains at least one immunoprotective antigenic substances.

As used herein, "a pathogenic organism" is a bacterium, virus, fungus, or protozoan that causes a disease or medical condition in an animal which it has infected.

As used herein, "an adjuvant" is a substance that accentuates, increases, or enhances the immune response to an immunogen or antigen. As used herein, an increase, or accentuation or enhancement means a 2-fold or more, for example, 2, 3, 4, 5, 10, 20, 30, 40, 50, 60, 70, 80, 90, 100, or 1000-fold or more increase in the amount of antibody produced, for example, in the response to an antigen administered in the presence of an adjuvant as compared to in the absence of an adjuvant. An increase, accentuation or enhancement also means at least 5% or more antibody production, for example, 5, 6, 10, 20, 30, 40, 50, 60 70, 80, 90 or 100% or more, for example, in response to an antigen administered in the presence versus the absence of an adjuvant. Adjuvants typically enhance both the humoral and cellular immune response but an increased response to either in the absence of the other qualifies to define an adjuvant. Moreover, adjuvants and their uses are well known to immunologists and are typically employed to enhance the immune response when doses of immunogen are limited or when the immunogen is poorly immunogenic or when the route of administration is sub-optimal. Thus the term 'adjuvanting amount' is that quantity of adjuvant capable of enhancing the immune response to a given immunogen or antigen. The mass that equals an adjuvanting amount will vary and is dependant on a variety of factors including but not limited to the characteristics of the immunogen, the quantity of immunogen administered, the host species, the route of administration, and the protocol for administering the immunogen. The adjuvanting amount can readily be quantified by routine experimentation given a particular set of circumstances. This is well within the ordinarily skilled artisan's purview and typically employs the use of routine dose response determinations to varying amounts of administered immunogen and adjuvant. Responses are measured by determining serum antibody titers raised in response to the immunogen using enzyme linked immunosorbant assays, radio immune assays, hemagglutination assays and the like.

As used herein, a “transgenic plant cell” refers to a plant cell which stably expresses a foreign gene, wherein the foreign gene is integrated into the plant cell chromosome and does not carry with it a viral vector sequence unique to a virus, where the foreign gene is passed onto the next cell generation and is capable of being expressed from the host plant cell chromosome. In addition, “transgenic plant material” refers to a “transgenic cell suspension” comprising one or a plurality of “transgenic plant cells” obtained by well-known cell culture techniques (Street, HE. 1973, Plant tissue and cell culture: botanical monographs. Vol II, University of Calif., Berkeley).

As used herein, a “trangenic plant” refers to a plant, the cells of which stably express a “heterologous” foreign gene, wherein the foreign gene is integrated into the plant cell chromosome and does not carry with it a viral vector sequence unique to a virus, where the foreign gene is passed onto the next plant generation and is capable of being expressed from the host plant cell chromosome. A “transgenic plant” comprises a “plurality of transgenic plant cells”. A “transgenic plant” refers to the whole plant, or a part thereof including, but not limited to, roots, stems, leaves, stalks, seeds, fruit, tubers, flowers, pollen, and the like. Examples of heterologous foreign genes include, but are not limited to, Norwalk virus capsid protein (NVCP), Avian Influenza hemagglutination antigen (AIV-HA), Newcastle Disease Virus neuraminidase (NDV-HN), zona pellucida glycoprotein 3 (ZP3), and Hepatitis B surface Antigen (HBsAg).

Transgenic plant is herein defined as a plant cell culture, plant cell line, plant, or progeny thereof derived from a transformed plant cell or protoplast, wherein the genome of the transformed plant contains foreign DNA, introduced by laboratory techniques, not originally present in a native, non-transgenic plant cell of the same species. The terms “transgenic plant” and “transformed plant” have sometimes been used in the art as synonymous terms to define a plant whose DNA contains an exogenous DNA molecule.

As used herein, an “edible plant” refers to a plant which may be consumed by an animal, has nutritional value and is not toxic. An “edible plant” may be a “food” which is a plant or a material obtained from a plant which is ingested by humans or other animals. The term “food” is intended to include plant material which may be fed to humans and other animals or a processed plant material which is fed to humans and other animals. Materials obtained from a plant are intended to include a component of a plant which is eventually ingested by a human or other animal. Examples of “edible plant” include, but are not limited to, tomato plants, rice plants, wheat plants, corn plants, carrot plants, potato plants, apple plants, soybean plants, alfalfa plants, medicago plants, vegetable plants, and fruit plants or any of the edible plants described herein.

In some cases an “edible plant” is “capable of being ingested for its nutritional value”, which refers to a plant or portion thereof that provides a source of metabolizable energy, supplementary or necessary vitamins or co-factors, roughage or otherwise beneficial effect upon ingestion by an animal. Thus, where the animal to be treated by the methods of the present invention is an herbivore capable of bacterial-aided digestion of cellulose, such a food might be represented by a transgenic grass plant. Other edible plants include vegetables and fruits. Similarly, although transgenic lettuce plants, for example, do not substantially contribute energy sources, building block molecules such as proteins, carbohydrates or fats, nor other necessary or supplemental vitamins or cofactors, a lettuce plant transgenic for the nucleic acid molecules described herein used as food for an animal would fall under the definition of a food as used herein if the ingestion of the lettuce contributed roughage to the benefit of the animal, even if the animal could not digest the cellulosic content of lettuce. An “edible plant” therefore excludes tobacco.

As used herein, “immune response” refers to a response made by the immune system of an organism to a substance, which includes but is not limited to foreign or self proteins. There are three general types of “immune response” including, but not limited to mucosal, humoral and cellular “immune responses.” A “mucosal immune response” results from the production of secretory IgA (sIgA) antibodies in secretions that bathe all mucosal surfaces of the respiratory tract, gastrointestinal tract and the genitourinary tract and in secretions from all secretory glands (McGhee, J. R. et al., 1983, *Annals NY Acad. Sci.* 409). These sIgA antibodies act to prevent colonization of pathogens on a mucosal surface (Williams, R. C. et al., *Science* 177, 697 (1972); McNabb, P. C. et al., *Ann. Rev. Microbiol.* 35, 477 (1981)) and thus act as a first line of defense to prevent colonization or invasion through a mucosal surface. The production of sIgA can be stimulated either by local immunization of the secretory gland or tissue or by presentation of an antigen to either the gut-associated lymphoid tissue (GALT or Peyer's patches) or the bronchial-associated lymphoid tissue (BALT; Cebra, J. J. et al., *Cold Spring Harbor Symp. Quant. Biol.* 41, 210 (1976); Bienenstock, J. M., *Adv. Exp. Med. Biol.* 107, 53 (1978); Weisz-Carrington, P. et al., *J. Immunol* 123, 1705 (1979); McCaughan, G. et al., *Internal Rev. Physiol* 28, 131 (1983)). Membranous microfold cells, otherwise known as M cells, cover the surface of the GALT and BALT and may be associated with other secretory mucosal surfaces. M cells act to sample antigens from the luminal space adjacent to the mucosal surface and transfer such antigens to antigen-presenting cells (dendritic cells and macrophages), which in turn present the antigen to a T lymphocyte (in the case of T-dependent antigens), which process the antigen for presentation to a committed B cell. B cells are then stimulated to proliferate, migrate and ultimately be transformed into an antibody-secreting plasma cell producing IgA against the presented antigen. When the antigen is taken up by M cells overlying the GALT and BALT, a generalized mucosal immunity results with sIgA against the antigen being produced by all secretory tissues in the body (Cebra et al., supra; Bienenstock et al., supra; Weinz-Carrington et al., supra; McCaughan et al., supra). Oral immunization is therefore an important route to stimulate a generalized mucosal immune response and, in addition, leads to local stimulation of a secretory immune response in the oral cavity and in the gastrointestinal tract.

An “immune response” may be measured using techniques known to those of skill in the art. For example, serum, blood or other secretions may be obtained from an organism for which an “immune response” is suspected to be present, and assayed for the presence of the above mentioned immunoglobulins using an enzyme-linked immuno-absorbant assay (ELISA; U.S. Pat. No. 5,951,988; Ausubel et al., *Short Protocols in Molecular Biology* $3^{rd}$ Ed. John Wiley & Sons, Inc. 1995). According to the present invention, a protein of the present invention can be said to stimulate an “immune response” if the quantitative measure of immunoglobulins in an animal treated with a protein of interest detected by ELISA is statistically different (for example, is increased or decreased by 2-fold or more, for example, 2, 3, 4, 5, 10, 20, 30, 40, 50, 60, 70, 80, 90, 100, or 1000-fold or more increase or decrease in the amount of antibody produced. An increase or decrease also means at least 5% or more antibody production, for example, 5, 6, 10, 20, 30, 40, 50, 60 70, 80, 90 or 100% or more, or at least 5% or more of a decrease in antibody production) from the measure of immunoglobulins detected in an animal not treated with a protein of interest, wherein said immunoglobulins are specific for the protein of interest. A statistical test known in the art and useful to determining the difference in measured immunoglobulin levels includes, but is not limited to ANOVA, Student's T-test, and the like, wherein the P value is at least <0.1, <0.05, <0.01, <0.005, <0.001, and even <0.0001.

An "immune response" may be measured using other techniques such as immunohistochemistry using labeled antibodies which are specific for portions of the immunoglobulins raised during the "immune response". Tissue (e.g., ovarian tissue) from an animal to which a protein of interest has been administered according to the invention may be obtained and processed for immunohistochemistry using techniques well known in the art (Ausubel et al., *Short Protocols in Molecular Biology* $3^{rd}$ Ed. John Wiley & Sons, Inc. 1995). Microscopic data obtained by immunohistochemistry may be quantitated by scanning the immunohistochemically stained tissue sample and quantitating the level of staining using a computer software program known to those of skill in the art including, but not limited to NIH Image (National Institutes of Health, Bethesda, Md.). According to the present invention, a protein of the present invention can be said to stimulate an "immune response" if the quantitative measure of immunohistochemical staining in an animal treated with a protein of interest is statistically different (as defined by an increase or decrease discussed hereinabove) from the measure of immunohistochemical staining detected in an animal not treated with the protein of interest, wherein said histochemical staining requires binding specific for that protein. A statistical test known in the art may be used to determine the difference in measured immunohistochemical staining levels including, but not limited to ANOVA, Student's T-test, and the like, wherein the P value is at least <0.1, <0.05, <0.01, <0.005, <0.001, and even <0.0001.

A "mucosal immune response" may be "detected" using any of the above referenced techniques. For example, an ELISA assay may be employed using anti-IgA antibodies to detect and measure the mucosal-specific immunoglobulins (Dickinson, B. L. & Clements, J. D. Dissociation of *Escherichia coli* heat-labile enterotoxin adjuvanticity from ADP-ribosyltransferase activity. *Infect Immun* 63, 1617–1623 (1995)).

A "humoral immune response" comprises the production of antibodies in response to an antigen or antigens. A cellular immune response includes responses such as a helper T-cell ($CD4^+$) response and a cytotoxic T-cell lymphocyte ($CD8^+$) response. A mucosal immune response (or secretory immune response) comprises the production of secretory (sIgA) antibodies. An immune response can comprise one or a combination of these responses.

As used herein, "animal" refers to an organism classified within the phylogenetic kingdom Animalia. As used herein, an "animal" also refers to a mammal. Animals, useful in the present invention, include, but are not limited to mammals, marsupials, mice, dogs, cats, cows, humans, deer, horses, sheep, livestock, poultry, chickens, turkeys, ostrich, fish, fin fish, shell fish, and the like.

As used herein, "monocotyledonous" refers to a type of plant whose embryos have one cotyledon or seed leaf. Examples of "monocots" include, but are not limited to lilies; grasses; corn; grains, including oats, wheat and barley; orchids; irises; onions and palms.

As used herein, "dicotyledonous" refers to a type of plant whose embryos have two seed halves or cotyledons. Examples of "dicots" include, but are not limited to tobacco; tomato; the legumes including alfalfa; oaks; maples; roses; mints; squashes; daisies; walnuts; cacti; violets and buttercups.

As used herein, "vector" refers to a nucleic acid molecule capable of transporting another nucleic acid to which it has been linked. One type of vector is a "plasmid", which refers to a circular double stranded nucleic acid loop into which additional nucleic acid segments can be ligated. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant nucleic acid techniques are often in the form of plasmids. In the present specification, "plasmid" and "vector" can be used interchangeably as the plasmid is the most commonly used form of vector.

As used herein, "promoter" refers to a sequence of DNA, usually upstream (5') of the coding region of a structural gene, which controls the expression of the coding region by providing recognition and binding sites for RNA polymerase and other factors which may be required for initiation of transcription. The selection of the promoter will depend upon the nucleic acid sequence of interest. A "plant-functional promoter" refers to a "promoter" which is capable of supporting the initiation of transcription in plant cells. "Plant-functional promoters" useful in the present invention include, but are not limited to the 35S promoter of the cauliflower mosaic virus (CaMV); promoters of seed storage protein genes such as Zma10Kz or Zmag12, light inducible genes such as ribulose bisphosphate carboxylase small subunit (rbcS), stress induced genes such as alcohol dehydrogenase (Adh1), or "housekeeping genes" that express in all cells (such as Zmact, a maize actin gene); the tomato E8 promoter; ubiquitin; mannopine synthetase (mas); rice actin 1; soybean seed protein glycinin (Gy1); soybean vegetative storage protein (vsp); and granule-bound starch synthase (gbss). Other "plant-functional promoters" include promoters for genes which are known to give high expression in edible plant parts, such as the patatin gene promoter from potato.

As used herein, "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. A promoter sequence is "operably-linked" to a gene when it is in sufficient proximity to the transcription start site of a gene to regulate transcription of the gene.

As used herein, "administered" refers to the delivery of the transgenic plant material, cells, compositions, and pharmaceutical formulations of the present invention to an animal in such a manner so to guarantee that the "delivered" material contacts a mucosal surface of the animal to which it was administered. Routes of "delivery" useful in the present invention include, but are not limited to oral delivery, nasal delivery, intraperitoneal delivery, intramuscular, intravenous or subcutaneous delivery rectal or vaginal delivery (e.g., by suppository, or topical administration), or a route of delivery wherein the delivered material directly contacts a mucosal surface (i.e., "mucosal delivery"). As used herein, "pharmaceutically acceptable" means a non-toxic material that does not interfere with the effectiveness of the biological activity of the active ingredient(s). The characteristics of the carrier will depend on the route of administration.

As used herein, a "mucosal surface", "mucosal membrane", or "mucosa" refers to the well known medical definition of these structures, which is the surface or lining of a structure comprising an epithelium, lamina propria, and, in the digestive tract, a layer of smooth muscle. Examples of "mucosal surfaces" include, but are not limited to the inner coat of the bronchi, the mucous layer of the tympanic cavity, the inner mucous coat of the colon, the inner layer of the ductus deferens, the inner coat of the esophagus, the mucous coat of the small intestine, the mucous coat of the larynx, the mucous membrane of the tongue, the pituitary membrane, the mucous membrane of the oral cavity, the mucous membrane of the pharynx, the inner mucous layer of the trachea, the lining of the auditory tube, the mucous layer of the uterine tube, the inner layer of the ureter, the inner layer of the urethra, the endometrium, the mucous membrane of the vagina, the mucous layer of the stomach, the inner coat of the urinary bladder, and the mucous membrane of the seminal vesicle.

As used herein, a "carrier" refers to an inert and non-toxic material suitable for accomplishing or enhancing delivery of the vaccine of the present invention into an animal. Examples of a carrier include, but are not limited to water, phosphate buffered saline, or saline, and further may include an adjuvant. Adjuvants such as incomplete Freund's adjuvant, aluminum phosphate, aluminum hydroxide, or alum are materials well known in the art.

The present invention also provides pharmaceutical and veterinary compositions comprising an immunoprotective particle of the present invention in combination with one or more pharmaceutically acceptable adjuvants carriers, diluents, and excipients. Such pharmaceutical compositions may also be referred to as vaccines and are formulated in a manner well known in the pharmaceutical vaccine arts.

"Administering" or "administer" is defined as the introduction of a substance into the body of an animal and includes oral, nasal, rectal, vaginal and parenteral routes. The claimed compositions may be administered individually or in combination with other therapeutic agents via any route of administration, including but not limited to subcutaneous (SQ) intramuscular (IM), intravenous (IV), mucosal, nasal or oral. The compositions may be administered via the SQ or IM route. Especially preferred is the mucosal route, and most preferred is the oral route.

As used herein, "an effective amount or dosage of the vaccine" is an amount necessary to stimulate an innate immune response as defined herein and as detected by the assays described herein as in a human or animal sufficient for the human or animal to effectively resist a challenge mounted by a pathogen. For example, in one embodiment, "an effective amount or dosage of the vaccine" causes an increase in the amount of antibody that binds to the immunoprotective antigen of the vaccine. As used herein, an increase means a 2-fold or more, for example, 2, 3, 4, 5, 10, 20, 30, 40, 50, 60, 70, 80, 90, 100, or 1000-fold or more increase in the amount of antibody produced by the vaccinated subject as compared to an unvaccinated subject. An increase also means at least 5% or more antibody production, for example, 5, 6, 10, 20, 30, 40, 50, 60 70, 80, 90 or 100% or more, by a vaccinated subject as compared to an unvaccinated subject. The dosages administered to such human or animal will be determined by a physician or veterinarian in light of the relevant circumstances including the particular immunoprotective particle or combination of particles, the condition of the human or animal, and the chosen route of administration. The dosage ranges presented herein are not intended to limit the scope of the invention in any way and are presented as general guidance for the skilled practitioner. The effective dosage can be estimated initially either in cell culture assays, or in animal models, usually mice, rabbits, dogs, or pigs. The animal model is also used to achieve a desirable concentration range and route of administration. Such information can then be used to determine useful dosages and routes for administration in humans.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight and gender of the subject; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

The particular dosages of an antigenic composition of the invention will depend on many factors including, but not limited to the species, age, and general condition of the human or animal to which the composition is administered, and the mode of administration of the composition. An effective amount of the composition of the invention can be readily determined using only routine experimentation. In vitro and in vivo models (for example poultry) can be employed to identify appropriate doses. Generally, 0.1, 1.0, 1.5, 2.0, 5, 10, or 100 mg/kg of an antigen will be administered to a large mammal, such as a baboon, chimpanzee, or human. If desired, co-stimulatory molecules or adjuvants can also be provided before, after, or together with the antigenic compositions. Preferably, the dosage of antigen is administered in the range of 1 ng to 0.5 mg/kg bodyweight, more preferably, 1 mg to 50 mg/kg of body weight.

The efficacy of an edible vaccine according to the invention is determined by demonstrating that the administration of the vaccine prevents or ameliorates the symptoms of the disease being treated or caused by the pathogen of interest, by at least 5% , preferably 10–20% and more preferably, 25–100%.

"Bird" is herein defined as any warm-blooded vertebrate member of the class Aves having forelimbs modified into wings, scaly legs, a beak, and bearing young in hard-shelled eggs. For purposes of this specification, preferred groups of birds are domesticated chickens, turkeys, ostriches, ducks, geese, and comish game hens. A more preferred group is domesticated chickens and turkeys. The most preferred bird for purposes of this invention is the domesticated chicken, including broilers and layers.

The methods and compositions of the present invention are directed toward immunizing and protecting humans and animals, preferably domestic animals, such as birds (poultry), cows, sheep, goats, pigs, horses, cats, dogs and llamas, and most preferably birds. Certain of these animal species can have multiple stomachs and digestive enzymes specific for the decomposition of plant matter, and may otherwise readily inactivate other types of oral vaccines. While not meant to be a limitation of the invention, ingestion of transgenic plant cells, and compositions derived therefrom, can result in immunization of the animals at the site of the oral mucosa including the tonsils.

As used herein, "fruit" refers to the ovary of an angiosperm flower and the associated structures (e.g. the receptacle or parts of the floral tube) that enlarge and develop to form a mass of tissue surrounding the seeds. According to the invention, the particular tissues that are involved in fruit development vary with the species, but tissues involved in fruit development according to the invention, are always derived from the maternal parent of the progeny seeds.

As used herein, "ripe" refers to a stage of fruit development that is characterized by changes in pigmentation, the conversion of acids and starches to free sugars, and breakdown of cell walls that results in softening of the fruit.

As used herein, "fruit ripening conditions" refer to conditions under which the developmental processes involved in fruit ripening can occur, including cell division and expansion of maternal tissues that occurs after fertilization of ovaries. As used herein, for example, production of ethylene is a chemical signal that stimulates the genetic program for ripening in climacteric fruits such as tomato.

As used herein, "prior to the onset of fruit ripening" refers to a stage in fruit development wherein less than 10% (for example, 9.9, 9, 8, 7, 6, 5, 4, 3, 2, 1, 0.5%) of the fruit has undergone a change in pigmentation. "Prior to the onset of fruit ripening" also refers to a stage in fruit development wherein less than 10% (for example, 9.9, 9, 8, 7, 6, 5, 4, 3, 2, 1, 0.5%) of the acids and starches of a fruit are converted to sugar. "Prior to the onset of fruit ripening" also refers to a stage in fruit development wherein less than 10% (for example, 9.9, 9, 8, 7, 6, 5, 4, 3, 2, 1, 0.5%) of the cell wall material of a fruit is degraded.

As used herein, "incubating" includes growing a plant either in the field or in a controlled or uncontrolled laboratory or indoor setting. In one embodiment of the invention, an antigen is produced in a plant by "incubating", as defined herein, the plant under conditions wherein said plant expresses the antigen prior to the onset of fruit ripening.

DETAILED DESCRIPTION OF THE INVENTION

The invention relates to sequences encoding an antigen of interest, for example a plant optimized sequence encoding HN antigen of Newcastle Disease Virus or HA antigen of Avian Influenza Virus. The invention also relates to vectors, plant cells, transgenic plants and vaccines comprising the plant optimized sequences of the invention. The invention further relates to methods of protecting against viral infection, for example infection by Newcastle Disease Virus of Avian Influenza Virus. The invention also relates to methods of antigen production in transgenic plants.

Immunoprotective Antigens Useful According to the Invention

The invention provides for plant cells and transgenic plants expressing a heterologous foreign gene. A heterologous foreign gene of the invention can be any gene of interest including but not limited to Norwalk virus capsid protein (NVCP) (Genbank Accession Number: M87661, GenBank #AF093797, Genome for Norwalk Virus, Genbank Accession Number AAB50466, for NV capsid protein), Avian Influenza hemagluttination antigen (AIV-HA) (Genbank Accession Number U67783 and AAC58999), Newcastle Disease Virus neuraminidase (NDV-HN) (Genbank Accession Numbers NM-204389, NP-989720, NP-009086, and NM-007155) (Genbank Accession Number: AY510092 and AAS10195), zona pellucida glycoprotein 3(ZP3), Hepatitis B surface Antigen (HBsAg) (Genbank Accession Numbers AF134148, AAD31865, X58569, GenBank #AF090842), shigatoxin B (StxB) (Genbank #AJ132761), staphylococcus enterotoxin B (SEB)(GenBank #M11118), E. coli labile toxin B (LT-B) (GenBank#AB011677), and E. coli labile toxin A subunit (LT-A) (GenBank #AB011677).

Newcastle's disease virus (NDV) is a member of the *Paramyxovirus* genus of the *Paramyxoviridae*. Viruses in this genus are enveloped negative-strand RNA viruses that also include parainfluenza viruses like Sendai, respiratory syncytial, mumps and measles viruses (Kingsbury et al., 1978, Intervirology, 10:137–152). Virions are characterized by the presence of two surface glycoproteins including hemagglutinin neuraminidase (HN) a 74 kDA protein and a smaller fusion (F) protein. HN is involved in two important functions including cell attachment by recognition of sialic acid containing cell receptors, and neuraminidase activity cleaving sialic acid from progeny virus particles to prevent self-agglutination. The F protein mediates virus-to-cell and cell-to-cell fusion and hemolysis. See Scheid, A., and Choppin, P. W. (1973) J. Virology. 11, 263–271; Scheid, A, and Choppin, P. W. (1974) Virology 57, 470–490; Lamb, R. A., and Kolakofsky, D. (1996). Paramyxoviridae: the viruses and their replication, p. 577–604. In B. N. Fields, D. M. Knipe, and P. M. Howley (ed.), Fields virology, $3^{rd}$ ed. Lippincott-Raven Publishers, Philadelphia, Pa. Polyvalent sera prepared against either protein are capable of neutralizing the infectivity of the virus. See Mertz, D. C., Scheid, A., and Choppin, P. W. (1980) J. Exp. Med. 151, 275–288.

Avian influenza virus is described in Suarez et al., Virus Res. 1997, 51:115 and Sockett, Can. Med. Assoc. J., 1998, 158:369, incorporated herein by reference in their entirety. The hemagglutinin gene of avian influenza virus is described in Barun et al., 1998, Nuc. Acids. Res., 16:4181, incorporated herein by reference in its entirety.

Preparation of the Constructs of the Invention

An expression cassette according to the invention comprises a DNA sequence encoding at least one immunoprotective antigen operably linked to transcriptional and translational control regions functional in a plant cell. Preferably the invention provides plant expression cassettes that are useful for expressing immunoprotective antigen transgenes in plants. These cassettes comprise the following elements that are operably linked from 5' to 3':

A) a plant gene promoter sequence that naturally expresses in plants;

B) a nucleic acid sequence encoding an immunoprotective antigen of interest; and C) a 3'UTR.

Promoters useful in this embodiment are any known promoters that are functional in a plant. Many such promoters are well known to the ordinarily skilled artisan. Such promoters include promoters normally associated with other genes, and/or promoters isolated from any bacterial, viral, eukaryotic, or plant cell. It may be advantageous to employ a promoter that effectively directs the expression of the foreign coding sequence in the cell or tissue type chosen for expression. The use of promoter and cell type combinations for protein expression is generally known to those of skill in the art of molecular biology, for example, see Sambrook et al., In: Molecular Cloning: A Laboratory Manual, Cold Spring Harbor Laboratory, Cold Spring Harbor, N.Y., 1989. The promoters employed may be constitutive, or inducible, and can be used under the appropriate conditions to direct high level expression of the introduced DNA segment, such as is advantageous in the large-scale production of recombinant proteins or peptides. The term "constitutive" used in the context of a promoter means that the promoter is capable of directing transcription of an operably linked nucleic acid sequence in the absence of a stimulus (e.g., heat shock, chemicals, etc.). In contrast, an "inducible" promoter is one which is capable of directing a level of transcription of an operably linked nucleic acid sequence in the presence of a stimulus (e.g., heat shock, chemicals, etc.), wherein the level of the transcription is different from that in the absence of the stimulus. As used herein, "inducible" also refers to expressed in the presence of an exogenous or endogenous chemical (for example an alcohol, a hormone, or a growth factor), in the presence of light and/or in response to developmental changes. As used herein, "inducible" also refers to expressed in any tissue in the presence of a chemical inducer". As used herein, "chemical induction" according to the invention refers to the physical application of a exogenous or endogenous substance (including macromolecules e.g. proteins, or nucleic acids) to a plant or a plant organ (e.g. by spraying a liquid solution comprising a chemical inducer on leaves, application of a liquid solution to roots or exposing plants or plant organs to gas or vapor) which has the effect of causing the target promoter present in the cells of the plant or plant organ to increase the rate of transcription.

Some exemplary plant functional promoters, which can be used to express a structural gene of the present invention, are among the following: CaMV 35S and 19S promoters (U.S. Pat. Nos. 5,352,605 and 5,530,196); patatin promoter (U.S. Pat. No. 5,436,393); a B33 promoter sequence of a patatin gene derived from Solanum tuberosum, and which leads to a tuber specific expression of sequences fused to the B33 promoter (U.S. Pat. No. 5,436,393); tomato E8 promoter (WO 94/24298); tomato fruit promoters (U.S. Pat. No. 5,556,653); -a plant ubiquitin promoter system (U.S. Pat. No. 5,614,399 and 5,510,474); 5' cis-regulatory elements of abscisic acid-responsive gene expression (U.S. Pat. No. 5,824,865); promoter from a badnavirus, rice tungro bacilliform virus (RTBV) (U.S. Pat. No. 5,824,857); a chemically inducible promoter fragment from the 5' flanking region adjacent the coding region of a tobacco PR-1a gene (U.S. Pat. No. 5,789,214); a raspberry drul promoter (U.S. Pat. No. 5,783,394); strawberry promoters and genes (WO 98/31812); promoter is the napin promoter, the phaseolin promoter, and the DC3 promoter (U.S. Pat. No. 5,773,697); a LEA promoter (U.S. Pat. No. 5,723,765); 5' transcriptional regulatory region for sink organ specific expression (U.S. Pat. No. 5,723,757); G-box related sequence motifs, specifically Iwt and PA motifs, which function as cis-elements of promoters, to regulate the expression of heterologous genes in transgenic plants (U.S. Pat. No. 5,723,751); P119 promoters and their use (U.S. Pat. No. 5,633,440); Group 2 (Gp2) plant promoter sequences (U.S. Pat. No. 5,608,144); nucleic acid promoter fragments derived from several genes from corn, petunia and tobacco (U.S. Pat. No. 5,608,143); promoter sequences isolated from the nuclear gene for chloroplast GS2 glutamine synthetase and from two nuclear genes for cytosolic GS3 glutamine synthetase in the pea plant, Pisum sativum (U.S. Pat. No. 5,391,725); full-length transcript promoter from figwort mosaic virus (FMV) (U.S. Pat. No. 5,378,619); an isocitrate lyase promoter (U.S. Pat. No. 5,689,040); a microspore-specific regulatory element (U.S. Pat. No. 5,633,438); expression of heterologous genes in transgenic plants and plant cells using plant asparagine synthetase promoters (U.S. Pat. No. 5,595,896); a promoter region that drives expression of a 1450 base TR transcript in octopine-type crown gall tumors (U.S. Pat. No. 4,771,002); promoter sequences from the gene from the small subunit of ribulose-1,5-bisphosphate carboxylase (U.S. Pat. No. 4,962,028); the Arabidopsis histone H4 promoter (U.S. Pat. No. 5,491,288); a seed-specific plant promoter (U.S. Pat. No. 5,767,363); a 21 bp promoter element which is capable of imparting root expression capability to a rbcS-3A promoter, normally a green tissue specific promoter (U.S. Pat. No. 5,023,179); promoters of tissue-preferential transcription of associated DNA sequences in plants, particularly in the roots (U.S. Pat. No. 5,792,925); Brassica sp. polygalacturonase promoter (U.S. Pat. No. 5,689,053); a seed coat-specific cryptic promoter region (U.S. Pat. No. 5,824,863); a chemically inducible nucleic acid promoter fragment isolated from the tobacco PR-1a gene inducible by application of a benzo-1,2,3-thiadiazole, an isonicotinic acid compound, or a salicylic acid compound (U.S. Pat. No. 5,689,044); promoter fragment isolated from a cucumber chitinase/lysozyme gene that is inducible by application of benzo-1,2,3-thiadiazole (U.S. Pat. No. 5,654,414); a constitutive promoter from tobacco that directs expression in at least ovary, flower, immature embryo, mature embryo, seed, stem, leaf and root tissues (U.S. Pat. No. 5,824,872); alteration of gene expression in plants (U.S. Pat. No. 5,223,419); a recombinant promoter for gene expression in monocotyledenous plants (U.S. Pat. No. 5,290,924); method for using TMV to overproduce peptides and proteins (WO 95/21248); nucleic acid comprising shoot meristem-specific promoter and regulated sequence (WO 98/05199); phaseolin promoter and structural gene (EP-B-0122791); plant promoters [sub domain of CaMV 35S] (U.S. Pat. No. 5,097,025); use of tomato E8-derived promoters to express heterologous genes, e.g. 5-adenosylmethionine hydrolase in ripening fruit (WO 94/24294); method of using transactivation proteins to control gene expression in transgenic plants (U.S. Pat. No. 5,801,027); DNA molecules encoding inducible plant promoters and tomato Adh2 enzyme (U.S. Pat. No. 5,821,398); synthetic plant core promoter and upstream regulatory element (WO 97/47756); monocot having dicot wound inducible promoter (U.S. Pat. No. 5,684,239); selective gene expression in plants (U.S. Pat. No. 5,110,732); CaMV 35S enhanced mannopine synthase promoter and method for using the same (U.S. Pat. No. 5,106,739); seed specific transcription regulation (U.S. Pat. No. 5,420,034); seed specific promoter region (U.S. Pat. No. 5,623,067); DNA promoter fragments from wheat (U.S. Pat. No. 5,139,954); chimeric regulatory regions and gene cassettes for use in plants (WO 95/14098); production of gene products to high levels (WO 90/13658); HMG promoter expression system and post harvest production of gene products in plants and plant cell cultures (U.S. Pat. No. 5,670,349); gene expression system comprising the promoter region of the alpha amylase genes in plants (U.S. Pat. No. 5,712,112).

A preferred group of promoters is the cassava vein mosaic virus promoters described in U.S. patent application Ser. No. 09/202,838, herein incorporated by reference in its entirety; the phaseolin promoters described in U.S. Pat. No. 5,591,605, herein incorporated by reference in its entirety; rice actin promoters described in U.S. Pat. No. 5,641,876, herein incorporated by reference in its entirety; the per5 promoter described in WO 98/56921, herein incorporated by reference in its entirety; and the gamma zein promoters described in WO 00/12681.

A promoter DNA sequence is said to be "operably linked" to a coding DNA sequence if the two are situated such that the promoter DNA sequence influences the transcription of the coding DNA sequence. For example, if the coding DNA sequence codes for the production of a protein, the promoter DNA sequence would be operably linked to the coding DNA sequence if the promoter DNA sequence affects the expression of the protein product from the coding DNA sequence.

Construction of gene cassettes is readily accomplished utilizing well known methods, such as those disclosed in Sambrook et al. (1989); and Ausubel et al. (1987) *Current Protocols in Molecular Biology*, John Wiley and Sons, New York, N.Y. The present invention also includes DNA sequences having substantial sequence homology with the disclosed sequences encoding immunoprotective antigens such that they are able to have the disclosed effect on expression. As used in the present application, the term "substantial sequence homology" is used to indicate that a nucleotide sequence (in the case of DNA or RNA) or an amino acid sequence (in the case of a protein or polypeptide) exhibits substantial, functional or structural equivalence with another nucleotide or amino acid sequence. Any functional or structural differences between sequences having substantial sequence homology will be de minimis; that is they will not affect the ability of the sequence to function as indicated in the present application. Sequences that have substantial sequence homology with the sequences disclosed herein are usually variants of the disclosed sequence, such as mutations, but may also be synthetic sequences.

In most cases, sequences having 95% homology to the sequences specifically disclosed herein will function as equivalents, and in many cases considerably less homology, for example 75% or 80%, will be acceptable. Locating the parts of these sequences that are not critical may be time consuming, but is routine and well within the skill in the art. Exemplary techniques for modifying oligonucleotide sequences include using polynucleotide-mediated, site-directed mutagenesis. See Zoller et al. (1984); Higuchi et al. (1988); Ho et al. (1989); Horton et al. (1989); and *PCR Technology: Principles and Applications for DNA Amplification*, (ed.) Erlich (1989).

The invention provides for a plant optimized sequence encoding an immunoprotective antigen of interest. A plant-optimized coding sequence is designed with hybrid codon preference reflecting tomato and potato codon usage (Ausubel F., et al., eds. (1994) *Current Protocols in Molecular Biology, vol.* 3, p. A.1C.3 Haq T A, Mason H S, Clements J D, Arntzen C J (1995).

A plant optimized sequence of the invention can be prepared as described in U.S. Pat. No. 5,380,831, incorporated by reference herein in its entirety. In general, the frequency of codon usage for a target plant of interest is used to adjust the codon usage frequency of a target gene of interest, for example, NDV HN.

The native sequence is scanned for sequence motifs that might result in interference with expression in the target plant, such as poly-A addition sites, Shaw/Kamen degradation sites, splice junction sites, and anything related to RNA termination or potential hairpin formation, etc. Runs of A/T sequences are often avoided. In one embodiment, it is preferable to keep strings of A/T to four or fewer in a row, if possible, since most regulatory sites tend to contain runs of A's and T's (e.g. AATAAA consensus poly-A or ATTTA Shaw/Kamen). In general it is useful to scan for about 16 putative poly-A addition sequences based on identified sites from plants found in the literature. In certain embodiments, it is useful to search for C/G runs since they can stabilize hairpin stem formation. Since monocots tend to favor third position C's and G's somewhat more than dicots, the relevance of identification of C/G runs may depend on the host plant target for expression.

In one embodiment wherein a gene is expressed in both dicots and monocots, an overall plant codon usage frequency is used as a basis for sequence optimization.

For the purposes of the present invention the term membrane anchor sequence contemplates that which the ordinarily skilled artisan understands about the term. Membrane anchor sequences include transmembrane protein sequences and are found in many naturally occurring proteins. Such membrane anchor sequences vary in size but always are comprised of a series of amino acids with lipophilic or aliphatic side chains that favor the hydrophobic environment within the membrane. During RNA translation and post translational processing, the anchor sequences integrate and become embedded in the cell membrane and function to anchor, or loosely attach the protein to a cellular membrane component allowing hydrophilic portions of the protein to be exposed to, and interact with, the aqueous milieu inside or outside of the cell.

In preparing the constructs of this invention, the various DNA fragments may be manipulated, so as to provide for the DNA sequences in the proper orientation and, as appropriate, in the proper reading frame. Adapters or linkers may be employed for joining the DNA fragments or other manipulations may be involved to provide for convenient restriction sites, removal of superfluous DNA, removal of restriction sites, or the like.

In carrying out the various steps, cloning is employed, so as to amplify a vector containing the promoter/gene of interest for subsequent introduction into the desired host cells. A wide variety of cloning vectors are available, where the cloning vector includes a replication system functional in *E. coli* and a marker which allows for selection of the transformed cells. Illustrative vectors include pBR322, pUC series, pACYC184, Bluescript series (Stratagene) etc. Thus, the sequence may be inserted into the vector at an appropriate restriction site(s), the resulting plasmid used to transform the *E. coli* host (e.g., *E. coli* strains HB101, JM101 and DH5α), the *E. coli* grown in an appropriate nutrient medium and the cells harvested and lysed and the plasmid recovered. Analysis may involve sequence analysis, restriction analysis, electrophoresis, or the like. After each manipulation the DNA sequence to be used in the final construct may be restricted and joined to the next sequence, where each of the partial constructs may be cloned in the same or different plasmids.

Vectors are available or can be readily prepared for transformation of plant cells. In general, plasmid or viral vectors should contain all the DNA control sequences necessary for both maintenance and expression of a heterologous DNA sequence in a given host. Such control sequences generally include a leader sequence and a DNA sequence coding for translation start-signal codon, a translation terminator codon, and a DNA sequence coding for a 3' UTR signal controlling messenger RNA processing. Selection of appropriate elements to optimize expression in any particular species is a matter of ordinary skill in the art utilizing the teachings of this disclosure. Finally, the vectors should desirably have a marker gene that is capable of providing a phenotypical property which allows for identification of host cells containing the vector.

The activity of the foreign coding sequence inserted into plant cells is dependent upon the influence of endogenous plant DNA adjacent to the insert. Generally, the insertion of heterologous genes appears to be random using any transformation technique; however, technology currently exists for producing plants with site specific recombination of DNA into plant cells (see WO 91/09957). Any method or combination of methods resulting in the expression of the desired sequence or sequences under the control of the promoter is acceptable.

The present invention is not limited to any particular method for transforming plant cells. Technology for introducing DNA into plant cells is well-known to those of skill in the art. Four basic methods for delivering foreign DNA into plant cells have been described. Chemical methods (Graham and van der Eb, *Virology,* 54(02):536–539, 1973; Zatloukal, Wagner, Cotten, Phillips, Plank, Steinlein, Curiel, Bimstiel, *Ann. N.Y. Acad. Sci.,* 660:136–153, 1992); Physical methods including microinjection (Capecchi, *Cell,* 22(2):479–488, 1980), electroporation (Wong and Neumann, *Biochim. Biophys. Res. Commun.* 107(2):584–587, 1982; Fromm, Taylor, Walbot, *Proc. Natl. Acad. Sci.* USA, 82(17):5824–5828,1985; U.S. Pat. No. 5,384,253) and the gene gun (Johnston and Tang, *Methods Cell. Biol.,* 43(A): 353–365, 1994; Fynan, Webster, Fuller, Haynes, Santoro, Robinson, *Proc. Natl. Acad. Sci.* USA 90(24):11478–11482, 1993); Viral methods (Clapp, *Clin. Perinatol.,* 20(1):155–168, 1993; Lu, Xiao, Clapp, Li, Broxmeyer, *J. Exp. Med.* 178(6):2089–2096, 1993; Eglitis and Anderson, *Biotechniques,* 6(7):608–614, 1988; Eglitis, Kantoff, Kohn, Karson, Moen, Lothrop, Blaese, Anderson, *Avd. Exp. Med. Biol.,* 241:19–27, 1988); and Receptor-mediated methods (Curiel, Agarwal, Wagner, Cotten, *Proc. Natl. Acad. Sci.* USA, 88(19):8850–8854, 1991; Curiel, Wagner, Cotten, Birnstiel, Agarwal, Li, Loechel, Hu, *Hum. Gen. Ther.,* 3(2): 147–154, 1992; Wagner et al., *Proc. Natl. Acad. Sci.* USA, 89 (13):6099–6103, 1992).

The introduction of DNA into plant cells by means of electroporation is well-known to those of skill in the art. Plant cell wall-degrading enzymes, such as pectin-degrading enzymes, are used to render the recipient cells more susceptible to transformation by electroporation than untreated cells. To effect transformation by electroporation one may employ either friable tissues such as a suspension culture of cells, or embryogenic callus, or immature embryos or other organized tissues directly. It is generally necessary to partially degrade the cell walls of the target plant material to pectin-degrading enzymes or mechanically wounding in a controlled manner. Such treated plant material is ready to receive foreign DNA by electroporation.

Another method for delivering foreign transforming DNA to plant cells is by microprojectile bombardment. In this method, microparticles are coated with foreign DNA and delivered into cells by a propelling force. Such micro particles are typically made of tungsten, gold, platinum, and similar metals. An advantage of microprojectile bombardment is that neither the isolation of protoplasts (Cristou et al., 1988, *Plant Physiol.,* 87:671–674,) nor the susceptibility to *Agrobacterium* infection is required. An illustrative embodiment of a method for delivering DNA into maize cells by acceleration is a Biolistics Particle Delivery System, which can be used to propel particles coated with DNA or cells through a screen onto a filter surface covered with corn cells cultured in suspension. The screen disperses the particles so that they are not delivered to the recipient cells in large aggregates. For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of the microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids.

*Agrobacterium*-mediated transfer is a widely applicable system for introducing foreign DNA into plant cells because the DNA can be introduced into whole plant tissues, eliminating the need to regenerate an intact plant from a protoplast. The use of *Agrobacterium*-mediated plant integrating vectors to introduce DNA into plant cells is well known in the art. See, for example, the methods described in Fraley et al., 1985, *Biotechnology,* 3:629; Rogers et al., 1987, *Meth. in Enzymol.,* 153:253–277. Further, the integration of the Ti-DNA is a relatively precise process resulting in few rearrangements. The region of DNA to be transferred is defined by the border sequences, and intervening DNA is usually inserted into the plant genome as described in Spielmann et al., 1986, *Mol. Gen. Genet.,* 205:34; Jorgensen et al., 1987, *Mol. Gen. Genet.,* 207:471.

Modern *Agrobacterium* transformation vectors are capable of replication in *E. coli* as well as *Agrobacterium,* allowing for convenient manipulations. Moreover, recent technological advances in vectors for *Agrobacterium*-mediated gene transfer have improved the arrangement of genes and restriction sites in the vectors to facilitate construction of vectors capable of expressing various proteins or polypeptides. Convenient multi-linker regions flanked by a promoter and a polyadenylation site for direct expression of inserted polypeptide coding genes are suitable for present purposes. In addition, *Agrobacterium* containing both armed and disarmed Ti genes can be used for the transformations.

Transformation of plant protoplasts can be achieved using methods based on calcium phosphate precipitation, polyethylene glycol treatment, electroporation, and combinations of these treatments (see, e.g., Potrykus et al., 1985, *Mol. Gen. Genet.,* 199:183; Marcotte et al., *Nature,* 335:454, 1988). Application of these systems to different plant species depends on the ability to regenerate the particular species from protoplasts.

Once the plant cells have been transformed, selected and checked for antigen expression, it is possible in some cases to regenerate whole fertile plants. This will greatly depend on the plant species chosen. Methods for regenerating numerous plant species have been reported in the literature and are well known to the skilled artisan. For practice of the present invention, it is preferable to transform plant cell lines that can be cultured and scaled-up rapidly by avoiding the generally lengthy regeneration step. In addition the use of plant cell cultures avoids open field production and greatly reduces the chances of gene escape and food contamination. Tobacco suspension cell cultures such as NT-1 and BY-2 (An, G., 1985 *Plant Physiol.* 79, 568–570) are preferred because these lines are particularly susceptible to handling in culture, are readily transformed, produce stably integrated events and are amenable to cryopreservation.

The tobacco suspension cell line, NT-1, is suitable for the practice of the present invention. NT-1 cells were originally developed from *Nicotiana tabacum* L.cv. bright yellow 2. The NT-1 cell line is widely used and readily available; though, any tobacco suspension cell line is consistent with the practice of the invention. It is worth noting that the origins of the NT-1 cell line are unclear. Moreover, the cell line appears variable and is prone to change in response to culture conditions. NT-1 cells suitable for use in the examples below are available from the American Type Culture Collection under accession number ATCC No. 74840. See also U.S. Pat. No. 6,140,075, herein incorporated by reference.

Many plant cell culture techniques and systems ranging from laboratory-scale shaker flasks to multi-thousand liter bioreactor vessels have been described and are well know in the art of plant cell culture. See for example Fischer, R. et al, 1999 *Biotechnol. Appl. Biochem.* 30, 109–112 and Doran, P., 2000 *Current Opinions in Biotechnology* 11, 199–204. After the transformed plant cells have been cultured to the mass desired, they are harvested, gently washed and placed in a suitable buffer for sonication. Many different buffers are compatible with the present invention. In general the buffer is an aqueous isotonic buffered salt solution at or near a neutral pH value that does not contain any detergent. Preferred buffers include Dulbeccos Phosphate Buffered Saline and PBS containing 1 mM EDTA.

For sonication, the washed cells are placed in buffer in a range of about 0.01 gm/ml to about 5.0 gm/ml, preferably in a range of about 0.1 gm/ml to about 0.5 gm/ml (washed wet weight cells per volume of buffer). Many commercially available sonication instruments are consistent with the invention and sonication times range from about 5 to about 20 seconds, preferably about 15 to about 20 seconds. The resulting particles are membrane vesicles that may range in size from a few microns to several hundred microns and expose the recombinant, immunoprotective, anchored proteins.

An immunoprotective agent or antigen of interest is expressed and isolated according to methods well known in the art and described in the examples herein below.

In one embodiment, a method of producing an antigen of interest comprises preparing a transgenic plant comprising a vector encoding the antigen. The plant is incubated under conditions wherein the plant expresses the antigen prior to the onset of ripening of the plant. According to this embodiment, the plant has a fruit that ripens (including but not limited to tomato, banana, citrus, melon, strawberry, pineapple, stonefruit, mango, pumpkin, squash etc.) The antigen produced according to this method can be isolated from the plant, or from the fruit of the plant prior to administration. Alternatively, the antigen is not isolated from the plant but is administed in a crude, food-processed or raw form.The details of this method are described in the Examples below.

Plants Useful According to the Invention

The present invention also provides for a transgenic plant transformed with the constructs of the invention. Plants that can be used for practice of the present invention include any dicotyledon and monocotyledon. These include, but are not limited to, tobacco, tomato, potato, eggplant, pepino, yam, soybean, pea, sugar beet, lettuce, bell pepper, celery, carrot, asparagus, onion, grapevine, muskmelon, strawberry, rice, sunflower, rapeseed/canola, wheat, oats, maize, cotton, walnut, spruce/conifer, poplar and apple, berries such as strawberries, raspberries, alfalfa and banana. Since many edible plants used by humans for food or as components of animal feed are dicotyledenous plants, dicotyledons are typically employed, although monocotyledon transformation is also applicable especially in the production of certain grains useful for animal feed. It is particularly advantageous in certain disease prevention for human infants to produce a vaccine in a juice for ease of administration to humans such as juice of tomato, soybean, and carrot, or milk. Cells and seeds derived from these plant vaccines are also useful according to the invention.

Representative plants that have been transformed with this system and representative references are listed in Table A. Other plants having edible parts, or which can be processed to afford isolated protein, can be transformed by the same methods or routine modifications thereof.

TABLE A

| Plant | Reference |
|---|---|
| Tobacco | Barton, K. et al., (1983) Cell 32, 1033 |
| Tomato | Fillatti, J. et al., (1987) Bio/Technology 5, 726–730 |
| Potato | Hoekema, A. et al., (1989) Bio/Technology 7: 273–278 |
| Eggplant | Filipponee, E. et al., (1989) Plant Cell Rep. 8: 370–373 |
| Pepino | Atkinson, R. et al., (1991) Plant Cell Rep. 10: 208–212 |
| Yam | Shafer, W. et al., (1987) Nature. 327: 529–532 |
| Soybean | Delzer, B., et al., (1990) Crop Sci. 30: 320–322 |
| Pea | Hobbs, S. et al., (1989) Plant Cell Rep. 8: 274–277 |
| Sugar beet | Kallerhoff, J. et al., (1990) Plant Cell Rep. 9: 224–228 |
| Lettuce | Michelmore, R., et al., (1987) Plant Cell Rep. 6: 439–442 |
| Bell pepper | Liu, W. et al., (1990) Plant Cell Rep. 9: 360–364 |
| Celery | Liu, C-N. et al., (1992) Plant Mol. Biol. 1071–1087 |
| Carrot | Liu, C-N. et al, (1992) Plant Mol Biol. 1071–1087 |
| Asparagus | Delbriel, B. et al., (1993) Plant Cell Rep. 12: 129–132 |
| Onion | Dommisse, E. et al.; (1990) Plant Sci. 69: 249–257 |
| Grapevine | Baribault, T., et al., (1989) Plant Cell Rep. 8: 137–140 |
| Muskmelon | Fang, G., et al., (1990) Plant Cell Rep. 9: 160–164 |
| Strawberry | Nehra, N. et al., (1990) Plant Cell Rep. 9: 10–13 |
| Rice | Raineri, D. et al., (1990) Bio/Technology. 8: 33–38 |
| Sunflower | Schrammeijer, B. et al., (1990) Plant Cell Rep. 9: 55–60 |
| Rapeseed/ Canola | Pua, E. et al., (1987) Bio/Technology 5. 815 |
| Wheat | Mooney, P. et al., (1991) Plant Cell Tiss. Organ Cult. 25: 209–218 |
| Oats | Donson, J. et al., (1988) Virology. 162: 248–250 |
| Maize | Gould, J. et al., (1991) Plant Physiol. 95: 426–434 |
| Alfalfa | Chabaud, M. et al., (1988) Plant Cell Rep. 7: 512–516 |
| Cotton | Umbeck, P. et al., (1987) Bio/Technology. 5: 263–266 |
| Walnut | McGranahan, G. et al., (1990) Plant Cell Rep. 8: 512–516 |
| Spruce/ Conifer | Ellis, D. et al., (1989) Plant Cell Rep. 8: 16–20 |
| Poplar | Python, F. et al., (1987) Bio/Technology 5: 1323 |
| Apple | James, P. et al., (1989) Plant Cell Rep. 7: 658–661 |

A transgenic plant transformed with a vector described hereinabove is another aspect of the present invention.

Potato varieties FL 1607 ("Frito Lay 1607") and Desiree, and tomato variety Tanksley TA234TM2R are particularly preferred varieties, which have been transformed with binary vectors using the methods described herein. Of these transformed varieties, Desiree is the only commercial variety; the other varieties can be obtained from Frito-Lay (Rhinelander, Wis.) and Steve Tanksley (Dept. of Plant Breeding, Cornell Univ.). Potato variety FL1607 allows rapid transformation but is not a good agronomic variety as it suffers from hollow heart.

Tomato is preferred as a model system for expression of foreign proteins because of its ease of genetic transformation, and because fruit-specific, ripening dependent promoters are available for regulated expression (Giovannoni et al., 1989).

The invention includes whole plants, plant cells, plant organs, plant tissues, plant seeds, protoplasts, callus, cell cultures, and any group of plant cells organized into structural and/or functional units capable of expressing at least a polynucleotide of the invention. Preferably, whole plants, plant cells, plant organs, plant tissues, plant seeds, protoplasts, callus, cell cultures, and any group of plant cells produce 0.001, 0.01, 1, 5, 10, 25, 50, 100, 500, or 1000 μg of polypeptide of the invention per gram of total soluble plant material.

Use, Dosage and Administration of a Vaccine According to the Invention

Food plant produced antigens provide a less expensive source of antigen, that does not require animal-sourced components, for the preparation of vaccines.

The vaccines according to the invention are useful for protection against a pathogen of interest and against viral infection.

1. Administration

The invention provides for methods of administering a vaccine according to the invention to a mammal to prevent viral infection.

In one embodiment, a vaccine is administered orally (either by feeding or by oral gavage) to ensure inducing a mucosal immune response as well as to take advantage of cost and convenience. Conveniently, an oral administration step entails consuming a transgenic plant or plant part according to the invention. An edible vaccine according to the invention can be in the form of a plant part, an extract, a juice, a liquid, a powder or a tablet.

An vaccine according to the invention may also be administered by via an intranasal route in the form of a nasal spray. Alternatively, a vaccine according to the invention may be administered orally, intraperitoneally, intramuscularly, intravenously, or subcutaneously.

The invention provides for compositions comprising an edible vaccine admixed with a physiologically compatible carrier. As used herein, “physiologically compatible carrier” refers to a physiologically acceptable diluent such as water, phosphate buffered saline, or saline, and further may include an adjuvant. Adjuvants such as incomplete Freund’s adjuvant, aluminum phosphate, aluminum hydroxide, or alum are materials well known in the art.

The invention also provides for pharmaceutical compositions. In addition to the active ingredients, these pharmaceutical compositions may contain suitable pharmaceutically acceptable carrier preparations which can be used pharmaceutically.

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethyl-cellulose, or sodium carboxymethyl cellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hank’s solution, Ringer’s solution, or physiologically buffered saline. Aqueous injection suspensions may contain substances which increase the viscosity of the suspension, such as sodium carboxymethyl cellulose, sorbitol, or dextran. Additionally, suspensions of the active solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For nasal administration, penetrants appropriate to the particular barrier to be permeated are used in the formulation. Such penetrants are generally known in the art.

2. Manufacture and Storage

The pharmaceutical compositions of the present invention may be manufactured in a manner known in the art, e.g. by means of conventional mixing, dissolving, granulating, dragee-making, levitating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc . . . . Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in an acceptable carrier have been prepared, they can be placed in an appropriate container and labeled for treatment of an indicated condition with information including amount, frequency and method of administration.

3. Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, or in animal models, usually birds, mice, rabbits, dogs, or pigs. The animal model is also used to achieve a desirable concentration range and route of administration. Such information can then be use to determine useful doses and routes for administration in humans.

A therapeutically effective dose refers to that amount of protein or its antibodies, antagonists, or inhibitors which prevent or ameliorate the symptoms or conditions, for example caused by viral infection. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animals studies is used in formulating a range of dosage for human use. The dosage of such compounds lies preferably within a range of circulating concentrations that include the ED50 with little or no toxicity. The dosage varies within this range depending upon the dosage from employed, sensitivity of the patient, and the route of administration.

The exact dosage is chosen by the individual physician or veterinarian in view of the patient to be treated. Dosage and administration are adjusted to provide sufficient levels of the active moiety or to maintain the desired effect. Additional factors which may be taken into account include the severity of the disease state; age, weight and gender of the subject; diet, time and frequency of administration, drug combination(s), reaction sensitivities, and tolerance/response to therapy. Long acting pharmaceutical compositions might be administered every 3 to 4 days, every week, or once every two weeks depending on a half-life and clearance rate of the particular formulation.

In general, compositions contain from about 0.5% to about 50% of the compounds in total, depending on the desired doses and the type of composition to be used. The amount of the compounds, however, is best defined as the effective amount, that is, the amount of each compound which provides the desired dose to the subject in need of such treatment. The activity of the adjunctive combinations does not depend on the nature of the composition, so the composition is chosen and formulated solely for convenience and economy. Any of the combinations may be formulated in any desired form of composition.

Dosage amounts may vary from 0.1 to 100,000 micrograms of recombinant protein; transformed plant cell, or transformed transgenic plant per subject per day, for example, 1 ug, 10 ug, 100 ug, 500 ug, 1 mg, 10 mg, and even up to a total dose of about 1 g per subject per day, depending upon the route of administration. In one embodiment, the dosage is in the range of 1 ng to ) 0.5 mg per kilogram bodyweight. In another embodiment, the dosage is in the range of 1 μg to 50 μg per kilogram bodyweight. In another embodiment, the dosage is in the range of 1 to 25 μg per kilogram bodyweight. In another embodiment, the dosage is in the range of 2 to 25 μg per kg body weight. In another embodiment, the dosage is in the range of 2 to 15 μg per kg bodyweight. For example, in one embodiment HN antigen is administered subcutaneously in a range of 2.5 to 5 μg, and IN/ocularly in a range of 0.5 to 12 μg; HA antigen is administered subcutaneously at a dose of 1 to 5 mg, IN/ocuraly in a range of 24 to 26 μg; VP2 antigen is administered subcutaneously in a range of 8 to 17 μg, and LT antigen is administered orally in a range of 50 to 100 ng, subcutaneously in a range of 2–10 μg and IN/ocularly in a range of 2 to 10 μg; Guidance as to particular dosages and methods of delivery is provided in the literature. See U.S. Pat. Nos. 4,657,760; 5,206,344; or 5,225,212, hereby incorporated by reference. Those skilled in the art will employ different formulations for nucleotides than for proteins or their inhibitors. Similarly, delivery of polynucleotide or polypeptides will be specific to particular cells, conditions, locations, etc.

Testing the Efficacy of a Vaccine of the Invention

The efficacy of a vaccine according to the invention is determined by demonstrating that the administration of the vaccine prevents or ameliorates the symptoms of the viral infection being treated or prevented or the symptoms induced by the pathogen of interest, by at least 5%, preferably 10–20% and more preferably, 25–100%.

The efficacy of a vaccine according to the invention is determined by measuring antibody production in response to vaccination with a plant derived protein of interest, detection of the production of antibody in response to vaccination with a plant derived protein of interest, wherein the antibody inhibits hemagluttination, and assessing the mortality of a subject that has been inoculated and then challenged with a vaccine comprising an immunoprotective antigen of the invention (all as described hereinbelow).

Having now generally described the invention, the same will be more readily understood through reference to the following Examples which are provided by way of illustration, and are not intended to be limiting of the present invention, unless specified.

EXAMPLE 1

Vectors

Gene Construction: The coding sequence of the HN gene of NDV strain "Lasota" (GenBank accession AF077761) was analyzed for codon use and the presence of undesired sequence motifs that could mediate spurious mRNA processing and instability, or methylation of genomic DNA. See Adang M J, Brody M S, Cardineau G, Eagan N, Roush R T, Shewmaker C K, Jones A, Oakes J V, McBride K E (1993) The construction and expression of *Bacillus thuringiensis* cryIIIA gene in protoplasts and potato plants. *Plant Mol Biol* 21:1131–1145. A plant-optimized coding sequence was designed with hybrid codon preference reflecting tomato and potato codon usage (Ausubel F., et al., eds. (1994)*Current Protocols in Molecular Biology, vol.* 3, p. A.1C.3 Haq T A, Mason H S, Clements J D, Arntzen C J (1995) Oral immunization with a recombinant bacterial antigen produced in transgenic plants. *Science* 268:714–716). The designed sequence is shown in FIG. 1. The synthetic HN gene was assembled by a commercial supplier (Retrogen) and was received in two separate plasmids containing either the 5' (p4187-4203-1) or 3' (p42111-4235-1c-1) half of the gene cloned into pCR-Blunt.

Figure 3:
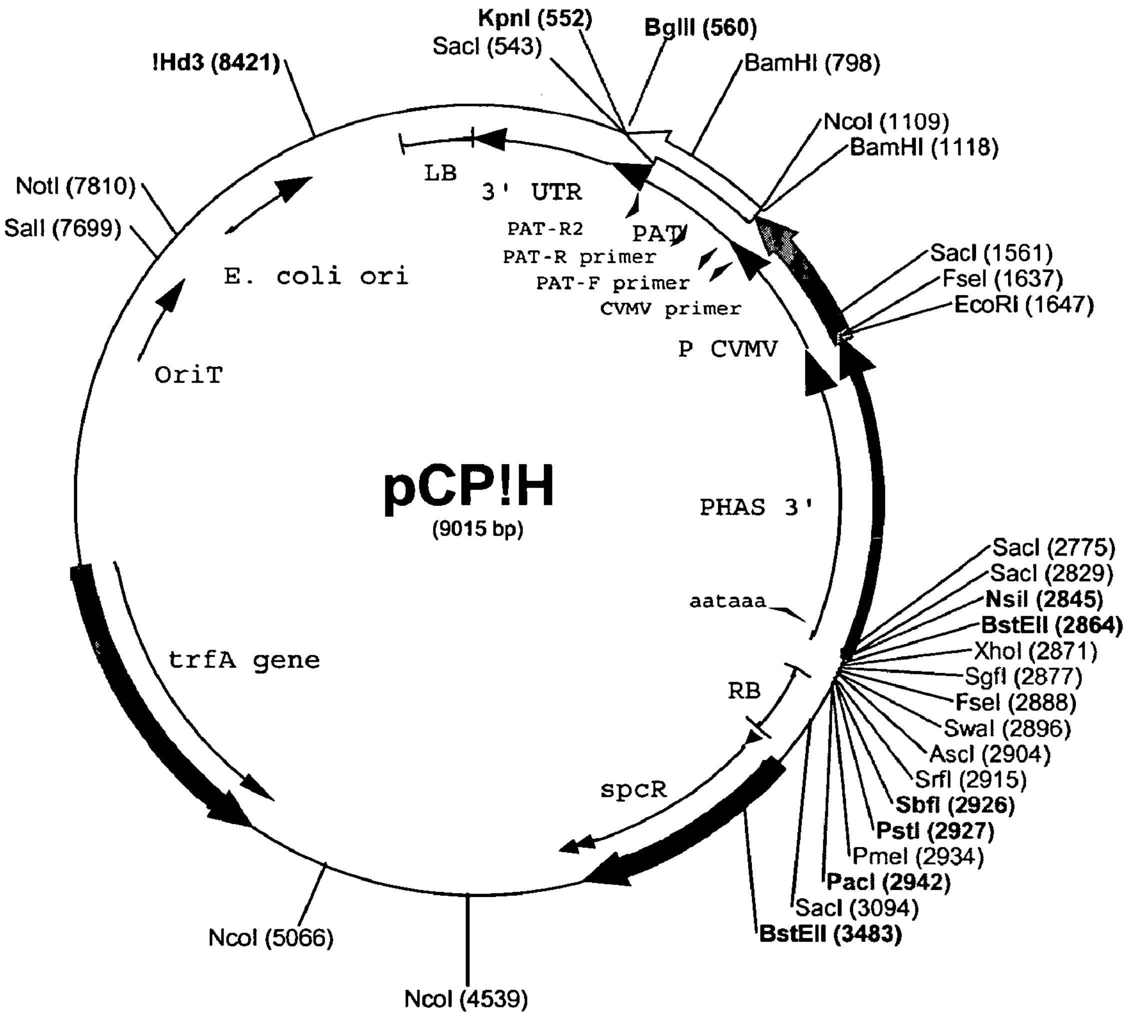
FIG. 3. Map of pCP!H which is a "template vector" used as a starting plasmid for a variety of plant expression vectors for expressing immunoprotective antigens.
Figure 4:
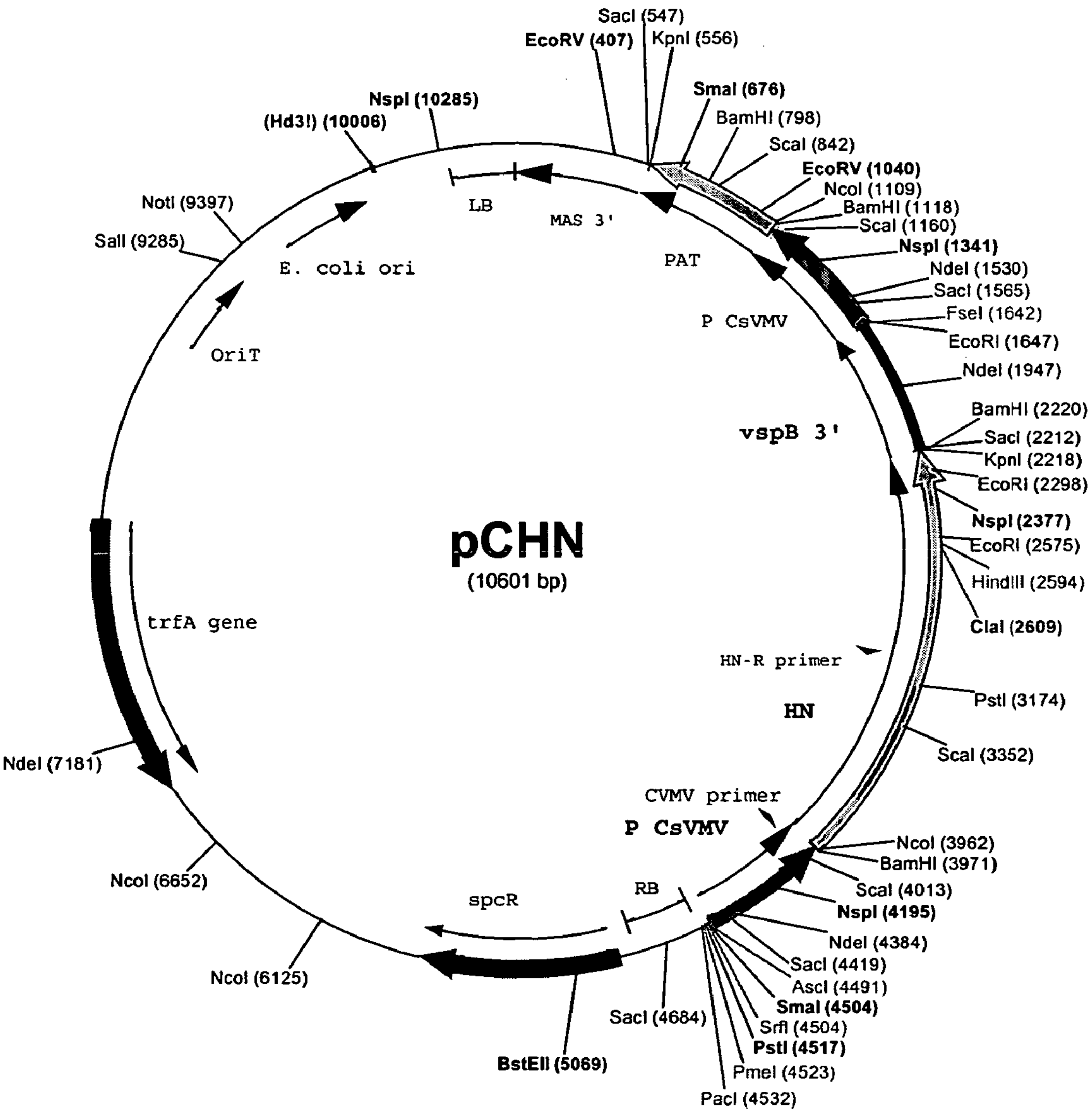
FIG. 4. Map of pCHN expression vector for NDV HN protein. This vector comprising the HN expression cassette includes the constitutive CsVMV promoter and is terminated by the soybean vspB 3' element.

Plasmid construction: Binary vectors for *Agrobacterium*-mediated plant transformations were constructed based on vector pBBV-PHAS-iaaH shown in FIG. 2, which uses the plant selection marker phosphinothricin acetyl transferase (PAT), described in U.S. Pat. Nos: 5,879,903; 5,637,489; 5,276,268; and 5,273,894 herein incorporated by reference, driven by the constitutive cassava vein mosaic virus promoter (CsVMV) described in WO 97/48819. The iaaH gene and the phaseolin promoter sequence were deleted by digestion of pBBV-PHAS-iaaH with PacI and religated to form pCVMV-PAT; then the single HindIII site was deleted by filling it with Klenow enzyme and religating to form pCP!H. The CsVMV promoter was end-tailored by PCR using primers CVM-Asc (5'-ATGGCGCGCCAGAAGGTAATTATCCAAG SEQ ID NO:5) and CVM-Xho (5'-ATCTCGAGCCATGGTTTGGATCCA SEQ ID NO:6) on template pCP!H, and the product was cloned in EcoRV-digested, T-tailed pBluescriptKS to make pKS-CVM7. A map of pCP!H is shown in FIG. 3. The HN expression cassette pKS-CHN was constructed by ligating the vector pKS-CVM7/NcoI-EcoRI with 3 insert fragments: the HN 5' half on NcoI/PstI, the HN 3' half on PstI/KpnI, and the soybean vspB 3' element on KpnI-EcoRI (Haq 1995). The binary T-DNA vector pCHN was then assembled by ligation of the vector pCP!H/AscI-EcoRI and the AscI-EcoRI fragment of pKS-CHN. A map of pCHN is shown in FIG. 4.

The granule bound starch synthase (GBSS) promoter, described in U.S. Pat. No. 5,824,798 herein incorporated by reference, was used to make other vectors. These constructs were made using a promoter fragment amplified from genomic DNA of *Solanum tuberosum* L. cv. "Desiree" using primers designed from the sequence in GenBank accession X83220 for the Chinese potato cultivar "Dongnong". A mutagenic primer "GSS-Nco" (5'-tgccatggtgatgtgtggtctacaa SEQ ID NO:7) was used to create a Nco I site overlapping the translation initiation codon, along with forward primer "GSS-1.8F" (5'-gatctgacaagtcaagaaaattg SEQ ID NO:8) complimentary to the 5' region at −1800 bp; the 1825 bp PCR product was cloned in T-tailed pBluescriptKS to make pKS-GBN, and sequenced. A mutagenic primer "GSS-Xho" (5'-agctcGAGCTGTGTGAGTGAGTG SEQ ID NO:9) was used to create a XhoI site just 3' of the transcription start site along with primer "GSS-1.8F"; the 1550 bp PCR product was cloned in T-tailed pBluescriptKS to make pKS-GBX, and sequenced.

Figure 5:
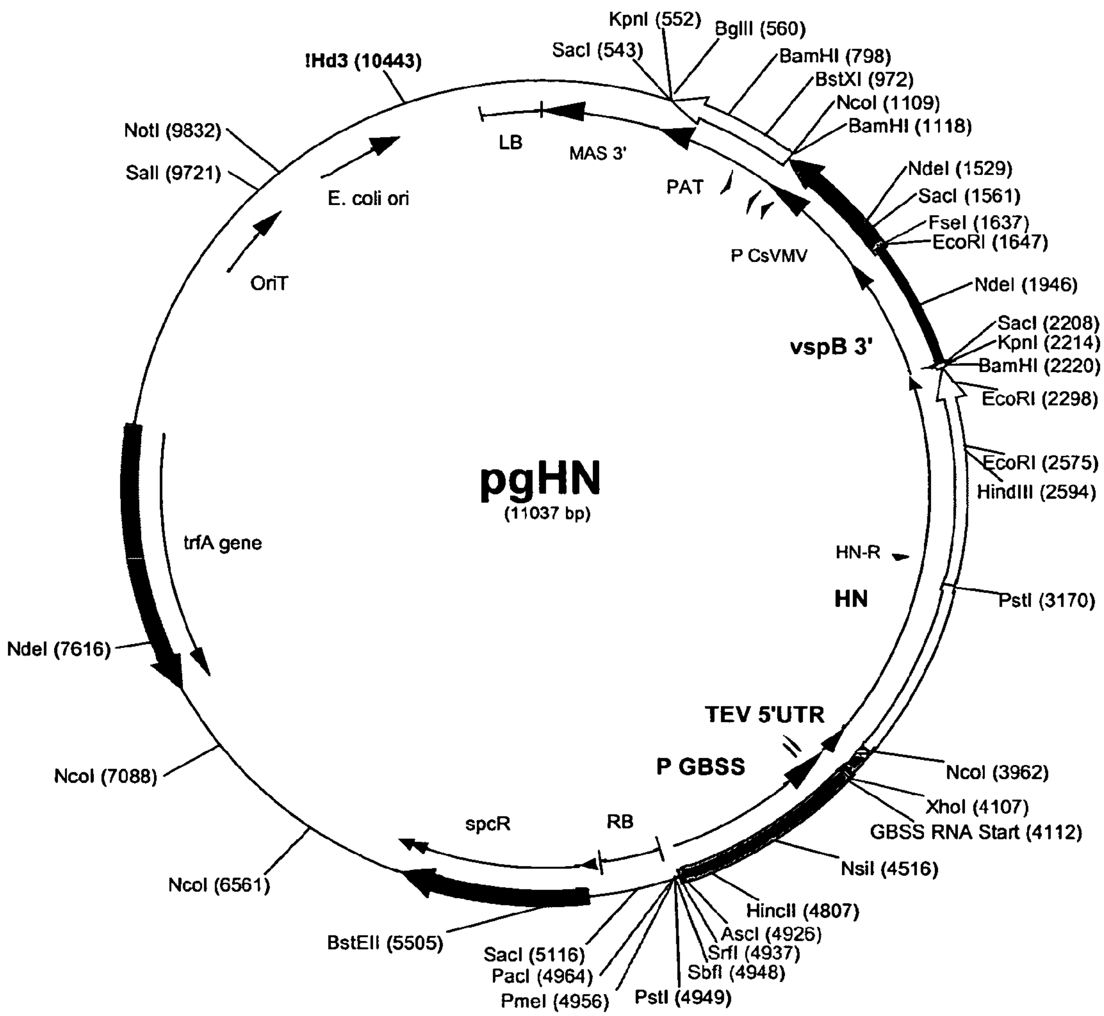
FIG. 5. Map of pgHN expression vector for NDV HN protein. This vector comprising the HN expression cassette includes the tuber-specific GBSS promoter with TEV 5' UTR and is terminated by the soybean vspB 3' element.
Figure 11:
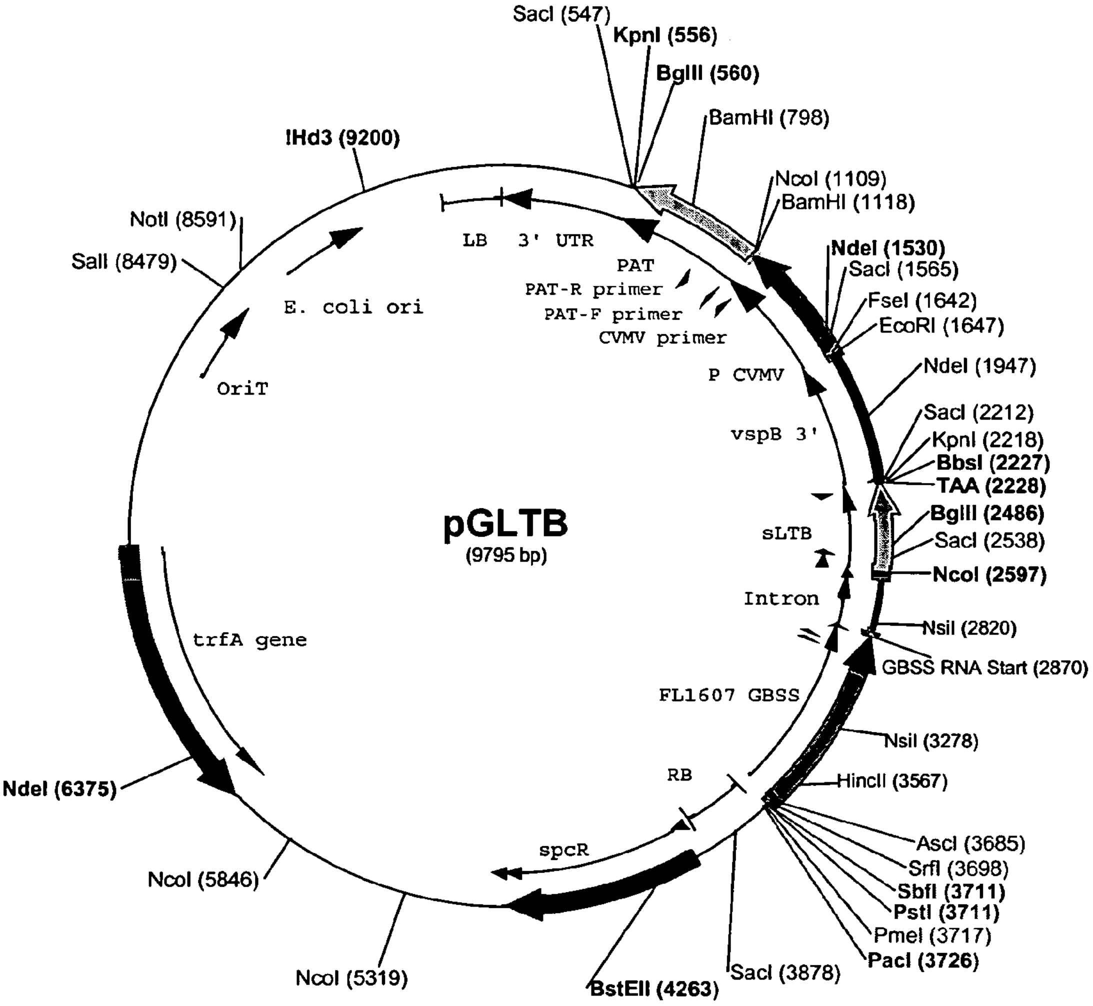
FIG. 11. Map of pGLTB intermediate vector.

A GBSS promoter expression cassette containing the TEV 5'UTR (untranslated region), described in U.S. Pat. No. 5,891,665 herein incorporated by reference, was assembled by ligation of vector pTH210 digested with HindIII/XhoI with the HindIII/XhoI fragment of pKS-GBX, which effected a substitution of the CaMV 35S promoter with the 811 bp GBSS promoter, to make pTH252A. See Haq T A, Mason H S, Clements J D, Arntzen C J (1995) Oral immunization with a recombinant bacterial antigen produced in transgenic plants. *Science* 268:714–716. The HN gene was inserted into pTH252A/NcoI-KpnI by ligation with the HN 5' half on NcoI/PstI and the HN 3' half on PstI/KpnI to make pHN252A. The binary T-DNA vector pgHN was made by ligation of the vector pGLTB (shown in FIG. 11) digested with NsiI and EcoRI with the fragments pHN252A/NsiI-KpnI and pTH210/KpnI-EcoRI. A map of pgHN is shown in FIG. 5.

Figure 6:
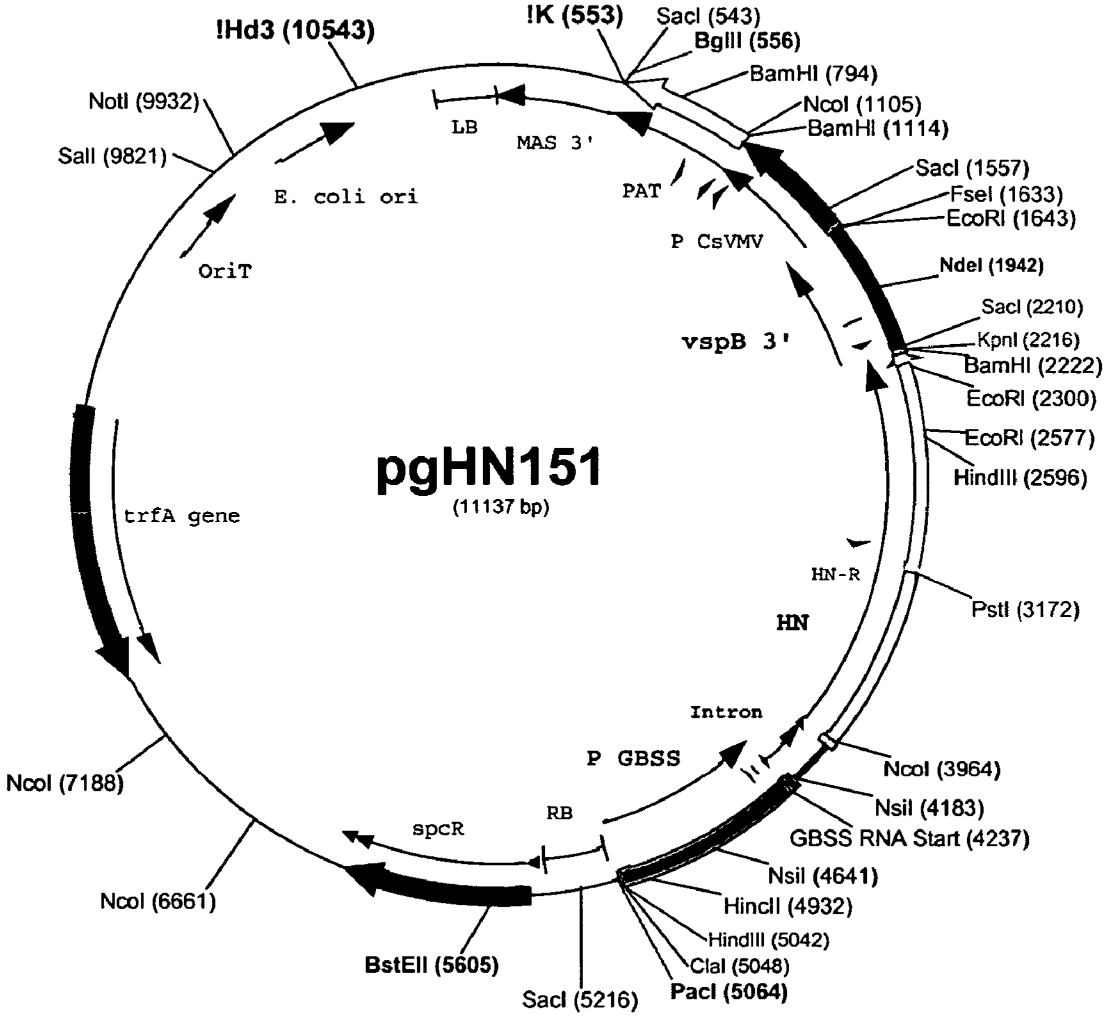
FIG. 6. Map of pgHN151 expression vector for NDV HN protein. The HN expression vector or cassette includes the tuber-specific GBSS promoter with its native 5' UTR and intron, and is terminated by the soybean vspB 3' element. The vector is derived from pBBV-PHAS-iaaH, which contains the plant selectable marker PAT, includes the CsVMV promoter and is terminated by the MAS 3' element. LB and RB, left and right T-DNA border elements delineate the boundaries of the DNA that is integrated into the plant genome.
Figure 12:
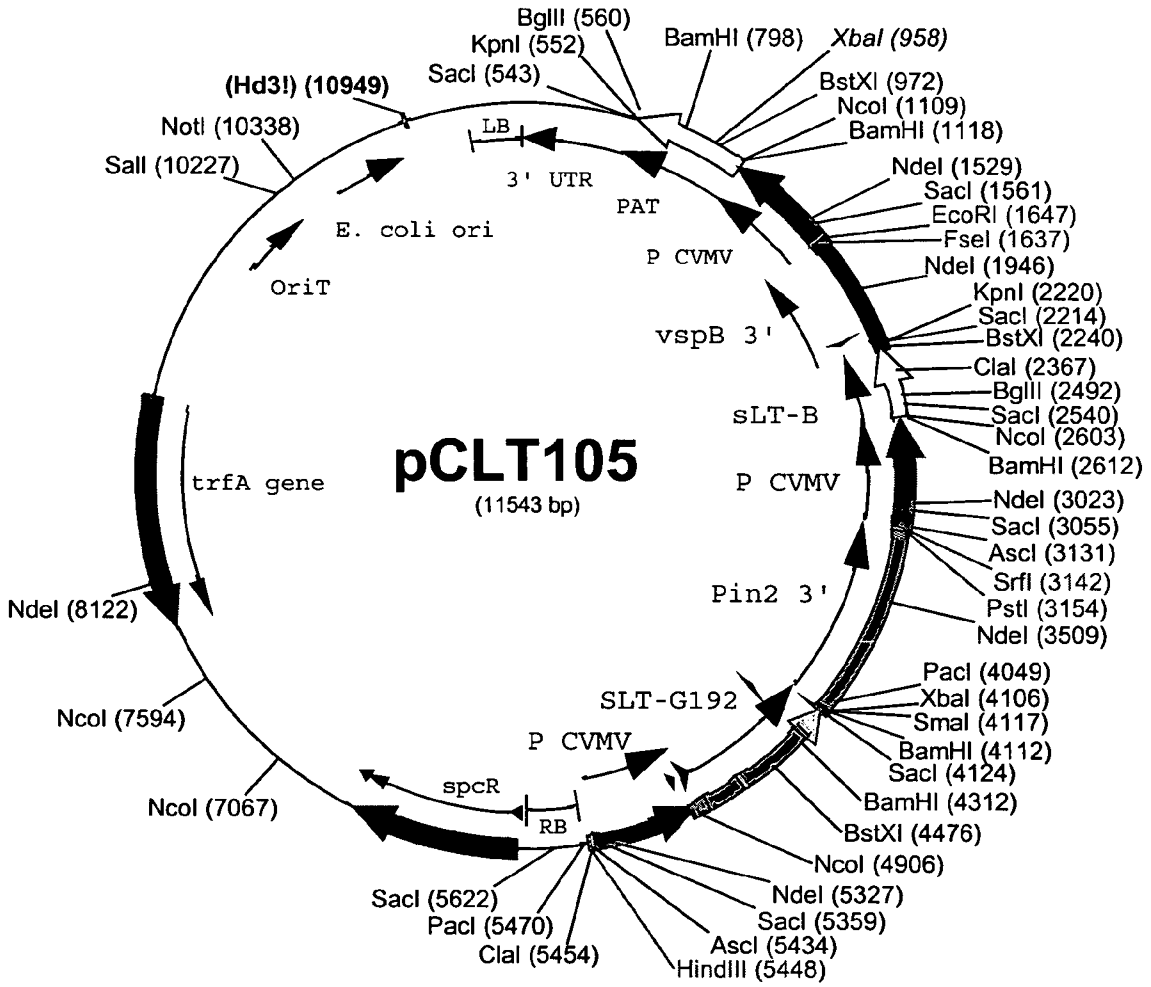
FIG. 12. Map of pCLT105 intermediate vector.

A GBSS promoter expression cassette containing the GBSS 5'UTR, described in U.S. Pat. No. 5,824,798 herein incorporated by reference, with its intron, was assembled by ligation of vector pTH210 (Haq 1995) digested with HindIII/NcoI with the HindIII/NcoI fragment of pKS-GBN, which effected a substitution of the (cauliflower mosaic virus) CaMV 35S promoter/TEV 5'UTR with the 1084 bp GBSS promoter/5'-UTR, to make pTH251A. The binary T-DNA vector pgHN151 was made by ligation of the vector pCLT105 (shown in FIG. 12) with fragments pTH251A/HindIII-NcoI and pHN252A/NcoI-KpnI. A map of pgHN151 is shown in FIG. 6.

Figure 7:
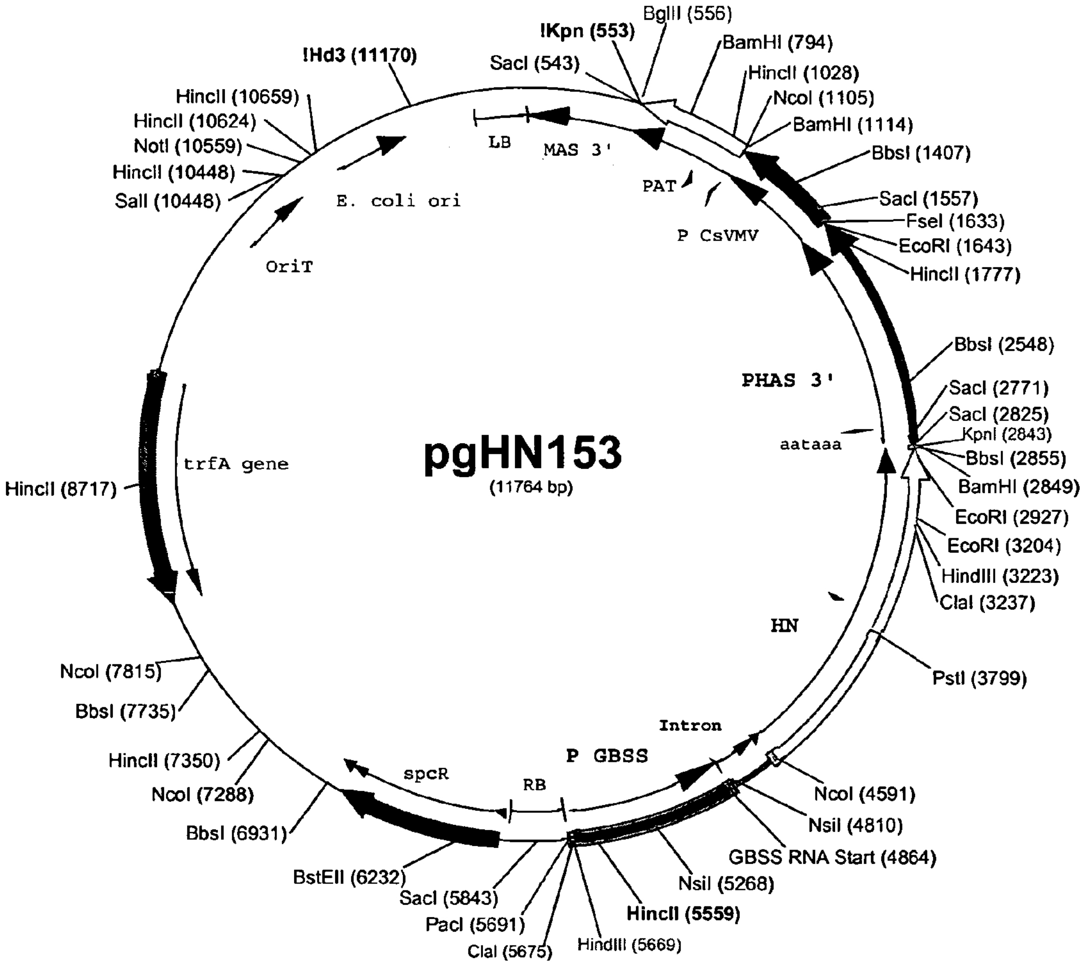
FIG. 7. Map of pgHN153 expression vector for NDV HN protein. The HN expression vector includes the tuber-specific GBSS promoter with its native 5' UTR and intron, and is terminated by the bean phaseolin 3' element. The vector is derived from pBBV-PHAS-iaaH, which contains the plant selectable marker PAT, includes the CsVMV promoter and is terminated by the MAS 3' element. LB and RB, left and right T-DNA border elements delineate the boundaries of the DNA that is integrated into the plant genome.

A GBSS promoter expression cassette containing the GBSS 5'UTR with its intron and the bean phaseolin 3' element (described in U.S. Pat. Nos. 5,270,200; 6,184,437; 6,320,101, herein incorporated by reference) was constructed. First, pCP!H was digested at the unique KpnI site, blunted with T4 DNA polymerase, and religated to make pCP!HK, which has the KpnI site removed. pCP!HK was digested with NsiI, followed by blunting with T4 DNA polymerase, and then digestion with PacI. The resulting vector was ligated with a 2848 bp fragment from pgHN151 digested with SacI, followed by blunting with T4 DNA polymerase, and then digestion with PacI, to make pgHN153. A map of pgHN153 is shown in FIG. 7.

Figure 8:
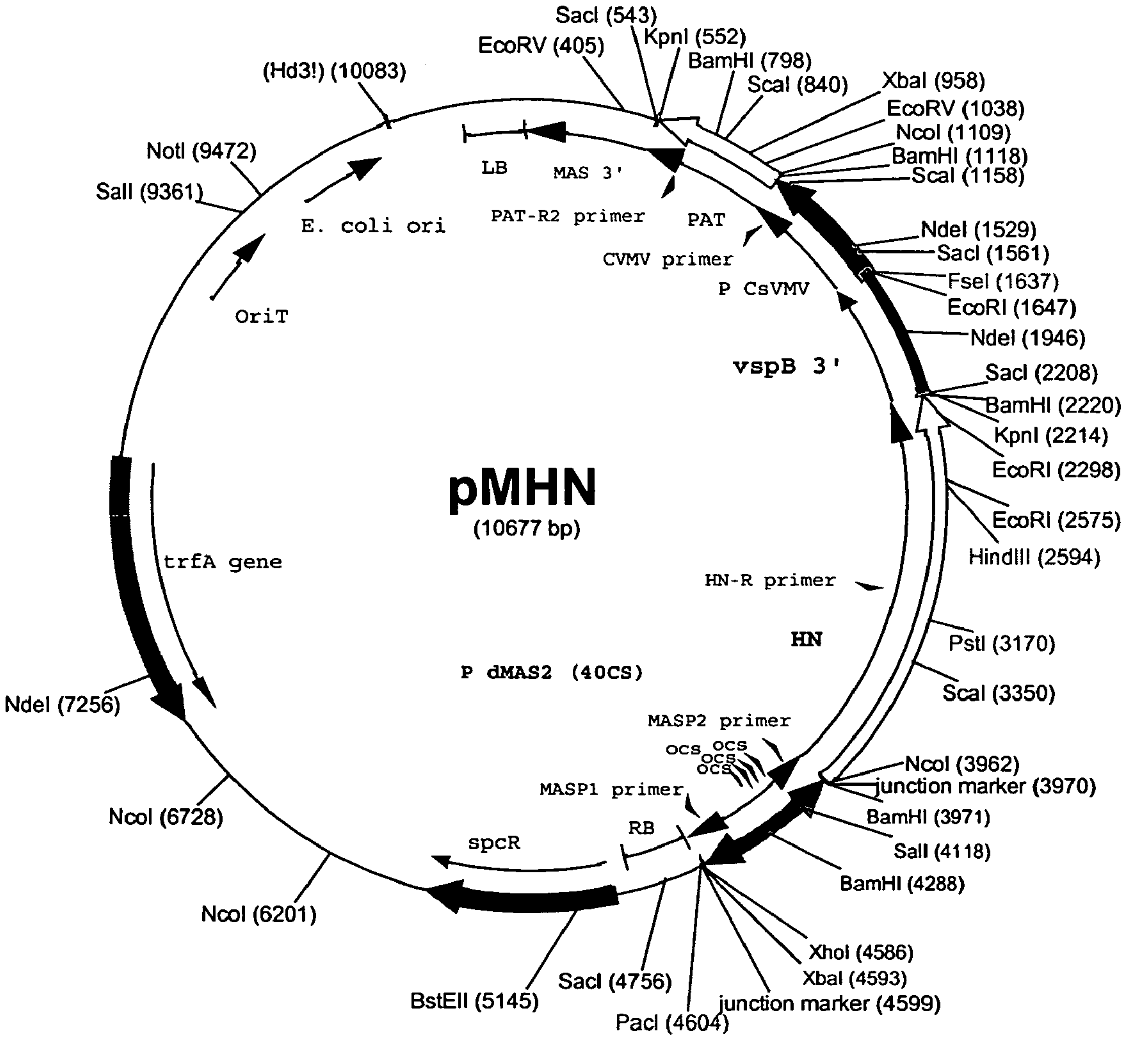
FIG. 8. Map of pMHN expression vector for NDV HN protein. The HN expression vector includes the constitutive 4OCSΔMAS promoter (P2 direction) and is terminated by the soybean vspB 3' element. The vector is derived from pBBV-PHAS-iaaH, which contains the plant selectable marker PAT, includes the CsVMV promoter and is terminated by the MAS 3' element. LB and RB, left and right T-DNA border elements delineate the boundaries of the DNA that is integrated into the plant genome.

A chimeric constitutive promoter (4OCSΔMAS U.S. Pat. Nos.: 5,001,060; 5,573,932 and 5,290,924 herein incorporated by reference) was used to construct another expression vector for HN. Plasmid, pAGM149, was digested with EcoRV and partial digestion with BamHI. This fragment was ligated with pCHN digested with PmeI/PstI and the 5' half of the synthetic HN gene obtained by digestion of pKS-CHN with BamHI/PstI. The resulting pMHN is shown in FIG. 8.

Figure 9:
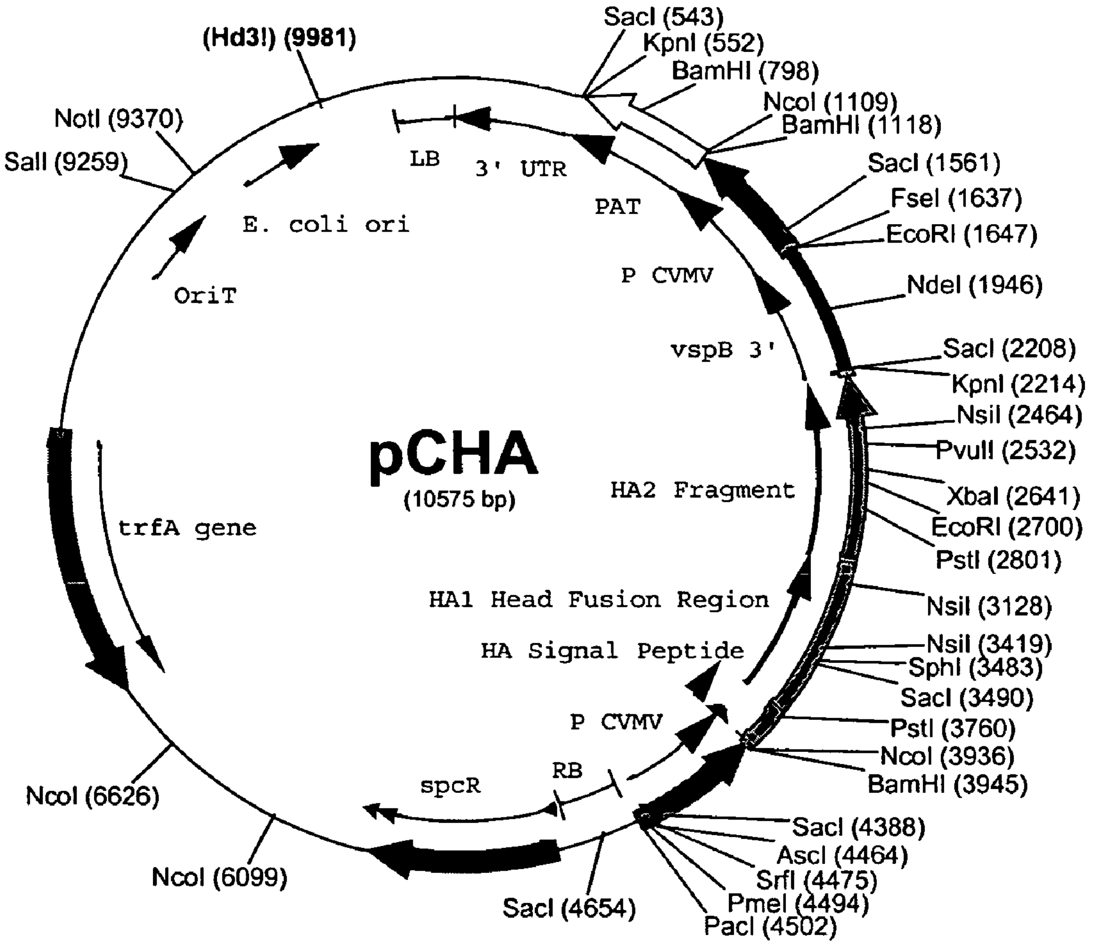
FIG. 9. Map of pCHA expression vector for the HA gene of the AIV A/turkey/Wisconsin/68 (H5N9).

A plasmid containing the HA gene of AIV A/turkey/Wisconsin/68 (H5N9) was obtained from David Suarez (SEPRL, Athens, Ga.). It was end-tailored by PCR to add restriction sites NcoI at the 5' and KpnI at the 3' end, and inserted into the vector pIBT210.1 (Haq et al., 1995), containing the 35S promoter, TEV 5'-UTR, and vspB 3' end. The expression cassette was transferred to the binary vector pGPTV-Kan (Becker et al., *Plant Mol Biol* 1992; 20: 1195–7) by digestion with HindIII and EcoRI (partial), to make pIBT-HAO. The HA gene/vspB3' end fragment from pIBT-HAO was obtained by digestion with NcoI and EcoRI (partial), and inserted into pKS-CVM7 to make pKS-CHA. The cassette containing the CsVMV promoter, HA gene, and vspB3' end was obtained from pKS-CHA by digestion with AscI and EcoRI (partial), and ligated with pCP!H to make pCHA, shown in FIG. 9.

A dicot expression vector containing the plant-optimized nucleotide sequence of NDV-HN was constructed. The completed construct contained the gene cassette; *Arabidopsis thaliana* (At) Ubiquitin 3 (Ubi3) promoter v2/Newcastle Disease Virus Hemagluttin Neuraminidase (NDV-HN)/vspb 3'UTR :: Cassava Vein Mosaic Virus (CsVMV) promoter/PAT selectable marker/*Arabidopsis thaliana* (At) ORF 25 3'UTR in a binary expression vector.

The expression cassette was assembled by completing a 3-way ligation (FIG. 48). The binary vector pCGUS was modified by removing the CsVMV promoter and GUS gene. A restriction enzyme digest with the enzymes HinDIII and KpnI (New England Biolabs) liberated a DNA fragment of 8310 bp. The NDV-HN gene was isolated from the plasmid pCHN as an NcoI/KpnI (New England Biolabs) restriction enzyme digestion DNA fragment of 1731 bp. Finally, the AtUbi3 promoter v2 was isolated from pDAB7121 as an NcoI/HindIII (New England Biolabs) restriction enzyme digestion. The resulting reaction produced a DNA fragment of 1732 bp. The DNA of all three enzyme digestions was excised from agarose gel via the "Qiaexll Gel Extraction Kit" (Qiagen). A 3-way ligation was completed using equimolar concentrations of all three DNA fragments. The ligation was catalyzed by the "T4 DNA Ligase" (New England Biolabs). The resulting ligation product was transformed into "One Shot Top10 Chemically Competent *E. coli*." (Invitrogen). Two colonies were isolated from this transformation. Initial screening via restriction enzyme digestion indicated that both clones produced the expected DNA banding pattern. The restriction enzyme reactions that were completed used the following enzymes; EcoRV, FspI, HinDIII, NcoI, SacI, ScaI (New England Biolabs). Further confirmation of the correct construct involved a sequencing reaction over the AtUbi 3' promoter v2/NDV-HN border. A sequencing reaction with the primer pUHN2 (tgg ttg gag cct agg gta ct) was completed using the "Beckman CEQ Quick Start Kit" (Beckman Coulter). The results of this sequencing reaction indicated that the AtUbi3' promoter v2 DNA fragment did ligate with the NDV-HN DNA fragment at the intended NcoI restriction site. Sequencing across the NDV-HN/pCGUS border and pCGUS/AtUbi3' promoter v2 border required additional steps. A PCR reaction of both borders was completed. The NDV-HN/pCGUS border and pCGUS/AtUbi3' promoter v2 border were PCR amplified using the "FailSafe PCR Kit" (Epicenter). Two reactions for the NDV-HN/pCGUS border were completed using the FailSafe buffer's B and C with the PCR primers KpnI 5' (act aat act taa tga taa ca) and KpnI 3' (ata cac tac ctc cac atg tt). The PCR reactions for the pCGUS/AtUbi3' promoter v2 border were completed using FailSafe buffer's B and C with the PCR primers HinDIII 5' (tgccggttttcaggtaac ata) and HinDIII 3' (agt tag gcc cga ata gtt tga a). All of the PCR reactions produced DNA fragments of the expected length (~600 bp). The PCR amplifications of the border regions were cloned into the "TOPO TA cloning kit with pCR2.1-TOPO" (Invitrogen). Clones containing the amplified border region were identified via an EcoRI restriction enzyme digestion (New England Biolabs). To confirm that the intended ligation at these border junctions did occur, a sequencing reaction was completed using the "Beckman CEQ Quick Start Kit" (Beckman Coulter) with the M13 reverse sequencing primer (aac agc tat gac cat g). The results of these sequencing reactions indicated that the correct ligation reaction did occur at the pCGUS/NDV-HN and the pCGUS/At Ubi 3 promoter v2 borders.

EXAMPLE 2

Preparation of Transgenic *Nicotiana tabacum*

Three to 4 days prior to transformation, a 1 week old NT-1 culture was sub-cultured to fresh medium by adding 2 ml of the NT-1 culture into 40 ml NT-1 media. The sub-culture was maintained in the dark at 25±1° C. on a shaker at 100 rpm.

NT-1 Medium

| Reagent | Per liter |
|---|---|
| MS salts | 4.3 g |
| MES stock (20X) | 50 ml |
| B1 inositol stock (100X) | 10 ml |
| Miller's I stock | 3 ml |
| 2,4-D (1 mg/ml) | 2.21 ml |
| Sucrose | 30 g |
| pH to 5.7 ± 0.03 | |

B1 Inositol Stock (100x)(1 liter)
Thiamine HCl (Vit B1)—0.1 g
MES (20x) (1 liter)
MES (2-N-morpholinoethanesulfonic acid)—10 g
Myoinositol—10 g
Miller's I (1 liter)
$KH_2PO_4$—60 g

*Agrobacterium tumefaciens* containing the expression vector of interest was streaked from a glycerol stock onto a plate of LB medium containing 50 mg/l spectinomycin. The bacterial culture was incubated in the dark at 30° C. for 24 to 48 hours. One well-formed colony was selected, and transferred to 3 ml of YM medium containing 50 mg/L spectinomycin. The liquid culture was incubated in the dark at 30° C. in an incubator shaker at 250 rpm until the $OD_{600}$ was 0.5–0.6. This took approximately 24 hrs.

LB Medium

| Reagent | Per liter |
|---|---|
| Bacto-tryptone | 10 g |
| Yeast extract | 5 g |
| NaCl | 10 g |
| Difco Bacto Agar | 15 g |

YM Medium

| Reagent | Per liter |
|---|---|
| Yeast extract | 400 mg |
| Mannitol | 10 g |
| NaCl | 100 mg |
| $MgSO_4.7H_2O$ | 200 mg |
| $KH_2PO_4$ | 500 mg |

(Alternatively, YM in powder form can be purchased (Gibco BRL; catalog #10090-011). To make liquid culture medium, add 11.1 g to 1 liter water.)

On the day of transformation, 1 µl of 20 mM acetosyringone was added per ml of NT-1 culture. The acetosyringone stock was made in ethanol the day of the transformation. The NT-1 cells were wounded to increase the transformation efficiency. For wounding, the suspension culture was drawn up and down repeatedly (20 times) through a 10 ml wide-bore sterile pipette. Four milliliters of the suspension was transferred into each of 10, 60×15 mm Petri plates. One plate was set aside to be used as a non-transformed control. Approximately, 50 to 100 µl of *Agrobacterium* suspension was added to each of the remaining 9 plates. The plates were wrapped with parafilm then incubated in the dark on a shaker at 100 rpm at 25±1° C. for 3 days.

Cells were transferred to a sterile, 50 ml conical centrifuge tube, and brought up to a final volume of 45 ml with NTC medium (NT-1 medium containing 500 mg/L carbenicillin, added after autoclaving). They were mixed, then centrifuged at 1000 rpm for 10 min in a centrifuge equipped with a swinging bucket rotor. The supernatant was removed, and the resultant pellet was resuspended in 45 ml of NTC. The wash was repeated. The suspension was centrifuged, the supernatant was discarded, and the pellet was resuspended in 40 ml NTC. Aliquots of 5 ml were plated onto each Petri plate (150×15 mm) containing NTCB10 medium (NTC medium solidified with 8 g/l Agar/Agar; supplemented with 10 mg/l bialaphos, added after autoclaving). Plates were wrapped with parafilm then maintained in the dark at 25°±1° C. Before transferring to the culture room, plates were left open in the laminar flow hood to allow excess liquid to evaporate. After 6 to 8 weeks, putative transformants appeared. They were selected and transferred to fresh NTCB5 (NTC medium solidified with 8 g/l Agar/Agar; supplemented with 5 mg/l bialaphos, added after autoclaving). The plates were wrapped with parafilm and cultured in the dark at 25°±1° C.

Putative transformants appeared as small clusters of callus on a background of dead, non-transformed cells. These calli were transferred to NTCB5 medium and allowed to grow for several weeks. Portions of each putative transformant were selected for ELISA analysis. After at least 2 series of analysis by ELISA, lines with the highest antigen levels were selected. The amount of callus material for each of the elite lines was then multiplied in plate cultures and occasionally in liquid cultures. The resulting transformed NT-1 cell lines expressed and accumulated the HN protein from Newcastle Disease Virus (Lasota strain), or transformed cell line CHA expressed the HA protein from Avian Influenza Virus. These lines contain an undetermined number of copies of the T-DNA region of the plasmids stably integrated into the nuclear chromosomal DNA. The transgenic CHN NT-1 cells accumulate HN at levels up to 1% of total soluble protein as determined by HN-specific ELISA.

Transgenic NT1 cell and potato lines selected for Bialaphos® resistance were propagated and evaluated for HN expression by ELISA. High-expressing NT1 cell lines were established in liquid suspension culture. Potato lines containing a constitutive promoter construct (pCHN, pMHN) were screened for expression in leaf tissue, and selected lines were transferred to soil and cultured in a greenhouse to obtain tubers for evaluation. Potato lines containing a tuber-specific GBSS promoter construct (pGHN, pGHN151, pGHN153) were screened for expression using microtubers developed in vitro.

Figure 19:
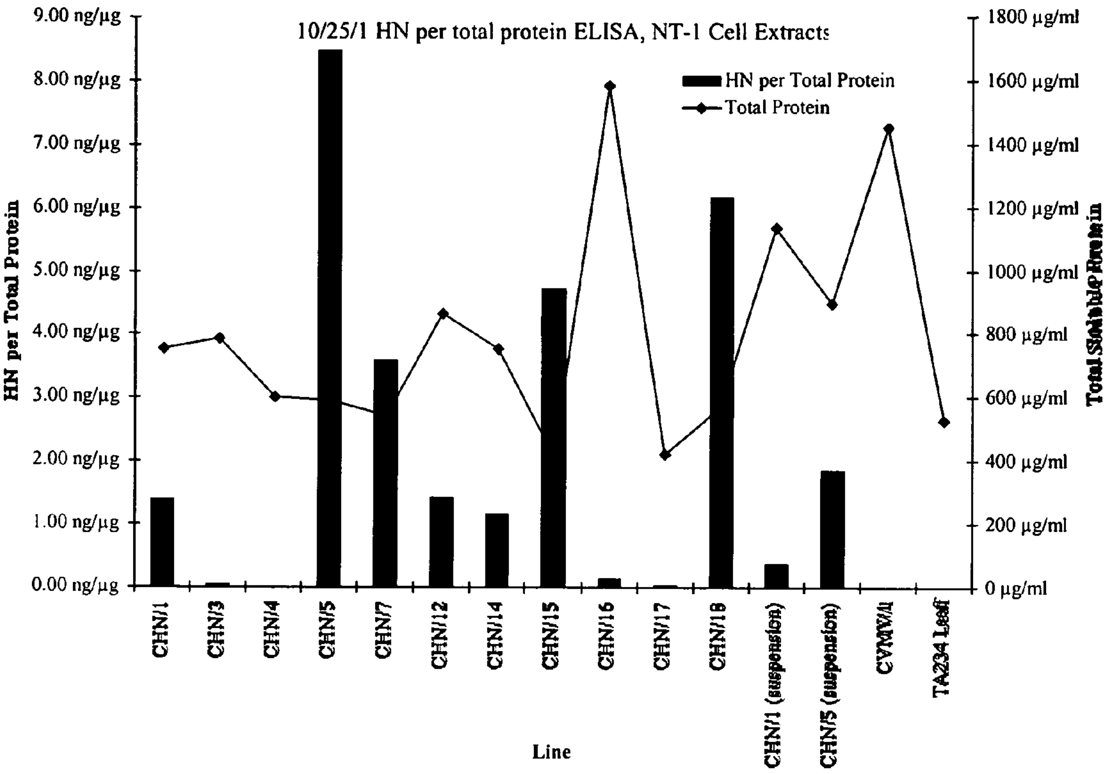
FIG. 19. Expression of NDV-HN in NT1 cells transformed with pCHN. Extracts f cells growing on solid media were assayed by ELISA for NDV-HN, using inactivated NDV as a reference standard. Total soluble protein (TSP) was assayed by the Bradford method (BioRad) using bovine serum albumin as a standard.
Figure 20:
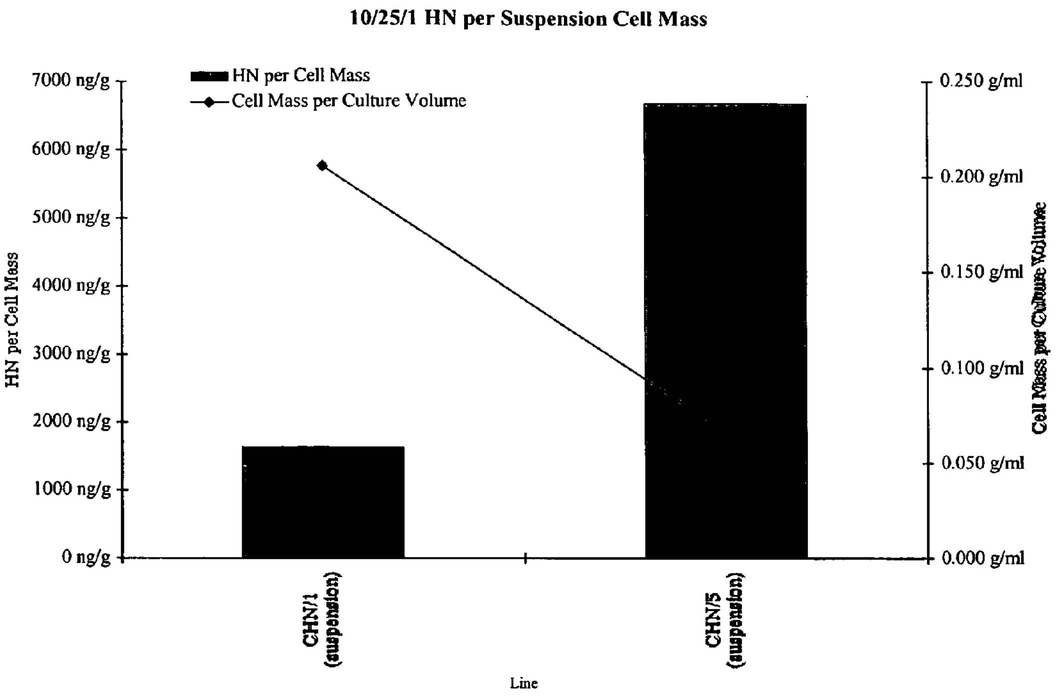
FIG. 20. Expression of HN per cell mass in pCHN-transformed NT1 lines.
Figure 21:
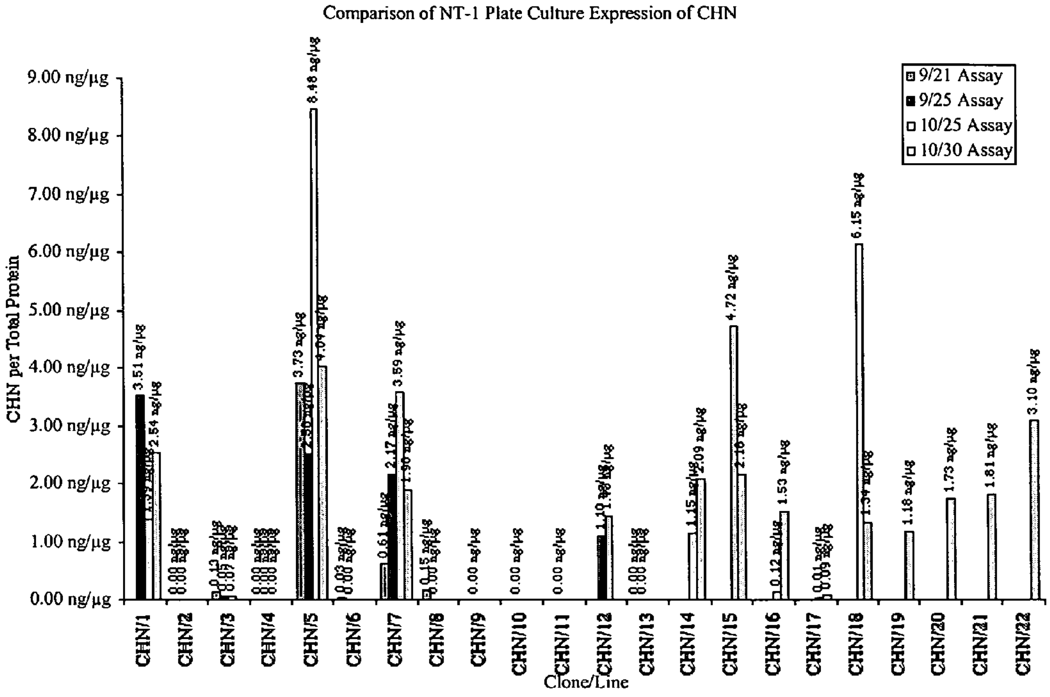
FIG. 21. Stability of expression of HN in pCHN-transformed NT1 cell lines.
Figure 22:
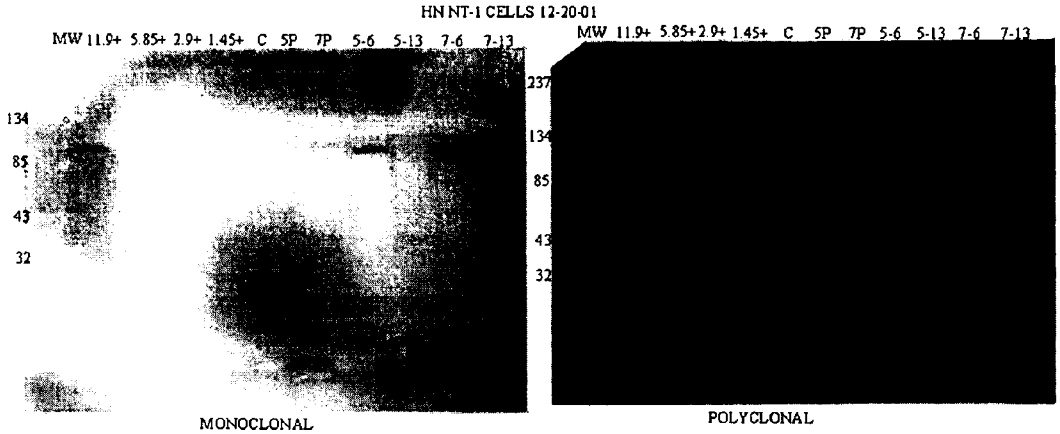
FIG. 22. Western blot of pCHN-transformed NT1 cells using HN-specific antibodies. NT1 cells cultured on solid media (5P, 7P) or in liquid suspension (5–6, 5–13, 7–6, 7–13) were extracted and subjected to SDS-PAGE, followed by Western blot probed with either monoclonal (left) or polyclonal (right) antibodies. MW, molecular weight markers, indicated by numbers at left in kDa. Lanes 11.9+, 5.85+, 2.99+, 1.45+ indicate amount (ng) of reference standard inactivated NDV run in those lanes. C, nontransgenic NT1 cell extract.

HN expression in pCHN-transformed NT1 lines using the CsVMV promoter. Expression of HN in NT1 cell lines assayed from callus growing on solid media is shown in FIG. 19. The highest expressing lines were CHN-5 (8.5 ng/μg TSP) and CHN-18 (6.2 ng/μg TSP). Lines CHN-1 and CHN-5 were established in liquid suspension culture. The expression of HN per unit cell mass in these cultures is shown in FIG. 20. Line CHN-5 showed expression of HN at 6.7 μg per g cell mass. The same cell lines shown in FIG. 20 were evaluated multiple times, and some new lines assayed at the last time point, stability of expression of HN in the NT1 lines (FIG. 21). Western blotting of extracts from lines CHN-5 and CHN-7 showed a single reactive band co-migrating with the reference standard when probed with monoclonal antibody, and showed an additional smaller band when probed with a polyclonal antiserum (FIG. 22).

Figure 23:
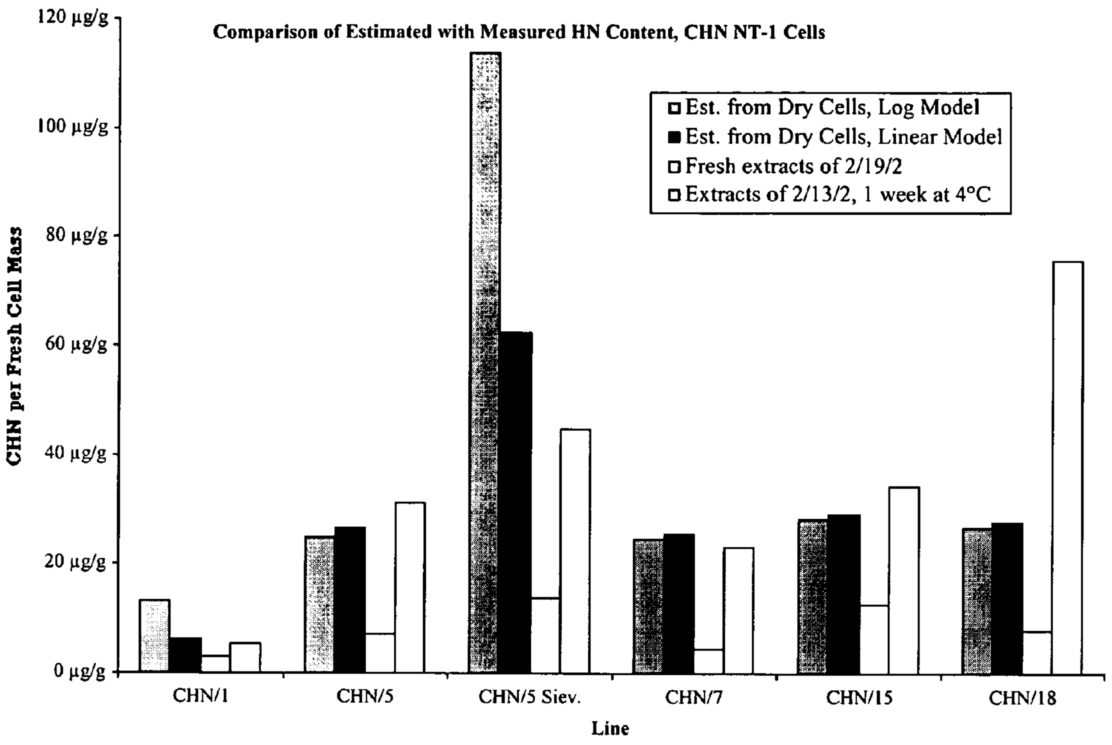
FIG. 23. HN antigen is maintained in freeze-dried pCHN-transformed NT1 cells and on storage of extracts at 4° C. NT1 cells were freeze-dried, extracted, and subjected to ELISA. The results for freeze-dried cells were analyzed by either a log or linear regression model, as indicated in the inset. The values are corrected to indicate HN content per mass of fresh weight cells using estimates of water loss on drying. Fresh cells were extracted and analyzed immediately (2/19/2) or stored at 4° C. for 1 week prior to assay.

Effects of freeze-drying of fresh cells and of storage of extracts at 4° C. In order to examine the effect of drying on antigen stability, freeze-dried NT1 cells were extracted and assayed by ELISA. Extracts of freeze-dried cells showed no loss or apparent increase in HN content per fresh cell mass (FIG. 23). Furthermore, extracts of fresh cells stored at 4° C. for one week showed an increase in HN content assayed by ELISA (FIG. 23). We have observed a similar effect with another membrane-bound viral protein, the hepatitis B surface antigen. It may result from oxidation of cysteine residues to form correct disulfide bonds, which results in display of the appropriate antigenic epitopes.

Figure 24:
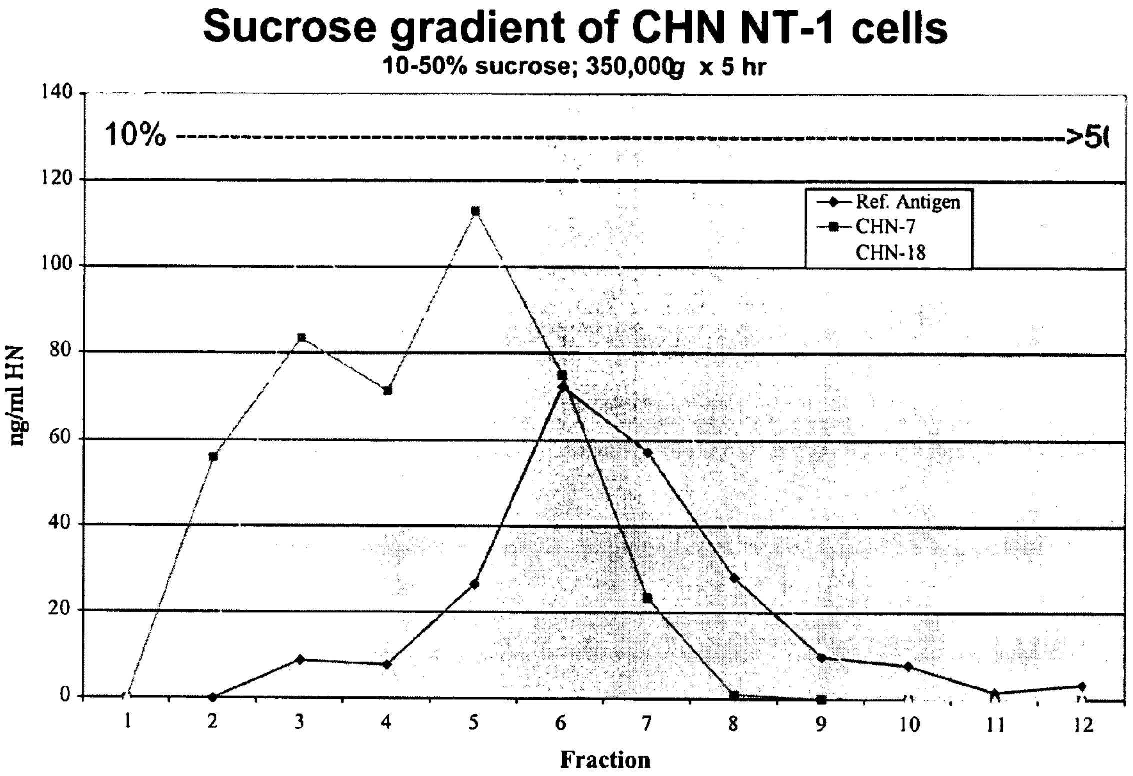
FIG. 24. Sucrose gradient analysis of RN antigen shows particulate character. Extracts of pCHN-transformed NT1 cell lines CHN-7 or CHN-18, or reference standard inactivated NDV were sedimented in 10–50% sucrose/PBS gradients at 350,000 g for 5 h. Fractions were collected and assayed by ELISA for HN. Fraction 1 is the top of gradient.

Particle behavior of plant-expressed HN antigen. In order to evaluate assembly of NT1 cell-expressed antigen to form particulate structures, sucrose gradient sedimentation was performed on crude cell extracts. The profiles shown in FIG. 24 indicate that the NT1 cell-derived HN showed 2 peaks of ELISA reactive material. One peak co-sedimented with inactivated virus particles, while the other peak sedimented more slowly but still showed particulate character. These data provide evidence that the HN protein is correctly inserted into the ER membrane.

Figure 13:
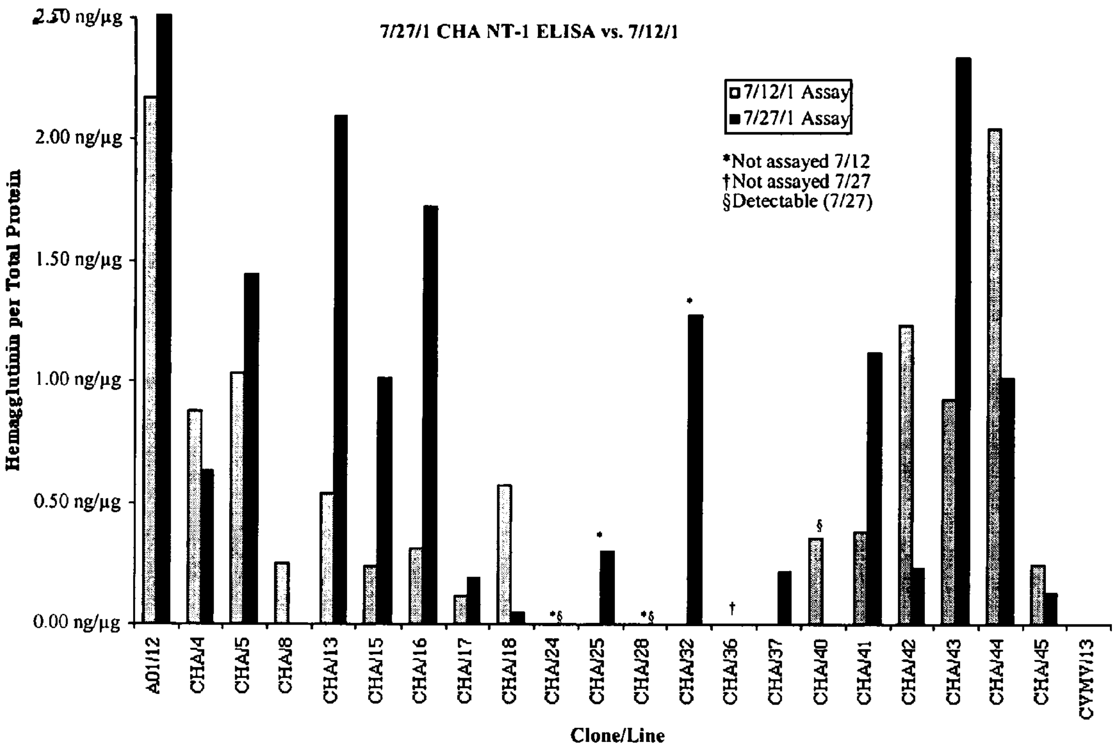
FIG. 13. HA expression in transgenic NT1 cell lines using pGPTV-HAO or pCHA. Callus cells growing on solid media were extracted and assayed for HA by ELISA and for total protein by the Bradford method. Data are presented as ng HA per μg total protein. A01/12, a high-expressing line selected from several pGPTV-HAO-transformed lines. CHA, lines transformed with pCHA. CVMV/13, a vector-only transformed line. Separate samples were extracted and assayed 7/12/01 or 7/27/01.
Figure 14:
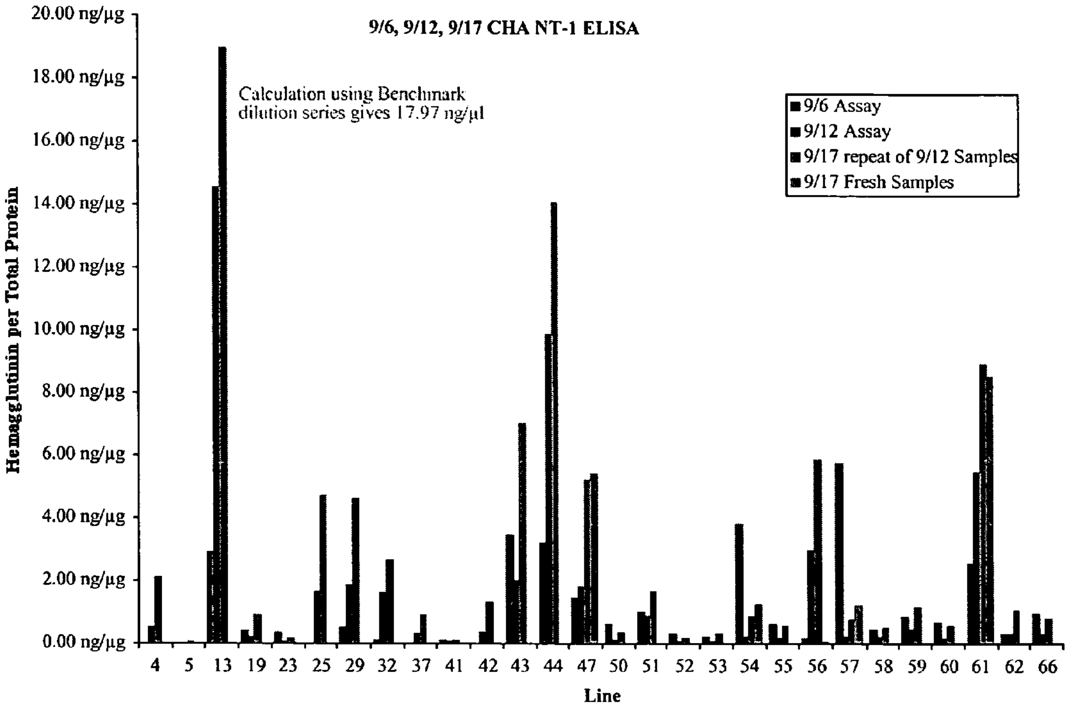
FIG. 14. Repeated assays of pCHA-transformed NT1 cell lines.
Figure 15:
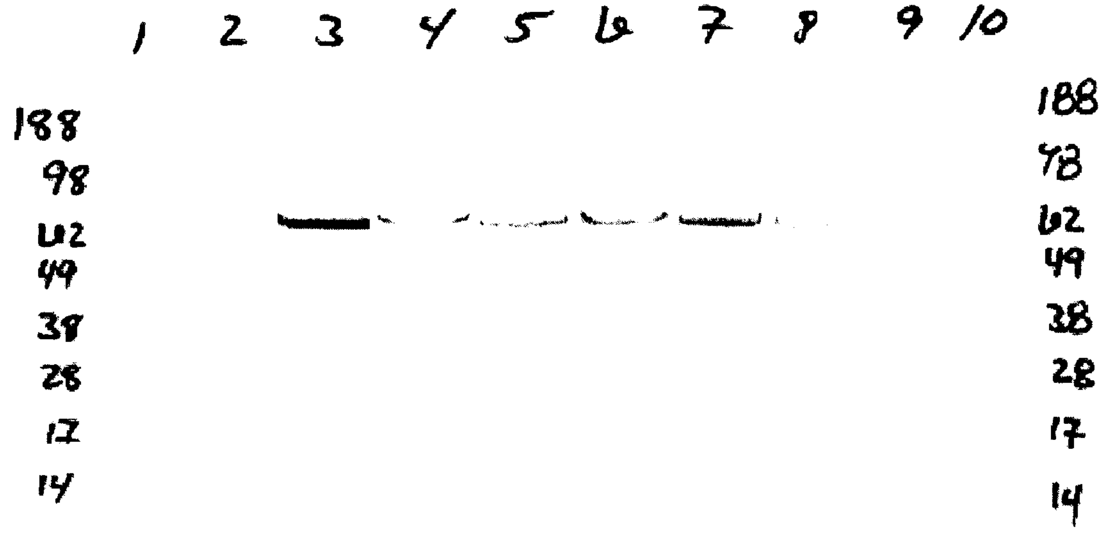
FIG. 15. Western blot for AIV HA expression in pCHA-transformed NT1 cell lines. NT1 cell lines were grown in liquid suspension culture, and extracts were resolved by SDS-PAGE, electro-transferred to PVDF membrane, and probed with chicken anti-AIV-H5 from USDA/SEPRL, which is also used as the detector antibody in the HA quantitation ELISA. Lanes 1 and 10, molecular size standards; lane 2, HN Reference Antigen at 1:800, 31.25 ng/well; lane 3, CHA—13 (1:2); lane 4, CHA—42 (1:2); lane 5, CHA—43 (1:2); lane 6, CHA—44 (1:2); lane 7, CHA—61 (1:2); lane 8, GPTV-HAO grown with Kanamycin (1:2); lane 9, GPTV-HAO grown without Kanamycin (1:2).

HN expression in pMHN-transformed NT1 lines using the (4ocs)ΔMAS promoter. HN expression in several NT1 cell lines transformed with pMHN, compared to pCHN-transformed NT1 cell lines, is shown in FIG. 25. Expression in pMHN-transformed lines was at least as high as in pCHN-transformed lines, with the highest accumulation of HN observed at approximately 30 μg per gram cell mass. Maximal HN expression in pCHN-transformed NT1 cells was less than 20 μg per gram cell mass. Bialaphos® resistant NT1 cell lines were also generated and assayed for HA expression by ELISA as described previously. In the first set of assays, only one pCHA-transformed line accumulated HA to a similar extent as the pGPTV-HAO line #12 that was previously generated (FIG. 13). In this experiment, the expression range was up to 2.5 ng/μg TSP. In repeated experiments with these and new pCHA-transformed lines, accumulation of HA ranged up to 18 ng/μg TSP in line CHA-13 (FIG. 14). Selected lines from this group were analyzed by Western blot. In all pCHA-lines tested, a reactive band at the expected size of ~68 kDa was observed (FIG. 15). These data show that the HA protein was correctly processed to remove the signal peptide, and accumulated in a stable form. Previous studies on pGPTV-HAO-transformed NT1 cells by non-denaturing Western blot (unpublished studies), showed that the HA assembled oligomeric structures, probably the native trimer that occurs on the surface of the AIV virion.

EXAMPLE 3

Cryopreservation

Cell Culture: NT-1 tobacco suspension cultures (non-transgenic and transgenic lines) were maintained in 250 ml Erlenmeyer flasks. Initially, the cells were cultured in a modified liquid Linsmaier and Skoog medium (LS) (1965). The medium, designated LSg, contained LS salts and vitamins, 30 g $l^{-1}$ glucose, and 0.05 mg $l^{-1}$ 2,4-dichlorophenoxyacetic acid (2,4-D). The pH of the medium was adjusted to 5.8. The cultures were transferred to fresh medium weekly by transferring 6 ml of 7-day-old cultures into 50 ml of LSg medium.

Based on poor growth of the cells in LSg medium, two additional media were investigated which were designated KCMS and NT-1. KCMS contained Murashige and Skoog (MS) (1962) salts, 1.3 mg $l^{-1}$ thiamine, 200 mg $l^{-1}$ $KH_2PO_4$, 30 g $l^{-1}$ sucrose, 0.2 mg $l^{-1}$ and 0.1 mg $l^{-1}$ kinetin. NT-1 medium contained MS salts, 180 mg $l^{-1}$ $KH_2PO_4$, 0.5 mg $l^{-1}$ 2-N-morpholinoethanesulfonic acid, 1 mg $l^{-1}$ thiamine, 100 mg $l^{-1}$ myoinositol, 30 g $l^{-1}$ sucrose, and 2.21 mg $l^{-1}$ 2,4-D. The pH of both media was adjusted to 5.7. For transfers to fresh medium, 2 ml of a 7-day-old culture were transferred into 48 ml of either KCMS or NT-1. All suspension cultures were maintained in the dark at 25° C. on an orbital shaker at 100 rpm Preculture: Three days after subculture (late exponential growth period), the cells were precultured in their respective medium (LSg, KCMS, or NT-1) by replacing one third of the medium with 1M mannitol (for final concentration of 0.3M), for 24 to 72 h.

Heat Shock Treatment: After preculture, cultures were placed on an orbital shaker at 100 rpm at 37° C. for 2 h. They were transferred back to the shaker at 25° C. for 4 h before vitrification.

Vitrification: The vitrification solution designated PVS2/100% contained 30% glycerol, 15% ethylene glycol, and 15% DMSO in a 0.4 M sucrose solution. A PVS2/20% solution was made by diluting PVS2/100%. Both solutions were adjusted to a pH of 5.8, autoclaved, then stored at 4° C.

To start the vitrification process, 4 ml of ice cold PVS2/20% was added to a 1 ml settled cell volume of cells. The preparation was incubated on ice for 5 min, then 1 ml of cold PVS2/100% was added at 1-minute intervals until a total volume of 9 ml was achieved. The preparations were centrifuged for 1 min at 7500–8000 rpm. The supernatant was discarded, then 0.5 ml of PVS2/100% was added at 2, 1-min intervals while the cells remained on ice. Then 1 ml of PVS2/100% was added 3 times at 1-min intervals. Half a milliliter of this mixture was then transferred into each of 6 cryogenic straws (Continental Plastic Corporation, Delavan, Wis.). The straws were heat sealed at each end with hot forceps, and immersed immediately into liquid nitrogen. The remaining 2 ml were not frozen and served as controls.

Recovery: After 1 h in liquid nitrogen, the vitrified cells were thawed in a 40° C. water bath for 3–5 sec, then immediately diluted with 7 ml of cold 1.2 M sucrose. The cells were kept on wet ice for 20 min, then centrifuged for 3 min at 7500–8000 rpm. Cells were transferred to 2 layers of filter paper (42.5 mm Whatman) on LSg or NT-1 solidified medium containing 0.75% agarose (Invitrogen Life Technologies, Carlsbad, Calif.) in 60×15 mm tissue culture plates. The cultures were maintained at 25° C. in the dark. Two days after plating, the cells were transferred to fresh NT-1 solidified medium. Transgenic lines were initially plated on medium without a selection agent until cell growth was well established and covered a small plate. They were then transferred to medium containing the appropriate selection.

Thereafter, the cells were transferred to fresh medium approximately every 2 wk. When cell growth nearly covered the surface of the medium in the plate, the cells were removed from the filter paper and transferred to larger plates (100×15 mm). When the callus again covered the plate, the cells were transferred to NT-1 medium solidified with 8 g $l^{-1}$ Agar (Sigma, St. Louis, Mo.) for maintenance.

EXAMPLE 4

Antigen Preparation

Whole wet NT-1 cells expressing either HN, HA or null control were harvested directly from cell culture and filtered to remove excess media by placing a Spectramesh 30 filter in a Buchner funnel and pouring cells and media through the filter using a slight vacuum. 0.5 grams of cells were placed in 2 mls of buffer (Dulbeccos Phosphate Buffered Saline and 1 mM EDTA), and then sonicated for 15 to 20 seconds on ice. Sonication was performed using a Branson 450 sonifier with a replaceable microtip at output control of 8, duty cycle 60 for varying amounts of time. Sonicates were then placed on ice until use.

EXAMPLE 5

Antigen Extraction

To examine whether non-detergent treatments could release ELISA signal from transformed NT-1 cells and allow retention of biological activity, a series of treatments were set up that involved comparison of treatments without detergent and various levels of sonication. The results were striking in that periods of sonication greater than 20 seconds in extraction buffer completely destroyed hemagglutination activity of HN from a pCHN bearing NT-1 cell line, but not ELISA signal. In contrast, sonication for only 20 seconds in DPBS not only released antigen detectable by ELISA signal, but the soluble protein extracts demonstrated excellent hemagglutination activity (see Table 1).

TABLE 1

Comparison of extraction methods on hemagglutination activity of plant-derived HN

| Sample | DPBS Sonic. 1.5 min | Ext. buffer Sonic. 1.5 min | DPBS Sonic. 15 sec | Ext. buffer F/T Sonic. 15 sec | DPBS F/T Sonic. 15 sec |
|---|---|---|---|---|---|
| pCHN-18-NT-1 | ≦2 | 256 | 4096 | 1024 | 1024 |
| pCHA-47-NT-1 | ≦2 | — | 64 | 16 | 16 |
| NT-1 | ≦2 | ≦2 | ≦2 | ≦2 | ≦2 |
| Native NDV[1] | 256 | 512 | 128 | nd | nd |

[1]Native NDV was sonicated for 2 minutes.
Ext. buffer—50 mM sodium ascorbate, 1 mM EDTA, 1 mM PMSF, and 0.1% Triton X-100 pH 7.2;
DPBS—Dulbeccos phosphate buffered saline;
sonic.—sonication;
F/T—freeze-thaw;
nd—not done for this experiment.

Plant-derived HN extracted without detergent was used as the antigen in hemagglutination inhibition assays to determine if polyclonal antibody produced to native virus could recognize and inhibit agglutination of RBC's by the plant-derived HN. The results indicate that native antibody will recognize the hemagglutination epitope of the plant-derived HN in a similar manner as native virus (Table 2). The data from Table 2 also demonstrates that control NT-1 cells or NT-1 cells expressing a non-hemagglutinating protein do not agglutinate red blood cells nor are affected by NDV specific serum. In this experiment, extracts of plant-derived protein were diluted to 4 HA units, and then treated with NDV specific polyclonal antisera. Four HA units is the standard amount of virus used for titration of serum.

TABLE 2

Comparison of hemagglutination inhibition (HAI) activity of plant-derived HN and native virus

| Sample | HN Concentration ELISA | Hemagglutination Titer | Hemagglutination Inhibition Titer (chicken anti-NDV polyclonal antibody) |
|---|---|---|---|
| NDV allantoic fluid (native) | 20 ug/ml | 4* | 4096 |
| NT control cell | None | ≦2 | ≦8 |
| pCHN-7-NT-1 | 1.5 ug/g fresh weight | >64 | 512 |
| CHN-18-NT-1 | 12 ug/g fresh weight | ≧4096 | 1024 |
| CLT-101-14-NT-1 | None | ≦2 | ≦8 |

*Stock virus is diluted such that 4 HA units, a 1:4 dilution of the stock will generate a positive HA but a dilution of 1:8 will not hemagglutinate. This is the concentration of virus used to titer antibody, the endpoint dilution of antibody that will interfere with 4 HA units of virus is considered to be the HAI titer of the antibody preparation.

The above data demonstrates that using an extraction method that does not utilize detergent and reduces the amount of cell disruption produces an extracellular fraction that retains hemagglutination activity for transformed NT-1 cell lines expressing HN or HA. To determine if HN protein from non-detergent extracted NT-1 cells had additional biological activity that may be relevant to vaccine efficacy, the HN extracts were examined for ability to bind to chicken cell receptors. Immuno-fluorescence staining indicated that CEF cells treated with native virus or pCHN-18 extracts were indistinguishable. Thus, plant-derived HN retains virus-like ability to bind to receptors on target cell surfaces.

The combined data from Tables 1 and 2, together with the hemagglutination and immunofluorescence assays discussed above, suggest that the HN protein derived transgenic NT-1 cells will retain both immunological and biological features if processed and formulated correctly. Most significant of the data provided above is that antisera to native virus will recognize plant-derived HN in HAI tests. Chickens that contain at least 4 fold higher titer of HAI activity above background are almost always certain of protection against challenge from virulent virus. To test whether the plant derived protein extracted in non-detergent as described above would generate antibody in target animals species both HA and HN protein were prepared and inoculated into chickens and rabbits.

EXAMPLE 6

Quantitative ELISA

HN

Quantitative ELISA for HN is performed by coating plates on the day prior to running the assay. 50 μl per well of Capture Antibody (Rabbit anti-HN in 50% glycerol, diluted (1:500) in 0.01M Borate Buffer) is added to each well of each flat bottom 96-well microtiter plate. The plate is covered and incubated at 2° C.–7° C. overnight, (12–18 hours). The coated ELISA plate(s) are allowed to equilibrate to room temperature (approximately 20–30 minutes) and then washed three times with 200–300 μl per well per wash with PBS-T. The entire plate is blocked to prevent non-specific reactions by adding 200 μl per well of 3% Skim Milk Blocking Solution. The plate(s) is(are) then incubated for 2 hours (+10 minutes) at 37° C.±2° C. (covered with a plate cover or equivalent). HN Reference antigen (Ag) in 1% Skim Milk Blocker is added to a concentration of 250 ng HN/ml; experimental antigens are diluted in 1% Blocker. The HN ELISA plate(s) are washed one time with PBS-T and 100 μl per well of diluted HN Reference Antigen and HN Test Samples are added to Row B. 50 μl per well of 1% Blocker is added to all remaining wells. The samples are serially diluted down the plate by transferring 50 μl per well from row B to row G, mixing 4–5 times with the pipette before each transfer. The plate(s) are covered and incubated 1 hour (+10 minutes) at 37° C.±2° C.; and the ELISA plate(s) are washed three times with PBS-T. Fifty μl of NDV HN 4A Ascites Fluid in 50% glycerol (1:2000) in 3% Blocker is added to each well and the plates are covered and incubated 1 hour (+10 minutes) at 37° C.±2° C. The ELISA plate(s) are washed three times with PBS-T and 50 μl of rabbit anti-Mouse IgG in 50% glycerol (1:3000) in 3% Blocker is added to each well. The plates are covered and incubated 1 hour (+10 minutes) at 37° C.±2° C. ELISA plate(s) are washed three times with PBS-T and 50 μl of ABTS Peroxidase Substrate Solution (equilibrated at RT (room temperature) for at least 30 minutes) is added to each well. The plates are covered and incubated at RT in the dark for 15–20 minutes. The Optical Density (OD) of the wells are read at a wavelength of 405 nm (with a 492 nm Reference Filter). The initial dilution of the HN Reference Antigen should be within 0.7–1.0 OD, this serves as the positive control for the ELISA.

HA

For quantitative ELISA of HA, the plates are coated on the day prior to running the assay. Fifty μl per well of Capture Antibody (goat anti-Hav5 in 50% glycerol, diluted (1:1000) in 0.01M Borate Buffer) is added to each well of flat bottom 96-well microtiter plate(s)). The plate(s) are covered and incubate at 2° C.–7° C. overnight, (12–18 hours). The coated ELISA plate(s) is(are) allowed to equilibrate to room temperature (approximately 20–30 minutes) and is(are) then washed three times with 200–300 μl per well per wash with PBS-T. The entire plate is blocked to prevent non-specific reactions by adding 200 μl per well of 3% Skim Milk Blocking Solution. The plate(s) is(are) then incubated for 2 hours (+10 minutes) at 37° C.±2° C. (covered with a plate cover or equivalent). AIV-HA (allanotoic fluid) reference Antigen is added in 1% Skim Milk Blocker to a concentration of 1000 ng HA/ml and experimental antigens are diluted in 1% Blocker. The HA ELISA plate(s) are washed one time with PBS-T and 100 μl per well of diluted HA reference antigen and HA Test Samples are added to Row B. 50 μl per well of 1% Blocker is added to all remaining wells. The samples are serially diluted down the plate by transferring 50 μl per well from row B to row G, mixing 4–5 times with the pipette before each transfer. The plate(s) are covered and incubated 1 hour (+10 minutes) at 37° C.±2° C. The ELISA plate(s) are washed three times with PBS-T. Fifty μl of chicken anti-AIV polyclonal antisera in 50% glycerol (1:2000) in 3% Blocker is added to each well and the plates are covered and incubated 1 hour (+10 minutes) at 37° C.±2° C. The ELISA plate(s) are washed three times with PBS-T and then 50 μl of goat anti-chicken IgG in 50% glycerol (1:3000) in 3% Blocker is added to each well. The plates are covered and incubated 1 hour (+10 minutes) at 37° C.±2° C. The ELISA plate(s) are washed three times with PBS-T and 50 μl of ABTS Peroxidase Substrate Solution (equilibrated at RT for at least 30 minutes) is added to each well. The plate(s) are covered and incubated at RT in the dark for 15–20 minutes. The Optical Density (OD) of the wells read at a wavelength of 405 nm (with a 492 nm Reference Filter). The initial dilution of the HA Reference Antigen should be within 0.7–1.0 OD, this serves as the positive control for the ELISA.

EXAMPLE 7

Serum ELISA

NDV-HN

Plates are coated with rabbit α-NDV pooled antiserum (Mixed 1:2 with 50% glycerol in water) diluted (1:2000) in 0.01 M borate buffer (100 μl/well). Plates are incubated overnight at 2–7° C., covered and then equilibrated for approximately 20–30 minutes at room temperature. Plates are washed 3× with PBS-T (1×PBS+0.05% Tween-20) at 300 μl/well with the Titertek M96 plate washer or equivalent. Plates are blocked with 5% skim milk in PBS-T (Blocking Buffer) (200 μl/well) and incubated for 2 hours at 37° C. Plates are washed 1× with PBS-T at 300 μl/well with the Titertek M96 plate washer or equivalent. NDV allantoic fluid is diluted 1:200 in Blocking Buffer. 100 μl/well of the diluted antigen is added to the plate, and plates are incubated for 1 hour at 37 ° C. Plates are washed 3× with PBS-T at 300 μl/well with the Titertek M96 plate washer or equivalent. Test chicken serum samples are diluted (1:50). Negative control serum is diluted (1:50) (Neg. Control 27NOV00). Positive control serum is diluted (1:10,000 or 1:20,000) (SPAFAS Chicken α-NDV serum). All serum samples are diluted in Blocking Buffer. 100 μl/well of Negative Control Serum is added to Column 1 Rows B-G; 200 μl/well of Positive Control Serum is added to Columns 2–3 Row A; 200 μl/well of Test Serum Samples is added to Rows A appropriate columns. This allows 4 samples per plate with 8 dilutions per sample. 100 μl/well of Blocking Buffer is added to all remaining wells The Positive Control Serum and the Test Serum Samples are serially two-fold diluted down the plate. The samples are diluted down the plate from Row A to Row H, discarding the remaining 100 μl/well. Plates are incubated for 1 hour at 37 ° C. and then washed 3× with PBS-T at 300 μl/well with the Titertek M96 plate washer or equivalent. The Goat α-Chicken IgG (H&L)-HRP is diluted (1:3000) in Blocking Buffer. 100 μl/well of the diluted conjugate is added to each plate. Once the conjugate is added to the plates, the ABTS substrate is equilibrated at RT in the dark. Plates are incubated for 1 hour at 37 ° C. and then washed 3× with PBS-T at 300 μl/well using the Titertek M96 plate washer or equivalent. 100 μl/well of pre-warmed ABTS substrate is added to each plate, waiting 2–3 minutes between plates. Plates are read at dual wavelength 405/490 nm on the Tecan Sunrise plate reader or equivalent when the first dilution of the positive control reaches an absorbance of between 0.7 and 1.0.

AIV-HA

Plates are coated with Rabbit α-HA pooled antiserum diluted (1:1000) in 0.01 M borate buffer and incubated overnight at 2–7° C., covered. Plates are equilibrated for approximately 20–30 minutes at room temperature and then washed 3× with PBS-T (PBS Stock+0.05% Tween-20) at 300 μl/well using the Titertek M96 plate washer or equivalent. The plates are blocked with 5% skim milk in PBS-T (Blocking Buffer) (200μl/well) and incubated for 1 hour at 37 ° C. The plates are washed 1× with PBS-T at 300 μl/well using the Titertek M96 plate washer or equivalent. Inactivated T/W/68 AIV Allantoic Fluid is diluted (1:100) in Blocking Buffer and 100 μl/well of the diluted antigen is added to the plate. Plates are incubated for 1 hour at 37° C. The plates are washed 3× with PBS-T at 300 μl/well using the Titertek M96 plate washer or equivalent. Test chicken serum samples are diluted (1:50). Negative control serum is diluted (1:50). Positive control serum is diluted (1:25600) (USDA/SEPRL Chicken α-AIV (T/W/68 antiserum) All serum is diluted in Blocking Buffer. 100 μl/well of Negative Control Serum is added to Column 1 Rows B-G; 200 μl/well of Positive Control Serum is added to Columns 2–3 Row A; 200 μl/well of Test Serum Samples is added to Row A in appropriate columns; 100 μl/well of Blocking Buffer is added to all remaining wells. The Positive Control Serum and the Test Serum Samples are serially diluted two-fold down the plate, discarding the remaining 100 μl/well. The plates are incubated for 1 hour at 37° C. The plates are washed 3× with PBS-T (300 μl/well) using the Titertek M96 plate washer or equivalent. Goat α-Chicken IgG (H&L)-HRP is diluted (1:3000) in Blocking Buffer and 100 μl/well of the diluted conjugate is added to each plate. Once the conjugate is added to the plates, the ABTS substrate is equilibrated at RT in the dark. The plates are incubated for 1 hour at 37° C. and then washed 3× with PBS-T at 300 μl/well using the Titertek M96 plate washer or equivalent. 100 μl/well of equilibrated ABTS substrate is added to each plate, leaving 2–3 minutes between plates. Plates are read at dual wavelength 405/490 nm on the Tecan Sunrise plate reader or equivalent when the first dilution of the positive control reaches an absorbance of between 0.7 and 1.0.

EXAMPLE 8

Antigenicity in Rabbits

To test whether the plant derived protein extracted in non-detergent as described above would generate antibody in target animals species both HA and HN protein were prepared and inoculated into rabbits. New Zealand White rabbits 3 months of age were inoculated with HA-AIV or HN-NDV according to the dose schedule provided in Table 3. For the primary inoculation the antigen was mixed with Complete Freund's Adjuvant (CFA) and Incomplete Freund's Adjuvant was used for all booster inoculations. The antibody titers induced by both proteins are provided in Table 4. The results indicate that after two inoculations HAI antibody titers were induced by both proteins. However, the titers of the AIV-HA inoculated rabbits were higher than those induced by the NDV-HN protein. This may be significant since the AIV/HA protein had lower overall biological activity (hemagglutination) per unit of AIV-HA protein than NDV-HN (Table 3 column 4). This may indicate that the AIV-HA protein derived from plants is more potent per unit of protein than the NDV-HN protein considering that the quantitation methods from both proteins are accurate. It also suggests that the AIV-HA protein formulated in this manner would be immunogenic in chickens.

TABLE 3

Dose levels for inoculation into rabbits

| Sample | Hemagglutination Endpoint Titers | ELISA Results (ug protein/ml) | BCA TSP[1] Results (mg/ml) | Hemag-glutination units per ug protein |
|---|---|---|---|---|
| NT Control | ≦2 | 0.00 | 1.44 | 0 |
| CHN-7 | 2048 | 13.53 | 2.48 | 3027 |
| CHN-18 | 1024 | 9.21 | 4.10 | 2223 |
| CHA-13 | 32 | 3.80 | 6.15 | 168 |
| CHA-47 | 16 | 2.88 | 5.25 | 111 |

[1]All NT-1 samples were provided from non freeze-dried material.
BCA—bicinchoninic acid, primary component of Pierce Chemical BCA protein assay kit;
TSP—total soluble protein.

TABLE 4

Serology Results from NT-1 derived AIV-HA and NDV-HN inoculated rabbits

| Treatment with | Sample | NDV HAI Titers | | | | NDV ELISA Titers | | | |
|---|---|---|---|---|---|---|---|---|---|
| NDV-HN | Number | Pre-Bleed | 6 week | 8 week | 10 week | Pre-Bleed | 6 week | 8 week | 10 week |
| Sup from NT Control Cells | 2723 | ≦8 | ≦8 | ≦8 | ≦8 | 0 | 0 | 0 | 0 |
| Sup from HN - 18 Cells | 2724 | ≦8 | 23 | 23 | 23 | 0 | 815 | 554 | 888 |
| Sup from HN - 18 Cells | 2725 | ≦8 | 11 | 23 | 23 | 0 | 0 | 585 | 591 |

TABLE 4-continued

Serology Results from NT-1 derived AIV-HA and NDV-HN inoculated rabbits

| | | | | | | | | | |
|---|---|---|---|---|---|---|---|---|---|
| Sup from HN - 7 Cells | 2726 | ≦8 | 45 | 23 | 23 | 0 | 607 | 461 | 0 |
| Sup from HN - 7 Cells | 2727 | ≦8 | 45 | 45 | 45 | 0 | 1396 | 2008 | 1270 |
| Treatment with | Sample | AIV HAI Titers | | | | AIV ELISA Titers | | | |
| AIV-HA | Number | Pre-Bleed | 6 week | 8 week | 10 week | Pre-Bleed | 6 week | 8 week | 10 week |
| Sup from NT Control Cells | 2723 | ≦8 | ≦8 | ≦8 | ≦8 | <25 | <25 | <25 | <25 |
| Sup from HA - 13 Cells | 2728 | ≦8 | 362 | 362 | 362 | <25 | 25600 | 25600 | 25600 |
| Sup from HA - 13 Cells | 2729 | ≦8 | 181 | 181 | 11 | <25 | 3200 | 3200 | <25 |
| Sup from HA - 47 Cells | 2730 | ≦8 | 181 | 362 | 724 | <25 | 12800 | 25600 | 25600 |
| Sup from HA - 47 Cells | 2731 | ≦8 | ≦8 | 362 | 362 | <25 | 50 | 12800 | 25600 |

To examine the efficacy of the plant derived antigens in chickens the HN protein was inoculated into chickens that were 2 days of age and 10 days of age. The dose concentrations used for these studies are provided in Table 5. All vaccine inoculum were formulated with the soluble fraction of NT-1 cells grown 15–20 days in shaker flasks at 25° C. Adjuvant used in both trials was MPL-TDM from Corixa, Inc. Intranasal groups were given MPL alone as the adjuvant.

EXAMPLE 9

Challenge in Poultry

Two-day old SPF chicks were inoculated by various routes using biologically active (hemagglutination positive) NDV-HN protein derived from NT-1 with the amount of HN protein per inoculation shown in Table 5. The serological and challenge results of this trial are provided in Table 6. All control groups responded as expected in that birds not receiving NDV-HN antigen in the inoculum had 100% mortality, whereas, control birds receiving 20 ug of native NDV by SQ had 100% survival. In the experimental treatment groups there was 75% protection in group #3 (SQ inoculation without adjuvant) and 80% protection in group #4 (SQ inoculation with adjuvant). The remaining treatment groups, which were inoculated by IN and oral routes, had 100% mortality. However, in group 6 two birds had a delay in mortality, indicating that these birds may have been sensitized to vaccination (see Table 9)

TABLE 5

Dose levels used per inoculation for poultry trial

| | ug HN/Bird | | |
|---|---|---|---|
| Group | Day 0 | Day 14 | Day 21 |
| NT Control (SQ) | 0 | 0 | 0 |
| NDV All. Fluid (SQ) | 20 | 20 | 20 |
| HN Tobacco (SQ) | 150 | 230 | 180 |
| HN Tobacco (IN) | 6 | 14 | 14 |
| HN Tobacco (OG) | 114 | 282 | 136 |
| HN Tobacco (OG + OF) | 114og + 700of* | 282og/1400of* | 136 + 2366* |
| Average hemagglutination units per ug HN | 3590 | 5810 | 6025 |

*Dose based on wet weight expression per mass cells mixed with feed;
IN—intranasal;
SQ—subcutaneous;
OG—oral gavage;
OF-on feed mixtures.

TABLE 6

Serology and challenge results from poultry trial

| | | NDV HAI titers | | | | | NDV ELISA titers | | | |
|---|---|---|---|---|---|---|---|---|---|---|
| Treatment | Sample Number | Day 14 | Day 21 | Day 28 | Pre Chall. | Post Chall. | Day 28 | Pre Chall. | Post Chall. | Surv. Chall. |
| 1. Control NT Cells | 924 | ≦8 | ≦8 | ≦8 | ≦8 | na | 0 | 0 | 0 | No |
| SQ | 1061 | ≦8 | ≦8 | ≦8 | ≦8 | na | 0 | 0 | 0 | No |
| | 1073 | ≦8 | ≦8 | ≦8 | ≦8 | na | 0 | 0 | 0 | No |
| | 1077 | ≦8 | ≦8 | ≦8 | ≦8 | na | 0 | 0 | 0 | No |
| | 1081 | ≦8 | ≦8 | ≦8 | ≦8 | na | 0 | 0 | 0 | No |
| 2. NDV HN allantoic | 1063 | 11 | 1448 | 2896 | 724 | 724 | 11956 | 9245 | 7294 | Yes |
| fluid SQ | 1068 | 11 | 1448 | 1024 | 724 | 362 | 9216 | 7639 | 6122 | Yes |
| | 1072 | 45 | 1448 | 1448 | 724 | 362 | 11592 | 7500 | 5937 | Yes |
| | 1083 | 23 | 724 | 724 | 181 | 91 | 5697 | 4919 | 3011 | Yes |
| | 1089 | 45 | 1024 | 1448 | 362 | 181 | 15181 | 7449 | 6085 | Yes |

TABLE 6-continued

Serology and challenge results from poultry trial

| Treatment | Sample Number | NDV HAI titers Day 14 | Day 21 | Day 28 | Pre Chall. | Post Chall. | NDV ELISA titers Day 28 | Pre Chall. | Post Chall. | Surv. Chall. |
|---|---|---|---|---|---|---|---|---|---|---|
| 3. NDV HN tobacco | 797 | 23 | 45 | 45 | ≦8 | 2896 | 0 | 0 | 19036 | Yes |
| SQ | 1066 | ≦8 | 16 | 45 | ≦8 | 724 | 450 | 0 | 15087 | Yes |
| | 1085 | ≦8 | ≦8 | 23 | ≦8 | na | 0 | 0 | na | No |
| | 1095 | ≦8 | 23 | 45 | ≦8 | 724 | 436 | 0 | 10043 | Yes |
| 4. ND V HN tobacco | 1067 | 11 | 45 | 45 | ≦8 | 181 | 592 | 0 | 4912 | Yes |
| MPL/TDM adjuvant | 1080 | ≦8 | 181 | 181 | 45 | 181 | 1911 | 871 | 5048 | Yes |
| SQ | 1093 | 11 | 45 | 45 | ≦8 | ≦8 | 0 | 0 | 0 | Yes |
| | 1094 | 11 | 91 | 91 | 11 | 11 | 747 | 199 | 0 | Yes |
| | **1098** | ≦8 | 23 | 45 | ≦8 | na | 0 | 0 | na | No |
| 5. NDV HN tobacco | 796 | ≦8 | ≦8 | ≦8 | ≦8 | na | 0 | 0 | na | No |
| IN | 925 | ≦8 | ≦8 | ≦8 | ≦8 | na | 0 | 0 | na | No |
| | 1065 | ≦8 | ≦8 | ≦8 | ≦8 | na | 0 | 0 | na | No |
| | 1084 | ≦8 | ≦8 | ≦8 | ≦8 | na | 0 | 0 | na | No |
| | 1092 | ≦8 | ≦8 | ≦8 | ≦8 | na | 0 | 0 | na | No |
| 6. NDV HN tobacco + MPL | 921 | ≦8 | ≦8 | ≦8 | ≦8 | na | 0 | 0 | na | No |
| adjuvant | **923** | ≦8 | 11 | ≦8 | ≦8 | na | 0 | 0 | na | No |
| IN | 1069 | ≦8 | ≦8 | ≦8 | ≦8 | na | 0 | 0 | na | No |
| | 1074 | ≦8 | 11 | ≦8 | ≦8 | na | 0 | 0 | na | No |
| | **1088** | ≦8 | 11 | 8 | ≦8 | na | 0 | 0 | na | No |
| 7. NDV HN tobacco | 723 | ≦8 | ≦8 | ≦8 | ≦8 | na | 0 | 0 | na | No |
| Oral gavage | 1062 | ≦8 | ≦8 | ≦8 | ≦8 | na | 0 | 0 | na | No |
| | 1075 | ≦8 | 8 | ≦8 | ≦8 | na | 0 | 0 | na | No |
| | 1079 | ≦8 | 8 | ≦8 | ≦8 | na | 0 | 0 | na | No |
| | 1086 | ≦8 | ≦8 | ≦8 | ≦8 | na | 0 | 0 | na | No |
| 8. NDV HN tobacco + MPL/ | 1070 | ≦8 | ≦8 | ≦8 | ≦8 | na | 0 | 0 | na | No |
| TDM adjuvant | 1082 | ≦8 | ≦8 | ≦8 | ≦8 | na | 0 | 0 | na | No |
| Oral gavage + On feed | 1091 | ≦8 | ≦8 | ≦8 | ≦8 | na | 0 | 0 | na | No |
| | 1097 | ≦8 | ≦8 | ≦8 | ≦8 | na | 0 | 0 | na | No |
| | 1100 | ≦8 | ≦8 | ≦8 | ≦8 | na | 0 | 0 | na | No |

All birds receive $10^2$ $EID_{50}$ Texas GB strain of NDV. Birds were challenged 24 days post last vaccination. Bird numbers bolded had a delayed onset to mortality see Table 9.

In a subsequent trial, eighteen 10-day old SPF birds were inoculated according to the schedule and dose amounts described in Table 7. Results of this trial are shown in Table 8. One control group (#3), a non-vaccinated non-challenged treatment was used to show that the housing and facility had no adverse affects on general health of the chickens. Control groups in this trial also responded as expected. Since birds from both trials were challenged at the same facility, treatment group #2 served as a positive control for both poultry trials. In the remaining groups, all of which were inoculated SQ with HN derived from NT-1 cells, there was 100% survival in group #7, 80% survival in each of groups 5 and 6, and 60% survival in group 4 (see Table 8).

TABLE 7

Dose levels of antigen used per inoculation

| Group | ug HN/Bird (Subcutaneous) Day 0 | Day 14 | Day 21 |
|---|---|---|---|
| NT Control | 0 | 0 | 0 |
| NDV All. Fluid | 20 | 20 | 20 |
| HN Tobacco (Low Dose) | 20 | 20 | 20 |

TABLE 7-continued

Dose levels of antigen used per inoculation

| Group | ug HN/Bird (Subcutaneous) Day 0 | Day 14 | Day 21 |
|---|---|---|---|
| HN Tobacco (High Dose) | 150 | 100 | 100 |
| Average hemagglutination units per ug HN | 3590 | 2625 | 2625 |

Conclusions: Using a procedure that provides recovery of hemagglutination of HA and HN protein, preparations for these plant-derived proteins were inoculated into two separate animal species by subcutaneous (SQ) route to determine if antibody could be induced that will inhibit hemagglutination (HAI antibody). In one trial, HN protein was formulated to have high hemagglutination activity to total soluble protein ratios. These materials were then inoculated by SQ, intranasal (IN) and by oral routes. The results indicate that both HA-AIV and HN-NDV protein derived from NT-1 cells will induce hemagglutination inhibition (H) antibody in rabbits when formulated in this manner. In addition, HN- NDV derived from NT-1 inoculated by SQ route in chickens will induce (HAI) antibodies and protect against virulent NDV challenge.

The results from these trials indicate that the HN-NDV protein derived from NT-1 cells is immunogenic in birds when inoculated by SQ. In most cases birds protected from challenge had a detectable HAI titer post challenge, however, there were exceptions to this observation. Two birds (bird #1093 and #1047, respectively) did not have a detectable HAI or ELISA titer after challenge but survived challenge (Tables 6 and 8).

vaccinated with Newcastle disease virus as determined by the under-agarose leukocyte-migration inhibition technique. *Avian Dis.* 35: 360–364).

In some cases, although there was a detectable titer at the end of the vaccination schedule at day 28, there was no protection to challenge. However, in all cases when this situation occurred there was no detectable antibody titer before (on the day of challenge) or after challenge indicating that these birds were not sensitized effectively (compare Tables 4 and 6). Differences observed between the two poultry trials may be attributed to the fact that antigen used

TABLE 8

Serology and challenge results

| Treatment | Sample Number | NDV HAI titer Day 21 | Day 28 | Pre Chall. | Post Chall. | NDV ELISA titers Day 21 | Day 28 | Pre Chall. | Post Chall. | Surv. Chall. |
|---|---|---|---|---|---|---|---|---|---|---|
| 1. Control allantoic | 1026 | ≦8 | ≦8 | ≦8 | na | 0 | 0 | 0 | na | No |
| fluid | 1027 | ≦8 | ≦8 | ≦8 | na | 0 | 0 | 0 | na | No |
| | 1028 | ≦8 | ≦8 | ≦8 | na | 0 | 0 | 0 | na | No |
| | 1029 | ≦8 | ≦8 | ≦8 | na | 0 | 0 | 0 | na | No |
| | 1030 | ≦8 | ≦8 | ≦8 | na | 0 | 0 | 0 | na | No |
| 2. NDV HN allantoic | 1031 | 362 | 91 | 181 | 91 | 9177 | 6937 | 5533 | 3551 | Yes |
| fluid | 1032 | 362 | 724 | 181 | 91 | 12393 | 16533 | 7909 | 6080 | Yes |
| 20 ug/dose | 1033 | 724 | 362 | 181 | 181 | 8622 | 15291 | 6766 | 6362 | Yes |
| | 1034 | 362 | 181 | 181 | 181 | 7875 | 10071 | 6487 | 5822 | Yes |
| | 1035 | 724 | 724 | 181 | 181 | 9681 | 16133 | 7537 | 6539 | Yes |
| 3. Control tobacco | 1036 | ≦8 | 23 | ≦8 | ≦8 | 0 | 0 | 0 | 0 | n/c |
| | 1037 | ≦8 | 11 | ≦8 | ≦8 | 0 | 0 | 0 | 0 | n/c |
| | 1038 | ≦8 | ≦8 | ≦8 | ≦8 | 0 | 0 | 0 | 0 | n/c |
| | 1039 | ≦8 | ≦8 | ≦8 | ≦8 | 0 | 0 | 0 | 0 | n/c |
| | 1040 | ≦8 | 23 | ≦8 | ≦8 | 0 | 0 | 0 | 0 | n/c |
| 4. NDV HN tobacco | 1041 | 11 | ≦8 | ≦8 | 1448 | 0 | 0 | 0 | 14042 | Yes |
| 20 ug/dose | 1042 | 23 | 11 | ≦8 | 2896 | 0 | 0 | 0 | 19263 | Yes |
| | 1043 | 32 | 11 | ≦8 | na | 0 | 0 | 0 | na | No |
| | 1044 | ≦8 | 11 | ≦8 | na | 0 | 0 | 0 | na | No |
| | 1045 | 23 | 11 | ≦8 | 1024 | 0 | 0 | 0 | 11770 | Yes |
| 5. NDV HN tobacco | 1046 | 23 | 23 | ≦8 | 1448 | 0 | 674 | 0 | 11243 | Yes |
| 20 ug/dose + MPL/ | 1047 | 23 | 23 | ≦8 | ≦8 | 0 | 963 | 0 | 0 | Yes |
| TDM | 1048 | 23 | 23 | ≦8 | na | 396 | 757 | 0 | na | No |
| emulsion adjuvant | 1049 | 45 | 23 | ≦8 | 362 | 0 | 804 | 0 | 6239 | Yes |
| | 1050 | 11 | 11 | ≦8 | 1448 | 0 | 398 | 0 | 15948 | Yes |
| 6. NDV HN tobacco | 1051 | 91 | 45 | 23 | 181 | 1096 | 1137 | 565 | 4547 | Yes |
| 250 ug/dose | 1052 | 45 | 45 | ≦8 | 181 | 1166 | 998 | 0 | 7376 | Yes |
| | 1053 | 23 | 23 | ≦8 | 2896 | 0 | 0 | 0 | 16712 | Yes |
| | 1054 | 23 | 23 | ≦8 | na | 646 | 838 | 0 | na | No |
| | 1055 | 45 | 45 | 23 | 91 | 705 | 563 | 448 | 4902 | Yes |
| 7. NDV HN tobacco | 1056 | 45 | 45 | 11 | 23 | 746 | 948 | 174 | 926 | Yes |
| 250 ug/dose + MPL/ | 1057 | 45 | 23 | 11 | 724 | 556 | 892 | 0 | 11542 | Yes |
| TDM | 1058 | 45 | 23 | 23 | 724 | 780 | 1588 | 630 | 9915 | Yes |
| emulsion adjuvant | 1059 | 91 | 64 | 23 | 91 | 2004 | 3090 | 1016 | 4690 | Yes |
| | 1060 | 45 | 45 | 11 | 181 | 916 | 1522 | 448 | 6620 | Yes |

All birds received $10^2$ $EID_{50}$ Texas GB strain of NDV, except group 1, which received $10^4$ $EID_{50}$ Texas GB strain of NDV and group 3, which was the non-challenge control. Birds were challenged 31 days post last vaccination. Bird numbers bolded had a delayed onset to mortality see Table 9.
n/c—nonchallenged.

Typically, a high titer response after challenge is indicative of a good sensitizing immunization, yet, it is not unprecedented with native or recombinant derived NDV antigen that birds will be protected without a detectable HAI or ELISA antibody titer (Winterfield, R. W., Dhillon, A. S., and L. J. Alby, 1979. Vaccination of Chickens against Newcastle Disease with Live and Inactivated Newcastle Disease Virus. *Poultry. Sci.* 59: 240–246). It is proposed that either a cellular immune response or a local immune response is involved with providing immune protection in a vaccinated bird where no humoral antibody response can be detected (Agrawal, P. K. and D. L. Reynolds. 1991. Evaluation of the cell mediated immune response of chickens in the first trial had a much higher biological activity per microgram of HN. Antigen used in this trial had at least a 2 fold higher level of hemagglutination activity per microgram of protein than antigen in the latter trial (compare Tables 5 and 7). This may be one reason why birds treated with non-adjuvanted antigen (group #3, Table 6) developed detectable ELISA and HAI titers by day 28, whereas, birds treated with non-adjuvanted antigen (group #4, Table 8) did not show ELISA titers by day 28. Another difference which may have contributed to the results is the age of the birds. Birds in the first trial were vaccinated at day 2 of age, whereas, birds in the second trial were vaccinated at day 10 of age.

TABLE 9

Death on days after challenge

| Group # | Treatment | Route | Chall. | D 1 | D 2 | D 3 | D 4 | D 5 | D 6 | D 7 | D 8 | D 9 | D 10 | D 11–14 | % Surv. |
|---|---|---|---|---|---|---|---|---|---|---|---|---|---|---|---|
| 1-018 | Control allantoic fluid | SQ | $10^4$ $EID_{50}$ | 0 | 0 | 3 | 2 | — | — | — | — | — | — | — | 0 |
| 2-018 | NDV HN allantoic fluid - 20 ug/dose | SQ | $10^2$ $EID_{50}$ | 0 | 0 | 0 | 0 | 0 | 0 | 0 | 0 | 0 | 0 | 0 | 100 |
| 3-018 | Control tobacco | SQ | None | 0 | 0 | 0 | 0 | 0 | 0 | 0 | 0 | 0 | 0 | 0 | 100 |
| 4-018 | NDV HN tobacco derived - 20 ug/dose | SQ | $10^2$ $EID_{50}$ | 0 | 0 | 0 | 0 | 1 | 0 | 0 | 0 | 1 | — | — | 60 |
| 5-018 | NDV HN tobacco derived - 20 ug/dose + MPL/TDM Emulsion adjuvant | SQ | $10^2$ $EID_{50}$ | 0 | 0 | 0 | 0 | 0 | 1 | 0 | 0 | 0 | 0 | 0 | 80 |
| 6-018 | NDV HN tobacco derived 250 ug/dose | SQ | $10^2$ $EID_{50}$ | 0 | 0 | 0 | 0 | 0 | 0 | 1 | 0 | 0 | 0 | 0 | 80 |
| 7-018 | NDV HN tobacco derived 250 ug/dose + MPL/TDM Emulsion adjuvant | SQ | $10^2$ $EID_{50}$ | 0 | 0 | 0 | 0 | 0 | 0 | 0 | 0 | 0 | 0 | 0 | 100 |
| 1-016 | Control tobacco | SQ | $10^2$ $EID_{50}$ | 0 | 0 | 0 | 4 | 1 | — | — | — | — | — | — | 0 |
| 2-016 | NDV HN allantoic fluid | SQ | $10^2$ $EID_{50}$ | 0 | 0 | 0 | 0 | 0 | 0 | 0 | 0 | 0 | 0 | 0 | 100 |
| 3-016 | NDV HN tobacco derived | SQ | $10^2$ $EID_{50}$ | 0 | 0 | 0 | 0 | 0 | 0 | 0 | 0 | 0 | 0 | 1 | 80 |
| 4-016 | NDV HN tobacco derived + MPL/ TDM Emulsion adjuvant | SQ | $10^2$ EID50 | 0 | 0 | 0 | 0 | 0 | 0 | 1 | 0 | 0 | 0 | 0 | 80 |
| 5-016 | NDV HN tobacco derived | IN | $10^2$ $EID_{50}$ | 0 | 0 | 0 | 2 | 3 | — | — | — | — | — | — | 0 |
| 6-016 | NDV HN tobacco derived + MPL adjuvant | IN | $10^2$ $EID_{50}$ | 0 | 0 | 0 | 3 | 0 | 0 | 0 | 2 | — | — | — | 0 |
| 7-016 | NDV HN tobacco derived | oral gav. | $10^2$ $EID_{50}$ | 0 | 0 | 0 | 3 | 2 | — | — | — | — | — | — | 0 |
| 8-016 | NDV HN tobacco derived + MPL/ TDM adj | oral | $10^2$ $EID_{50}$ | 0 | 0 | 0 | 2 | 3 | — | — | — | — | — | — | 0 |

Adjuvant also seems to be an important feature in formulating the antigen in these trials. Although the adjuvant effect was not evident when using higher doses of NT-1 derived NDV-HN (compare groups 3 and 4, Table 6 with groups 6 and 7, Table 8), there was a clear adjuvant effect when using a low dose of NDV-HN (compare groups 4 and 5, Table 8). In addition, although there was 100% mortality in groups inoculated by intranasal route, the group that received adjuvant had 2 birds (#923 and #1088) that did not die until day 8, which was 3 days after all negative control birds had succumbed to challenge (Table 9). The significance of the delay to mortality in the intranasal group receiving adjuvanted antigen is not significant, however, it is interesting that birds #923 and #1088 were two birds with detectable HAI antibody titers at day 21 of the trial and were treated with less antigen per dose than the other treatment groups (see Table 5).

It is clear from the data provided here that HN-NDV derived from transformed NT-1 cells is efficacious against virulent challenge to NDV. The immune response to the plant derived antigen has several similarities to immune response to native antigen. 1) Although the antibody titers are higher for native antigen pre-challenge, a 20 ug dose inoculated SQ will provide protection against challenge for both native and plant derived antigen. 2) Antibody titers must have similar duration of response in that in both studies challenge was performed 24 days and 31 days post vaccination. 3) All birds producing a positive HAI antibody response (above background) at the end of the vaccination schedule and post challenge were protected from NDV associated pathology.

No birds were protected from challenge when inoculated by oral or intranasal route. In the case of the oral administered birds, inoculums of 100 to 300 ug of HN-NDV soluble protein from NT-1 cells along with 700 to 2400 ug of HN-NDV feed as whole wet cells per inoculation did not elicit a detectable antibody titer after three doses nor were birds protected from challenge. Because the HN-NDV from NT-1 has definite binding capability to red blood cells and to (CEF) chick embryo fibroblasts, the ability to bind to native receptors did not supplement binding or delivery to antigen sampling sites on the bird mucosal surface in this study.

The data provided here show that HN-NDV antigen derived from transgenic NT-1 cell culture will protect against virulent challenge when administered SQ. Furthermore, despite feeding several milligrams of antigen in the oral treatment groups, no HAI antibody was induced in the systemic compartment and no protection against challenge was observed. Thus, as previous data have shown, antigens that do not have a natural affinity or invasiveness for the antigen presenting sites on the mucosal surface need to be targeted to those sites with the aid of a protein that does sensitize the mucosal surface.

EXAMPLE 10

Preparation and Analysis of Transgenic Potato

Binary vectors pCHN, pgHN, pMHN and pCHA were used to transform potato (cv. Desiree) and transgenic tubers analysed for expression of the recombinant HN antigen from NDV, or the recombinant HA antigen from Avian Influenza Virus.

Plant material. In vitro plants of *Solanum tuberosum* cv Desiree were provided by Dr. Steven Slack, Department of Plant Pathology, Cornell University. For propagation, nodal segments were transferred to a shoot propagation medium designated CM which contained MS salts (Murashige and Skoog, 1962), 100 mg/l myoinositol, 0.4 mg/l thiamine, 20 g/l sucrose, and 8 g/l Agar/Agar (Sigma Chemical Co., St. Louis, Mo.; catalog #A-1296). The pH of the medium was adjusted to pH 5.7 before the addition of the Agar/Agar. One nodal explant was placed in each test tube and maintained at 24°±1 ° C. under a photoperiod of 16 h (light)/8 h (dark) at 74 μE $m^{-2}s^{-1}$. The source of light for these cultures and those described throughout this report was from a mixture of cool and warm fluorescent bulbs (F40CW and F40WW) (Philips Lighting Co., www.lighting.philips.com/index.htm). Nodal explants were harvested and transferred to fresh medium every 6 weeks.

*Agrobacterium* preparation. *Agrobacterium tumefaciens* containing the gene construct of interest was streaked from a glycerol stock maintained at −80° C. onto Petri plates of LB medium which contained 10 g/l bacto tryptone, 5 g/l yeast extract, 10 g/l NaCl, 50 mg/l spectinomycin, and 15 g/l Difco Bacto Agar (Difco Laboratories, Detroit, Mich.; catalog #DF 0140-01). Four well-formed colonies were picked with a sterile pipet tip, then added to 50 ml of YM medium (Gibco BRL cat. #10090-011) containing 50 mg/l spectinomycin. Cultures were grown in a shaking incubator at 28° C. and 100 rpm for 24 hrs, or until the culture reached an $OD_{600}$ of 0.5–0.7. It takes approximately 24 hrs to reach this OD. When the desired OD was reached, the cells were centrifuged at 8000 rpm for 10 min at 20° C. The pellet was resuspended in MS liquid medium (MS salts, 2 mg/l glycine, 0.5 mg/l nicotinic acid, 0.5 mg/l pyridoxine, 0.4 mg/l thiamine, 0.25 mg/l folic acid, 0.05 mg/l d-biotin, 100 mg/l myoinositol, 30 g/l sucrose, pH 5.6) at the same original volume as the YM selective medium.

Infection. Stem internode segments 0.5–1 cm in length were excised from six-week-old in vitro plants and inoculated the same day. Approximately 100 internode explants were incubated per 50 ml of inoculum for 10 min, agitating occasionally. After the incubation, they were blotted onto sterile filter paper, then transferred to medium designated CIM which contained MS salts, 2 mg/l glycine, 0.5 mg/l nicotinic acid, 0.5 mg/l pyridoxine, 0.4 mg/l thiamine, 0.25 mg/l folic acid, 0.05 mg/l D-biotin, 100 mg/l myoinositol, 30 g/l sucrose (grade II; PhytoTechnology Laboratories, Shawnee Mission, Kans.), 1 mg/l benzyladenine (BA), 2 mg/l naphthaleneacetic acid (NAA) (added after autoclaving), and 6 g/l Agar/Agar (PhytoTechnology Laboratories, Shawnee Mission, Kans.). The pH of the medium was adjusted to 5.6 before the addition of the Agar/Agar. One hundred explants were cultured per 100×20 mm Petri plates. All cultures were maintained at 24°±1° C. under a photoperiod of 16 h (light)/8 h (dark) at 74 μE $m^{-2}s^{-1}$.

Plant regeneration. After 48 hrs of cocultivation, the explants were transferred to 3C5ZR bialaphos selective medium which contained MS salts, 0.1 mg/l thiamine, 0.5 mg/l nicotinic acid, 0.5 mg/l pyridoxine, 100 mg/l myoinositol, 30 g/l sucrose, 0.5 mg/l indole-3-acetic acid (IAA) (added after autoclaving), 3 mg/l zeatin riboside (added after autoclaving), 500 mg/l carbenicillin (added after autoclaving) (Agri-Bio, Miami, Fla), 5 mg/l bialaphos (added after autoclaving) (Duchefa, located on the world wide web at duchefa.com/), and 8 g/l Agar/Agar. The pH of the medium was adjusted to 5.9 before the addition of the Agar/Agar. Twenty-five internode segments were cultured per 100×20 mm Petri plate and the plates were sealed with Nesco film (Karlan Research Products, Santa Rosa, Calif.). Explants were transferred weekly for 1 month, then every 10–14 days. All cultures were maintained at 24°±1° C. under a photoperiod of 16 h (light)/8 h (dark) at 74 μE $m^{-2}S^{-1}$.

When regenerants were approximately 0.5–1 cm in length, they were excised and transferred to bialaphos selective rooting medium which contained the same components as CM with the addition of 500 mg/l carbenicillin (added after autoclaving) and 5 mg/l bialaphos (added after autoclaving). Five regenerants were cultured per GA7 Magenta box. Once the shoots rooted, the shoot tip from each plant was transferred to CM in test tubes for maintenance.

Microtubers. Microtubers were induced on plant material for an early indication of expression in tubers. This was especially applicable for transgenic lines containing genes driven by the tuber-specific promoter, GBSS. Nodal segments were placed on microtuber medium which contained 1/2 strength MS salts, 5 mg/l kinetin, 80 g/l sucrose, 0.25 mM ancymidol (added after autoclaving), 9 g/l Agar/Agar. The pH of the medium was adjusted to 5.85 prior to the addition of the Agar/Agar. The cultures were maintained in the dark at 18° C. The microtubers were analyzed by ELISA for antigen expression levels.

PCR analysis. Genomic DNA was isolated from leaves from 3–4-week-old putative transformants. Leaf samples were homogenized at room temperature in 500 μl of an extraction buffer containing 200 mM Tris HCl (pH 7.5), 250 mM NaCl, 25 mM EDTA, and 0.5% SDS. They were allowed to remain at room temperature for 1 hr, then centrifuged at 12,000 rpm for 5 min. The supernatant was removed to a new tube, 500 μl of isopropanol was added, then the samples either remained at room temperature for 5–10 min, or were placed at −20° C. overnight. They were then centrifuged at 13,000 rpm for 5 min, and the supernatant was discarded. The resultant pellet was washed with 70% ethanol, dried, then resuspended in 100 μl of TE buffer.

The primer set was designed such that the forward primer was in the CVMV promoter and the reverse primer (PAT R2) was in the PAT gene which resulted in a product size of approximately 500 bp. Amplified DNA fragments were run on a 1% agarose gel, stained with ethidium bromide, and visualized under a UV light.

ELISA analysis of leaves. Leaf material was harvested into tubes then placed on ice. Lines with the highest antigen levels were selected for propagation, then transferred to the greenhouse.

Greenhouse acclimation. Plants with well-formed root systems were transferred to Jiffy 7 pots. The pots were placed in trays and covered with plastic domes. After approximately 2 weeks, the domes were removed. The plants were transferred to 3 gallon pots containing Cornell soil mix when the roots systems had grown through the mesh on the Jiffy 7 pots.

HN expression in pCHN-transformed potato plants. Potato (*Solanum tuberosum* L. cv. Desiree) plants were transformed with pCHN, and regenerated Bialaphos® resistant plants were screened for expression of HN in leaves by ELISA. Several lines were selected based on leaf expression (FIG. 26), propagated, and transplanted to soil for greenhouse culture. At maturity, tubers were harvested, extracted, and assayed for HN content by ELISA (FIG. 26). HN accumulation varied among individual tubers from the same line, but in general expression was correlated with the HN content of leaves within each line (FIG. 26). The best expression was observed in tubers of lines 6, 21, 27, and 34, with the highest accumulation observed at ~11 μg HN per g fresh tuber mass.

Particle behavior of potato tuber-expressed HN antigen. In order to evaluate assembly of NT1 cell-expressed antigen to form particulate structures, sucrose gradient sedimentation was performed on pCHN-transformed potato tuber extracts. The profiles shown in FIG. 27 indicate that the tuber-derived HN showed 2 peaks of ELISA reactive material, similar to the NT1 cell-derived HN shown in FIG. 24.

HN expression in potato plants transformed with pGHN and pGHN151. Potato (*Solanum tuberosum* L. cv. Desiree) plants were transformed with pGHN or pGHN151, and regenerated Bialaphos® resistant plants were screened for expression of HN in microtubers by ELISA. Several pGHN-transformed lines were selected based on microtuber expression (FIG. 28), propagated, and transplanted to soil for greenhouse culture. Transformation with pGHN151 was relatively inefficient, resulting in only one line that showed expression in microtubers (GHN151-6), which was transplanted to soil for greenhouse culture. At maturity, tubers were harvested, extracted, and assayed for HN content by ELISA (FIG. 28). HN accumulation varied among individual tubers from the same line, but in general expression was correlated with the HN content of microtubers within each line (FIG. 29). The best expression was observed in tubers of lines GHN-1, 30, 47, and 54, with the highest accumulation observed at ~40 μg HN per g fresh tuber mass. Expression in tubers of line GHN 151-6 varied between 6 and 12 μg HN per g fresh tuber mass. It is possible that the intron-containing GBSS promoter construct pGHN151 was unstable in transgenic plants or in *Agrobacterium*, resulting in poor expression with this construct.

Figure 16:
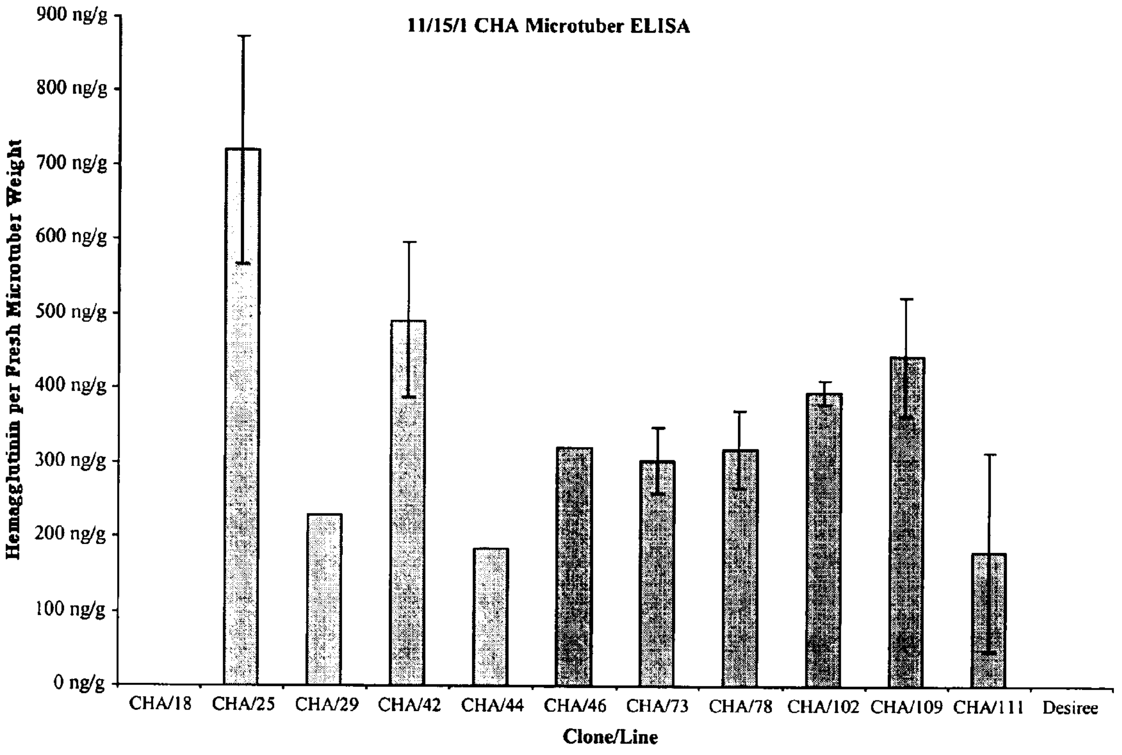
FIG. 16. HA expression in microtubers of pCHA-transformed potato plantlets. Microtubers were generated in vitro from stem nodes of tissue culture plantlets. Samples were extracted and assayed for HA by ELISA. Data are presented as ng HA per g fresh microtuber weight. Line numbers indicate independent transgenic lines. Desiree, a non-transformed line. Standard error bars represent standard deviation of multiple determinations.
Figure 17:
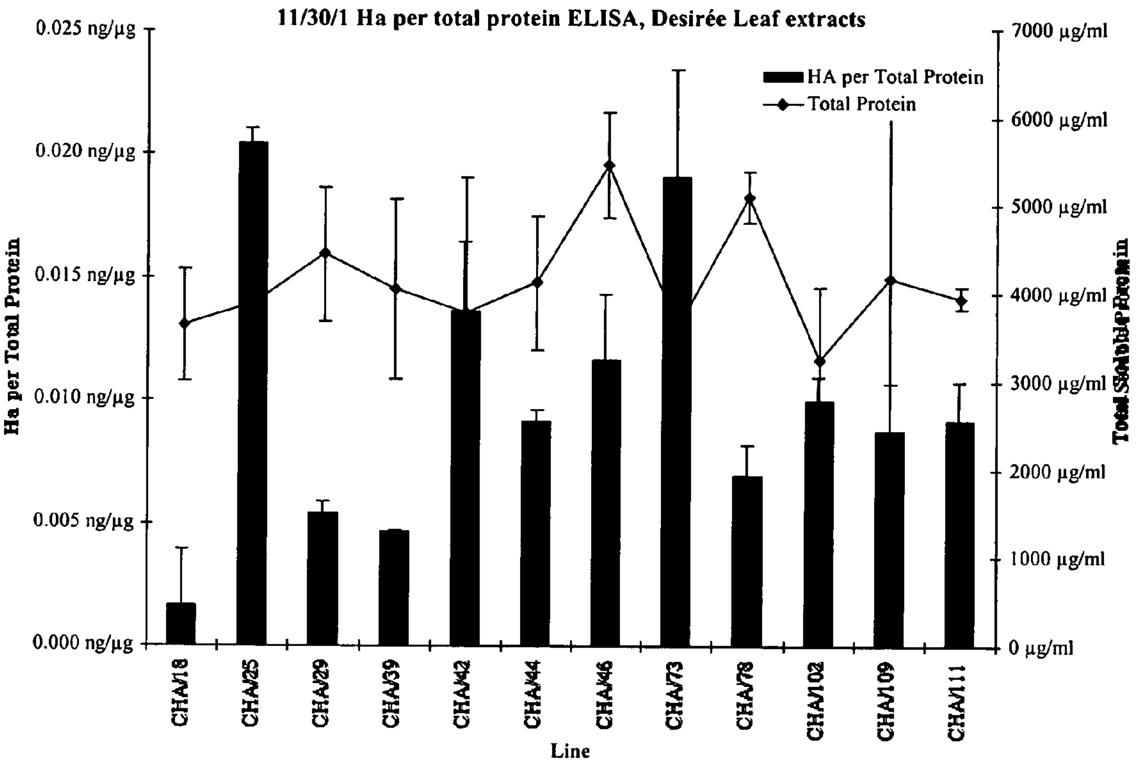
FIG. 17. HA expression in leaves of pCHA-transformed potato plants. Leaf samples from greenhouse-grown plants were extracted and assayed for HA by ELISA and for total protein by the Bradford method. Data are presented as ng HA per μg total protein. Line numbers indicate independent transgenic lines. Standard deviations of multiple determinations are shown.
Figure 18:
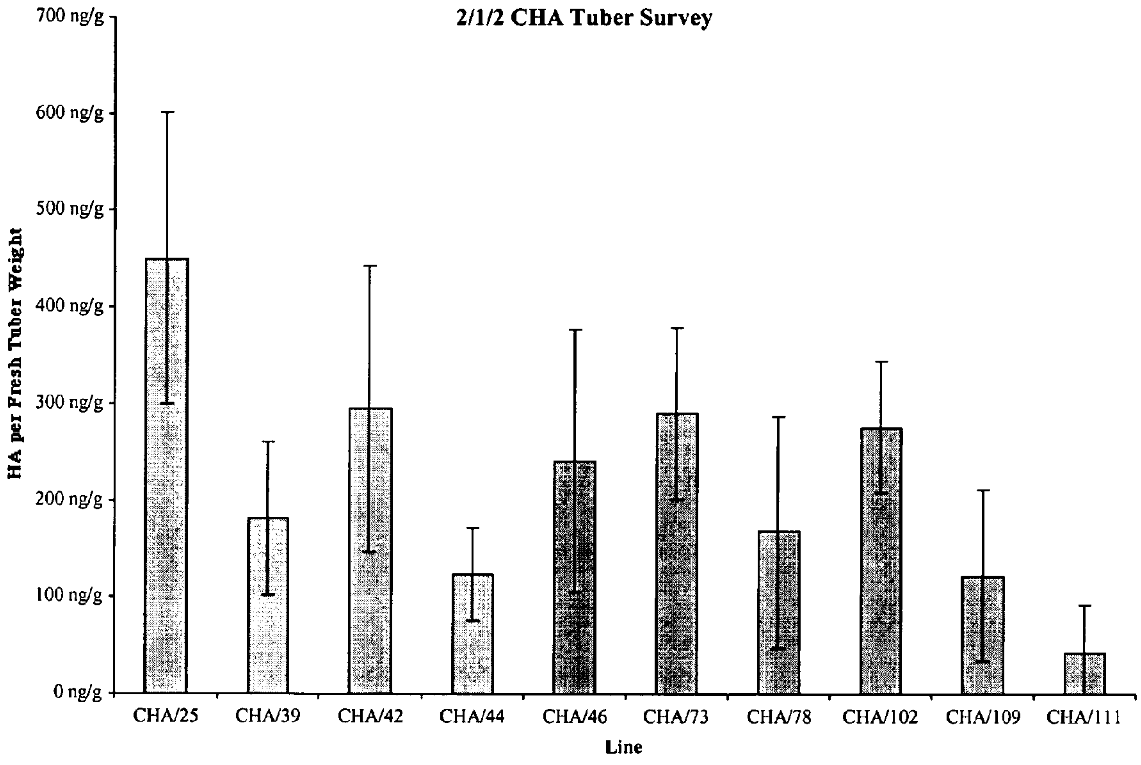
FIG. 18. HA expression in tubers of soil-grown pCHA-transformed potato plants. Greenhouse-grown plants were harvested and tubers sampled for extraction and ELISA for HA expression. Four replicate samples were analyzed, and the standard deviations are shown. Data are presented as ng HA per g fresh tuber weight.

ELISA analysis of tubers. Approximately 3–4 months after plants were transferred to soil, assorted tissue were harvested for analysis. FIG. 16 shows expression of HA in microtubers of pCHA transformed microtubers, which ranged up to 700 ng/g fresh weight. This is similar to the accumulation observed in pGPTV-HAO-transformed tubers (HA gene driven by CaMV 35S promoter), which was maximal at 1 ug/g fresh weight. Selected lines were transplanted to soil and grown in the greenhouse. Leaves of soil-grown plants were sampled and assayed by ELISA (FIG. 17). Expression of HA in leaves was very poor (<0.025 ng/μg TSP), which is consistent with the earlier assays with leaves of tissue culture plants. Tubers of mature plants were harvested, extracted, and evaluated for HA expression by ELISA. Accumulation of HA in tubers was maximally 500 ng/g fresh weight (FIG. 18). The expression observed in microtubers produced in vitro was well correlated with the expression in soil-grown tubers (FIGS. 16 and 18), thus the microtuber is a good model for expression of HA with pCHA.

EXAMPLE 11

Preparation and Analysis of Transgenic Tomato

Binary vectors pCHN, pMHN, and pUHN were used to transform tomato (variety TA234) and transgenic fruit and leaves analysed for expression of the recombinant HN protein from Newcastle Disease Virus.

Plant material. Seeds from a tomato line designated TA234 were used for transformations. TA234, originally known as Momor, is a verticillium and tobacco mosaic virus resistant line derived from the variety Moneymaker. Seeds were surface sterilized in 20% Clorox, for 20 min, rinsed 3 times with sterile distilled water, then cultured on 1/2 MSO medium (See below) in Magenta boxes. They were maintained at 24°±1° C., under a photoperiod of 16 h (light)/8 h (dark) at 74 μE $m^{-2}S^{-1}$. The source of light for these cultures and those described throughout this report was a mixture of cool and warm fluorescent bulbs (F40CW and F40WW) (Philips Lighting Co., located on the world wide web at lighting.philips.com/indez.htm). The seed cultures were maintained for 6–8 days depending upon the stage of cotyledon growth. Cotyledons were excised before the first true leaves emerged. If cotyledon sections were longer than 1 cm, they were cut into two 0.5 cm segments. Cotyledon sections were placed on feeder layer plates which were prepared one day prior to transformation. The feeder layer consisted of NT1 suspension cultured cells plated on KCMS medium (See below) which had been subcultured (2 mls of cells:48 ml of liquid KCMS) 7 days prior to plating. The plated suspension culture was covered with a sterile 7 cm Whatman filter paper. Cotyledon sections were placed on top of the filter paper.

*Agrobacterium* preparation. *Agrobacterium tumefaciens* containing the gene construct of interest was streaked from glycerol stocks maintained at −80° C. onto fresh plates of LB medium (See Appendix) containing the appropriate antibiotic. For DAS constructs, 50 mg/l spectinomycin was added to the LB medium. The cultures were incubated for 24–48 hrs at 28° C. The duration of the incubation time was dependent upon colony size. If pin-point colonies developed after 24 hrs, the cultures were incubated for an additional day.

When the colonies were of a well-formed size, liquid cultures were prepared. Four colonies were picked with a sterile pipet tip, then added to 50 ml of YM selective medium containing 50 mg/l spectinomycin for DAS constructs (See below). Cultures were grown in a shaking incubator at 28° C. and 100 rpm for 24 hrs, or until the culture reached an $OD_{600}$ of 0.5–0.6. It takes approximately 24 hrs to reach this OD. When the desired OD was reached, the cells were centrifuged at 8000 rpm for 10 min at 20° C. The pellet was resuspended in MS liquid medium at the same original volume as the YM selective medium.

Infection. Cotyledon explants were cultured on the feeder layer plates 1 day prior to infection with *Agrobacterium*. For infection, they were incubated in the *Agrobacterium* suspension for 10 min, then the suspension was removed. The explants were blotted on sterile paper towels, then placed with the adaxial sides down on the original feeder plate cultures. They were maintained at 19° C. in the dark for 48 hrs of cocultivation.

Plant regeneration: After cocultivation, cotyledon explants were cultured with the adaxial sides up on selective 2Z medium containing 3 mg/l bialaphos. The cultures were maintained at 24±2° C. under a 16-hr photoperiod of cool white fluorescent lights. Three weeks later, the cultures were transferred to 1Z medium containing 3 mg/l bialaphos (See below), then to fresh medium at 3 week intervals. When shoots began to regenerate, the cultures were transferred to the same 1Z medium with bialaphos in Magenta boxes. When shoots were 2 cm tall, they were transferred to selective rooting medium containing 2 mg/l bialaphos (See below) in Magenta boxes. Plants were maintained at 24±1° C. under a 16-hr photoperiod of cool white fluorescent lights. After approximately 3 weeks, cuttings from these plants were transferred again to selective rooting medium containing bialaphos, however, timentin was not included to determine if there was *Agrobacterium* contamination present.

Analysis. Plants that rooted on selective rooting medium were selected for ELISA analysis. Leaf material was harvested, transferred to 2 ml conical screw cap tubes, and placed on ice. ELISA was performed at least twice before selecting the lines containing the highest antigen level. The elite lines were propagated and transferred to the greenhouse.

Greenhouse acclimation. Plants were transferred to the greenhouse when they had a well-developed root system. The agar medium was washed off the roots before transferring the plants to 6-inch pots containing Cornell mix. They were covered with plastic domes. During the next week, the domes were gradually lifted to acclimate the plants. After approximately 5 weeks, the plants are transferred to 3-gallon pots containing Cornell mix.

Media Ingredients

| | Per liter |
|---|---|
| 1/2 MSO | |
| MS salts | 2.15 g |
| Myoinositol | 100 mg |
| Thiamine HCl stock (0.4 mg/ml) | 5 ml |
| Pyridoxine HCl stock (0.5 mg/ml) | 1 ml |
| Nicotinic acid stock (0.5 mg/ml) | 1 ml |
| Sucrose | 10 g |
| pH to 5.8 ± 0.03 | |
| Agar/Agar | 8 g |
| KCMS | |
| MS salts | 4.3 g |
| Thiamine HCl stock (1 mg/ml) | 1.3 ml |
| Myoinositol | 100 mg |
| 2,4-D stock (1 mg/ml) | 200 µl |
| $KH_2PO_4$ | 200 mg |
| Kinetin stock (1 mg/ml) | 100 µl |
| Sucrose | 30 g |
| pH to 5.5 ± 0.03 | |
| Agargel | 5.2 g |
| LB | |
| Bacto-tryptone | 10 g |
| Yeast extract | 5 g |
| NaCl | 10 g |
| Difco Bacto Agar | 15 g |
| YM | |
| Yeast extract | 400 mg |
| Mannitol | 10 g |
| NaCl | 100 mg |
| $MgSO_4.7H_20$ | 200 mg |
| $KH_2PO_4$ | 500 mg |
| MS Liquid Medium | |
| MS salts | 4.3 g |
| Myoinositol | 100 mg |
| Glycine | 2 mg |
| Nicotinic acid | 0.5 mg |
| Pyridoxine HCl | 0.5 mg |
| Thiamine HCl | 0.4 mg |
| Folic acid | 0.25 mg |
| D-biotin | 0.05 mg |
| Sucrose | 30 g |
| pH 5.6 | |
| 2Z | |
| MS salts | 4.3 g |
| Myoinositol | 100 mg |
| Nitsch vitamins stock (1000X)* | 1 ml |
| Sucrose | 20 g |
| pH to 6.0 ± 0.3 | |
| Agargel | 5.2 g |
| Selective Rooting Medium | |
| MS salts | 4.3 g |
| Nitsch vitamins stock (1000x)* | 1 ml |
| Sucrose | 30 g |
| pH to 6.0 + 0.03 | |
| Difco Bacto Agar | 8 g |

Alternatively, YM in powder form can be purchased (Gibco BRL; catalog #10090-011). To make liquid culture medium, add 11.1 g to 1 liter water.

Add the following filter-sterilized components per liter after autoclaving:

Bialaphos: 2 ml of a 1 mg/ml stock solution

Timentin: 3 ml of a 100 mg/ml stock solution

Nitsch Vitamins Stock (1000x)

| | Per 50 ml |
|---|---|
| Glycine | 0.1 g |
| Nicotinic acid | 0.5 g |
| Pyridoxine HCl | 0.025 g |
| Thiamine HCl | 0.025 g |
| Folic acid | 0.025 g |
| d-biotin | 0.002 g |

Adjust pH to 7.0 to clear solution.

EXAMPLE 12

Tomato as a Production System of Edible Vaccines

Assembly of a Synthetic HN Gene. A HN expression cassette that includes the promoter of the Casava vein mosaic virus (CsVMV) and terminated by the 3' element of the Soybean Vegetative Storage Protein (VSP) was assembled and inserted into binary vectors by the Mason Laboratory (The Boyce Thompson Institute for Plant Research (BTI)) for *Agrobacterium*-mediated plant transformations. The vector carries the gene encoding the plant selection marker phosphinothricin acetyl transferase (PAT, described in U.S. Pat. Nos: 5,879,903; 5,637,489; 5,276,268; and 5,273,894) (FIG. 30).

Tomato Transformation and Regeneration. *Agrobacterium*-mediated transformation of tomato cotyledons (variety Tanksley TA234TM2R) was performed according to Frary and Earle [12] by the Van Eck Laboratory (BTI). Regenerating explants were transferred to fresh medium every 3 weeks. Green shoots were transferred to GA-7 boxes (Magenta Corporation, Chicago, Ill.) containing rooting media (MS salts 4.3 g, 1 ml/l Nitsch vitamins 1000×, 30 g/l sucrose, 8 g/l difco bacto agar, pH 6.0, supplemented with 50 mg/l kanamycin, 300 mg/l timentin and 4 mg/l IBA) when they were approximately 1 cm tall. Rooted plantlets were transferred to soil and maintained at 28° C. under a 12 hours photoperiod.

Protein Extraction and Elisa Analysis. Crude protein extracts were made by homogenizing 1 mg of fresh leaf, fruit or NT1 cell material per 5 µL of PBS or 1 mg of dried leaf, fruit or NT1 cell material per 10 µL of PBS in a QBiogene (Carlsbad, Calif., USA) Fast Prep machine. Insoluble material was removed by centrifugation at 14,000 rpm in an Eppendorf 5415C microcentrifuge at 4° C. for 5 minutes. The resulting sample supernatants were kept on ice during analysis and subsequently stored at −80° C.

Ninety-six well, microtiter plates (Costar 3590, Fisher Scientific, Pa., USA check) were coated with 100 µl per well of a 1 in 1,000 dilution of SPAFAS chicken anti-NDV polyclonal antibody (Benchmark Biolabs, Nebr.) in 0.01 M borate buffer. The plates were covered and incubated overnight at 4° C. The plates were equilibrated to room temperature for 30 minutes then washed three times with 300 µl per well phosphate buffered saline with 0.05% Tween-20 (PBST). The plates were blocked with 200 µl per well, 3% skim milk in PBST at 37° C. for two hours then washed three times with PBST before 50 µl per well of protein extracts were added. ELISAs were performed on two replicates on a series of two-fold dilutions of the crude extracts in 5% skim milk+PBS+0.05% Tween-20. The plates were incubated for one hour at 37° C. before washing three times with PBST. One hundred microliters of the primary antibody, HN Mab 4A (Benchmark Biolabs), diluted 1 in 250 in 1% skim milk in PBST, was added to each well and incubated for one hour at 37° C. The plates were then washed three times with PBST before 100 μl per well of goat, anti-mouse IgG horse radish peroxidase (HRP) conjugate (Sigma, St Louis, Mo., USA) diluted 1 in 3,000 in 1% skim milk in PBST was added and left to incubate at 37° C. for one hour. The plates were washed four times with PBST before 50 μl per well of TMB Peroxidase EIA Substrate kit (BioRad) was added and incubated for five minutes at room temperature. Absorbance at 450 nm was measured in a ThermoMax Micropla reader. ELISA data obtained by anti-HN ELISA was converted to microgram per gram of fresh weight by reference to a standard curve constructed using purified HN (Benchmark Biolabs).

The top four lines based on HN expression in the leaves were used for fruit analysis.

Nucleic Acid Extraction. Ten milliliters of extraction buffer (4% p-amino salicylic acid, 1% 1,5 naphthalenedisulfonic acid, disodium salt hydrate), 3 ml CTAB buffer, and 10 ml buffer-saturated phenol (pH 4.3) were added to a 50 ml falcon tube and heated at 70° C. in a water bath for 10 minutes. About 3.5 g of individual tomato fruit were ground in liquid nitrogen then added to the heated tube and vortexed vigorously for 30 seconds. Ten milliliters of chloroform: isoamylalcohol (24:1) was added. The resulting slurry was vortexed for 30 seconds before centrifuging for 20 minutes at 10,000 rpm at 4° C. The aqueous phase was transferred to a 50 mL falcon tube, mixed with 2 volumes of ethanol, and precipitated for 15 minutes at room temperature. The extract was then centrifuged for 15 minutes at 10,000 rpm at 4° C. before the supernatant was discarded. The resulting nucleic acid pellet was resuspended in 2 ml DEPC treated water, mixed with an equal volume of 4 M LiCl, and precipitated at −20° C. overnight. The extract was centrifuged at 10,000 rpm at 4° C. for 20 minutes. The supernatant containing genomic DNA was removed to a different tube, precipitated with 2 volumes of ethanol and stored at −20° C. overnight. Meanwhile, the RNA pellet was resuspended in DEPC treated water and stored at −20° C. The following day, the DNA pellet was centrifuged down at 10,000 rpm at 4° C. for 20 minutes and resuspended in water containing 1 μg/ml Rnase A.

Southern Analysis. Fifteen micrograms of tomato genomic or 330 ng of pCHN plasmid DNA were digested with 5 units of restriction enzyme EcoRI per μg DNA at 37° C. for 20 to 24 hours. Uncut and digested samples were run overnight in a 1.0% TAE agarose gel. The gel was prepared for transfer by one 20 minute depurination wash (0.25 MHCI), two 30 minute denaturation washes (1.5 M NaCl, 0.5 M NaOH) and two 30 minute neutralization washes (0.5 M TrisHCl, pH 7, 3 MNaCl). DNA was then transferred to a nylon membrane (Zeta-Probe blotting membranes, Bio-Rad, Hercules, Calif., USA) by capillary transfer and fixed by UV cross-linkage using a Bio-Rad GS Gene Linker. A PCR labeled probe was made by using the primer set HNa (CCG AGC AGT TTC ACA AGT GG, SEQ ID NO: 10) and HNb (CCT GAT CTT GCT TCA CGT ACA, SEQ ID NO:11) on a pCHN template. DIG labeled dCTP was incorporated into the 1734 bp amplicon using the Roche Molecular Biochemical DIG PCR Probe Synthesis kit according to manufacturer's instructions. The amplification was performed over 37 cycles using an iCycler Gradient Thermo Cycler (BioRad, Hercules, Calif., USA). The template was initially melted at 94° C. for 5 minutes followed by 35 cycles of 94° C. for 30 seconds, 56° C. for 30 seconds, and 72° C. for 90 seconds. A final extension step was performed at 72° C. for 5 minutes before soaking at 4° C. Hybridization bottles and 10 ml DIG Easy Hyb (Roche Scientific, Mannheim, Germany) per membrane were pre-warmed to 45° C. in a hybridization oven. Membranes were prehybridized for 60 minutes at 45° C. and hybridized overnight at 45° C. with a probe concentration of 5 μl/ml DIG Easy Hyb.

Post hybridization washes and detection were performed as per manufacturer's instructions (Roche—DIG wash and block buffer set and DIG Luminescent Detection Kit). Labeled membranes were visualized after exposure to film.

Northern Analysis. Thirty micrograms of total RNA from tomato transfonnants and wild type plants and 1.25 μg of ladder (high range RNA ladder, MBI Fermentas, Hanover, Md.) were denatured with formaldehyde/formamide and run for two hours in a 1% agarose 3-(N-morpholino) propanesulfonic acid (MOPS) formaldehyde gel at 80V. The RNA was transferred to zeta probe membrane (BioRad, Hercules, Calif., USA) by upward capillary action and fixed by UV cross-linkage. The membrane was then stained with 0.04% methylene blue in 0.5M sodium acetate to determine if RNA transfer was successful and to confirm that RNA concentrations in all samples were similar. A PCR labeled, DNA probe was made using the primer set HNa and HNb on a pCHN template. DIG labeled dCTP was incorporated into the 1734 bp amplicon as per manufacturer's instructions (PCR DIG Probe Synthesis kit, Roche Scientific, Mannheim, Germany). The amplifications were performed as described for Southern analysis. Hybridization bottles and 10 ml DIG Easy Hyb (Roche) per membrane were pre-warmed to 45° C. in a hybridization oven. Membranes were pre-hybridized for at least 90 minutes at 45° C. and hybridized overnight with a probe concentration of 7.5 μl/ml DIG Easy Hyb. Post hybridization washes and detection were performed as per manufacturer's instructions (Roche—DIG wash and block buffer set and DIG Luminescent Detection Kit). Labeled membranes were visualized after exposure to film.

Western Analysis. Purified HN supplied by Benchmark Biolabs and NT1 cell line 119 transformed with pCHN (supplied by BTI) were used as positive controls. Twenty microliters of protein extracts were added to 4 μl 6×SDS gel loading buffer (300mM Tris-HCl, pH 6.8, 600 mM DTT, 12% SDS, 0.6% bromophenol blue, 60% glycerol), boiled for 10 minutes and loaded into a 15% sodium dodecyl sulfate polyacrylamide gel. The gel was run in tris-glycine buffer (25 mM Tris, 250 mM Glycine, pH 8.3, 0.1% SDS) at 30 milliamps per gel until the dye front ran about 5 mm from the gel bottom. The separated proteins were transferred from the gel to a PVDF membrane using a BioRad Trans Blot Cell (50 V for 2 hours or overnight at 7 V). All membrane washes were performed in PBST (PBS+0.1% Tween-20) at room temperature unless otherwise stated. The membrane was blocked with 5% skim milk+PBS+0.1% Tween-20 overnight at 4° C. or for two hours at room temperature using slow rotation in a hybridization incubator (Fisher Scientific, Tustin, Calif., USA). The membrane was washed twice briefly before incubating for one hour at 37° C. with a 1 in 50,000 dilution of the primary antibody, mouse anti-HN Mab14F antiserum (Benchmark Biolabs) in 1% skim milk+PBS+0.1% Tween-20. The membrane was briefly rinsed in PBST before a 15 minute wash and three 5 minute washes then incubated in a 1 in 30,000 dilution of an anti-rabbit IgG horseradish peroxidase (HRP) conjugate (Sigma) for an hour at 37° C. with slow rotation. The membrane was rinsed, then subjected to a 15 minute wash and three 5 minute washes. Detection was performed using the Amersham ECL+kit as per manufacturer's instructions.

Haemagglutination Activity. To make a 1% chicken red blood cell (cRBC) standardized solution, cRBCs in Alsevers solution (Colorado Serum, Colo.) were transferred into a 15 ml conical tube and centrifuged at 250 g for 10 minutes. The supernatant was aspirated and the pellet resuspended in 10 ml Dulbecco's phosphate-buffered saline without calcium and magnesium (DPBS) (Cellgro, Mediatech, Inc, Kansas City, Mo.). The suspension was centrifuged at 250 g for 10 minutes. The washes and resuspensions were repeated until the supernatant was clear. Once this was achieved the cells were pelleted and the supernatant aspirated to leave the packed RBC pellet. The pellet was then diluted in 1% DPBS-(volume to volume). Four hundred microliters of the 1% RBC solution was transferred to a small tube, 1.6 ml of deionized water was added before being vortexed at high speed for 20 seconds to lyse the cells. A cRBC solution was not used unless the absorbance at 540 nm of the lysed cells was 0.4–0.5. A 96-well, U bottom plate (Falcon) was sprayed with antistatic spray before 50 μl per well of DPBS was added. Fifty microliters of the samples, including the positive control of NDV HN and negative control of DPBS, was added to the first row, mixed through repeated pipetting then serially diluted by transferring 50 μl to the next row. Fifty microliters of the standardized cRBC was added to each well before the dilutions were incubated on a plate shaker at 600 rpm for 20–30 seconds. The plates were then incubated at 5° C. for an hour before the control NDV HN wells were checked for haemagglutination. Once this was achieved the final read was made. The HA titer was taken as the reciprocal of the highest dilution that was positive for agglutination.

Analysis. Fruit ripening is a developmentally and genetically regulated process that is characterized by many biochemical and physiological changes, including increases in the rate of ethylene biosynthesis and respiration, chlorophyll degradation, pigment accumulation, textural modifications such as fruit softening, changes in the levels of sugars and organic acids, and production of volatile aromatic compounds (Brady C J. *Annu Rev. Plant Physiol.* 1987; 38: 155–178). There is a distinct relationship between fruit pH and solids content (mainly sugars, Benton Jones J. *Tomato plant culture: in the field, greenhouse, and home garden.* New York: CRC Press, 1999). The degree of ripeness is also a factor that affects pH. Ripening of wild type TA234 caused the fruit pH to decrease significantly ($\alpha$=0.05) (FIG. 31) and the total soluble protein to generally decrease (FIG. 32). Although the extent of decrease varies, this has been found in other studies (Benton Jones J. *Tomato plant culture: in the field, greenhouse, and home garden.* New York: CRC Press, 1999).

Figure 33:
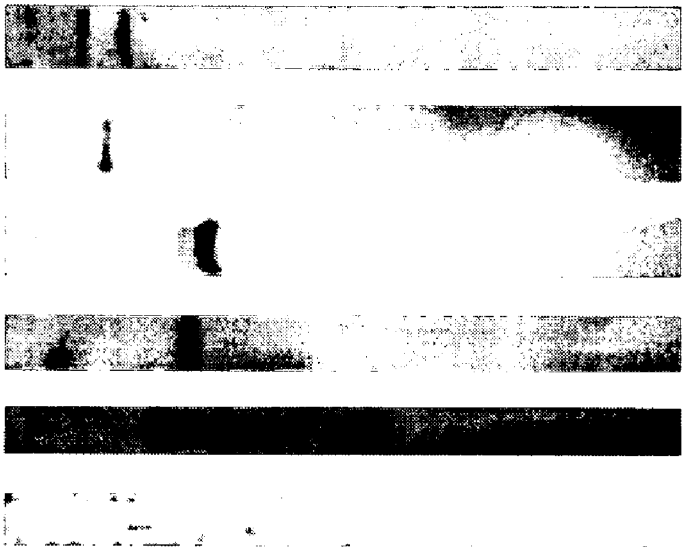
FIG. 33. Southern analysis of $T_0$ CHN tomato lines. The positive control is an EcoRI digest of the plasmid pCHN loaded to indicate the intensity of 2 copies of the HN gene per genome while the negative control is DNA from wild type TA234 tomato.

The four lines expressing the highest level of HN in leaf tissue had varying phenotypes. The phenotypes of lines CHN-1, CHN-12 and CHN-32 were indistinguishable from control plants while line CHN-10 showed traits indicative of polyploidy such as thick, wrinkly leaves and late flower set and fruit development. Comparing the intensity of signals between the plasmid controls and the genomic samples in Southern analysis, the lines had between 1 and 4 copies of the transgene (FIG. 33) with CHN-1 having two copies, CHN-10 four copies, CHN-12 having one copy, and CHN-32 having 2 copies. Since CHN-10 is likely a polyploid line, it will not be used in further studies or for production of vaccine batches.

Figure 34:
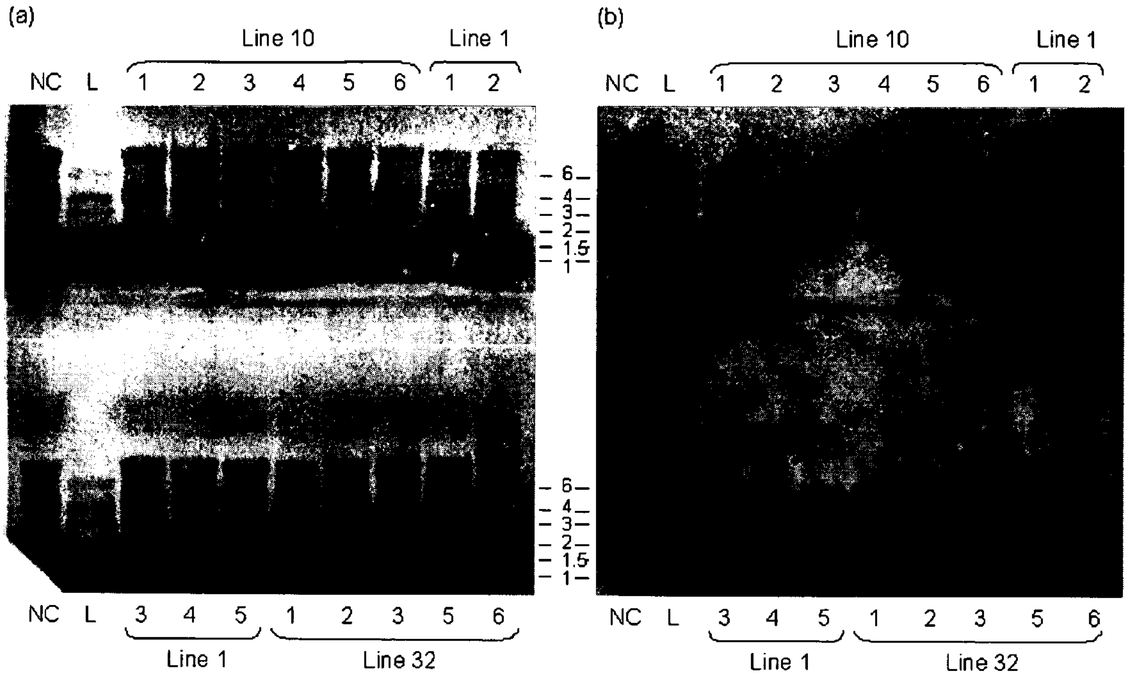
FIG. 34. Total RNA from wild type and transgenic tomato fruit. (a) Methylene blue stain of membrane. (b) Northern analysis. NC represents the negative control, total RNA from wild type fruit; L, MBI Fermentas (Hanover, MD) high range RNA ladder; 1–6. corresponding ripening stage of fruit.

Methylene blue staining of the northern membrane before the pre-hybridization and hybridization steps revealed the transfer of RNA from the gel to the membrane was successful and that there were similar concentrations of RNA in each of the samples (FIG. 34*a*). Northern analysis of total RNA specific for the HN gene demonstrated no band in the wild type negative control however a band of about 5000 nucleotides was seen in the transgenic tomato lines (FIG. 34*b*). Since the HN gene expression cassette with promoter and terminator is 2,832 bp and the expression cassettes within the T-DNA combined are 4323 bp, the transcript is larger than expected and was thought due to read through of the VSP 3' termination signal during transcription of the HN gene. Transcript prevalence varied at different stages of fruit ripening within a line and between lines. Line CHN-10 displayed a distinct decrease in HN-specific mRNA content as the fruit ripened (FIG. 34*b*). However since only one fruit was sampled for northern analysis no pattern could be discerned between RNA prevalence and stage of ripening in the other CHN tomato lines.

Figure 35:
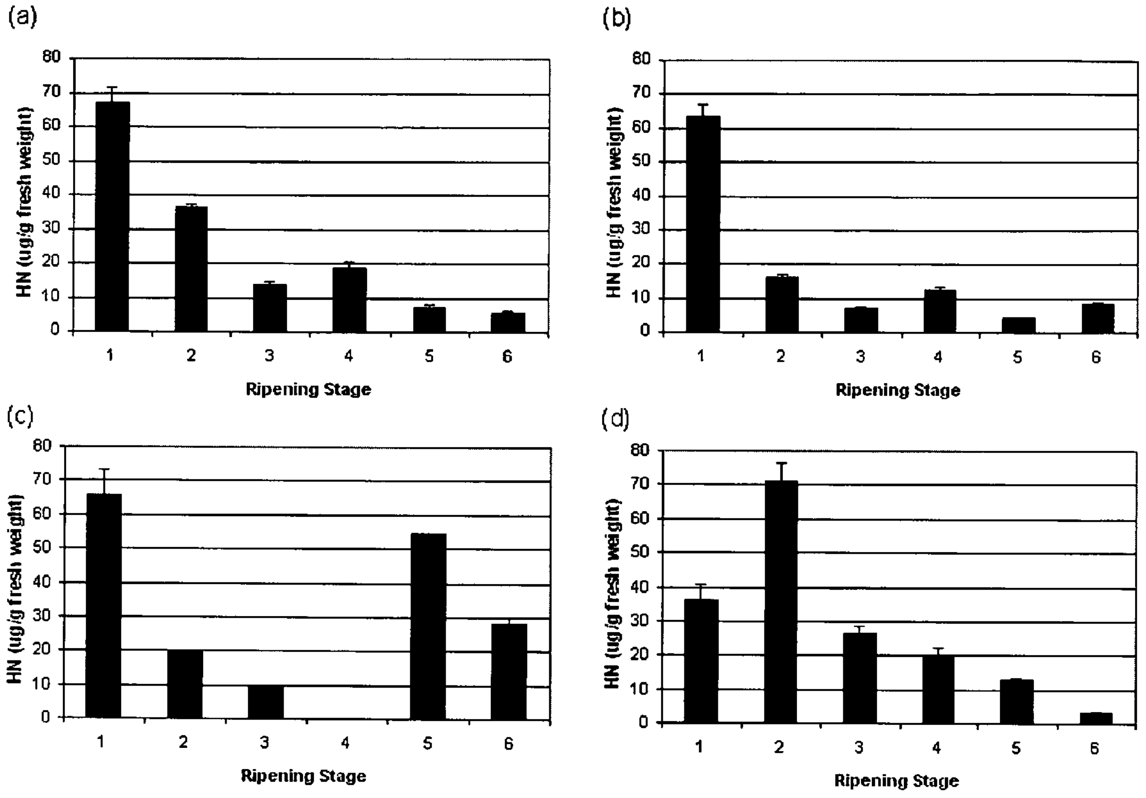
FIG. 35. ELISA analysis of HN concentration in ripening CHN tomato fruit. (a) Tomato line CHN-1. (b) Tomato line CHN-10. (c) Tomato line CHN-12. (d) Tomato line CHN-32. Except in line CHN-12 where only stage 1 fruit had three reps, bars represent the mean of 3 samples from 3 different fruit, error bars indicate the standard error of the mean.

Anti-HN ELISA of transgenic lines revealed a trend of decreasing concentration as the fruit ripened (FIG. 35). Stages 4 and 5 had significantly less HN per gram fresh weight than stage 1 fruit in lines CHN-1 (FIG. 35*a*) and CHN-10 (FIG. 35*b*) and stage 2 fruit in CHN-32 (FIG. 35*c*) ($\alpha$=0.05). HN concentration was not significantly different at the same stage between different varieties ($\alpha$=0.05). HN concentration varied between 71.1 and 3.5 μg/g fresh weight with the highest concentration in each line being 67.2 μg/g fresh weight in stage 1 fruit of CHN-1, 63.3 μg/g fresh weight in stage 1 fruit of CHN-10, 65.4 μg/g fresh weight in stage 1 fruit of CHN-12 and 71.1 μg/g fresh weight in stage 2 fruit of CHN-32. The best stage to harvest a HN tomato crop would therefore be at the green or early breaker stage.

Figure 36:
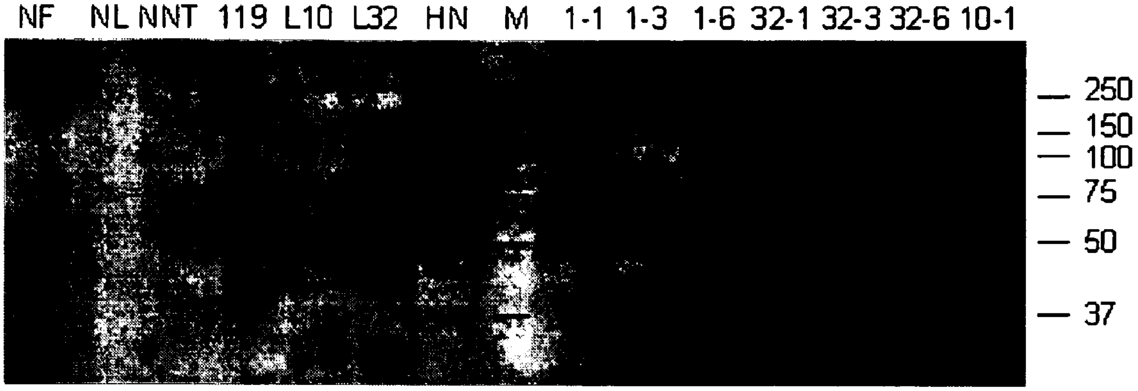
FIG. 36. Western analysis of crude protein extracts from wild type and transgenic tomato fruit and leaves and NT1 cell extracts. NF, represents tomato fruit negative control—wild type fruit; NL tomato leaf negative control—wild type leaf; NNT NT1 cell negative control—non-transformed cell lines; 119, transgenic NT1 cell line 119; L10, leaf from transgenic tomato line 10; L32, leaf from tomato line 32; HN, animal derived Lasota NDV virus; M, Bio-Rad's precision plus protein all blue standard; 1-1. fruit from line CHN-1, stage 1 of ripening; 1-3, fruit from line CHN-1, stage 3 of ripening; 1-6, fruit from line CHN-1, stage 6 of ripening; 32-1, fruit from line CHN-32, stage 1 of ripening; 32-3, fruit from line CHN-32, stage 3 of ripening; 32-6, fruit from line CHN-32, stage 6 of ripening; 10-1, fruit from CHN-10, stage 1 of ripening. Protein size is give in kDa. and leaves and NT1 cell extracts.

Western analysis of the Lasota NDV HN positive control while overloaded, revealed bands around 49, 74, 78, 90,120, 200, 250 and larger than 250 kDa (FIG. 36). The 78 kDa band was designated HN monomers, the smaller bands degradation products. The 90 kDa band was thought a different glycosylation form and the 120 kDa and larger bands as HN polymers. Western analysis of transgenic fruit at different stages was difficult due to the low expression of HN, however two bands around 78 and 70 kDa were visible. These bands were also present in the leaves of transgenic tomato plants and in the NT1 cell line 119 but were not present in the tomato or NT1 cell line negative controls. It was thought the 78 and 70 kDa bands represented different glycosylation forms of the HN antigen or the 70 kDa band a truncated version of the HN monomer. Additional bands thought to be degradation products were visible around 20 and 48 kDa in leaf samples of transgenic tomatoes and 48 kDa in the NT1 119 line.

NF, represents tomato fruit negative control—wild type fruit; NL tomato leaf negative control—wild type leaf; NNT NT1 cell negative control—non-transformed cell lines; 119, transgenic NT1 cell line 119; L10, leaf from transgenic tomato line 10; L32, leaf from tomato line 32; HN, animal derived Lasota NDV virus; M, Bio-Rad's precision plus protein all blue standard; 1-1, fruit from line CHN-1, stage 1 of ripening; 1–3, fruit from line CHN-1, stage 3 ripening; 1-6, fruit from line CHN-1, stage 6 of ripening; 32-1, fruit from line CHN-32, stage 1 of ripening; 32-3, fruit from line CHN-32, stage 3 of ripening; 32-6, fruit from line CHN-32, stage 6 of ripening; 10-1, fruit from CHN-10, stage 1 of ripening. Protein size is give in kDa.

Haemagglutination assays of the freeze-dried green fruit and leaves of the transgenic tomato revealed haemagglutination activity in all lines (FIG. 37). Activity was highest in the leaves in lines CHN-1, CHN-12 and CHN-32 with CHN-10 being the only line to have higher activity in the fruit. Line CHN-32 displayed the highest haemagglutination activities of 512 and 2,048 in the fruit and leaves (FIG. 37*a*) as well as the highest haemagglutination activity of 10,928 units per microgram HN (FIG. 37*b*). The CHN-1 line had the second highest haemagglutination activities of 128 and 256 in the fruit and leaves as well as the second highest activity of 3,994 units per µg HN (FIGS. 37*a* and *b*). Despite being mis-processed during transcription, the synthetic HN gene was translated into a functional protein.

Although CHN-10 had higher HN activity in the fruit, the target organ for animal trials and vaccine delivery, the probable polyploid status of this line in addition to its slowness to flower and fruit made it an unlikely candidate for future studies. Taking into account HN expression levels and HN activity in the four lines, the CHN-1 and CHN-32 lines were chosen for future analysis.

Western analysis, ELISA and haemagglutinin activity assays show that tomato is capable of expressing a HN protein of the correct size (78 kDa) that is antigenic in ELISAs and retains haemagglutination activity. The optimal time to harvest tomato fruit expressing HN under the control of the CsVMV promoter was the early stage of fruit ripening. This decreased the time to harvest by 2 weeks and increased HN expression approximately 15-fold. Despite the protein being correctly processed, northern analysis reveals that the gene is not processed correctly at the DNA level. The 5,000 nucleotide transcript is likely due to read through of the HN gene terminator. Lines CHN-1 and CHN-32 were deemed the best lines for progression to additional studies.

EXAMPLE 13

HN expression during Maturation of Tomato Fruit

HN levels in maturing tomato fruit to determine if immature fruit are capable of expressing higher levels of HN than stage one tomatoes.

The fruit of red-fleshy tomato varieties is said to be mature when it has completed growth but is still completely green. This stage of ripeness is known as "green" or "stage one". Tomatoes are usually picked at this stage then ripened with ethylene. The stages following include "breakers" or "stage two" when there is a definite break in color from green to tannish-yellow or pink (vine ripened tomatoes are picked at this stage); "turning" or "stage three" when more than 10% but less than 30% (for example, 11, 12, 13, 14, 15, 20, 25, 29%) of the surface of the tomato shows a definite change in color from green to tannish-yellow, pink or red; "pink" or "stage four" when more than 30% but less than 60% (for example, 31, 32, 33, 34, 35, 40, 45, 50, 55, 59%) of the surface of the fruit is pink or red in color; "light red" or "stage five" when more than 60% but less than 90% (for example, 61, 62, 63, 64, 65, 70. 75, 80, 85, 89%) of the surface of the fruit is pinkish-red or red; "red" or "stage six" when more than 90% (for example, 91, 92, 93, 94, 95, 99, 100%) of the surface of the fruit is red.

Expression of the synthetic, plant optimized, gene for the Newcastle disease virus haemagglutinin neuraminidase (HN) protein driven by the Casava Vein Mosaic Virus promoter (CsVMV), decreased as the tomato fruit ripened. It was determined that in stage one green tomato fruit, HN expression was approximately 12 µg/g fresh weight (FW) and that this steadily decreased as the tomato ripened to stage six red tomato fruit to an approximate value of 2.5 µg/g FW.

One $T_1$, plant from each of the elite lines in the $T_0$ CHN generation (CHN-1, CHN-32) was germinated and allowed to grow. When flowering began, cross-pollination was prevented by each flower being self-pollinated by hand and enclosed in a paper towel. The individual flower was dated and allowed to fruit. Three fruit from each plant line were harvested at one week post-pollination, two weeks post-pollination, four weeks post-pollination, six weeks post-pollination, and finally at stage one green fruit (about eight weeks post pollination). Fruit diameter (mm) and fresh mass (g) were recorded before ELISA analysis of the HN content and lyophilization. To measure the diameter of the tomato fruit, a vernier caliper was applied to the widest part of the tomato fruit perpendicular to the stem and the measurement in millimeters recorded. Mass was determined using a gram balance.

HNELISA. SPAFAS chicken α-NDV polyclonal antibody diluted 1:1500 in 0.01M borate buffer was used to coat a 96 well ELISA plate. One hundred microliters of the dilution was pipetted into each well before the plate was covered, and left overnight at 4° C. The next morning the plate was allowed to equilibrate for 30 minutes at 24° C., before being washed three times with PBST (0.05% tween). A solution of 3% skim milk was made and 200 µl added to each well. The plate was placed at 37° C. and allowed to block for two hours.

To collect a sample, a coring tool (size 1) was pushed through the center of the tomato along the horizontal axis. Any gelatinous material or seeds were excluded from the sample. Using a scalpel, approximately 1 cm of the tomato was collected and placed into the sample tube that was then placed on ice. The actual sample weight was calculated by subtracting the individual tube weight from the total mass then 20× tomato extraction buffer (4M Nacl (final concentration 100 mM), 0.5M EDTA (final concentration 1 mM), 20% Triton-x 100 (final concentration 10%), Leupeptin (final concentration 10 µg/ml), 0.5M NaPi, pH 7.0 (final concentration 50 mM), brought to volume with milliQ water) (mass by volume) was added to the tube. A ceramic bead was added to the sample tube and the sample homogenized using a fast prep machine at speed 4.0 for 30 seconds. The homogenized samples were centrifuged and then set aside on ice while the standard curve was prepared.

After the plate had blocked for two hours it was washed three times with PBST (PBS plus 0.05% tween). For the NDV HN standard curve, 100 µl of 232 ng/ml NDV purified stock (1:80) was pipetted into the second well of the second row. Fifty microliters of 1% skim milk was pipetted into the remaining wells of the second row and each of the wells in rows 3–8 of the microtiter plate. Fifty microliters of each plant sample was then added to the 1% skim milk in wells 3–11 of the second row. The purified NDV as well as the plant samples were then serially diluted down the plate by pipetting 50 µl out of row two and into row three and so on down the plate. The samples were mixed in the wells by pipetting up and down after each dilution step. The initial concentration of the samples was a 40-fold dilution. The plate was placed back into the 37° C. incubator for 1 hour.

After incubating for one hour the plate was washed three times with PBST and the primary antibody added. The primary antibody NDV HN Mab 4A was diluted to a concentration of 1:250 in 1% skim milk and 100 µl added to each well. This was allowed to incubate for one hour at 37° C. Next the plate was washed three times with PBST and the secondary antibody goat anti-mouse IgG, was added to each well at a concentration of 1:3000 in 1% skim milk. This was allowed to incubate for one hour at 37° C.

The plate was washed four times with PBST and 50 µl TMB substrate was added to each well. After five minutes had elapsed the TMB was neutralized with 1N $H_2SO_4$. The plate was then read on a spectrophotometer at a wavelength of 450 nm.

The percent water loss was determine by removing the seeds from each tomato fruit, measuring the mass, freezing at −20° C., lyophilizing, then reweighing the tomato fruit.

To take into account the increase in fruit size in addition to HN concentration, the HN content of a tomato fruit at each of the maturation stages selected was calculated by multiplying the fruit HN concentration by the fruit mass. In addition, the data generated from this study was used to calculate the possible number of doses produced from the CHN elite lines if fruit were harvested at stage one or at four weeks post pollination. In this model it was assumed that the same number of fruit would be produced from a plant harvested when fruit were at stage three and a plant harvested when fruit were four weeks post pollination and that one dose would be 50 μg of antigen.

Results

Fruit Physiology

As expected, fruit size, mass and percent water loss increased with time (FIGS. 38, 39, and 40). Only small variations were observed between repetitions of measurements taken at the same maturation stage within the same plant line. No significant difference was seen between line 1 and 32 at the same stage in maturation (α=0.05).

HN Content of Maturing Fruit

Concentration of HN in maturing fruit peaked at two weeks post pollination then decreased as the fruit matured (FIG. 41). There was no significant difference between the two tomato lines at the same stage of maturation nor between the HN content in the first four weeks after pollination (α=0.05). There was significantly more HN in fruit two weeks post pollination than in fruit six weeks after pollination and when mature and in the stage 1 of ripening (α=0.05).

To take into account the increase in fruit size in addition to HN content, the amount of HN of a tomato fruit at each of the maturation stages selected was calculated. The HN content within a fruit peaked at four weeks post pollination (723 μg for line CHN-1 and 630.9 μg for line CHN-32) before decreasing with further fruit maturation (FIG. 42). There was no significant difference between lines at the same stage of maturation (α=0.05).

Calculations were made for the number of doses produced by the HN elite lines if fruit were harvested at stage 1 or four weeks post pollination (Table 10). It was assumed the same number of fruit would be produced from each harvest and that one dose would be 50 μg of antigen. These data indicate that if 33 fruit are harvested at stage one, 126 doses would be produced; and if fruit were harvested four weeks post pollination, 486 doses would be produced. Thus harvest time is reduced by four weeks and there is a 286% increase in doses yielded.

TABLE 10

Effect of harvest time on number of HN doses produced.

| Characteristic | Stage 1 | Four Weeks Post Pollination |
|---|---|---|
| Antigen Concentration (μg/g) | 2.5 | 18.4 |
| Average Weight (g/fruit) | 76.2 | 40 |
| Number of Fruit Harvested | 33 | 33 |
| Total Mass of Fruit Produced (g) | 2514.6 | 1320 |
| Total Mass of Antigen (mg) | 6.3 | 24.3 |
| Number of 50 μg Doses | 126 | 486 |

Although HN concentration peaked at 38.8–42 μg/g fresh weight in tomato fruit two weeks post pollination, no significant difference was found in HN concentration in the first four weeks after pollination (α=0.05). When mass was taken into account however, tomato fruit that were four weeks post pollination averaged between 631–723 μg HN, which was a significantly higher amount of HN than the other maturation stages tested (a=0.05). Since percentage of water loss between fruit at stage one of ripening and two and four weeks post pollination did not varying greatly (total difference of 2.6%) the significantly higher antigen content at four weeks pollination was not a factor of varying water content or dilution of antigen. These data suggest that the best time to harvest tomato fruit expressing HN under the control of the CsVMV promoter is four weeks post pollination.

To identify easily when fruit are four weeks post pollination, fruit mass and diameter were recorded throughout their maturation. Fruit four weeks post pollination averaged a mass of 40 g and a diameter between 42 and 45 mm. Fruit size is affected by genetics, temperature, day length and plant age. The small standard errors of our means indicated that genetics is not presently an issue with regards to plant-by-plant variation in fruit size. However the effect of stress (due to change in temperature, day length and plant age) means that fruit size may not always prove an accurate indication of time post pollination. Large temperature fluctuations, day length and plant age should therefore be kept in mind, when approximating time of pollination using fruit size.

To calculate the benefit of harvesting earlier in the maturation of tomato fruit we constructed a conservative model that assumed 33 fruit are harvested from one plant over an average production period, and one dose of HN would be 50 μg. The model was deemed conservative since one dose is likely to be less than 50 μg and plants that have fruit harvested four weeks post pollination would have reduced metabolic burden and would likely produce more fruit than plants that have fruit harvested at a later stage. These data suggest that by harvesting the fruit at four weeks post pollination, the time required for fruit to be ready for harvest is reduced by four weeks and there is a 286% increase in doses yielded.

Tomato therefore is capable of expressing large quantities of HN when harvested at an optimal time in fruit maturation.

EXAMPLE 14

Preparation of CHN-18 Master Seed

Master Seed Passage: Master Seed passage 2 was used for DNA extraction.

DNA Extraction and PCR Amplification: DNA extraction was performed as described herein. PCR amplification for the HN and PAT gene expression cassettes were conducted separately. There was a 24 bp overlap between the PCR products of HN and PAT expression cassettes.

For HN gene cassette amplification, 50 μL PCR reaction contained 2.5 units of Takara Ex Tag DNA polymerase (Takara Shuzo Co, Shiga, Japan, catalog #RR001A), 0.2 μM of each primers (CHN01/CHN03), 5 μL of 10× reaction buffer containing $MgCl_2$, 0.2 mM of each dNTP, and 200 ng of genomic DNA. The PCR was performed with a Gen Amp PCR 9700 system, manufactured by Applied Biosystem (Foster City, Calif.) at the following condition: 94° C. for 5 min for 1 cycle, 94° C. for 30 sec, 60° C. 30 sec and 72° C. for 3 min 30 sec for 40 cycles, 72° C. for 7 min.

For PAT gene cassette amplification, a 50 μL PCR reaction contained 2.5 units of Takara Ex Tag DNA polymerase (Takara Shuzo Co, Shiga, Japan, catalog #RR001A), 0.2 μM of each primers (CHN02/CHN04), 5 μL of 10× reaction buffer containing $MgCl_2$, 0.2 mM of each dNTP, and 200 ng of genomic DNA were used. The PCR was performed with a Gen Amp PCR 9700 system, manufactured by Applied Biosystem (Foster City, Calif.) at the following condition: 94° C. for 5 min for 1 cycle, 94° C. for 30 sec, 56° C. 30 sec and 72° C. for 40 cycles, 72° C. for 7 min.

Cloning of PCR Products: After agarose gel electrophoresis and visual observation, PCR products were purified using MiniElute PCR Purification Kit (Qiagen, Valencia, Calif. Catalog #28004) according to the manufacturer's protocol. Purified PCR products were cloned into pCR® II-TOPO vector using TOPO TA Cloning® kit (Invitrogen, Carlsbad, Calif., Catalog #051302) according to the manufacturer's protocol.

Plasmid DNA Extraction Plasmid DNA was extracted using Qiaprep Spin Minprep kit (Qiagen, Valencia, Calif., catalog #27106) according to the manufacturer's protocol.

DNA Sequencing and Analysis: Plasmid DNAs containing cloned PCR products were sent to Lark Technologies Inc (Houston, Tex.) for sequencing using ABI PRISM® BigDye™ Primer Cycle Sequencing Kits (Applied Biosystem, Foster City, Calif.). DNA sequences were analyzed using Vector NTI program (InforMax, Frederick, Md.).

RESULTS

DNA sequences from the HN and PAT cassettes were assembled and compared with the sequences from a virtual plasmid map of pCHN. DNA sequences of all the genetic elements including the CsVMV promoter, HN and PAT coding sequences, vspB 3' UTR, and MAS 3' UTR were identical to the ones in the virtual plasmid map pCHN. Based on the virtual plasmid map pCHN, the PCR product including the whole gene insert in CHN-18 Master Seed using primer CHN01/CHN02 was 4757 bp. However, the actual cloned and sequenced PCR product including the whole gene insert in CHN-18 Master Seed was 4768 bp. By sequence comparison, 7 additional DNA bases were located in the junction region (poly cloning site) between the PAT coding sequences and MAS 3' UTR, another additional 4 DNA bases were located outside of the 3' end of MAS3' UTR (FIG. 43). The inconsistenct DNA base number between the virtual plasmid map and the actual sequencing data most likely occurred during the virtual creation of plasmid map pCHN. Open reading frame analysis of the entire insert sequence indicated there were only the expected HN and PAT open reading frames, and the 11 DNA bases did not result in any changes in the existing HN and PAT open reading frame and did not create any new opening reading frames.

CONCLUSIONS

By comparison with the virtual sequence from plasmid map pCHN, the actual DNA sequence of the whole gene insert in CHN-18 Master Seed was identical to what was expected except for extra 11 DNA bases outside all the genetic elements in the gene insert. These 11 DNA bases do not have any effect on the existing HN and PAT open reading frames.

The principles, preferred embodiments and modes of operation of the present invention have been described in the foregoing specification and examples. The invention that is intended to be protected herein, however, is not to be construed as limited to the particular forms specifically disclosed, since they are to be regarded as illustrative rather than restrictive. Variations and changes may be made by those skilled in the art without departing from the spirit and scope of the invention.

The practice of the present invention will employ, unless otherwise indicated, conventional techniques of molecular biology, cell biology, microbiology and recombinant DNA techniques, which are within the skill of the art. Such techniques are explained fully in the literature. See, e.g., Sambrook, Fritsch & Maniatis, 1989, *Molecular Cloning: A Laboratory Manual*, Second Edition; *Oligonucleotide Synthesis* (M. J. Gait, ed., 1984); *Nucleic Acid Hybridization* (B. D. Harnes & S. J. Higgins, eds., 1984); *A Practical Guide to Molecular Cloning* (B. Perbal, 1984); (Harlow, E. and Lane, D.) Using Antibodies: A Laboratory Manual (1999) Cold Spring Harbor Laboratory Press; and a series, *Methods in Enzymology* (Academic Press, Inc.); *Short Protocols In Molecular Biology*, (Ausubel et al., ed., 1995).

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

---

We claim:

1. An isolated plant-codon optimized nucleic acid molecule encoding the HN antigen of Newcastle Disease Virus comprising the sequence of SEQ ID NO:1.

2. A recombinant expression vector comprising SEQ ID NO:1.

3. The vector of claim 2, wherein a plant-functional promoter is operably linked to SEQ ID NO:1.

4. A transgenic plant cell transformed with the vector of claim 2.

5. The plant cell of claim 4, wherein said plant cell is a potato plant cell, a tomato plant cell or a tobacco plant cell.

6. A transgenic plant transformed with the vector of claim 2.

* * * * *

SEQUENCE LISTING

```
<160> NUMBER OF SEQ ID NOS: 26

<210> SEQ ID NO 1
<211> LENGTH: 1760
<212> TYPE: DNA
<213> ORGANISM: Newcastle disease virus
```

-continued

<400> SEQUENCE: 1

```
ccatggaccg agcagtttca caagtggctc ttgagaatga tgagagggaa gccaagaaca     60
cttggaggct tatctttcgg atagccattc tctttcttac tgttgtcacc ctagcaatct    120
ctgttgcatc attactctat tctatgggag caagcacccc ctcagactta gttggcatac    180
ccacacgaat ctctagggct gaagagaaga ttaccagtac cctaggctcc aaccaggatg    240
ttgtggaccg aatctacaaa caagttgcac ttgaaagtca acttgcatta ctcaacacag    300
aaactaccat catgaatgca atcaccagcc tatcctatca gatcaatggg gctgccaaca    360
attcaggttg gggagcccca attcatgatc cagactacat tggaggtatt ggcaaagaac    420
tcattgtaga tgatgcttca gatgttacat ctttctatcc ttcagctttc caggaacatc    480
tgaacttcat tcctgcaccc acaactggga gtgggtgcac tcggataccc tcatttgaca    540
tgagtgctac acactattgc tatacacaca atgtcattct atctggctgt cgtgaccatt    600
ctcactctta tcagtactta gcacttggag ttcttcgtac atctgctact ggtagagtgt    660
tcttctcaac tcttcgcagt atcaatcttg atgatacaca gaatcgcaaa agttgctctg    720
tatctgctac acctttgggc tgtgatatgc tatgcagtaa agtaacagaa actgaagaag    780
aggactacaa ttctgcagtc cctacaagga tggtgcatgg cagattgggt tttgatggtc    840
aataccatga gaaagatttg gatgtcacta cattgtttgg ggattgggta gctaactatc    900
caggagttgg aggtggtagc ttcattgact ccagagtctg gttctctgtc tatggtggtt    960
tgaaacctaa cagtcctagt gatactgtgc aagagggaaa gtatgttatc tacaagaggt   1020
acaatgatac ttgtcctgat gagcaagact atcagattcg aatggctaag tcatcataca   1080
aaccaggaag atttggaggt aagaggatac aacaagctat tctcagtatc aaggttagca   1140
catcattggg agaagatcca gtccttactg ttccaccaaa cactgtaaca ttgatgggag   1200
ctgagggaag gattcttact gttggtacta gccactttct ctatcaacgt ggaagttcct   1260
actttagccc agcgttactg tatccaatga ctgtgagcaa caagacagct acattacatt   1320
caccatatac tttcaatgcc tttacaagac ctggatcgat tccttgccaa gcttcagcta   1380
gatgtccgaa ttcgtgtgtg actggagttt acactgatcc ttaccctttg atcttctacc   1440
gtaatcatac cttgagaggg gtgtttggaa caatgttaga tggtgttcaa gctaggttga   1500
atcctgcctc tgctgtgttt gattctacat ccagatcaag gataaccaga gtttcctcta   1560
gttctactaa ggcagcatac actacctcca catgtttcaa agttgtaaag acgaacaaga   1620
cctattgtct gagcatagct gagatttcta acactctctt tggggaattc agaattgttc   1680
cacttttggt ggagattctg aaagatgatg gtgtacgtga agcaagatca ggttaagtct   1740
tcggatccgg taccgagctc                                               1760
```

<210> SEQ ID NO 2
<211> LENGTH: 577
<212> TYPE: PRT
<213> ORGANISM: Newcastle disease virus

<400> SEQUENCE: 2

```
Met Asp Arg Ala Val Ser Gln Val Ala Leu Glu Asn Asp Glu Arg Glu
1               5                   10                  15

Ala Lys Asn Thr Trp Arg Leu Ile Phe Arg Ile Ala Ile Leu Phe Leu
            20                  25                  30

Thr Val Val Thr Leu Ala Ile Ser Val Ala Ser Leu Leu Tyr Ser Met
        35                  40                  45
```

-continued

```
Gly Ala Ser Thr Pro Ser Asp Leu Val Gly Ile Pro Thr Arg Ile Ser
    50                  55                  60

Arg Ala Glu Glu Lys Ile Thr Ser Thr Leu Gly Ser Asn Gln Asp Val
65                  70                  75                  80

Val Asp Arg Ile Tyr Lys Gln Val Ala Leu Glu Ser Pro Leu Ala Leu
                85                  90                  95

Leu Asn Thr Glu Thr Thr Ile Met Asn Ala Ile Thr Ser Leu Ser Tyr
            100                 105                 110

Gln Ile Asn Gly Ala Ala Asn Asn Ser Gly Trp Gly Ala Pro Ile His
        115                 120                 125

Asp Pro Asp Tyr Ile Gly Gly Ile Gly Lys Glu Leu Ile Val Asp Asp
    130                 135                 140

Ala Ser Asp Val Thr Ser Phe Tyr Pro Ser Ala Phe Gln Glu His Leu
145                 150                 155                 160

Asn Phe Ile Pro Ala Pro Thr Thr Gly Ser Gly Cys Thr Arg Ile Pro
                165                 170                 175

Ser Phe Asp Met Ser Ala Thr His Tyr Cys Tyr Thr His Asn Val Ile
            180                 185                 190

Leu Ser Gly Cys Arg Asp His Ser His Ser Tyr Gln Tyr Leu Ala Leu
        195                 200                 205

Gly Val Leu Arg Thr Ser Ala Thr Gly Arg Val Phe Phe Ser Thr Leu
    210                 215                 220

Arg Ser Ile Asn Leu Asp Asp Thr Gln Asn Arg Lys Ser Cys Ser Val
225                 230                 235                 240

Ser Ala Thr Pro Leu Gly Cys Asp Met Leu Cys Ser Lys Val Thr Glu
                245                 250                 255

Thr Glu Glu Glu Asp Tyr Asn Ser Ala Val Pro Thr Arg Met Val His
            260                 265                 270

Gly Arg Leu Gly Phe Asp Gly Gln Tyr His Glu Lys Asp Leu Asp Val
        275                 280                 285

Thr Thr Leu Phe Gly Asp Trp Val Ala Asn Tyr Pro Gly Val Gly Gly
    290                 295                 300

Gly Ser Phe Ile Asp Ser Arg Val Trp Phe Ser Val Tyr Gly Gly Leu
305                 310                 315                 320

Lys Pro Asn Ser Pro Ser Asp Thr Val Gln Glu Gly Lys Tyr Val Ile
                325                 330                 335

Tyr Lys Arg Tyr Asn Asp Thr Cys Pro Asp Glu Gln Asp Tyr Gln Ile
            340                 345                 350

Arg Met Ala Lys Ser Ser Tyr Lys Pro Gly Arg Phe Gly Gly Lys Arg
        355                 360                 365

Ile Gln Gln Ala Ile Leu Ser Ile Lys Val Ser Thr Ser Leu Gly Glu
    370                 375                 380

Asp Pro Val Leu Thr Val Pro Pro Asn Thr Val Thr Leu Met Gly Ala
385                 390                 395                 400

Glu Gly Arg Ile Leu Thr Val Gly Thr Ser His Phe Leu Tyr Gln Arg
                405                 410                 415

Gly Ser Ser Tyr Phe Ser Pro Ala Leu Leu Tyr Pro Met Thr Val Ser
            420                 425                 430

Asn Lys Thr Ala Thr Leu His Ser Pro Tyr Thr Phe Asn Ala Phe Thr
        435                 440                 445

Arg Pro Gly Ser Ile Pro Cys Gln Ala Ser Ala Arg Cys Pro Asn Ser
    450                 455                 460
```

-continued

```
Cys Val Thr Gly Val Tyr Thr Asp Pro Tyr Pro Leu Ile Phe Tyr Arg
465                 470                 475                 480

Asn His Thr Leu Arg Gly Val Phe Gly Thr Met Leu Asp Gly Val Gln
                485                 490                 495

Ala Arg Leu Asn Pro Ala Ser Ala Val Phe Asp Ser Thr Ser Arg Ser
            500                 505                 510

Arg Ile Thr Arg Val Ser Ser Ser Ser Thr Lys Ala Ala Tyr Thr Thr
        515                 520                 525

Ser Thr Cys Phe Lys Val Val Lys Thr Asn Lys Thr Tyr Cys Leu Ser
    530                 535                 540

Ile Ala Glu Ile Ser Asn Thr Leu Phe Gly Glu Phe Arg Ile Val Pro
545                 550                 555                 560

Leu Leu Val Glu Ile Leu Lys Asp Asp Gly Val Arg Glu Ala Arg Ser
                565                 570                 575

Gly
```

<210> SEQ ID NO 3
<211> LENGTH: 1647
<212> TYPE: DNA
<213> ORGANISM: Avian influenza virus

<400> SEQUENCE: 3

```
gaccaaatct gcatcggtta tcatgcaaac aattcaacaa aacaagttga cacaatcatg     60

gagaagaatg tgacggtcac acatgctcaa gatatactgg aaaaagagca caacgggaaa    120

ctctgcagtc tcaaaggagt gaggcccctc attctgaagg attgcagtgt ggctggatgg    180

cttcttggga acccaatgtg tgatgagttc ctaaatgtac cggaatggtc atatattgta    240

gagaaggaca atccaaccaa tggcttatgt tatccgggag acttcaatga ttatgaagaa    300

ctgaagtatt taatgagcaa cacaaaccat tttgagaaaa ttcaaataat ccctaggaac    360

tcttggtcca atcatgatgc ctcatcagga gtgagctcag catgcccata caatggtagg    420

tcttcctttt tcaggagtgt ggtgtggttg atcaagaaga gtaatgtata cccaacaata    480

aagaggacct acaataacac caatgtagag gaccttctga tattgtgggg aatccatcac    540

cctaatgatg cagcggaaca aacggaactc tatcagaact cgaacactta tgtgtctgta    600

ggaacatcaa cactaaatca gaggtcaatt ccagaaatag ctaccaggcc caaagtgaat    660

ggacaaagtg gaagaataga atttttctgg acaatactaa ggccgaacga tgcaatcagc    720

tttgaaagta atgggaactt tatagctcct gaatatgcat acaagatagt taaaaaggga    780

gattcagcaa tcatgagaag cgaactggag tatggcaact gtgataccaa atgtcagacc    840

ccagtgggtg ctataaattc cagtatgcct tttcacaatg ttcatcccct taccattgga    900

gagtgtccca aatatgtcaa atcagataaa ctggtccttg caacaggact gaggaacgtg    960

cctcagagag aaacaagagg tctgtttgga gcaatagcag gattcataga agggggtgg    1020

caaggaatgg tagatggatg gtatggttac catcatagca acgagcaggg aagtggatat   1080

gctgcagaca aagagtccac tcagaaagca atcgacggga tcaccaataa agtcaactca   1140

atcattgaca aaatgaacac tcaattcgaa gccgttggga aagaattcaa caacttagaa   1200

aggagaatag aaaatttgaa taagaaaatg gaagatggat ttctagatgt atggacttac   1260

aatgcagaac ttctggtgct catggaaaat gaaagaactc tggatttcca tgattcatat   1320

gtcaagaacc tatacgataa ggtccgactc cagctgagag ataatgcaaa agaattgggc   1380

aatgggtgtt tggagttctc ccacaaatgt gacaatgaat gcatggaaag tgtgagaaac   1440
```

-continued

```
ggaacgtatg actatccaca atactcagaa gaatcaaggc tgaacagaga ggaaatagat   1500

ggagtcaaat tggagtcaat gggcacctat cagatactat caatttactc aacagtggcg   1560

agttccctag cactggcaat catggtagct ggtctgtctt tttggatgtg ctccaatgga   1620

tcattgcaat gcagaatttg catctag                                       1647
```

<210> SEQ ID NO 4
<211> LENGTH: 548
<212> TYPE: PRT
<213> ORGANISM: Avian influenza virus

<400> SEQUENCE: 4

```
Asp Gln Ile Cys Ile Gly Tyr His Ala Asn Asn Ser Thr Lys Gln Val
1               5                   10                  15

Asp Thr Ile Met Glu Lys Asn Val Thr Val Thr His Ala Gln Asp Ile
            20                  25                  30

Leu Glu Lys Glu His Asn Gly Lys Leu Cys Ser Leu Lys Gly Val Arg
        35                  40                  45

Pro Leu Ile Leu Lys Asp Cys Ser Val Ala Gly Trp Leu Leu Gly Asn
    50                  55                  60

Pro Met Cys Asp Glu Phe Leu Asn Val Pro Glu Trp Ser Tyr Ile Val
65                  70                  75                  80

Glu Lys Asp Asn Pro Thr Asn Gly Leu Cys Tyr Pro Gly Asp Phe Asn
                85                  90                  95

Asp Tyr Glu Glu Leu Lys Tyr Leu Met Ser Asn Thr Asn His Phe Glu
            100                 105                 110

Lys Ile Gln Ile Ile Pro Arg Asn Ser Trp Ser Asn His Asp Ala Ser
        115                 120                 125

Ser Gly Val Ser Ser Ala Cys Pro Tyr Asn Gly Arg Ser Ser Phe Phe
    130                 135                 140

Arg Ser Val Val Trp Leu Ile Lys Lys Ser Asn Val Tyr Pro Thr Ile
145                 150                 155                 160

Lys Arg Thr Tyr Asn Asn Thr Asn Val Glu Asp Leu Leu Ile Leu Trp
                165                 170                 175

Gly Ile His His Pro Asn Asp Ala Ala Glu Gln Thr Glu Leu Tyr Gln
            180                 185                 190

Asn Ser Asn Thr Tyr Val Ser Val Gly Thr Ser Thr Leu Asn Gln Arg
        195                 200                 205

Ser Ile Pro Glu Ile Ala Thr Arg Pro Lys Val Asn Gly Gln Ser Gly
    210                 215                 220

Arg Ile Glu Phe Phe Trp Thr Ile Leu Arg Pro Asn Asp Ala Ile Ser
225                 230                 235                 240

Phe Glu Ser Asn Gly Asn Phe Ile Ala Pro Glu Tyr Ala Tyr Lys Ile
                245                 250                 255

Val Lys Lys Gly Asp Ser Ala Ile Met Arg Ser Glu Leu Glu Tyr Gly
            260                 265                 270

Asn Cys Asp Thr Lys Cys Gln Thr Pro Val Gly Ala Ile Asn Ser Ser
        275                 280                 285

Met Pro Phe His Asn Val His Pro Leu Thr Ile Gly Glu Cys Pro Lys
    290                 295                 300

Tyr Val Lys Ser Asp Lys Leu Val Leu Ala Thr Gly Leu Arg Asn Val
305                 310                 315                 320

Pro Gln Arg Glu Thr Arg Gly Leu Phe Gly Ala Ile Ala Gly Phe Ile
                325                 330                 335
```

-continued

```
Glu Gly Gly Trp Gln Gly Met Val Asp Gly Trp Tyr Gly Tyr His His
            340                 345                 350

Ser Asn Glu Gln Gly Ser Gly Tyr Ala Ala Asp Lys Glu Ser Thr Gln
        355                 360                 365

Lys Ala Ile Asp Gly Ile Thr Asn Lys Val Asn Ser Ile Ile Asp Lys
    370                 375                 380

Met Asn Thr Gln Phe Glu Ala Val Gly Lys Glu Phe Asn Asn Leu Glu
385                 390                 395                 400

Arg Arg Ile Glu Asn Leu Asn Lys Lys Met Glu Asp Gly Phe Leu Asp
                405                 410                 415

Val Trp Thr Tyr Asn Ala Glu Leu Leu Val Leu Met Glu Asn Glu Arg
            420                 425                 430

Thr Leu Asp Phe His Asp Ser Tyr Val Lys Asn Leu Tyr Asp Lys Val
        435                 440                 445

Arg Leu Gln Leu Arg Asp Asn Ala Lys Glu Leu Gly Asn Gly Cys Leu
    450                 455                 460

Glu Phe Ser His Lys Cys Asp Asn Glu Cys Met Glu Ser Val Arg Asn
465                 470                 475                 480

Gly Thr Tyr Asp Tyr Pro Gln Tyr Ser Glu Glu Ser Arg Leu Asn Arg
                485                 490                 495

Glu Glu Ile Asp Gly Val Lys Leu Glu Ser Met Gly Thr Tyr Gln Ile
            500                 505                 510

Leu Ser Ile Tyr Ser Thr Val Ala Ser Ser Leu Ala Leu Ala Ile Met
        515                 520                 525

Val Ala Gly Leu Ser Phe Trp Met Cys Ser Asn Gly Ser Leu Gln Cys
    530                 535                 540

Arg Ile Cys Ile
545
```

<210> SEQ ID NO 5
<211> LENGTH: 28
<212> TYPE: DNA
<213> ORGANISM: Artificial Sequence
<220> FEATURE:
<223> OTHER INFORMATION: PCR primer CVM-Asc

<400> SEQUENCE: 5
atggcgcgcc agaaggtaat tatccaag 28

<210> SEQ ID NO 6
<211> LENGTH: 24
<212> TYPE: DNA
<213> ORGANISM: Artificial Sequence
<220> FEATURE:
<223> OTHER INFORMATION: PCR primer CVM-Xho

<400> SEQUENCE: 6
atctcgagcc atggtttgga tcca 24

<210> SEQ ID NO 7
<211> LENGTH: 25
<212> TYPE: DNA
<213> ORGANISM: Artificial Sequence
<220> FEATURE:
<223> OTHER INFORMATION: Mutagenic primer GSS-Nco

<400> SEQUENCE: 7
tgccatggtg atgtgtggtc tacaa 25

-continued

<210> SEQ ID NO 8
<211> LENGTH: 23
<212> TYPE: DNA
<213> ORGANISM: Artificial Sequence
<220> FEATURE:
<223> OTHER INFORMATION: Forward primer GSS-1.8F

<400> SEQUENCE: 8
gatctgacaa gtcaagaaaa ttg 23

<210> SEQ ID NO 9
<211> LENGTH: 23
<212> TYPE: DNA
<213> ORGANISM: Artificial Sequence
<220> FEATURE:
<223> OTHER INFORMATION: Mutagenic primer GSS-Xho

<400> SEQUENCE: 9
agctcgagct gtgtgagtga gtg 23

<210> SEQ ID NO 10
<211> LENGTH: 20
<212> TYPE: DNA
<213> ORGANISM: Artificial Sequence
<220> FEATURE:
<223> OTHER INFORMATION: Primer HNa

<400> SEQUENCE: 10
ccgagcagtt tcacaagtgg 20

<210> SEQ ID NO 11
<211> LENGTH: 21
<212> TYPE: DNA
<213> ORGANISM: Artificial Sequence
<220> FEATURE:
<223> OTHER INFORMATION: Primer HNb

<400> SEQUENCE: 11
cctgatcttg cttcacgtac a 21

<210> SEQ ID NO 12
<211> LENGTH: 4767
<212> TYPE: DNA
<213> ORGANISM: Artificial Sequence
<220> FEATURE:
<223> OTHER INFORMATION: DNA Sequence of the whole gene insert in CHN-18 Master Seed

<400> SEQUENCE: 12
gaggtctaca ggccaaattc gctcttagcc gtacaatatt actcaccgga tcggccgctt 60
aattaagttt aaaccctgca ggaaagcccg ggcaaaggcg cgccagaagg taattatcca 120
gatgtagcat caagaatcca atgtttacgg gaaaaactat ggaagtatta tgtgagctca 180
gcaagaagca gatcaatatg cggcacatat gcaacctatg ttcaaaaatg aagaatgtac 240
agatacaaga tcctatactg ccagaatacg aagaagaata cgtagaaatt gaaaaagaag 300
aaccaggcga agaaaagaat cttgaagacg taagcactga cgacaacaat gaaaagaaga 360
agataaggtc ggtgattgtg aaagagacat agaggacaca tgtaaggtgg aaaatgtaag 420
ggcggaaagt aaccttatca caaaggaatc ttatccccca ctacttatcc ttttatattt 480
ttccgtgtca tttttgccct tgagttttcc tatataagga accaagttcg gcatttgtga 540
aaacaagaaa aaatttggtg taagctattt tctttgaagt actgaggata caacttcaga 600
gaaatttgta agtttgtgga tccaaaccat ggaccgagca gtttcacaag tggctcttga 660

-continued

```
gaatgatgag agggaagcca agaacacttg gaggcttatc tttcggatag ccattctctt    720
tcttactgtt gtcaccctag caatctctgt tgcatcatta ctctattcta tgggagcaag    780
caccccctca gacttagttg gcatacccac acgaatctct agggctgaag agaagattac    840
cagtacccta ggctccaacc aggatgttgt ggaccgaatc tacaaacaag ttgcacttga    900
aagtccactt gcattactca acacagaaac taccatcatg aatgcaatca ccagcctatc    960
ctatcagatc aatggggctg ccaacaattc aggttgggga gccccaattc atgatccaga   1020
ctacattgga ggtattggca aagaactcat tgtagatgat gcttcagatg ttacatcttt   1080
ctatccttca gctttccagg aacatctgaa cttcattcct gcacccacaa ctgggagtgg   1140
gtgcactcgg ataccctcat ttgacatgag tgctacacac tattgctata cacacaatgt   1200
cattctatct ggctgtcgtg accattctca ctcttatcag tacttagcac ttggagttct   1260
tcgtacatct gctactggta gagtgttctt ctcaactctt cgcagtatca atcttgatga   1320
tacacagaat cgcaaaagtt gctctgtatc tgctacacct ttgggctgtg atatgctatg   1380
cagtaaagta acagaaactg aagaagagga ctacaattct gcagtcccta caaggatggt   1440
gcatggcaga ttgggttttg atggtcaata ccatgagaaa gatttggatg tcactacatt   1500
gtttggggat tgggtagcta actatccagg agttggaggt ggtagcttca ttgactccag   1560
agtctggttc tctgtctatg gtggtttgaa acctaacagt cctagtgata ctgtgcaaga   1620
gggaaagtat gttatctaca agaggtacaa tgatacttgt cctgatgagc aagactatca   1680
gattcgaatg gctaagtcat catacaaacc aggaagattt ggaggtaaga ggatacaaca   1740
agctattctc agtatcaagg ttagcacatc attgggagaa gatccagtcc ttactgttcc   1800
accaaacact gtaacattga tgggagctga gggaaggatt cttactgttg gtactagcca   1860
ctttctctat caacgtggaa gttcctactt tagcccagcg ttactgtatc caatgactgt   1920
gagcaacaag acagctacat tacattcacc atatactttc aatgccttta caagacctgg   1980
atcgattcct tgccaagctt cagctagatg tccgaattcg tgtgtgactg gagtttacac   2040
tgatccttac cctttgatct tctaccgtaa tcataccttg agaggggtgt ttggaacaat   2100
gttagatggt gttcaagcta ggttgaatcc tgcctctgct gtgtttgatt ctacatccag   2160
atcaaggata accagagttt cctctagttc tactaaggca gcatacacta cctccacatg   2220
tttcaaagtt gtaaagacga acaagaccta ttgtctgagc atagctgaga tttctaacac   2280
tctctttggg gaattcagaa ttgttccact tttggtggag attctgaaag atgatggtgt   2340
acgtgaagca agatcaggtt aagtcttcgg atccggtacc gagctctctc aacaatctag   2400
ctagagtttg ctcctatcta tatgtaataa ggtatgctga tatgcactat tcaaatagga   2460
gcattagcta tgtttgttaa tgtcacttta tgttatgtgg gtaagtcacc taagacactc   2520
cacgtaccta cttgttgtct cttacgcggc tttaataaat cttctgccct tgttccatat   2580
ttactaatta tccctttctt cactaaaaga aaattgttat cattaagtat tagtctttag   2640
aacatatgag gtctttaatt gggtaggttt tacaaattaa ctaatataaa atgtcataaa   2700
atccacgtgg ttaaacaaat gcagaaaatc gacgtcgtct attggaccga cagttgctat   2760
taatataatg ggccaccata gtagactgac aaataaatta cctgacaaca tcgtttcaca   2820
aaaaaacaaa cacaaaaagg gagtgcattt tccagggcat tttgtaata aaaaacagat   2880
aaaagggagt gcaatagaaa tataggggtg tggaaatagt gatttgagca cgtcttgaag   2940
cgaattcgcg gccggccaga aggtaattat ccaagatgta gcatcaagaa tccaatgttt   3000
acgggaaaaa ctatggaagt attatgtgag ctcagcaaga agcagatcaa tatgcggcac   3060
```

-continued

```
atatgcaacc tatgttcaaa aatgaagaat gtacagatac aagatcctat actgccagaa   3120
tacgaagaag aatacgtaga aattgaaaaa gaagaaccag gcgaagaaaa gaatcttgaa   3180
gacgtaagca ctgacgacaa caatgaaaag aagaagataa ggtcggtgat tgtgaaagag   3240
acatagagga cacatgtaag gtggaaaatg taagggcgga aagtaacctt atcacaaagg   3300
aatcttatcc cccactactt atccttttat atttttccgt gtcatttttg cccttgagtt   3360
ttcctatata aggaaccaag ttcggcattt gtgaaaacaa gaaaaaattt ggtgtaagct   3420
attttctttg aagtactgag gatacaactt cagagaaatt tgtaagtttg tggatccaaa   3480
ccatggcttc tccggagagg agaccagttg agattaggcc agctacagca gctgatatgg   3540
ccgcggtttg tgatatcgtt aaccattaca ttgagacgtc tacagtgaac tttaggacag   3600
agccacaaac accacaagag tggattgatg atctagagag gttgcaagat agataccctt   3660
ggttggttgc tgaggttgag ggtgttgtgg ctggtattgc ttacgctggg ccctggaagg   3720
ctaggaacgc ttacgattgg acagttgaga gtactgttta cgtgtcacat aggcatcaaa   3780
ggttgggcct aggatccaca ttgtacacac atttgcttaa gtctatggag gcgcaaggtt   3840
ttaagtctgt ggttgctgtt ataggccttc caaacgatcc atctgttagg ttgcatgagg   3900
ctttgggata cacagcccgg ggtacattgc gcgcagctgg atacaagcat ggtggatggc   3960
atgatgttgg tttttggcaa agggattttg agttgccagc tcctccaagg ccagctaggc   4020
cagttaccca gatctgaggt accctgagct cggtcacctg tccaacagtc tcagggttaa   4080
tgtctatgta tcttaaataa tgttgtcggt attttgtaat ctcatataga ttttcactgt   4140
gcgacgcaaa aatattaaat aaatattatt attatctacg ttttgattga gatatcatca   4200
atattataat aaaaatatcc attaaacacg atttgataca aatgacagtc aataatctga   4260
tttgaatatt tattaattgt aacgaattac ataaagatcg aatagaaaat actgcactgc   4320
aaatgaaaat taacacatac taataaatgc gtcaaatatc tttgccaaga tcaagcggag   4380
tgagggcctc atatccggtc tcagttacaa gcacggtatc cccgaagcgc gctccaccaa   4440
tgccctcgac atagatgccg ggctcgacgc tgaggacatt gcctaccttg agcatggtct   4500
cagcgccggc tttaagctca atcccatccc aatctgaata tcctatcccg cgcccagtcc   4560
ggtgtaagaa cgggtctgtc catccacctc tgttgcggcc aattctgatc tggcccccat   4620
ttggacgtga atgtagacac gtcgatataa agatttccga attagaataa tttgtttatt   4680
gctttcgcct ataaatacga cggatcgtaa tttgtcgttt tatcaaaatg tactttcatt   4740
ttataataac gctgcggaca tctacat                                        4767
```

<210> SEQ ID NO 13
<211> LENGTH: 681
<212> TYPE: DNA
<213> ORGANISM: Hepatitis B virus

<400> SEQUENCE: 13

```
atggagaaca tcacatcagg attcctagga cccctgctcg tgttacaggc ggggtttttc     60
ttgttgacaa gaatcctcac aataccgcag agtctagact cgtggtggac ttctctcaat    120
tttctagggg gatcacccgt gtgtcttggc caaaattcgc agtccccaac ctccaatcac    180
tcaccaacct cctgtcctcc aatctgtcct ggttatcgct ggatgtgtct gcggcgtttt    240
atcatattcc tcttcatcct gctgctatgc ctcatcttct tattggttct tctggattat    300
caaggtatgt tgcccgtttg tcctctaatt ccaggatcaa caacaaccag tacgggacca    360
tgcaaaacct gcacgactcc tgctcaaggg aactctatgt ttccctcatg ttgctgtaca    420
```

-continued

```
aaacctacgg atgggaattg cacctgtatt cccatcccat cgtcctgggc tttcgcaaaa    480

tacctatggg agtgggcctc agtccgtttc tcttggctca gtttactagt gccatttgtt    540

cagtggttcg tagggctttc ccccactgtt tggctttcag ctatatggat gatgtggtat    600

tgggggccaa gtctgtacag catcgtgagt ccctttatac cgctgttacc aattttcttt    660

tgtctctggg tatacattta a                                              681
```

```
<210> SEQ ID NO 14
<211> LENGTH: 226
<212> TYPE: PRT
<213> ORGANISM: Hepatitis B virus

<400> SEQUENCE: 14

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Ser Pro Val Cys
        35                  40                  45

Leu Gly Gln Asn Ser Gln Ser Pro Thr Ser Asn His Ser Pro Thr Ser
    50                  55                  60

Cys Pro Pro Ile Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

Leu Leu Asp Tyr Gln Gly Met Leu Pro Val Cys Pro Leu Ile Pro Gly
            100                 105                 110

Ser Thr Thr Thr Ser Thr Gly Pro Cys Lys Thr Cys Thr Thr Pro Ala
        115                 120                 125

Gln Gly Asn Ser Met Phe Pro Ser Cys Cys Cys Thr Lys Pro Thr Asp
    130                 135                 140

Gly Asn Cys Thr Cys Ile Pro Ile Pro Ser Ser Trp Ala Phe Ala Lys
145                 150                 155                 160

Tyr Leu Trp Glu Trp Ala Ser Val Arg Phe Ser Trp Leu Ser Leu Leu
                165                 170                 175

Val Pro Phe Val Gln Trp Phe Val Gly Leu Ser Pro Thr Val Trp Leu
            180                 185                 190

Ser Ala Ile Trp Met Met Trp Tyr Trp Gly Pro Ser Leu Tyr Ser Ile
        195                 200                 205

Val Ser Pro Phe Ile Pro Leu Leu Pro Ile Phe Phe Cys Leu Trp Val
    210                 215                 220

Tyr Ile
225
```

```
<210> SEQ ID NO 15
<211> LENGTH: 1467
<212> TYPE: DNA
<213> ORGANISM: Homo sapiens

<400> SEQUENCE: 15

cgcagttgtg cacaccccag cccaggctct ggcaggctgc caggcggggc tcgccgcctt     60

cgcagtgcac gttgtccagc aggatgtgtc cggtgccata gccgaagaag gcgttggtgg    120

tggcggccat ggccgccccg cagcccagct gacgacagac cacagcggca tccggcagcc    180

cccagtcgtc gtcacacacg gtgccccaca ggccactgtg caggatctcc actcggccct    240
```

-continued

```
gacacagggt ggagccagcc atcctgagac gtccgtacag cccgtactgg tggagtgtca    300

ggaggccact ctgatggtca tggtcagcaa agaccttttt ggcaccggga agctcatcag    360

ggctgctgac ctcaccttgg gcccagaggc ctgtgagcct ctggtctcca tggacacaga    420

agatgtggtc aggtttgagg ttggactcca cgagtgtggc aacagcatgc aggtaactga    480

cgatgccctg gtgtacagca ccttcctgct ccatgacccc cgccccgtgg gaaacctgtc    540

catcgtgagg actaaccgcg cagagattcc catcgagtgc cgctacccca ggcagggcaa    600

tgtgagcagc caggccatcc tgcccacctg gttgcccttc aggaccacgg tgttctcaga    660

ggagaagctg actttctctc tgcgtctgat ggaggagaac tggaacgctg agaagaggtc    720

ccccaccttc cacctgggag atgcagccca cctccaggca gaaatccaca ctggcagcca    780

cgtgccactg cggttgtttg tggaccactg cgtggccaca ccgacaccag accagaatgc    840

ctccccttat cacaccatcg tggacttcca tggctgtctt gtcgacggtc tcactgatgc    900

ctcttctgca ttcaaagttc ctcgacccgg gccagataca ctccagttca cagtggatgt    960

cttccacttt gctaatgact ccagaaacat gatatacatc acctgccacc tgaaggtcac   1020

cctagctgag caggacccag atgaactcaa caaggcctgt tccttcagca agccttccaa   1080

cagctggttc ccagtggaag gctcggctga catctgtcaa tgctgtaaca aaggtgactg   1140

tggcactcca agccattcca ggaggcagcc tcatgtcatg agccagtggt ccaggtctgc   1200

ttcccgtaac cgcaggcatg tgacagaaga agcagatgtc accgtggggc cactgatctt   1260

cctggacagg aggggtgacc atgaagtaga gcagtgggct ttgccttctg acacctcagt   1320

ggtgctgctg ggcgtaggcc tggctgtggt ggtgtccctg actctgactg ctgttatcct   1380

ggttctcacc aggaggtgtc gcactgcctc ccaccctgtg tctgcttccg aataaaagaa   1440

gaaagcaata aaaaaaaaaa aaaaaaa                                       1467
```

<210> SEQ ID NO 16
<211> LENGTH: 373
<212> TYPE: PRT
<213> ORGANISM: Homo sapiens

<400> SEQUENCE: 16

```
Met Val Met Val Ser Lys Asp Leu Phe Gly Thr Gly Lys Leu Ile Arg
1               5                   10                  15

Ala Ala Asp Leu Thr Leu Gly Pro Glu Ala Cys Glu Pro Leu Val Ser
            20                  25                  30

Met Asp Thr Glu Asp Val Val Arg Phe Glu Val Gly Leu His Glu Cys
        35                  40                  45

Gly Asn Ser Met Gln Val Thr Asp Asp Ala Leu Val Tyr Ser Thr Phe
    50                  55                  60

Leu Leu His Asp Pro Arg Pro Val Gly Asn Leu Ser Ile Val Arg Thr
65                  70                  75                  80

Asn Arg Ala Glu Ile Pro Ile Glu Cys Arg Tyr Pro Arg Gln Gly Asn
                85                  90                  95

Val Ser Ser Gln Ala Ile Leu Pro Thr Trp Leu Pro Phe Arg Thr Thr
            100                 105                 110

Val Phe Ser Glu Glu Lys Leu Thr Phe Ser Leu Arg Leu Met Glu Glu
        115                 120                 125

Asn Trp Asn Ala Glu Lys Arg Ser Pro Thr Phe His Leu Gly Asp Ala
    130                 135                 140

Ala His Leu Gln Ala Glu Ile His Thr Gly Ser His Val Pro Leu Arg
145                 150                 155                 160
```

-continued

```
Leu Phe Val Asp His Cys Val Ala Thr Pro Thr Pro Asp Gln Asn Ala
                165                 170                 175

Ser Pro Tyr His Thr Ile Val Asp Phe His Gly Cys Leu Val Asp Gly
            180                 185                 190

Leu Thr Asp Ala Ser Ser Ala Phe Lys Val Pro Arg Pro Gly Pro Asp
        195                 200                 205

Thr Leu Gln Phe Thr Val Asp Val Phe His Phe Ala Asn Asp Ser Arg
    210                 215                 220

Asn Met Ile Tyr Ile Thr Cys His Leu Lys Val Thr Leu Ala Glu Gln
225                 230                 235                 240

Asp Pro Asp Glu Leu Asn Lys Ala Cys Ser Phe Ser Lys Pro Ser Asn
                245                 250                 255

Ser Trp Phe Pro Val Glu Gly Ser Ala Asp Ile Cys Gln Cys Cys Asn
            260                 265                 270

Lys Gly Asp Cys Gly Thr Pro Ser His Ser Arg Arg Gln Pro His Val
        275                 280                 285

Met Ser Gln Trp Ser Arg Ser Ala Ser Arg Asn Arg Arg His Val Thr
    290                 295                 300

Glu Glu Ala Asp Val Thr Val Gly Pro Leu Ile Phe Leu Asp Arg Arg
305                 310                 315                 320

Gly Asp His Glu Val Glu Gln Trp Ala Leu Pro Ser Asp Thr Ser Val
                325                 330                 335

Val Leu Leu Gly Val Gly Leu Ala Val Val Val Ser Leu Thr Leu Thr
            340                 345                 350

Ala Val Ile Leu Val Leu Thr Arg Arg Cys Arg Thr Ala Ser His Pro
        355                 360                 365

Val Ser Ala Ser Glu
    370
```

<210> SEQ ID NO 17
<211> LENGTH: 1740
<212> TYPE: DNA
<213> ORGANISM: Avian influenza virus

<400> SEQUENCE: 17

```
atggaaagaa tagtgattgc ccttgcaata atcaacattg tcaaaggtga ccaaatctgc      60

attggttatc atgcaaacaa ttcaacagag caggttgaca caatcatgga gaagaatgtg     120

acggtcacac atgctcagga catactggaa aaagagcaca atgggaaact ctgcagtctt     180

aaaggagtga ggcccctcat tctgaaggat tgcagtgtcg ctgggtggct tcttggaaac     240

ccaatgtgtg atgaattcct gaatgtaccg gaatggtcat acattgtgga aaaagataat     300

ccagtcaatg gcctgtgcta tccaggagac ttcaacgatt atgaagaact gaagcattta     360

atgagcagca caaaccattt tgagaaaatt cagataattc ctaggaactc ttggtccacc     420

catgatgcct catcaggagt gagctcagca tgcccataca atggtaggtc ttccttttttc     480

aggaatgtag tgtggttgat caagaagaat aatgcgtacc caacaataaa gaggacctac     540

aacaacacca atgtagaaga ccttttaata ttatggggaa tccaccaccc taatgatgca     600

gcagaacaaa caaaactcta ccagaactcg aacacttatg tgtctgtagg aacatcaaca     660

ctgaatcaga ggtcaatccc agaaatagcc accagaccca aagtgaacgg acaaagtgga     720

agaatggaat ttttttggac aatactaagg ccgaacgatg caatcagctt tgaaagtaat     780

gggaacttta tagctcctga atatgcgtac aagattgtta aaaaaggaga ttcagcaatc     840

atgaaaagtg aactggagta tggtaactgt gataccaaat gtcagacccc agtgggtgct     900
```

-continued

```
ataaattcca gtatgccttt ccacaatgtt catcccctta ccattgggga gtgccccaag    960

tatgtcaaat cggacaaact ggtccttgca acaggactaa gaaacgtacc ccaaagagaa   1020

acaagaggcc tatttggagc aatagcagga ttcatagaag gaggatggca aggaatggta   1080

gatggatggt atggatacca tcatagcaat gagcagggaa gtggatatgc tgcagacaaa   1140

gaatctaccc agaaagcaat cgatgggatc accaataaag taaactcaat cattgacaaa   1200

atgaacactc aattcgaagc cgttgggaaa gaattcaaca acctagaaag gagaatagaa   1260

aatttgaata agaaaatgga agatgggttt ttagatgtat ggacttacaa tgcagaactt   1320

ctagtgctca tggaaaacga aagaactctg gatttccatg attcaaatgt caagaactta   1380

tacgataagg tccgactcca gctgagagac aatgcaaaag aattaggcaa cgggtgcttt   1440

gaattctacc acaagtgtga caatgaatgc atggaaagtg tgagaaatgg aacgtatgac   1500

tatccacaat actcagaaga atcaagactg aacagggagg aaatagacgg agtcaaattg   1560

gaatcaatgg gcacttatca gatactatca atctactcaa cagtggcgag ttccctagca   1620

ctggcaatca tggtagctgg tctatctttt tggatgtgct ccaatggatc attgcagtgc   1680

agaatttgca tctagaattg tgagttcaga ttataattaa aaacacccta gtttctactg   1740
```

```
<210> SEQ ID NO 18
<211> LENGTH: 564
<212> TYPE: PRT
<213> ORGANISM: Avian influenza virus

<400> SEQUENCE: 18

Met Glu Arg Ile Val Ile Ala Leu Ala Ile Ile Asn Ile Val Lys Gly
1               5                   10                  15

Asp Gln Ile Cys Ile Gly Tyr His Ala Asn Asn Ser Thr Glu Gln Val
            20                  25                  30

Asp Thr Ile Met Glu Lys Asn Val Thr Val Thr His Ala Gln Asp Ile
        35                  40                  45

Leu Glu Lys Glu His Asn Gly Lys Leu Cys Ser Leu Lys Gly Val Arg
    50                  55                  60

Pro Leu Ile Leu Lys Asp Cys Ser Val Ala Gly Trp Leu Leu Gly Asn
65                  70                  75                  80

Pro Met Cys Asp Glu Phe Leu Asn Val Pro Glu Trp Ser Tyr Ile Val
                85                  90                  95

Glu Lys Asp Asn Pro Val Asn Gly Leu Cys Tyr Pro Gly Asp Phe Asn
            100                 105                 110

Asp Tyr Glu Glu Leu Lys His Leu Met Ser Ser Thr Asn His Phe Glu
        115                 120                 125

Lys Ile Gln Ile Ile Pro Arg Asn Ser Trp Ser Thr His Asp Ala Ser
    130                 135                 140

Ser Gly Val Ser Ser Ala Cys Pro Tyr Asn Gly Arg Ser Ser Phe Phe
145                 150                 155                 160

Arg Asn Val Val Trp Leu Ile Lys Lys Asn Asn Ala Tyr Pro Thr Ile
                165                 170                 175

Lys Arg Thr Tyr Asn Asn Thr Asn Val Glu Asp Leu Leu Ile Leu Trp
            180                 185                 190

Gly Ile His His Pro Asn Asp Ala Ala Glu Gln Thr Lys Leu Tyr Gln
        195                 200                 205

Asn Ser Asn Thr Tyr Val Ser Val Gly Thr Ser Thr Leu Asn Gln Arg
    210                 215                 220
```

-continued

```
Ser Ile Pro Glu Ile Ala Thr Arg Pro Lys Val Asn Gly Gln Ser Gly
225                 230                 235                 240

Arg Met Glu Phe Phe Trp Thr Ile Leu Arg Pro Asn Asp Ala Ile Ser
                245                 250                 255

Phe Glu Ser Asn Gly Asn Phe Ile Ala Pro Glu Tyr Ala Tyr Lys Ile
            260                 265                 270

Val Lys Lys Gly Asp Ser Ala Ile Met Lys Ser Glu Leu Glu Tyr Gly
        275                 280                 285

Asn Cys Asp Thr Lys Cys Gln Thr Pro Val Gly Ala Ile Asn Ser Ser
    290                 295                 300

Met Pro Phe His Asn Val His Pro Leu Thr Ile Gly Glu Cys Pro Lys
305                 310                 315                 320

Tyr Val Lys Ser Asp Lys Leu Val Leu Ala Thr Gly Leu Arg Asn Val
                325                 330                 335

Pro Gln Arg Glu Thr Arg Gly Leu Phe Gly Ala Ile Ala Gly Phe Ile
            340                 345                 350

Glu Gly Gly Trp Gln Gly Met Val Asp Gly Trp Tyr Gly Tyr His His
        355                 360                 365

Ser Asn Glu Gln Gly Ser Gly Tyr Ala Ala Asp Lys Glu Ser Thr Gln
    370                 375                 380

Lys Ala Ile Asp Gly Ile Thr Asn Lys Val Asn Ser Ile Ile Asp Lys
385                 390                 395                 400

Met Asn Thr Gln Phe Glu Ala Val Gly Lys Glu Phe Asn Asn Leu Glu
                405                 410                 415

Arg Arg Ile Glu Asn Leu Asn Lys Lys Met Glu Asp Gly Phe Leu Asp
            420                 425                 430

Val Trp Thr Tyr Asn Ala Glu Leu Leu Val Leu Met Glu Asn Glu Arg
        435                 440                 445

Thr Leu Asp Phe His Asp Ser Asn Val Lys Asn Leu Tyr Asp Lys Val
    450                 455                 460

Arg Leu Gln Leu Arg Asp Asn Ala Lys Glu Leu Gly Asn Gly Cys Phe
465                 470                 475                 480

Glu Phe Tyr His Lys Cys Asp Asn Glu Cys Met Glu Ser Val Arg Asn
                485                 490                 495

Gly Thr Tyr Asp Tyr Pro Gln Tyr Ser Glu Glu Ser Arg Leu Asn Arg
            500                 505                 510

Glu Glu Ile Asp Gly Val Lys Leu Glu Ser Met Gly Thr Tyr Gln Ile
        515                 520                 525

Leu Ser Ile Tyr Ser Thr Val Ala Ser Ser Leu Ala Leu Ala Ile Met
    530                 535                 540

Val Ala Gly Leu Ser Phe Trp Met Cys Ser Asn Gly Ser Leu Gln Cys
545                 550                 555                 560

Arg Ile Cys Ile
```

<210> SEQ ID NO 19
<211> LENGTH: 1734
<212> TYPE: DNA
<213> ORGANISM: Newcastle disease virus

<400> SEQUENCE: 19

```
atggaccgcg ccgttagcca agttgcgtta gagaatgatg aaagagaggc aaaaaataca      60

tggcgcttga tattccggat tgcaatctta ttcttaacag tagtgacctt ggctatatct     120

gtagcctccc ttttatatag catgggggct agcacaccta gcgatcttgt aggcataccg     180
```

-continued

```
actaggattt ccagggcaga agaaaagatt acatctacac ttggttccaa tcaagatgta    240
gtagatagga tatataagca agtggccctt gagtctccgt tggcattgtt aaaaactgag    300
accacaatta tgaacgcaat aacatctctc tcttatcaga ttaatggagc tgcaaacaac    360
agcgggtggg ggcacctat ccatgaccca gattatatag gggggatagg caaagaactc    420
attgtagatg atgctagtga tgtcacatca ttctatccct ctgcatttca agaacatctg    480
aattttatcc cggcgcctac tacaggatca ggttgcactc gaatacccte atttgacatg    540
agtgctaccc attactgcta cacccataat gtaatattgt ctggatgcag agatcactca    600
cattcatatc agtatttagc acttggtgtg ctccggacat ctgcaacagg gggggtattc    660
ttttctactc tgcgttccat caacctggac gacacccaaa atcggaagtc ttgcagtgtg    720
agtgcaactc ccctgggttg tgatatgctg tgctcgaaag tcacggagac agaggaagaa    780
gattataact cagctgtccc tacgcggatg gtacatggga ggttagggtt cgacggccag    840
taccacgaaa aggacctaga tgtcacaaca ttattcgggg actgggtggc caactaccca    900
ggagtagggg gtggatcttt tattgacagc cgcgtatggt tctcagttta cggagggtta    960
aaacccaatt cacccagtga cactgtacag gaagggaaat atgtgatata caagcaatac   1020
aatgacacat gcccagatga gcaagactac cagattcgaa tggccaagtc ttcgtataag   1080
cctggacggt ttggtgggaa acgcatacag caggctatct tatctatcaa ggtgtcaaca   1140
tccttaggcg aagacccggt actgactgta ccgcccaaca cagtcacact catgggggcc   1200
gaaggcagaa ttctcacagt agggacatct catttcttgt atcaacgagg gtcatcatac   1260
ttctctcccg cgttattata tcctatgaca gtcagcaaca aaacagccac tcttcatagt   1320
ccttatacat tcaatgcctt cactcggcca ggtagtatcc cttgccaggc ttcagcaaga   1380
tgccccaacc cgtgtgttac tggagtctat acagatccat atcccctaat cttctataga   1440
aaccacacct tgcgaggggt attcgggaca atgcttgatg gtgtacaagc aagacttaac   1500
cctgcgtctg cagtattcga tagcacatcc cgcagtcgca ttactcgagt gagttcaagc   1560
agtaccaaag cagcatacac aacatcaact tgttttaaag tggtcaagac taataagacc   1620
tattgtctca gcattgctga aatatctaat actctcttcg gagaattcag aatcgtcccg   1680
ttactagttg agatcctcaa agatgacggg gttagagaag ccaggtctgg ctag         1734
```

<210> SEQ ID NO 20
<211> LENGTH: 577
<212> TYPE: PRT
<213> ORGANISM: Newcastle disease virus

<400> SEQUENCE: 20

```
Met Asp Arg Ala Val Ser Gln Val Ala Leu Glu Asn Asp Glu Arg Glu
1               5                   10                  15

Ala Lys Asn Thr Trp Arg Leu Ile Phe Arg Ile Ala Ile Leu Phe Leu
            20                  25                  30

Thr Val Val Thr Leu Ala Ile Ser Val Ala Ser Leu Leu Tyr Ser Met
        35                  40                  45

Gly Ala Ser Thr Pro Ser Asp Leu Val Gly Ile Pro Thr Arg Ile Ser
    50                  55                  60

Arg Ala Glu Glu Lys Ile Thr Ser Thr Leu Gly Ser Asn Gln Asp Val
65                  70                  75                  80

Val Asp Arg Ile Tyr Lys Gln Val Ala Leu Glu Ser Pro Leu Ala Leu
                85                  90                  95
```

-continued

```
Leu Lys Thr Glu Thr Thr Ile Met Asn Ala Ile Thr Ser Leu Ser Tyr
            100                 105                 110

Gln Ile Asn Gly Ala Ala Asn Asn Ser Gly Trp Gly Ala Pro Ile His
        115                 120                 125

Asp Pro Asp Tyr Ile Gly Gly Ile Gly Lys Glu Leu Ile Val Asp Asp
    130                 135                 140

Ala Ser Asp Val Thr Ser Phe Tyr Pro Ser Ala Phe Gln Glu His Leu
145                 150                 155                 160

Asn Phe Ile Pro Ala Pro Thr Thr Gly Ser Gly Cys Thr Arg Ile Pro
                165                 170                 175

Ser Phe Asp Met Ser Ala Thr His Tyr Cys Tyr Thr His Asn Val Ile
            180                 185                 190

Leu Ser Gly Cys Arg Asp His Ser His Ser Tyr Gln Tyr Leu Ala Leu
        195                 200                 205

Gly Val Leu Arg Thr Ser Ala Thr Gly Gly Val Phe Phe Ser Thr Leu
    210                 215                 220

Arg Ser Ile Asn Leu Asp Asp Thr Gln Asn Arg Lys Ser Cys Ser Val
225                 230                 235                 240

Ser Ala Thr Pro Leu Gly Cys Asp Met Leu Cys Ser Lys Val Thr Glu
                245                 250                 255

Thr Glu Glu Glu Asp Tyr Asn Ser Ala Val Pro Thr Arg Met Val His
            260                 265                 270

Gly Arg Leu Gly Phe Asp Gly Gln Tyr His Glu Lys Asp Leu Asp Val
        275                 280                 285

Thr Thr Leu Phe Gly Asp Trp Val Ala Asn Tyr Pro Gly Val Gly Gly
    290                 295                 300

Gly Ser Phe Ile Asp Ser Arg Val Trp Phe Ser Val Tyr Gly Gly Leu
305                 310                 315                 320

Lys Pro Asn Ser Pro Ser Asp Thr Val Gln Glu Gly Lys Tyr Val Ile
                325                 330                 335

Tyr Lys Gln Tyr Asn Asp Thr Cys Pro Asp Glu Gln Asp Tyr Gln Ile
            340                 345                 350

Arg Met Ala Lys Ser Ser Tyr Lys Pro Gly Arg Phe Gly Gly Lys Arg
        355                 360                 365

Ile Gln Gln Ala Ile Leu Ser Ile Lys Val Ser Thr Ser Leu Gly Glu
    370                 375                 380

Asp Pro Val Leu Thr Val Pro Pro Asn Thr Val Thr Leu Met Gly Ala
385                 390                 395                 400

Glu Gly Arg Ile Leu Thr Val Gly Thr Ser His Phe Leu Tyr Gln Arg
                405                 410                 415

Gly Ser Ser Tyr Phe Ser Pro Ala Leu Leu Tyr Pro Met Thr Val Ser
            420                 425                 430

Asn Lys Thr Ala Thr Leu His Ser Pro Tyr Thr Phe Asn Ala Phe Thr
        435                 440                 445

Arg Pro Gly Ser Ile Pro Cys Gln Ala Ser Ala Arg Cys Pro Asn Pro
    450                 455                 460

Cys Val Thr Gly Val Tyr Thr Asp Pro Tyr Pro Leu Ile Phe Tyr Arg
465                 470                 475                 480

Asn His Thr Leu Arg Gly Val Phe Gly Thr Met Leu Asp Gly Val Gln
                485                 490                 495

Ala Arg Leu Asn Pro Ala Ser Ala Val Phe Asp Ser Thr Ser Arg Ser
            500                 505                 510
```

-continued

```
Arg Ile Thr Arg Val Ser Ser Ser Ser Thr Lys Ala Ala Tyr Thr Thr
        515                 520                 525

Ser Thr Cys Phe Lys Val Val Lys Thr Asn Lys Thr Tyr Cys Leu Ser
    530                 535                 540

Ile Ala Glu Ile Ser Asn Thr Leu Phe Gly Glu Phe Arg Ile Val Pro
545                 550                 555                 560

Leu Leu Val Glu Ile Leu Lys Asp Asp Gly Val Arg Glu Ala Arg Ser
                565                 570                 575

Gly


<210> SEQ ID NO 21
<211> LENGTH: 1377
<212> TYPE: DNA
<213> ORGANISM: Gallus gallus

<400> SEQUENCE: 21

atgctgggtg agctggaagc aggcgggatg caaggcggcc gcgtggtgct ggggctcctg      60

tgctgcttgg tggccggggt gggctcctac acgccctggg acatctcctg ggcagcacga     120

ggggacccct ctgcctggtc ctggggggcc gaggcgcact cacgggccgt ggccggctcg     180

cacccggtgg ccgtgcagtg ccaagaggcg cagctggtgg tgacggtgca cagggacctc     240

ttcgggaccg ggcgtctcat caacgctgct gacctgactc tgggcccggc tgcctgcaag     300

cactcctcgc tcaacgccgc acacaacacc gtcaccttcg ccgccggcct ccacgagtgc     360

ggcagcgtcg tgcaggtgac gccagacacc ctcatctacc gcacgctcat caactacgac     420

cccagccctg ctagcaaccc cgtcatcatc cgcaccaacc ctgctgtcat ccccatcgag     480

tgccactacc ccaggaggga gaacgtgagc agcaatgcca tccggcccac ctggtccccc     540

ttcaactccg cactgtcagc cgaggagagg ctggtgttct ccctgcgcct catgagtgat     600

gactggagca cagagagacc cttcaccggc ttccagctgg gcgacatcct caacatccag     660

gccgaggtca gcactgagaa ccatgtgccc ctgcggctct ttgtggacag ctgtgtggct     720

gccctgagcc ctgacggtga ctcctcgccc cactacgcca tcattgactt caacgggtgc     780

ttagtggatg ggagagtgga tgatactagc tctgccttca tcacaccccg gccacgggag     840

gatgtgctga ggttcaggat cgatgtcttc aggtttgcgg gggacaacag gaacctgatc     900

tacatcacct gccacctgaa ggtgacccca gcagaccaag gcccagaccc tcagaacaag     960

gcttgctcct tcaataaagc cagaaacacc tgggtgccag tggaaggcag ccgggatgtc    1020

tgcaactgct gtgagacagg caactgcgag ccgcctgcgc tctcccggag gctcaacccc    1080

atggagagat ggcagagccg ccgcttccgt cgtgatgccg ggaaagaggt tgcagctgat    1140

gtggtcattg gccccgtgtt gctctcggcg gacccgggag ctgtgggaca gcaggaggag    1200

ggtggtgacg gtgcggcggt gatggtgccc agcgtgggga cggggctggt gtgcgtggcc    1260

gtggctgtag ctctggctgc cgttggggtg gctgtatgta ttgcacgcaa gggatgcacc    1320

cgaacctcaa ctgcggtgtg agtgcagggc gagccgtgaa taaagcctgg aaaggcc       1377


<210> SEQ ID NO 22
<211> LENGTH: 446
<212> TYPE: PRT
<213> ORGANISM: Gallus gallus
```

-continued

<400> SEQUENCE: 22

Met Leu Gly Glu Leu Glu Ala Gly Gly Met Gln Gly Gly Arg Val Val
1 5 10 15

Leu Gly Leu Leu Cys Cys Leu Val Ala Gly Val Gly Ser Tyr Thr Pro
20 25 30

Trp Asp Ile Ser Trp Ala Ala Arg Gly Asp Pro Ser Ala Trp Ser Trp
35 40 45

Gly Ala Glu Ala His Ser Arg Ala Val Ala Gly Ser His Pro Val Ala
50 55 60

Val Gln Cys Gln Glu Ala Gln Leu Val Val Thr Val His Arg Asp Leu
65 70 75 80

Phe Gly Thr Gly Arg Leu Ile Asn Ala Ala Asp Leu Thr Leu Gly Pro
85 90 95

Ala Ala Cys Lys His Ser Ser Leu Asn Ala Ala His Asn Thr Val Thr
100 105 110

Phe Ala Ala Gly Leu His Glu Cys Gly Ser Val Val Gln Val Thr Pro
115 120 125

Asp Thr Leu Ile Tyr Arg Thr Leu Ile Asn Tyr Asp Pro Ser Pro Ala
130 135 140

Ser Asn Pro Val Ile Ile Arg Thr Asn Pro Ala Val Ile Pro Ile Glu
145 150 155 160

Cys His Tyr Pro Arg Arg Glu Asn Val Ser Ser Asn Ala Ile Arg Pro
165 170 175

Thr Trp Ser Pro Phe Asn Ser Ala Leu Ser Ala Glu Glu Arg Leu Val
180 185 190

Phe Ser Leu Arg Leu Met Ser Asp Asp Trp Ser Thr Glu Arg Pro Phe
195 200 205

Thr Gly Phe Gln Leu Gly Asp Ile Leu Asn Ile Gln Ala Glu Val Ser
210 215 220

Thr Glu Asn His Val Pro Leu Arg Leu Phe Val Asp Ser Cys Val Ala
225 230 235 240

Ala Leu Ser Pro Asp Gly Asp Ser Ser Pro His Tyr Ala Ile Ile Asp
245 250 255

Phe Asn Gly Cys Leu Val Asp Gly Arg Val Asp Asp Thr Ser Ser Ala
260 265 270

Phe Ile Thr Pro Arg Pro Arg Glu Asp Val Leu Arg Phe Arg Ile Asp
275 280 285

Val Phe Arg Phe Ala Gly Asp Asn Arg Asn Leu Ile Tyr Ile Thr Cys
290 295 300

His Leu Lys Val Thr Pro Ala Asp Gln Gly Pro Asp Pro Gln Asn Lys
305 310 315 320

Ala Cys Ser Phe Asn Lys Ala Arg Asn Thr Trp Val Pro Val Glu Gly
325 330 335

Ser Arg Asp Val Cys Asn Cys Cys Glu Thr Gly Asn Cys Glu Pro Pro
340 345 350

Ala Leu Ser Arg Arg Leu Asn Pro Met Glu Arg Trp Gln Ser Arg Arg
355 360 365

Phe Arg Arg Asp Ala Gly Lys Glu Val Ala Ala Asp Val Val Ile Gly
370 375 380

Pro Val Leu Leu Ser Ala Asp Pro Gly Ala Val Gly Gln Gln Glu Glu
385 390 395 400

Gly Gly Asp Gly Ala Ala Val Met Val Pro Ser Val Gly Thr Gly Leu
405 410 415

-continued

```
Val Cys Val Ala Val Ala Val Ala Leu Ala Ala Val Gly Val Ala Val
            420                 425                 430

Cys Ile Ala Arg Lys Gly Cys Thr Arg Thr Ser Thr Ala Val
        435                 440                 445


<210> SEQ ID NO 23
<211> LENGTH: 3024
<212> TYPE: DNA
<213> ORGANISM: Anas sp.

<400> SEQUENCE: 23

catgcacacc tgaaagctta tgcaaagatt aacgaggaat cactggatag ggctaggaga     60

ttgctttggt ggcattacaa ttgtttactg tggggagaag ctaacgttac taattatatt    120

tctcggcttc gcacttggct atcaacacct gagagataca gaggccgaga tgccccaacc    180

attgaagcaa tcactagacc aatccaagtg gctcagggag gcagaaaaac atcttcgggt    240

actagaaaac ctcgtggact cgaacctaga agaagaaaag ttaaaaccac agttgtctat    300

gggagaagac gttcaaagtc cagggatagg agagcccctt caccccaacg tgcgggctcc    360

cctctcccgc gtagttcgag cagccacaga agatctccct cgcctaggaa atagattacc    420

tgctaggcat caccttggta aattgtcagg attatatcaa atgaagggat gtacatttaa    480

ccctgaatgg aaagtacctg atatttcgga tactcatttt gatatgcaaa tagtaaatga    540

gtgcccttcc cgaaattgga aatatctgac tccagccaaa ttctggccca agagcatttc    600

ctactttcct gtacaggcag ggttaaagc taagtaccct gacaatgtga tgcaacatga    660

atcaatagta ggtaaatatt taaccaggct ctatgaagca ggaatccttt ataagcggat    720

atctaaacat ttggtcacat ttaaaggtca gccttataat tgggaacttc aataccttgt    780

caagcaacat caagttcctg atgggtcaac aacctgcaaa atcaatggac gtgcggagaa    840

tcgaaggagg agaactcctg ctaaatcaat tagcaggccg catgatccca aaagggacag    900

tcacatggtc gggcaaattt ccaacaatag atcacatatt agaccatgtg caaacaatgg    960

aggaaataaa cactcttcaa aaccaagggg cttggcctgc tggggcggga aggagagcag   1020

gattaaccaa tcctgctcct caagagattc ctcagcccca gtggactccc gaagaagatc   1080

agaaagctcg cgaagctttt cgtcgttatc aagaagagag accaccagag accaccacaa   1140

ttcctcccac atctccaacg cagtggaaac tgcaacccgg ggacgatcca ctcctgggaa   1200

acaagtctct gctcgagact cacccgcttt accagaatac cgagccagcc gtgtctgtaa   1260

taaagactcc tccactgaga aagaaaatgt ctggtacctt cgggggaata ctagctggcc   1320

taatcggatt actggtaagc tttttcttgt tgataaaaat tctagaaata cttcggaggc   1380

tagattggtg gtggatttct ctcagttctc caaagggaaa aatgcaatgc gctttccaag   1440

atactggagc ccaaacctct ccacattacg tcggatcttg cccgtgggga tgcccaggat   1500

ttctctggac ttatctcagg ctttttatca tcttcctctt aatcctgcta gtagcagcag   1560

gcttgctgta tctgacggac aacgggtcta ctattttagg aaagctccga tgggagtcgg   1620

tcttagccct ttcctcctcc atctcttcac tactgccctc ggatccgaaa tcgctcgtcg   1680

ctttaatgtt tggactttta cttatatgga tgacttcctc ctctgccacc caaacgctcg   1740

tcaccttaac tcaattagcc acgctgtctg ctctttttta caagagctag gaataagaat   1800

aaactttgac aaaactactc catcaccagt caacgaaatt agattcctcg gttatcaaat   1860

tgatcaacga ttcatgaaga ttgaagaaag cagatggaaa gaattacgga ctgtaattaa   1920

aaagataaaa attggagaat ggtatgactg gaaatgtatt cagagatttg tcgggcattt   1980
```

-continued

```
aaactttgtg ttgccattta ccaaaggtaa catagaaatg ttaaaaccaa tgtatgctgc   2040

tataactcat aaagtcaatt ttagcttctc ttctgcctat aggactttgc tgtacaaatt   2100

aactatgggt gtttgtaaat tatcaatcaa accaaagtcc tctgtacctt tgccacgtgt   2160

agctacggat gctaccccaa cacatggcgc aatatcccat atcaccggcg ggagcgcagt   2220

gtttgctttt tcaaaggtca gagatataca tatacaggaa ttgctgatgg tatgtttagc   2280

taaattaatg attaagccta gatgcatact aaccgattct acctttgttt gtcacaaacg   2340

ttatcagacg ttaccatgga attttgcagt gtttgccaaa caattgttat cttctatacc   2400

attgtacttt gtaccgagca aatataatcc tgctgacggc ccatccaggc acaaaccgcc   2460

tgattggacg gctgttacat acacccctct ctcgaaagca atatatattc cacataggct   2520

atgtggaact taagaattac acccctctcc ttcggagctg cctgccaagg tatctttacg   2580

tctacattgc tgttgtcgtg tttgactgta cctttggtat gtaccattgt ttatgattct   2640

tgcttatata tggatatcaa tgcttctaga gccttagcca atgtttatga tttgccagat   2700

gatttcttcc caaaaattga tgatcttgta agggatgcga aggatgcttt agaaccttat   2760

tggagatcag attcaataaa gaaacatgtt ttaattgcaa ctcactttgt ggatcttatt   2820

gaagacttct ggcaaactac tcagggtatg catgaaatag ctgaagcctt aagagcagtt   2880

ataccaccta ctacaacacc agttcccgca ggatatctga ttcagcacga agaggctgag   2940

gagattcctc tgggagattt atttaaacat caggaagaaa ggatagttag tttccaaccg   3000

gattatccta ttactgcacg aatt                                          3024
```

```
<210> SEQ ID NO 24
<211> LENGTH: 10575
<212> TYPE: DNA
<213> ORGANISM: Artificial Sequence
<220> FEATURE:
<223> OTHER INFORMATION: pCHA vector sequence
<220> FEATURE:
<221> NAME/KEY: misc_feature
<222> LOCATION: (8466)..(8467)
<223> OTHER INFORMATION: n is a, c, g, or t

<400> SEQUENCE: 24
```

```
ggccgcaaca gaggtggatg gacagacccg ttcttacacc ggactgggcg cgggatagga     60

tattcagatt gggatgggat tgagcttaaa gccggcgctg agaccatgct caaggtaggc    120

aatgtcctca gcgtcgagcc cggcatctat gtcgagggca ttggtggagc gcgcttcggg    180

gataccgtgc ttgtaactga gaccggatat gaggccctca ctccgcttga tcttggcaaa    240

gatatttgac gcatttatta gtatgtgtta attttcattt gcagtgcagt attttctatt    300

cgatctttat gtaattcgtt acaattaata aatattcaaa tcagattatt gactgtcatt    360

tgtatcaaat cgtgtttaat ggatattttt attataatat tgatgatatc tcaatcaaaa    420

cgtagataat aataatattt atttaatatt tttgcgtcgc acagtgaaaa tctatatgag    480

attacaaaat accgacaaca ttatttaaga tacatagaca ttaaccctga gactgttgga    540

cagagctcat tggtacctca gatctgggta actggcctaa ctggccttgg aggagctggc    600

aactcaaaat ccctttgcca aaaaccaaca tcatgccatc caccatgctt gtatccagct    660

gcgcgcaatg taccccgggc tgtgtatccc aaagcctcat gcaacctaac agatggatcg    720

tttggaaggc ctataacagc aaccacagac ttaaaacctt gcgcctccat agacttaagc    780

aaatgtgtgt acaatgtgga tcctaggccc aacctttgat gcctatgtga cacgtaaaca    840

gtactctcaa ctgtccaatc gtaagcgttc ctagccttcc agggcccagc gtaagcaata    900
```

-continued

```
ccagccacaa caccctcaac ctcagcaacc aaccaagggt atctatcttg caacctctct    960

agatcatcaa tccactcttg tggtgtttgt ggctctgtcc taaagttcac tgtagacgtc   1020

tcaatgtaat ggttaacgat atcacaaacc gcggccatat cagctgctgt agctggccta   1080

atctcaactg gtctcctctc cggagaagcc atggtttgga tccacaaact tacaaatttc   1140

tctgaagttg tatcctcagt acttcaaaga aaatagctta caccaatttt ttcttgtttt   1200

cacaaatgcc gaacttggtt ccttatatag gaaaactcaa gggcaaaaat gacacggaaa   1260

aatataaaag gataagtagt gggggataag attcctttgt gataaggtta ctttccgccc   1320

ttacattttc caccttacat gtgtcctcta tgtctctttc acaatcaccg accttatctt   1380

cttcttttca ttgttgtcgt cagtgcttac gtcttcaaga ttcttttctt cgcctggttc   1440

ttctttttca atttctacgt attcttcttc gtattctggc agtataggat cttgtatctg   1500

tacattcttc atttttgaac ataggttgca tatgtgccgc atattgatct gcttcttgct   1560

gagctcacat aatacttcca tagtttttcc cgtaaacatt ggattcttga tgctacatct   1620

tggataatta ccttctggcc ggccgcgaat tcgcttcaag acgtgctcaa atcactattt   1680

ccacacccct atatttctat tgcactccct tttaactgtt ttttattaca aaaatgccct   1740

ggaaaatgca ctcccttttt gtgtttgtta tttagtgaaa cgatgttgtc aggtaattta   1800

tttgtcagtc tactatggtg gcccattata ttaatagcaa ctgtcggtcc aatagacgac   1860

gtcgattttc tgcatttgtt taaccacgtg gattttatga cattttatat tagttaattt   1920

gtaaaaccta cccaattaaa gacctcatat gttctaaaga ctaatactta atgataacaa   1980

ttttctttta gtgaagaaag ggataattag taaatatgga acaagggcag aagatttatt   2040

aaagccggta agagacaaca acgtaggtac gtggagtgtc ttaggtgact tacccacata   2100

acataaagtg acattaacaa acatagctaa tgctcctatt tgaatagtgc atatcagcat   2160

accttattac atatagatag gagcaaactc tagctagatt gttgagagag ctcggtacct   2220

taaaatctga actcacaatc ctagatgcaa attctgcact gcaatgatcc attggagcac   2280

atccaaaaag acagaccagc taccatgatt gccagtgcta gggaactcgc cactgttgag   2340

tagattgata gtatctgata ggtgcccatt gactccaatt tgactccatc tatttcctct   2400

ctgttcagcc ttgattcttc tgagtattgt ggatagtcat acgttccgtt tctcacactt   2460

tccatgcatt cattgtcaca tttgtggtag aactcaaaac acccattgcc caattctttt   2520

gcattatctc tcagctggag tcggacctta tcgtataggt tcttgacata tgaatcatgg   2580

aaatccagag ttctttcatt ttccatgagc accagaagtt ctgcattgta agtccataca   2640

tctagaaatc catcttccat tttcttattc aaattttcta ttctcctttc taagttgttg   2700

aattctttcc caacggcttc gaattgagtg ttcattttgt caatgattga gttgacttta   2760

ttggtgatcc cgtcgattgc tttctgagtg gactctttgt ctgcagcata tccacttccc   2820

tgctcgttgc tatgatggta accataccat ccatctacca ttccttgcca ccccccttct   2880

atgaatcctg ctattgctcc aaacagacct cttgtttctc tctgaggcac gttcctcagt   2940

cctgttgcaa ggaccagttt atctgatttg acatatttgg gacactctcc aatggtaagg   3000

ggatgaacat tgtgaaaagg catactggaa tttatagcac ccactggggt ctgacatttg   3060

gtatcacagt tgccatactc cagttcgctt ctcatgattg ctgaatctcc ctttttaact   3120

atcttgtatg catattcagg agctataaag ttcccattac tttcaaagct gattgcatcg   3180

ttcggcctta gtattgtcca gaaaaattct attcttccac tttgtccatt cactttgggc   3240

ctggtagcta tttctggaat tgacctctga tttagtgttg atgttcctac agacacataa   3300
```

-continued

```
gtgttcgagt tctgatagag ttccgtttgt tccgctgcat cattagggtg atggattccc   3360
cacaatatca gaaggtcctc tacattggtg ttattgtagg tcctctttat tgttgggtat   3420
gcattactct tcttgatcaa ccacaccaca ttcctgaaaa aggaagatct accattgtat   3480
gggcatgctg agctcactcc tgatgaggca tcatgattgg accaagagtt cctagggatt   3540
atttgaattt tctcaaaatg gtttgtgttg ctcattaaat acttcagttc ttcataatca   3600
ttgaagtctc ccggataaca taagccattg gttggattgt ccttctctac aatatatgac   3660
cattccggta catttaggaa ctcatcacac attgggttcc caagaagcca tccagccaca   3720
ctgcaatcct tcagaatgag gggcctcact cctttgagac tgcagagttt cccgttgtgc   3780
tctttttcca gtatatcttg agcatgtgtg accgtaacat tcttctccat gattgtgtca   3840
acttgttttg ttgaattgtt tgcatgataa ccgatgcaga tttggtcacc tttgacaacg   3900
ctgattattg caagggcaat cactattctt tccatccatg gtttggatcc acaaacttac   3960
aaatttctct gaagttgtat cctcagtact tcaaagaaaa tagcttacac caatttttttc   4020
ttgttttcac aaatgccgaa cttggttcct tatataggaa aactcaaggg caaaaaatgac   4080
acggaaaaat ataaaaggat aagtagtggg ggataagatt cctttgtgat aaggttactt   4140
tccgccctta cattttccac cttacatgtg tcctctatgt ctctttcaca atcaccgacc   4200
ttatcttctt cttttcattg ttgtcgtcag tgcttacgtc ttcaagattc ttttcttcgc   4260
ctggttcttc tttttcaatt tctacgtatt cttcttcgta ttctggcagt ataggatctt   4320
gtatctgtac attcttcatt tttgaacata ggttgcatat gtgccgcata ttgatctgct   4380
tcttgctgag ctcacataat acttccatag tttttcccgt aaacattgga ttcttgatgc   4440
tacatcttgg ataattacct tctggcgcgc ctttgcccgg gctttcctgc agggtttaaa   4500
cttaattaag cggccgatcc ggtgagtaat attgtacggc taagagcgaa tttggcctgt   4560
agacctcaat tgcgagcttt ctaatttcaa actattcggg cctaactttt ggtgtgatga   4620
tgctgactgg caggatatat accgttgtaa tttgagctcg tgtgaataag tcgctgtgta   4680
tgtttgtttg attgtttctg ttggagtgca gcccatttca ccggacaagt cggctagatt   4740
gatttagccc tgatgaactg ccgaggggaa gccatcttga gcgcggaatg ggaatggatc   4800
gaaccgggag cacaggatga cgcctaacaa ttcattcaag ccgacaccgc ttcgcggcgc   4860
ggcttaattc aggagttaaa catcatgagg gaagcggtga tcgccgaagt atcgactcaa   4920
ctatcagagg tagttggcgt catcgagcgc catctcgaac cgacgttgct ggccgtacat   4980
ttgtacggct ccgcagtgga tggcggcctg aagccacaca gtgatattga tttgctggtt   5040
acggtgaccg taaggcttga tgaaacaacg cggcgagctt tgatcaacga ccttttggaa   5100
acttcggctt cccctggaga gagcgagatt ctccgcgctg tagaagtcac cattgttgtg   5160
cacgacgaca tcattccgtg gcgttatcca gctaagcgcg aactgcaatt tggagaatgg   5220
cagcgcaatg acattcttgc aggtatcttc gagccagcca cgatcgacat tgatctggct   5280
atcttgctga caaaagcaag agaacatagc gttgccttgg taggtccagc ggcggaggaa   5340
ctctttgatc cggttcctga acaggatcta tttgaggcgc taaatgaaac cttaacgcta   5400
tggaactcgc cgcccgactg ggctggcgat gagcgaaatg tagtgcttac gttgtcccgc   5460
atttggtaca gcgcagtaac cggcaaaatc gcgccgaagg atgtcgctgc cgactgggca   5520
atggagcgcc tgccggccca gtatcagccc gtcatacttg aagctaggca ggcttatctt   5580
ggacaagaag atcgcttggc ctcgcgcgca gatcagttgg aagaatttgt tcactacgtg   5640
aaaggcgaga tcaccaaggt agtcggcaaa taatgtctaa caattcgttc aagccgacgc   5700
```

-continued

```
cgcttcgcgg cgcggcttaa ctcaagcgtt agagagctgg ggaagactat gcgcgatctg   5760
ttgaaggtgg ttctaagcct cgtacttgcg atggcatttc gatcgaaagg ggtacaaatt   5820
cccactaagc gctcgggggc tgagaaagcc cagtaaggaa acaactgtag gttcgagtcg   5880
cgagatcccc cggaaccaaa ggaagtaggt taaacccgct ccgatcaggc cgagccacgc   5940
caggccgaga acattggttc ctgtaggcat cgggattggc ggatcaaaca ctaaagctac   6000
tggaacgagc agaagtcctc cggccgccag ttgccaggcc gtaaaggtga gcagaggcac   6060
gggaggttgc cacttgcggg tcagcacggt tccgaacgcc atggaaaccg cccccgccag   6120
gcccgctgcg acgccgacag gatctagcgc tgcgtttggt gtcaacacca acagcgccac   6180
gcccgcagtt ccgcaaatag cccccaggac cgccatcaat cgtatcgggc tacctagcag   6240
agcggcagag atgaacacga ccatcagcgg ctgcacagcg cctaccgtcg ccgcgacccg   6300
cccggcaggc ggtagaccga aataaacaac aagctccaga atagcgaaat attaagtgcg   6360
ccgaggatga agatgcgcat ccaccagatt cccgttggaa tctgtcggac gatcatcacg   6420
agcaataaac ccgccggcaa cgcccgcagc agcataccgg cgacccctcg gcctcgctgt   6480
tcgggctcca cgaaaacgcc ggacagatgc gccttgtgag cgtccttggg gccgtcctcc   6540
tgtttgaaga ccgacagccc aatgatctcg ccgtcgatgt aggcgccgaa tgccacggca   6600
tctcgcaacc gttcagcgaa cgcctccatg ggctttttct cctcgtgctc gtaaacggac   6660
ccgaacatct ctggagcttt cttcagggcc gacaatcgga tctcgcggaa atcctgcacg   6720
tcggccgctc caagccgtcg aatctgagcc ttaatcacaa ttgtcaattt taatcctctg   6780
tttatcggca gttcgtagag cgcgccgtgc gcccgagcga tactgagcga agcaagtgcg   6840
tcgagcagtg cccgcttgtt cctgaaatgc cagtaaagcg ctggctgctg aacccccagc   6900
cggaactgac cccacaaggc cctagcgttt gcaatgcacc aggtcatcat tgacccaggc   6960
gtgttccacc aggccgctgc ctcgcaactc ttcgcaggct tcgccgacct gctcgcgcca   7020
cttcttcacg cgggtggaat ccgatccgca catgaggcgg aaggtttcca gcttgagcgg   7080
gtacggctcc cggtgcgagc tgaaatagtc gaacatccgt cgggccgtcg gcgacagctt   7140
gcggtacttc tcccatatga atttcgtgta gtggtcgcca gcaaacagca cgacgatttc   7200
ctcgtcgatc aggacctggc aacgggacgt tttcttgcca cggtccagga cgcggaagcg   7260
gtgcagcagc gacaccgatt ccaggtgccc aacgcggtcg gacgtgaagc ccatcgccgt   7320
cgcctgtagg cgcgacaggc attcctcggc cttcgtgtaa taccggccat tgatcgacca   7380
gcccaggtcc tggcaaagct cgtagaacgt gaaggtgatc ggctcgccga taggggtgcg   7440
cttcgcgtac tccaacacct gctgccacac cagttcgtca tcgtcggccc gcagctcgac   7500
gccggtgtag gtgatcttca cgtccttgtt gacgtggaaa atgaccttgt tttgcagcgc   7560
ctcgcgcggg attttcttgt tgcgcgtggt gaacagggca gagcgggccg tgtcgtttgg   7620
catcgctcgc atcgtgtccg gccacggcgc aatatcgaac aaggaaagct gcatttcctt   7680
gatctgctgc ttcgtgtgtt tcagcaacgc ggcctgcttg gcctcgctga cctgttttgc   7740
caggtcctcg ccggcggttt ttcgcttctt ggtcgtcata gttcctcgcg tgtcgatggt   7800
catcgacttc gccaaacctg ccgcctcctg ttcgagacga cgcgaacgct ccacggcggc   7860
cgatggcgcg ggcagggcag gggagccag ttgcacgctg tcgcgctcga tcttggccgt   7920
agcttgctgg accatcgagc cgacggactg gaaggtttcg cggggcgcac gcatgacggt   7980
gcggcttgcg atggtttcgg catcctcggc ggaaaacccc gcgtcgatca gttcttgcct   8040
gtatgccttc cggtcaaacg tccgattcat tcaccctcct tgcgggattg ccccgactca   8100
```

-continued

```
cgccggggca atgtgccctt attcctgatt tgacccgcct ggtgccttgg tgtccagata   8160
atccacctta tcggcaatga agtcggtccc gtagaccgtc tggccgtcct tctcgtactt   8220
ggtattccga atcttgccct gcacgaatac cagcgacccc ttgcccaaat acttgccgtg   8280
ggcctcggcc tgagagccaa aacacttgat gcggaagaag tcggtgcgct cctgcttgtc   8340
gccggcatcg ttgcgccact cttcattaac cgctatatcg aaaattgctt gcggcttgtt   8400
agaattgcca tgacgtacct cggtgtcacg ggtaagatta ccgataaact ggaactgatt   8460
atggcnnctc gaaattccct cggtcttgcc ttgctcgtcg gtgatgtact tcaccagctc   8520
cgcgaagtcg ctcttcttga tggagcgcat ggggacgtgc ttggcaatca cgcgcacccc   8580
ccggccgttt tagcggctaa aaaagtcatg gctctgccct cgggcggacc acgcccatca   8640
tgaccttgcc aagctcgtcc tgcttctctt cgatcttcgc cagcagggcg aggatcgtgg   8700
catcaccgaa ccgcgccgtg cgcgggtcgt cggtgagcca gagtttcagc aggccgccca   8760
ggcggcccag gtcgccattg atgcgggcca gctcgcggac gtgctcatag tccacgacgc   8820
ccgtgatttt gtagccctgg ccgacggcca gcaggtaggc cgacaggctc atgccggccg   8880
ccgccgcctt ttcctcaatc gctcttcgtt cgtctggaag gcagtacacc ttgataggtg   8940
ggctgccctt cctggttggc ttggtttcat cagccatccg cttgccctca tctgttacgc   9000
cggcggtagc cggccagcct cgcagagcag gattcccgtt gagcaccgcc aggtgcgaat   9060
aagggacagt gaagaaggaa cacccgctcg cgggtgggcc tacttcacct atcctgcccg   9120
gctgacgccg ttggatacac caaggaaagt ctacacgaac cctttggcaa aatcctgtat   9180
atcgtgcgaa aaaggatgga tataccgaaa aaatcgctat aatgaccccg aagcagggtt   9240
atgcagcgga aaagatccgt cgaccctttc cgacgctcac cgggctggtt gccctcgccg   9300
ctgggctggc ggccgtctat ggccctgcaa acgcgccaga aacgccgtcg aagccgtgtg   9360
cgagacaccg cggccgccgg cgttgtggat accacgcgga aaacttggcc ctcactgaca   9420
gatgaggggc ggacgttgac acttgagggg ccgactcacc cggcgcggcg ttgacagatg   9480
aggggcaggc tcgatttcgg ccggcgacgt ggagctggcc agcctcgcaa atcggcgaaa   9540
acgcctgatt ttacgcgagt ttcccacaga tgatgtggac aagcctgggg ataagtgccc   9600
tgcggtattg acacttgagg ggcgcgacta ctgacagatg aggggcgcga tccttgacac   9660
ttgaggggca gagtgatgac agatgagggg cgcacctatt gacatttgag ggctgtcca   9720
caggcagaaa atccagcatt tgcaagggtt tccgcccgtt tttcggccac cgctaacctg   9780
tcttttaacc tgcttttaaa ccaatattta taaaccttgt ttttaaccag ggctgcgccc   9840
tggcgcgtga ccgcgcacgc cgaagggggg tgcccccct tctcgaaccc tcccggcccg   9900
ctaacgcggg cctcccatcc ccccaggggc tgcgcccctc ggccgcgaac ggcctcaccc   9960
caaaaatggc aggccaagct agcttgcttg gtcgttccgg tacgtaccgt gaacgtcggc  10020
tcgattgtac ctgcgttcaa atactttgcg atcgtgttgc gcgcctgccc ggtgcgtcgg  10080
ctgatctcac ggatcgactg cttctctcgc aacgccatcc gacggatgat gtttaaaagt  10140
cccatgtgga tcactccgtt gccccgtcgc tcaccgtgtt ggggggaagg tgcacatggc  10200
tcagttctca atggaaatta tctgcctaac cggctcagtt ctgcgtagaa accaacatgc  10260
aagctccacc gggtgcaaag cggcagcggc ggcaggatat attcaattgt aaatggcttc  10320
atgtccggga aatctacatg gatcagcaat gagtatgatg gtcaatatgg agaaaaagaa  10380
agagtaatta ccaatttttt ttcaattcaa aaatgtagat gtccgcagcg ttattataaa  10440
atgaaagtac attttgataa aacgacaaat tacgatccgt cgtatttata ggcgaaagca  10500
```

-continued

```
ataaacaaat tattctaatt cggaaatctt tatttcgacg tgtctacatt cacgtccaaa  10560

tgggggcggc gaatt                                                   10575


<210> SEQ ID NO 25
<211> LENGTH: 10677
<212> TYPE: DNA
<213> ORGANISM: Artificial Sequence
<220> FEATURE:
<223> OTHER INFORMATION: pMHN vector sequence
<220> FEATURE:
<221> NAME/KEY: misc_feature
<222> LOCATION: (8568)..(8569)
<223> OTHER INFORMATION: n is a, c, g, or t

<400> SEQUENCE: 25

ggccgcaaca gaggtggatg gacagacccg ttcttacacc ggactgggcg cgggatagga     60

tattcagatt gggatgggat tgagcttaaa gccggcgctg agaccatgct caaggtaggc    120

aatgtcctca gcgtcgagcc cggcatctat gtcgagggca ttggtggagc gcgcttcggg    180

gataccgtgc ttgtaactga gaccggatat gaggccctca ctccgcttga tcttggcaaa    240

gatatttgac gcatttatta gtatgtgtta attttcattt gcagtgcagt attttctatt    300

cgatctttat gtaattcgtt acaattaata aatattcaaa tcagattatt gactgtcatt    360

tgtatcaaat cgtgtttaat ggatattttt attataatat tgatgatatc tcaatcaaaa    420

cgtagataat aataatattt atttaatatt tttgcgtcgc acagtgaaaa tctatatgag    480

attacaaaat accgacaaca ttatttaaga tacatagaca ttaaccctga gactgttgga    540

cagagctcat tggtacctca gatctgggta actggcctaa ctggccttgg aggagctggc    600

aactcaaaat ccctttgcca aaaaccaaca tcatgccatc caccatgctt gtatccagct    660

gcgcgcaatg taccccgggc tgtgtatccc aaagcctcat gcaacctaac agatggatcg    720

tttggaaggc ctataacagc aaccacagac ttaaaacctt gcgcctccat agacttaagc    780

aaatgtgtgt acaatgtgga tcctaggccc aacctttgat gcctatgtga cacgtaaaca    840

gtactctcaa ctgtccaatc gtaagcgttc ctagccttcc agggcccagc gtaagcaata    900

ccagccacaa caccctcaac ctcagcaacc aaccaagggt atctatcttg caacctctct    960

agatcatcaa tccactcttg tggtgtttgt ggctctgtcc taaagttcac tgtagacgtc   1020

tcaatgtaat ggttaacgat atcacaaacc gcggccatat cagctgctgt agctggccta   1080

atctcaactg gtctcctctc cggagaagcc atggtttgga tccacaaact tacaaatttc   1140

tctgaagttg tatcctcagt acttcaaaga aaatagctta caccaatttt ttcttgtttt   1200

cacaaatgcc gaacttggtt ccttatatag gaaaactcaa gggcaaaaat gacacggaaa   1260

aatataaaag gataagtagt gggggataag attcctttgt gataaggtta ctttccgccc   1320

ttacattttc caccttacat gtgtcctcta tgtctctttc acaatcaccg accttatctt   1380

cttcttttca ttgttgtcgt cagtgcttac gtcttcaaga ttcttttctt cgcctggttc   1440

ttctttttca atttctacgt attcttcttc gtattctggc agtataggat cttgtatctg   1500

tacattcttc atttttgaac ataggttgca tatgtgccgc atattgatct gcttcttgct   1560

gagctcacat aatacttcca tagtttttcc cgtaaacatt ggattcttga tgctacatct   1620

tggataatta ccttctggcc ggccgcgaat tcgcttcaag acgtgctcaa atcactattt   1680

ccacacccct atatttctat tgcactccct tttaactgtt ttttattaca aaaatgccct   1740

ggaaaatgca ctcccttttt gtgtttgtta tttagtgaaa cgatgttgtc aggtaattta   1800

tttgtcagtc tactatggtg gcccattata ttaatagcaa ctgtcggtcc aatagacgac   1860
```

-continued

```
gtcgattttc tgcatttgtt taaccacgtg gattttatga cattttatat tagttaattt   1920
gtaaaaccta cccaattaaa gacctcatat gttctaaaga ctaatactta atgataacaa   1980
ttttctttta gtgaagaaag ggataattag taaatatgga acaagggcag aagatttatt   2040
aaagccggta agagacaaca acgtaggtac gtggagtgtc ttaggtgact tacccacata   2100
acataaagtg acattaacaa acatagctaa tgctcctatt tgaatagtgc atatcagcat   2160
accttattac atatagatag gagcaaactc tagctagatt gttgagagag ctcggtaccg   2220
gatccgaaga cttaacctga tcttgcttca cgtacaccat catctttcag aatctccacc   2280
aaaagtggaa caattctgaa ttccccaaag agagtgttag aaatctcagc tatgctcaga   2340
caataggtct tgttcgtctt tacaactttg aaacatgtgg aggtagtgta tgctgcctta   2400
gtagaactag aggaaactct ggttatcctt gatctggatg tagaatcaaa cacagcagag   2460
gcaggattca acctagcttg aacaccatct aacattgttc caaacacccc tctcaaggta   2520
tgattacggt agaagatcaa agggtaagga tcagtgtaaa ctccagtcac acacgaattc   2580
ggacatctag ctgaagcttg gcaaggaatc gatccaggtc ttgtaaaggc attgaaagta   2640
tatggtgaat gtaatgtagc tgtcttgttg ctcacagtca ttggatacag taacgctggg   2700
ctaaagtagg aacttccacg ttgatagaga aagtggctag taccaacagt aagaatcctt   2760
ccctcagctc ccatcaatgt tacagtgttt ggtggaacag taaggactgg atcttctccc   2820
aatgatgtgc taaccttgat actgagaata gcttgttgta tcctcttacc tccaaatctt   2880
cctggtttgt atgatgactt agccattcga atctgatagt cttgctcatc aggacaagta   2940
tcattgtacc tcttgtagat aacatacttt ccctcttgca cagtatcact aggactgtta   3000
ggtttcaaac caccatagac agagaaccag actctggagt caatgaagct accacctcca   3060
actcctggat agttagctac ccaatcccca aacaatgtag tgacatccaa atctttctca   3120
tggtattgac catcaaaacc caatctgcca tgcaccatcc ttgtagggac tgcagaattg   3180
tagtcctctt cttcagtttc tgttacttta ctgcatagca tatcacagcc caaaggtgta   3240
gcagatacag agcaactttt gcgattctgt gtatcatcaa gattgatact gcgaagagtt   3300
gagaagaaca ctctaccagt agcagatgta cgaagaactc caagtgctaa gtactgataa   3360
gagtgagaat ggtcacgaca gccagataga atgacattgt gtgtatagca atagtgtgta   3420
gcactcatgt caaatgaggg tatccgagtg cacccactcc cagttgtggg tgcaggaatg   3480
aagttcagat gttcctggaa agctgaagga tagaaagatg taacatctga agcatcatct   3540
acaatgagtt ctttgccaat acctccaatg tagtctggat catgaattgg ggctccccaa   3600
cctgaattgt tggcagcccc attgatctga taggataggc tggtgattgc attcatgatg   3660
gtagtttctg tgttgagtaa tgcaagtgga ctttcaagtg caacttgttt gtagattcgg   3720
tccacaacat cctggttgga gcctagggta ctggtaatct tctcttcagc cctagagatt   3780
cgtgtgggta tgccaactaa gtctgagggg gtgcttgctc ccatagaata gagtaatgat   3840
gcaacagaga ttgctagggt gacaacagta agaaagagaa tggctatccg aaagataagc   3900
ctccaagtgt tcttggcttc cctctcatca ttctcaagag ccacttgtga aactgctcgg   3960
tccatggttt ggatccgcga tttggtgtat cgagattggt tatgaaattc agatgctagt   4020
gtaatgtatt ggtaatttgg gaagatataa taggaagcaa ggctatttat ccatttctga   4080
aaaggcgaaa tggcgtcacc gcgagcgtca cgctctagtc gaccatgtac gtaagcgctt   4140
acgtttttgg tggacccct cgaccatgta cgtaagcgct tacgtttttg gtggaccccc   4200
tcgaccatgt acgtaagcgc ttacgttttt ggtggacccc ctcgaccatg tacgtaagcg   4260
```

-continued

```
cttacgtttt tggtggaccc cctcgacgga tccccccctcg accctagacg tatctattca   4320
aaagtcgtta atggctgcgg atcaagaaaa agttggaata gaaacagaat acccgcgaaa   4380
ttcaggcccg gttgccatgt cctacacgcc gaaataaacg accaaattag tagaaaaata   4440
aaaactagct cagatactta cgtcacgtct tgcgcactga tttgaaaaat ctcaatataa   4500
acaaagacgg ccacaagaaa aaaccaaaac accgatattc attaatctta tctagtttct   4560
caaaaaaatt catatcttcc acaccctcga gatctagata aacttaatta agcggccgat   4620
ccggtgagta atattgtacg gctaagagcg aatttggcct gtagacctca attgcgagct   4680
ttctaatttc aaactattcg ggcctaactt ttggtgtgat gatgctgact ggcaggatat   4740
ataccgttgt aatttgagct cgtgtgaata agtcgctgtg tatgtttgtt tgattgtttc   4800
tgttggagtg cagcccattt caccggacaa gtcggctaga ttgatttagc cctgatgaac   4860
tgccgagggg aagccatctt gagcgcggaa tgggaatgga tcgaaccggg agcacaggat   4920
gacgcctaac aattcattca agccgacacc gcttcgcggc gcggcttaat tcaggagtta   4980
aacatcatga gggaagcggt gatcgccgaa gtatcgactc aactatcaga ggtagttggc   5040
gtcatcgagc gccatctcga accgacgttg ctggccgtac atttgtacgg ctccgcagtg   5100
gatggcggcc tgaagccaca cagtgatatt gatttgctgg ttacggtgac cgtaaggctt   5160
gatgaaacaa cgcggcgagc tttgatcaac gaccttttgg aaacttcggc ttcccctgga   5220
gagagcgaga ttctccgcgc tgtagaagtc accattgttg tgcacgacga catcattccg   5280
tggcgttatc cagctaagcg cgaactgcaa tttggagaat ggcagcgcaa tgacattctt   5340
gcaggtatct tcgagccagc cacgatcgac attgatctgg ctatcttgct gacaaaagca   5400
agagaacata gcgttgcctt ggtaggtcca gcggcggagg aactctttga tccggttcct   5460
gaacaggatc tatttgaggc gctaaatgaa accttaacgc tatggaactc gccgcccgac   5520
tgggctggcg atgagcgaaa tgtagtgctt acgttgtccc gcatttggta cagcgcagta   5580
accggcaaaa tcgcgccgaa ggatgtcgct gccgactggg caatggagcg cctgccggcc   5640
cagtatcagc ccgtcatact tgaagctagg caggcttatc ttggacaaga agatcgcttg   5700
gcctcgcgcg cagatcagtt ggaagaattt gttcactacg tgaaaggcga gatcaccaag   5760
gtagtcggca aataatgtct aacaattcgt tcaagccgac gccgcttcgc ggcgcggctt   5820
aactcaagcg ttagagagct ggggaagact atgcgcgatc tgttgaaggt ggttctaagc   5880
ctcgtacttg cgatggcatt tcgatcgaaa ggggtacaaa ttcccactaa gcgctcgggg   5940
gctgagaaag cccagtaagg aaacaactgt aggttcgagt cgcgagatcc cccggaacca   6000
aaggaagtag gttaaacccg ctccgatcag gccgagccac gccaggccga gaacattggt   6060
tcctgtaggc atcgggattg gcggatcaaa cactaaagct actggaacga gcagaagtcc   6120
tccggccgcc agttgccagg ccgtaaaggt gagcagaggc acgggaggtt gccacttgcg   6180
ggtcagcacg gttccgaacg ccatggaaac cgcccccgcc aggcccgctg cgacgccgac   6240
aggatctagc gctgcgtttg gtgtcaacac caacagcgcc acgcccgcag ttccgcaaat   6300
agcccccagg accgccatca atcgtatcgg gctacctagc agagcggcag agatgaacac   6360
gaccatcagc ggctgcacag cgcctaccgt cgccgcgacc cgcccggcag gcggtagacc   6420
gaaataaaca acaagctcca gaatagcgaa atattaagtg cgccgaggat gaagatgcgc   6480
atccaccaga ttcccgttgg aatctgtcgg acgatcatca cgagcaataa acccgccggc   6540
aacgcccgca gcagcatacc ggcgacccct cggcctcgct gttcgggctc cacgaaaacg   6600
ccggacagat gcgccttgtg agcgtccttg gggccgtcct cctgtttgaa gaccgacagc   6660
```

-continued

```
ccaatgatct cgccgtcgat gtaggcgccg aatgccacgg catctcgcaa ccgttcagcg   6720
aacgcctcca tgggcttttt ctcctcgtgc tcgtaaacgg acccgaacat ctctggagct   6780
ttcttcaggg ccgacaatcg gatctcgcgg aaatcctgca cgtcggccgc tccaagccgt   6840
cgaatctgag ccttaatcac aattgtcaat tttaatcctc tgtttatcgg cagttcgtag   6900
agcgcgccgt gcgcccgagc gatactgagc gaagcaagtg cgtcgagcag tgcccgcttg   6960
ttcctgaaat gccagtaaag cgctggctgc tgaaccccca gccggaactg accccacaag   7020
gccctagcgt ttgcaatgca ccaggtcatc attgacccag gcgtgttcca ccaggccgct   7080
gcctcgcaac tcttcgcagg cttcgccgac ctgctcgcgc cacttcttca cgcgggtgga   7140
atccgatccg cacatgaggc ggaaggtttc cagcttgagc gggtacggct cccggtgcga   7200
gctgaaatag tcgaacatcc gtcgggccgt cggcgacagc ttgcggtact tctcccatat   7260
gaatttcgtg tagtggtcgc cagcaaacag cacgacgatt tcctcgtcga tcaggacctg   7320
gcaacgggac gttttcttgc cacggtccag gacgcggaag cggtgcagca gcgacaccga   7380
ttccaggtgc ccaacgcggt cggacgtgaa gcccatcgcc gtcgcctgta ggcgcgacag   7440
gcattcctcg gccttcgtgt aataccggcc attgatcgac cagcccaggt cctggcaaag   7500
ctcgtagaac gtgaaggtga tcggctcgcc gataggggtg cgcttcgcgt actccaacac   7560
ctgctgccac accagttcgt catcgtcggc ccgcagctcg acgccggtgt aggtgatctt   7620
cacgtccttg ttgacgtgga aaatgacctt gttttgcagc gcctcgcgcg ggattttctt   7680
gttgcgcgtg gtgaacaggg cagagcgggc cgtgtcgttt ggcatcgctc gcatcgtgtc   7740
cggccacggc gcaatatcga acaaggaaag ctgcatttcc ttgatctgct gcttcgtgtg   7800
tttcagcaac gcggcctgct tggcctcgct gacctgtttt gccaggtcct cgccggcggt   7860
ttttcgcttc ttggtcgtca tagttcctcg cgtgtcgatg gtcatcgact tcgccaaacc   7920
tgccgcctcc tgttcgagac gacgcgaacg ctccacggcg gccgatggcg cgggcagggc   7980
agggggagcc agttgcacgc tgtcgcgctc gatcttggcc gtagcttgct ggaccatcga   8040
gccgacggac tggaaggttt cgcggggcgc acgcatgacg gtgcggcttg cgatggtttc   8100
ggcatcctcg gcggaaaacc ccgcgtcgat cagttcttgc ctgtatgcct tccggtcaaa   8160
cgtccgattc attcaccctc cttgcgggat tgccccgact cacgccgggg caatgtgccc   8220
ttattcctga tttgacccgc ctggtgcctt ggtgtccaga taatccacct tatcggcaat   8280
gaagtcggtc ccgtagaccg tctggccgtc cttctcgtac ttggtattcc gaatcttgcc   8340
ctgcacgaat accagcgacc ccttgcccaa atacttgccg tgggcctcgg cctgagagcc   8400
aaaacacttg atgcggaaga agtcggtgcg ctcctgcttg tcgccggcat cgttgcgcca   8460
ctcttcatta accgctatat cgaaaattgc ttgcggcttg ttagaattgc catgacgtac   8520
ctcggtgtca cgggtaagat taccgataaa ctggaactga ttatggcnnc tcgaaattcc   8580
ctcggtcttg ccttgctcgt cggtgatgta cttcaccagc tccgcgaagt cgctcttctt   8640
gatggagcgc atggggacgt gcttggcaat cacgcgcacc ccccggccgt tttagcggct   8700
aaaaaagtca tggctctgcc ctcgggcgga ccacgcccat catgaccttg ccaagctcgt   8760
cctgcttctc ttcgatcttc gccagcaggg cgaggatcgt ggcatcaccg aaccgcgccg   8820
tgcgcgggtc gtcggtgagc cagagtttca gcaggccgcc caggcggccc aggtcgccat   8880
tgatgcgggc cagctcgcgg acgtgctcat agtccacgac gcccgtgatt ttgtagccct   8940
ggccgacggc cagcaggtag gccgacaggc tcatgccggc cgccgccgcc ttttcctcaa   9000
tcgctcttcg ttcgtctgga aggcagtaca ccttgatagg tgggctgccc ttcctggttg   9060
```

-continued

```
gcttggtttc atcagccatc cgcttgccct catctgttac gccggcggta gccggccagc   9120

ctcgcagagc aggattcccg ttgagcaccg ccaggtgcga ataagggaca gtgaagaagg   9180

aacacccgct cgcgggtggg cctacttcac ctatcctgcc cggctgacgc cgttggatac   9240

accaaggaaa gtctacacga accctttggc aaaatcctgt atatcgtgcg aaaaaggatg   9300

gatataccga aaaaatcgct ataatgaccc cgaagcaggg ttatgcagcg gaaaagatcc   9360

gtcgaccctt tccgacgctc accgggctgg ttgccctcgc cgctgggctg gcggccgtct   9420

atggccctgc aaacgcgcca gaaacgccgt cgaagccgtg tgcgagacac cgcggccgcc   9480

ggcgttgtgg ataccacgcg gaaaacttgg ccctcactga cagatgaggg gcggacgttg   9540

acacttgagg ggccgactca cccggcgcgg cgttgacaga tgaggggcag gctcgatttc   9600

ggccggcgac gtggagctgg ccagcctcgc aaatcggcga aaacgcctga ttttacgcga   9660

gtttcccaca gatgatgtgg acaagcctgg ggataagtgc cctgcggtat tgacacttga   9720

ggggcgcgac tactgacaga tgaggggcgc gatccttgac acttgagggg cagagtgatg   9780

acagatgagg ggcgcaccta ttgacatttg aggggctgtc cacaggcaga aaatccagca   9840

tttgcaaggg tttccgcccg tttttcggcc accgctaacc tgtcttttaa cctgctttta   9900

aaccaatatt tataaacctt gtttttaacc agggctgcgc cctggcgcgt gaccgcgcac   9960

gccgaagggg ggtgcccccc cttctcgaac cctcccggcc cgctaacgcg ggcctcccat  10020

ccccccaggg gctgcgcccc tcggccgcga acggcctcac cccaaaaatg gcaggccaag  10080

ctagcttgct tggtcgttcc ggtacgtacc gtgaacgtcg gctcgattgt acctgcgttc  10140

aaatactttg cgatcgtgtt gcgcgcctgc ccggtgcgtc ggctgatctc acggatcgac  10200

tgcttctctc gcaacgccat ccgacggatg atgtttaaaa gtcccatgtg gatcactccg  10260

ttgccccgtc gctcaccgtg ttggggggaa ggtgcacatg gctcagttct caatggaaat  10320

tatctgccta accggctcag ttctgcgtag aaaccaacat gcaagctcca ccgggtgcaa  10380

agcggcagcg gcggcaggat atattcaatt gtaaatggct tcatgtccgg gaaatctaca  10440

tggatcagca atgagtatga tggtcaatat ggagaaaaag aaagagtaat taccaatttt  10500

ttttcaattc aaaaatgtag atgtccgcag cgttattata aaatgaaagt acattttgat  10560

aaaacgacaa attacgatcc gtcgtattta taggcgaaag caataaacaa attattctaa  10620

ttcggaaatc tttatttcga cgtgtctaca ttcacgtcca aatgggggcg gcgaatt     10677
```

```
<210> SEQ ID NO 26
<211> LENGTH: 10603
<212> TYPE: DNA
<213> ORGANISM: Artificial Sequence
<220> FEATURE:
<223> OTHER INFORMATION: pCHN vector sequence
<220> FEATURE:
<221> NAME/KEY: misc_feature
<222> LOCATION: (8828)..(8829)
<223> OTHER INFORMATION: n is a, c, g, or t

<400> SEQUENCE: 26
```

```
tgcgtagaaa ccaacatgca agctccaccg ggtgcaaagc ggcagcggcg gcaggatata     60

ttcaattgta aatggcttca tgtccgggaa atctacatgg atcagcaatg agtatgatgg    120

tcaatatgga gaaaaagaaa gagtaattac caattttttt tcaattcaaa aatgtagatg    180

tccgcagcgt tattataaaa tgaaagtaca ttttgataaa acgacaaatt acgatccgtc    240

gtatttatag gcgaaagcaa taaacaaatt attctaattc ggaaatcttt atttcgacgt    300

gtctacattc acgtccaaat gggggcggcg aattggccgc aacagaggtg gatggacaga    360
```

-continued

```
cccgttctta caccggactg ggcgcgggat aggatattca gattgggatg ggattgagct    420
taaagccggc gctgagacca tgctcaaggt aggcaatgtc ctcagcgtcg agcccggcat    480
ctatgtcgag ggcattggtg gagcgcgctt cggggatacc gtgcttgtaa ctgagaccgg    540
atatgaggcc ctcactccgc ttgatcttgg caaagatatt tgacgcattt attagtatgt    600
gttaattttc atttgcagtg cagtattttc tattcgatct ttatgtaatt cgttacaatt    660
aataaatatt caaatcagat tattgactgt catttgtatc aaatcgtgtt taatggatat    720
ttttattata atattgatga tatctcaatc aaaacgtaga taataataat atttatttaa    780
tatttttgcg tcgcacagtg aaaatctata tgagattaca aaataccgac aacattattt    840
aagatacata gacattaacc ctgagactgt tggacagagc tcattggtac ctcagatctg    900
ggtaactggc ctaactggcc ttggaggagc tggcaactca aaatcccttt gccaaaaacc    960
aacatcatgc catccaccat gcttgtatcc agctgcgcgc aatgtacccc gggctgtgta   1020
tcccaaagcc tcatgcaacc taacagatgg atcgtttgga aggcctataa cagcaaccac   1080
agacttaaaa ccttgcgcct ccatagactt aagcaaatgt gtgtacaatg tggatcctag   1140
gcccaacctt tgatgcctat gtgacacgta aacagtactc tcaactgtcc aatcgtaagc   1200
gttcctagcc ttccagggcc cagcgtaagc aataccagcc acaacaccct caacctcagc   1260
aaccaaccaa gggtatctat cttgcaacct ctctagatca tcaatccact cttgtggtgt   1320
ttgtggctct gtcctaaagt tcactgtaga cgtctcaatg taatggttaa cgatatcaca   1380
aaccgcggcc atatcagctg ctgtagctgg cctaatctca actggtctcc tctccggaga   1440
agccatggtt tggatccaca aacttacaaa tttctctgaa gttgtatcct cagtacttca   1500
aagaaaatag cttacaccaa atttttttctt gttttcacaa atgccgaact tggttcctta   1560
tataggaaaa ctcaagggca aaaatgacac ggaaaaatat aaaaggataa gtagtggggg   1620
ataagattcc tttgtgataa ggttactttc cgcccttaca ttttccacct tacatgtgtc   1680
ctctatgtct ctttcacaat caccgacctt atcttcttct tttcattgtt gtcgtcagtg   1740
cttacgtctt caagattctt ttcttcgcct ggttcttctt tttcaatttc tacgtattct   1800
tcttcgtatt ctggcagtat aggatcttgt atctgtacat tcttcatttt tgaacatagg   1860
ttgcatatgt gccgcatatt gatctgcttc ttgctgagct cacataatac ttccatagtt   1920
tttcccgtaa acattggatt cttgatgcta catcttggat aattaccttc tggccggccg   1980
cgaattcgct tcaagacgtg ctcaaatcac tatttccaca cccctatatt tctattgcac   2040
tcccttttaa ctgtttttta ttacaaaaat gccctggaaa atgcactccc tttttgtgtt   2100
tgttatttag tgaaacgatg ttgtcaggta atttatttgt cagtctacta tggtggccca   2160
ttatattaat agcaactgtc ggtccaatag acgacgtcga ttttctgcat ttgtttaacc   2220
acgtggattt tatgacattt tatattagtt aatttgtaaa acctacccaa ttaaagacct   2280
catatgttct aaagactaat acttaatgat aacaattttc ttttagtgaa gaaagggata   2340
attagtaaat atggaacaag ggcagaagat ttattaaagc cggtaagaga caacaacgta   2400
ggtacgtgga gtgtcttagg tgacttaccc acataacata aagtgacatt aacaaacata   2460
gctaatgctc ctatttgaat agtgcatatc agcatacctt attacatata gataggagca   2520
aactctagct agattgttga gagagctcgg taccggatcc gaagacttaa cctgatcttg   2580
cttcacgtac accatcatct ttcagaatct ccaccaaaag tggaacaatt ctgaattccc   2640
caaagagagt gttagaaatc tcagctatgc tcagacaata ggtcttgttc gtctttacaa   2700
ctttgaaaca tgtggaggta gtgtatgctg ccttagtaga actagaggaa actctggtta   2760
```

-continued

```
tccttgatct ggatgtagaa tcaaacacag cagaggcagg attcaaccta gcttgaacac   2820
catctaacat tgttccaaac acccctctca aggtatgatt acggtagaag atcaaagggt   2880
aaggatcagt gtaaactcca gtcacacacg aattcggaca tctagctgaa gcttggcaag   2940
gaatcgatcc aggtcttgta aaggcattga aagtatatgg tgaatgtaat gtagctgtct   3000
tgttgctcac agtcattgga tacagtaacg ctgggctaaa gtaggaactt ccacgttgat   3060
agagaaagtg gctagtacca acagtaagaa tccttccctc agctcccatc aatgttacag   3120
tgtttggtgg aacagtaagg actggatctt ctcccaatga tgtgctaacc ttgatactga   3180
gaatagcttg ttgtatcctc ttacctccaa atcttcctgg tttgtatgat gacttagcca   3240
ttcgaatctg atagtcttgc tcatcaggac aagtatcatt gtacctcttg tagataacat   3300
actttccctc ttgcacagta tcactaggac tgttaggttt caaaccacca tagacagaga   3360
accagactct ggagtcaatg aagctaccac ctccaactcc tggatagtta gctacccaat   3420
ccccaaacaa tgtagtgaca tccaaatctt tctcatggta ttgaccatca aaacccaatc   3480
tgccatgcac catccttgta gggactgcag aattgtagtc ctcttcttca gtttctgtta   3540
ctttactgca tagcatatca cagcccaaag gtgtagcaga tacagagcaa cttttgcgat   3600
tctgtgtatc atcaagattg atactgcgaa gagttgagaa gaacactcta ccagtagcag   3660
atgtacgaag aactccaagt gctaagtact gataagagtg agaatggtca cgacagccag   3720
atagaatgac attgtgtgta tagcaatagt gtgtagcact catgtcaaat gagggtatcc   3780
gagtgcaccc actcccagtt gtgggtgcag gaatgaagtt cagatgttcc tggaaagctg   3840
aaggatagaa agatgtaaca tctgaagcat catctacaat gagttctttg ccaatacctc   3900
caatgtagtc tggatcatga attggggctc cccaacctga attgttggca gccccattga   3960
tctgatagga taggctggtg attgcattca tgatggtagt ttctgtgttg agtaatgcaa   4020
gtggactttc aagtgcaact tgtttgtaga ttcggtccac aacatcctgg ttggagccta   4080
gggtactggt aatcttctct tcagccctag agattcgtgt gggtatgcca actaagtctg   4140
agggggtgct tgctcccata gaatagagta atgatgcaac agagattgct agggtgacaa   4200
cagtaagaaa gagaatggct atccgaaaga taagcctcca agtgttcttg gcttccctct   4260
catcattctc aagagccact tgtgaaactg ctcggtccat ggtttggatc cacaaactta   4320
caaatttctc tgaagttgta tcctcagtac ttcaaagaaa atagcttaca ccaaattttt   4380
tcttgttttc acaaatgccg aacttggttc cttatatagg aaaactcaag ggcaaaaatg   4440
acacggaaaa atataaaagg ataagtagtg ggggataaga ttcctttgtg ataaggttac   4500
tttccgccct tacattttcc accttacatg tgtcctctat gtctctttca caatcaccga   4560
ccttatcttc ttcttttcat tgttgtcgtc agtgcttacg tcttcaagat tcttttcttc   4620
gcctggttct tctttttcaa tttctacgta ttcttcttcg tattctggca gtataggatc   4680
ttgtatctgt acattcttca tttttgaaca taggttgcat atgtgccgca tattgatctg   4740
cttcttgctg agctcacata atacttccat agtttttccc gtaaacattg gattcttgat   4800
gctacatctt ggataattac cttctggcgc gcctttgccc gggctttcct gcagggttta   4860
aacttaatta agcggccgat ccggtgagta atattgtacg gctaagagcg aatttggcct   4920
gtagacctca attgcgagct ttctaatttc aaactattcg ggcctaactt ttggtgtgat   4980
gatgctgact ggcaggatat ataccgttgt aatttgagct cgtgtgaata agtcgctgtg   5040
tatgtttgtt tgattgtttc tgttggagtg cagcccattt caccggacaa gtcggctaga   5100
ttgatttagc cctgatgaac tgccgagggg aagccatctt gagcgcggaa tgggaatgga   5160
```

-continued

```
tcgaaccggg agcacaggat gacgcctaac aattcattca agccgacacc gcttcgcggc   5220
gcggcttaat tcaggagtta aacatcatga gggaagcggt gatcgccgaa gtatcgactc   5280
aactatcaga ggtagttggc gtcatcgagc gccatctcga accgacgttg ctggccgtac   5340
atttgtacgg ctccgcagtg gatggcggcc tgaagccaca cagtgatatt gatttgctgg   5400
ttacggtgac cgtaaggctt gatgaaacaa cgcggcgagc tttgatcaac gaccttttgg   5460
aaacttcggc ttcccctgga gagagcgaga ttctccgcgc tgtagaagtc accattgttg   5520
tgcacgacga catcattccg tggcgttatc cagctaagcg cgaactgcaa tttggagaat   5580
ggcagcgcaa tgacattctt gcaggtatct tcgagccagc cacgatcgac attgatctgg   5640
ctatcttgct gacaaaagca agagaacata gcgttgcctt ggtaggtcca gcggcggagg   5700
aactctttga tccggttcct gaacaggatc tatttgaggc gctaaatgaa accttaacgc   5760
tatggaactc gccgcccgac tgggctggcg atgagcgaaa tgtagtgctt acgttgtccc   5820
gcatttggta cagcgcagta accggcaaaa tcgcgccgaa ggatgtcgct gccgactggg   5880
caatggagcg cctgccggcc cagtatcagc ccgtcatact tgaagctagg caggcttatc   5940
ttggacaaga agatcgcttg gcctcgcgcg cagatcagtt ggaagaattt gttcactacg   6000
tgaaaggcga gatcaccaag gtagtcggca aataatgtct aacaattcgt tcaagccgac   6060
gccgcttcgc ggcgcggctt aactcaagcg ttagagagct ggggaagact atgcgcgatc   6120
tgttgaaggt ggttctaagc ctcgtacttg cgatggcatt tcgatcgaaa ggggtacaaa   6180
ttcccactaa gcgctcgggg gctgagaaag cccagtaagg aaacaactgt aggttcgagt   6240
cgcgagatcc cccggaacca aaggaagtag gttaaacccg ctccgatcag gccgagccac   6300
gccaggccga gaacattggt tcctgtaggc atcgggattg gcggatcaaa cactaaagct   6360
actggaacga gcagaagtcc tccggccgcc agttgccagg ccgtaaaggt gagcagaggc   6420
acgggaggtt gccacttgcg ggtcagcacg gttccgaacg ccatggaaac cgcccccgcc   6480
aggcccgctg cgacgccgac aggatctagc gctgcgtttg gtgtcaacac caacagcgcc   6540
acgcccgcag ttccgcaaat agcccccagg accgccatca atcgtatcgg gctacctagc   6600
agagcggcag agatgaacac gaccatcagc ggctgcacag cgcctaccgt cgccgcgacc   6660
cgcccggcag gcggtagacc gaaataaaca acaagctcca gaatagcgaa atattaagtg   6720
cgccgaggat gaagatgcgc atccaccaga ttcccgttgg aatctgtcgg acgatcatca   6780
cgagcaataa acccgccggc aacgcccgca gcagcatacc ggcgacccct cggcctcgct   6840
gttcgggctc cacgaaaacg ccggacagat gcgccttgtg agcgtccttg gggccgtcct   6900
cctgtttgaa gaccgacagc ccaatgatct cgccgtcgat gtaggcgccg aatgccacgg   6960
catctcgcaa ccgttcagcg aacgcctcca tgggcttttt ctcctcgtgc tcgtaaacgg   7020
acccgaacat ctctggagct ttcttcaggg ccgacaatcg gatctcgcgg aaatcctgca   7080
cgtcggccgc tccaagccgt cgaatctgag ccttaatcac aattgtcaat tttaatcctc   7140
tgtttatcgg cagttcgtag agcgcgccgt gcgcccgagc gatactgagc gaagcaagtg   7200
cgtcgagcag tgcccgcttg ttcctgaaat gccagtaaag cgctggctgc tgaaccccca   7260
gccggaactg accccacaag gccctagcgt ttgcaatgca ccaggtcatc attgacccag   7320
gcgtgttcca ccaggccgct gcctcgcaac tcttcgcagg cttcgccgac ctgctcgcgc   7380
cacttcttca cgcgggtgga atccgatccg cacatgaggc ggaaggtttc cagcttgagc   7440
gggtacggct cccggtgcga gctgaaatag tcgaacatcc gtcgggccgt cggcgacagc   7500
ttgcggtact tctcccatat gaatttcgtg tagtggtcgc cagcaaacag cacgacgatt   7560
```

-continued

```
tcctcgtcga tcaggacctg gcaacgggac gttttcttgc cacggtccag gacgcggaag   7620
cggtgcagca gcgacaccga ttccaggtgc ccaacgcggt cggacgtgaa gcccatcgcc   7680
gtcgcctgta ggcgcgacag gcattcctcg gccttcgtgt aataccggcc attgatcgac   7740
cagcccaggt cctggcaaag ctcgtagaac gtgaaggtga tcggctcgcc gataggggtg   7800
cgcttcgcgt actccaacac ctgctgccac accagttcgt catcgtcggc ccgcagctcg   7860
acgccggtgt aggtgatctt cacgtccttg ttgacgtgga aaatgacctt gttttgcagc   7920
gcctcgcgcg ggattttctt gttgcgcgtg gtgaacaggg cagagcgggc cgtgtcgttt   7980
ggcatcgctc gcatcgtgtc cggccacggc gcaatatcga acaaggaaag ctgcatttcc   8040
ttgatctgct gcttcgtgtg tttcagcaac gcggcctgct tggcctcgct gacctgtttt   8100
gccaggtcct cgccggcggt ttttcgcttc ttggtcgtca tagttcctcg cgtgtcgatg   8160
gtcatcgact tcgccaaacc tgccgcctcc tgttcgagac gacgcgaacg ctccacggcg   8220
gccgatggcg cgggcagggc agggggagcc agttgcacgc tgtcgcgctc gatcttggcc   8280
gtagcttgct ggaccatcga gccgacggac tggaaggttt cgcggggcgc acgcatgacg   8340
gtgcggcttg cgatggtttc ggcatcctcg gcggaaaacc ccgcgtcgat cagttcttgc   8400
ctgtatgcct tccggtcaaa cgtccgattc attcaccctc cttgcgggat tgccccgact   8460
cacgccgggg caatgtgccc ttattcctga tttgacccgc ctggtgcctt ggtgtccaga   8520
taatccacct tatcggcaat gaagtcggtc ccgtagaccg tctggccgtc cttctcgtac   8580
ttggtattcc gaatcttgcc ctgcacgaat accagcgacc ccttgcccaa atacttgccg   8640
tgggcctcgg cctgagagcc aaaacacttg atgcggaaga agtcggtgcg ctcctgcttg   8700
tcgccggcat cgttgcgcca ctcttcatta accgctatat cgaaaattgc ttgcggcttg   8760
ttagaattgc catgacgtac ctcggtgtca cgggtaagat taccgataaa ctggaactga   8820
ttatggcnnc tcgaaattcc ctcggtcttg ccttgctcgt cggtgatgta cttcaccagc   8880
tccgcgaagt cgctcttctt gatggagcgc atggggacgt gcttggcaat cacgcgcacc   8940
ccccggccgt tttagcggct aaaaaagtca tggctctgcc ctcgggcgga ccacgcccat   9000
catgaccttg ccaagctcgt cctgcttctc ttcgatcttc gccagcaggg cgaggatcgt   9060
ggcatcaccg aaccgcgccg tgcgcgggtc gtcggtgagc cagagtttca gcaggccgcc   9120
caggcggccc aggtcgccat tgatgcgggc cagctcgcgg acgtgctcat agtccacgac   9180
gcccgtgatt ttgtagccct ggccgacggc cagcaggtag gccgacaggc tcatgccggc   9240
cgccgccgcc ttttcctcaa tcgctcttcg ttcgtctgga aggcagtaca ccttgatagg   9300
tgggctgccc ttcctggttg gcttggtttc atcagccatc cgcttgccct catctgttac   9360
gccggcggta gccggccagc ctcgcagagc aggattcccg ttgagcaccg ccaggtgcga   9420
ataagggaca gtgaagaagg aacacccgct cgcgggtggg cctacttcac ctatcctgcc   9480
cggctgacgc cgttggatac accaaggaaa gtctacacga accctttggc aaaatcctgt   9540
atatcgtgcg aaaaaggatg gatataccga aaaaatcgct ataatgaccc cgaagcaggg   9600
ttatgcagcg gaaaagatcc gtcgaccctt tccgacgctc accgggctgg ttgccctcgc   9660
cgctgggctg gcggccgtct atggccctgc aaacgcgcca gaaacgccgt cgaagccgtg   9720
tgcgagacac cgcggccgcc ggcgttgtgg ataccacgcg gaaaacttgg ccctcactga   9780
cagatgaggg gcggacgttg acacttgagg ggccgactca cccggcgcgg cgttgacaga   9840
tgaggggcag gctcgatttc ggccggcgac gtggagctgg ccagcctcgc aaatcggcga   9900
aaacgcctga ttttacgcga gtttcccaca gatgatgtgg acaagcctgg ggataagtgc   9960
```

-continued

```
cctgcggtat tgacacttga ggggcgcgac tactgacaga tgaggggcgc gatccttgac  10020

acttgagggg cagagtgatg acagatgagg ggcgcaccta ttgacatttg aggggctgtc  10080

cacaggcaga aaatccagca tttgcaaggg tttccgcccg tttttcggcc accgctaacc  10140

tgtcttttaa cctgctttta aaccaatatt tataaacctt gtttttaacc agggctgcgc  10200

cctggcgcgt gaccgcgcac gccgaagggg ggtgcccccc cttctcgaac cctcccggcc  10260

cgctaacgcg ggcctcccat ccccccaggg gctgcgcccc tcggccgcga acggcctcac  10320

cccaaaaatg gcaggccaag ctagcttgct tggtcgttcc ggtacgtacc gtgaacgtcg  10380

gctcgattgt acctgcgttc aaatactttg cgatcgtgtt gcgcgcctgc ccggtgcgtc  10440

ggctgatctc acggatcgac tgcttctctc gcaacgccat ccgacggatg atgtttaaaa  10500

gtcccatgtg gatcactccg ttgccccgtc gctcaccgtg ttggggggaa ggtgcacatg  10560

gctcagttct caatggaaat tatctgccta accggctcag ttc                     10603
```